(12) United States Patent
Honda et al.

(10) Patent No.: US 7,361,744 B2
(45) Date of Patent: Apr. 22, 2008

(54) OLIGOSACCHARIDE DERIVATIVE

(75) Inventors: Takeshi Honda, Tokyo (JP); Akira Okuno, Tokyo (JP); Masanori Izumi, Tokyo (JP); Xiaoliu Li, Tokyo (JP)

(73) Assignee: Sankyo Company Limited, Chuo-Ku, Tokyo (JP)

( * ) Notice: Subject to any disclaimer, the term of this patent is extended or adjusted under 35 U.S.C. 154(b) by 314 days.

(21) Appl. No.: 11/193,655

(22) Filed: Jul. 28, 2005

(65) Prior Publication Data

US 2006/0025350 A1 Feb. 2, 2006

Related U.S. Application Data

(63) Continuation of application No. PCT/JP2004/000879, filed on Jan. 29, 2004.

(30) Foreign Application Priority Data

Jan. 30, 2003 (JP) ............... 2003-022800

(51) Int. Cl.
- *C07H 15/00* (2006.01)
- *C07H 17/00* (2006.01)
- *C07H 17/02* (2006.01)
- *A01N 43/04* (2006.01)
- *A61H 31/70* (2006.01)
- *C07G 3/00* (2006.01)
- *C07G 11/00* (2006.01)

(52) U.S. Cl. ............... 536/17.4; 514/25; 514/27; 514/61; 536/4.1; 536/18.5

(58) Field of Classification Search .............. None
See application file for complete search history.

(56) References Cited

U.S. PATENT DOCUMENTS 6,596,696 B1 7/2003 Uchida et al.
2004/0006046 A1 1/2004 Uchida et al.

FOREIGN PATENT DOCUMENTS

WO   WO 00/50494 A1   8/2000
WO   WO 01/94367 A1   12/2001

OTHER PUBLICATIONS

Toru Yamashita et al., "New Polyhydroxylated Pyrrolidine, Piperidine, and Pyrrolizidine Alkaloids from *Scilla sibirica*," Journal of Natural Products, vol. 65, No. 12, pp. 1875-1881, Dec. 2002, published on web Nov. 1, 2002.

Riichiro Uchida et al., "Synthesis of New N-Containing Maltooligosaccharides, α-Amylase Inhibitors, and Their Biological Acitivities," Chemical & Pharmaceutical Bulletin, vol. 47, No. 2, pp. 187-193, Feb. 1999.

Japanese Patent Office, International Search Report for PCT/JP2004/000879, May 18, 2004.

Undated English translation of the International Preliminary Report on Patentability for corresponding application No. PCT/JP2004/000879.

*Primary Examiner*—Shaojia Anna Jiang
*Assistant Examiner*—Layla Bland
(74) *Attorney, Agent, or Firm*—Morgan & Finnegan, LLP

(57) ABSTRACT

Compounds having the formula (I):

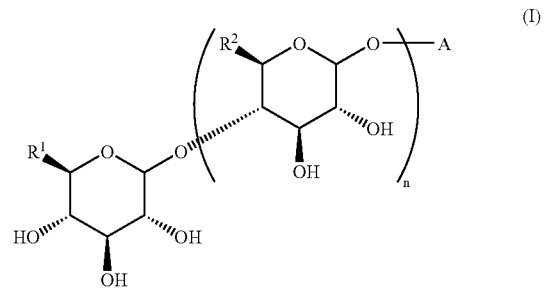

wherein A represents a group such as a cyclic group, $R^1$ and $R^2$ represent groups such as alkyl groups or hydroxymethyl groups, and n represents 1 or 2, or pharmacologically acceptable salts thereof or pharmacologically acceptable esters thereof have superior activity and stability, and are useful for the treatment and/or prevention of diabetes mellitus, or the like.

22 Claims, No Drawings

OLIGOSACCHARIDE DERIVATIVE

This is a continuation of prior application serial no. PCT/JP2004/000879, filed 29 Jan. 2004.

TECHNICAL FIELD

The present invention relates to a novel oligosaccharide derivative, its pharmacologically acceptable salts and its pharmacologically acceptable esters.

The present invention also relates to an oligosaccharide derivative having actions including α-amylase inhibitory action, blood glucose lowering action and lipid lowering action, its pharmacologically acceptable salts and its pharmacologically acceptable esters.

Moreover, the present invention relates to a therapeutic drug and/or preventive drug for a disease such as, hyperglycemia, post prandial hyperglycemia, impaired glucose tolerance (IGT), diabetes mellitus, obesity, hyperlipemia, fatty liver, hepatomegaly, diabetic complications, neuropathy, arteriosclerosis, cataract or diabetic nephropathy (and preferably a therapeutic drug and/or preventive drug for hyperglycemia or diabetes mellitus) containing as its active ingredient an oligosaccharide derivative, its pharmacologically acceptable salts or its pharmacologically acceptable esters.

Moreover, the present invention relates to a preventive drug or therapeutic drug for the aforementioned diseases containing as its active ingredient the aforementioned compound, a composition for preventing or treating the aforementioned diseases containing as its active ingredient the aforementioned compound, the use of the aforementioned compound to produce a pharmaceutical for preventing or treating the aforementioned diseases, or a prevention or treatment method for the aforementioned diseases in which a pharmacologically effective amount of the aforementioned compound is administered to a mammal (and preferably to a human).

BACKGROUND ART

In the past, digestive enzyme inhibitors such as Basen (Takeda Pharmaceutical), containing voglibose, and Glucobay (Bayer), containing acarbose, have actually been used clinically as effective therapeutic drugs for hyperglycemia. However, since both compounds inhibit α-glucosidase, they have the disadvantages of causing adverse side effects such as abdominal distention, flatulence, increased abdominal wind, soft stools, diarrhea and abdominal pain. Moreover, they have also been reported to cause liver function disorders.

On the other hand, effects causing inhibition of the absorption of nutrients are known to be obtainable by inhibiting not only α-glucosidase, but α-amylase as well, and compounds are known that lower blood glucose levels without causing the aforementioned adverse side effects unique to α-glucosidase inhibitors. However, the α-amylase activity of these compounds is weak, and there are no compounds known that have adequate α-amylase inhibitory activity.

Compounds having a partial structure (sugar derivative) that is in common with the oligosaccharide derivative of the present invention that demonstrate α-amylase inhibitory activity have been disclosed (see, for example, International Publication WO 00/50434 and International Publication WO 01/94367). However, these compounds differ from the compound of the present invention in that they are required to have a deoxynojirimycin backbone or a hexahydro-3,5,6-trihydroxy-1H-azepine backbone.

DISCLOSURE OF THE INVENTION

α-amylase inhibitors are required to be resistant to degradation in the digestive tract (and particularly the small intestine) and demonstrate stable action. However, since previously reported α-amylase inhibitors cannot be said to demonstrate adequate stability in the small intestine, there is a possibility that they cannot demonstrate adequate pharmacological effects stably. In addition, this instability in the digestive tract (and particularly the small intestine) results in the risk of having some form of effect on liver function resulting from absorption of their degradation products.

Therefore, the inventors of the present invention conducted extensive research for the purpose of developing a therapeutic drug and/or preventive drug for diseases such as hyperglycemia and diabetes mellitus that has superior α-amylase inhibitory activity and high stability, and found that a novel oligosaccharide derivative has superior α-amylase inhibitory action, blood glucose lowering action and lipid lowering action, improves diseases such as hyperglycemia, post prandial hyperglycemia, hyperglycemia, impaired glucose tolerance (IGT), diabetes mellitus, obesity, hyperlipemia, fatty liver, hepatomegaly, diabetic complications, neuropathy, arteriosclerosis, cataract and diabetic nephropathy, and has high stability, thereby leading to completion of the present invention.

Namely, the present invention provides an oligosaccharide derivative, its pharmacologically acceptable salts and its pharmacologically acceptable esters, which are useful as therapeutic drugs or preventive drugs for diseases such as hyperglycemia, post prandial hyperglycemia, impaired glucose tolerance (IGT), diabetes mellitus, obesity, hyperlipemia, fatty liver, hepatomegaly, diabetic complications (such as retinopathy, nephropathy and neuropathy), neuropathy, arteriosclerosis, cataract and diabetic nephropathy.

The present invention relates to a compound represented by the following general formula (I):

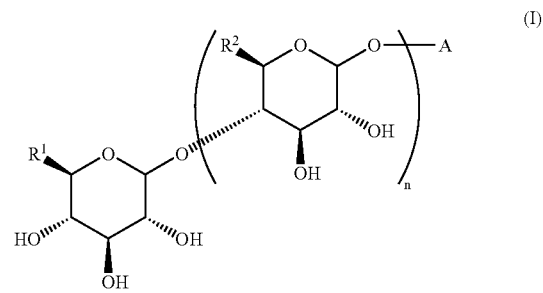

(wherein A represents the following general formula (A1), (A2) or (A3):

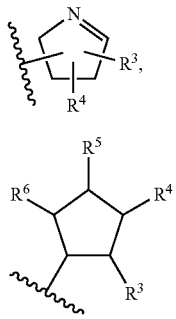

(A2)

(A3)

R¹ and R² may be the same or different and each represent a C1-C6 alkyl group, hydroxymethyl group, C1-C6 alkoxymethyl group or C1-C6 haloalkyl group, R³, R⁴, R⁵ and R⁶ may be the same or different and each represent a C1-C6 alkyl group, C1-C6 alkoxy group, C1-C6 hydroxyalkyl group, C1-C6 haloalkyl group, amino group (which amino group may be substituted with one or two C1-C6 alkyl groups or C1-C6 hydroxyalkyl groups), hydroxyl group, hydrogen atom or halogen atom, R⁷ represents a C1-C6 alkyl group, C1-C6 alkoxy group, C1-C6 hydroxyalkyl group, C1-C6 haloalkyl group, hydroxyl group or hydrogen atom, and n represents an integer of 1 or 2), its pharmacologically acceptable salts or its pharmacologically acceptable esters.

In the present invention, a "C1-C3 alkyl group" refers to a linear or branched alkyl group having 1 to 3 carbon atoms, examples of which include methyl, ethyl, n-propyl and isopropyl groups. In R¹, R², R³, R⁴, R⁵ and R⁶, the C1-C3 alkyl group is preferably a methyl group.

In the present invention, a "C1-C6 alkyl group" refers to a linear or branched alkyl group having 1 to 6 carbon atoms, examples of which include the groups indicated as examples of the aforementioned "C1-C3 alkyl group" as well as n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl groups. In the substituents of R¹, R², R³, R⁴, R⁵, R⁶, R⁷ and the amino group of R³, R⁴, R⁵ and R⁶, the C1-C6 alkyl group is preferably an alkyl group having 1 to 3 carbon atoms, and most preferably a methyl group.

In the present invention, a "halogen atom" refers to a fluorine atom, chlorine atom, bromine atom or iodine atom, and is preferably a fluorine atom in R³, R⁴, R⁵, R⁶, R⁸, R⁹ and R¹¹.

In the present invention, a "C1-C3 haloalkyl group" or "C1-C6 haloalkyl group" respectively refer to groups in which the aforementioned "C1-C3 alkyl group" or "C1-C6 alkyl group" is substituted with the aforementioned "halogen atom(s)". Examples of the "C1-C3 haloalkyl group" include trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl and 2,2-dibromoethyl groups, and it is preferably a fluoromethyl group in R¹, R², R³, R⁴, R⁵, R⁶, R⁷ and R¹⁰. Examples of the "C1-C6 haloalkyl group" include the aforementioned examples of the "C1-C3 haloalkyl group" as well as 4-iodobutyl, 4-fluorobutyl, 4-chlorobutyl, 5-iodopentyl, 5-fluoropentyl, 5-chloropentyl, 6-iodohexyl, 6-fluorohexyl and 6-chlorohexyl groups, and it is preferably a C1-C3 haloalkyl group and more preferably a fluoromethyl group in R¹, R², R³, R⁴, R⁵, R⁶, R⁷ and R¹⁰.

In the present invention, a "C1-C3 hydroxyalkyl group" or "C1-C6 hydroxyalkyl group" respectively refers to a group in which the aforementioned "C1-C3 alkyl group" or "C1-C6 alkyl group" is substituted with a hydroxyl group. Examples of the "C1-C3 hydroxyalkyl group" include hydroxymethyl, hydroxyethyl and hydroxypropyl groups, and it is preferably a hydroxymethyl group in R³, R⁴, R⁵, R⁶, R⁷, R¹⁰ and R¹¹. Examples of the "C1-C6 hydroxyalkyl group" include the aforementioned examples of the "C1-C3 hydroxyalkyl group" as well as hydroxybutyl, hydroxypentyl and hydroxyhexyl groups, and it is preferably a C1-C3 hydroxyalkyl group, and more preferably a hydroxymethyl group, in R³, R⁴, R⁵, R⁶, R⁷, R¹⁰ and R¹¹.

In the present invention, a "C1-C3 alkoxy group" or "C1-C6 alkoxy group" respectively refers to a group in which a "C1-C3 alkyl group" or "C1-C6 alkyl group" is bonded to an oxygen atom. Examples of the "C1-C3 alkoxy group" include methoxy, ethoxy, n-propoxy and isopropoxy groups. Examples of the "C1-C6 alkoxy group" include the aforementioned examples of a "C1-C3 alkoxy group" as well as n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy groups, and it is preferably a C1-C3 alkoxy group, and more preferably a methoxy group, in R³, R⁴, R⁵, R⁶ and R⁷.

In the present invention, a "C1-C3 alkoxymethyl group" or "C1-C6 alkoxymethyl group" respectively refers to a group in which the aforementioned "C1-C3 alkoxy group" or "C1-C6 alkoxy group" is bonded to a methyl group. Examples of the "C1-C3 alkoxymethyl group" include methoxymethyl, ethoxymethyl, n-propoxymethyl and isopropoxymethyl groups, and it is preferably a methoxymethyl group in R¹ and R². Examples of a "C1-C6 alkoxymethyl group" include the aforementioned examples of the "C1-C3 alkoxymethyl group" as well as n-butoxymethyl, isobutoxymethyl, s-butoxymethyl, tert-butoxymethyl, n-pentoxymethyl, isopentoxymethyl, 2-methylbutoxymethyl, neopentoxymethyl, n-hexyloxymethyl, 4-methylpentoxymethyl, 3-methylpentoxymethyl, 2-methylpentoxymethyl, 3,3-dimethylbutoxymethyl, 2,2-dimethylbutoxymethyl, 1,1-dimethylbutoxymethyl, 1,2-dimethylbutoxymethyl, 1,3-dimethylbutoxymethyl and 2,3-dimethylbutoxymethyl groups, and it is preferably a "C1-C3 alkoxymethyl group", and more preferably a methoxymethyl group, in R¹ and R².

Oligosaccharide derivatives having the general formulas (I), (Ia) and (Ib) of the present invention can be converted to an acid addition salt in the case of having a basic group in accordance with ordinary methods. Examples of such salts include salts of halogenated hydroacids such as hydrofluoric acid, hydrochloric acid, hydrobromic acid and hydroiodic acid; inorganic acid salts such as nitrates, perchlorates, sulfates and phosphates; salts of lower alkanesulfonic acids such as methanesulfonic acid, trifluoromethanesulfonic acid and ethanesulfonic acid; salts of arylsulfonic acids such as benzenesulfonic acid and p-toluenesulfonic acid; salts of amino acids such as glutamic acid and aspartic acid; and, salts of carboxylic acids such as acetic acid, fumaric acid, tartaric acid, oxalic acid, maleic acid, malic acid, succinic acid, benzoic acid, mandelic acid, ascorbic acid, lactic acid, gluconic acid and citric acid. The aforementioned salt is preferably a salt of a halogenated hydroacid, and most preferably a hydrochloride.

Moreover, oligosaccharide derivatives having the aforementioned general formulas (I), (Ia) and (Ib) can be converted to a metal salt in accordance with ordinary methods since they have a hydroxyl group. Examples of such salts include salts of alkali metals such as lithium, sodium and potassium; salts of alkaline earth metals such as calcium, barium and magnesium; and, aluminium salts. The aforementioned metal salt is preferably an alkali metal salt.

Oligosaccharide derivatives having the aforementioned general formulas (I), (Ia) and (Ib) of the present invention can be converted to pharmacologically acceptable esters in accordance with ordinary methods. There are no particular limitations on such esters provided they can be used medically and their pharmacological acceptability is comparable to that of the oligosaccharide derivatives of the aforementioned general formulas (I), (Ia) and (Ib).

Examples of ester residues of oligosaccharide derivatives having the aforementioned general formulas (I), (Ia) and (Ib) of the present invention include C1-C6 alkyl groups (wherein said alkyl groups may be substituted with a trialkylsilyl group), C7-C16 aralkyl groups, C1-C5 alkyl groups substituted with C1-C6 alkanoyloxy groups, C1-C5 alkyl groups substituted with C1-C6 alkyloxycarbonyloxy groups, C1-C5 alkyl groups substituted with C5-C7 cycloalkyloxycarbonyloxy groups, C1-C5 alkyl groups substituted with C6-C10 aryloxycarbonyloxy groups, and 2-oxy-1,3-dioxolen-4-yl groups having a C1-C6 alkyl group as a substituent at the 5-position.

Here, C1-C6 alkyl groups are preferably linear or branched alkyl groups having 1 to 4 carbon atoms, and more preferably are methyl, ethyl, propyl, isopropyl, butyl or isobutyl groups, and most preferably are methyl groups or ethyl groups.

C1-C5 alkyl groups refer to linear or branched alkyl groups having 1 to 5 carbon atoms, preferably methyl, ethyl, propyl, isopropyl, butyl or isobutyl groups, and most preferably methyl or ethyl groups.

C5-C7 cycloalkyl groups refer to 5- to 7-member saturated cyclic hydrocarbon groups, examples of which include cyclopentyl, cyclohexyl and cyclobutyl groups, and preferably cyclohexyl groups.

C6-C10 aryl groups refer to aromatic hydrocarbon groups having 6 to 10 carbon atoms, examples of which include phenyl, indenyl and naphthyl groups, and preferably phenyl groups.

C7-C16 aralkyl groups refer to groups in which the aforementioned "C6-C10 aryl group" is bonded to the aforementioned "C1-C6 alkyl group", examples of which include benzyl, α-naphtylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl, and 6-naphthylhexyl groups. They are preferably "aralkyl groups" in which the number of carbons of the "alkyl group" is 1 to 4, and more preferably benzyl groups in $R^1$ and $R^2$.

Specific preferable examples of ester residues include methyl, ethyl, propyl, isopropyl, butyl, isobutyl, t-butyl, benzyl, acetoxymethyl, 1-(acetoxy)ethyl, propionyloxymethyl, 1-(propionyloxy)ethyl, butyryloxymethyl, 1-(butyryloxy)ethyl, isobutyryloxymethyl, 1-(isobutyryloxy)ethyl, valeryloxymethyl, 1-(valeryloxy)ethyl, isovaleryloxymethyl, 1-(isovaleryloxy)ethyl, pivaloyloxymethyl, 1-(pivaloyloxy)ethyl, methoxycarbonyloxymethyl, 1-(methoxycarbonyloxy)ethyl, ethoxycarbonyloxymethyl, 1-(ethoxycarbonyloxy)ethyl, propoxycarbonyloxymethyl, 1-(propoxycarbonyloxy)ethyl, isopropoxycarbonyloxymethyl, 1-(isopropoxycarbonyloxy) ethyl, butoxycarbonyloxymethyl, 1-(butoxycarbonyloxy)ethyl, isobutoxycarbonyloxymethyl, 1-(isobutoxycarbonyloxy)ethyl, t-butoxycarbonyloxymethyl, 1-(t-butoxycarbonyloxy)ethyl, cyclopentanecarbonyloxymethyl, 1-(cyclopentanecarbonyloxy)ethyl, cyclohexanecarbonyloxymethyl, 1-(cyclohexanecarbonyloxy)ethyl, cyclopentyloxycarbonyloxymethyl, 1-(cyclopentyloxycarbonyloxy)ethyl, cyclohexyloxycarbonyloxymethyl, 1-(cyclohexyloxycarbonyloxy)ethyl, benzoyloxymethyl, 1-(benzoyloxy)ethyl, phenoxycarbonyloxymethyl, 1-(phenoxycarbonyloxy)ethyl, (5-methyl-2-oxo-1,3-dioxolen-4-yl)methyl or 2-trimethylsilylethyl group.

Furthermore, oligosaccharide derivatives having the aforementioned general formulas (I), (Ia) and (Ib) have various isomers. For example, optical isomers can be present in portion A and the bonding portion of the sugar in oligosaccharide derivatives having the aforementioned general formulas (I), (Ia) and (Ib). In the aforementioned general formulas (I), (Ia) and (Ib), these stereoisomers based on asymmetric carbons and the racemic and non-racemic mixtures of these isomers are all indicated with a single formula. Thus, the present invention includes these isomers and mixtures of these isomers in various proportions.

Moreover, in the case oligosaccharide derivatives having the aforementioned general formulas (I), (Ia) and (Ib), their salts or their esters form solvates (for example, hydrates), the present invention includes these as well.

Moreover, compounds converted to oligosaccharide derivatives having the aforementioned general formulas (I), (Ia) and (Ib) that are metabolized in the living body, their salts or their esters (for example, so-called pro-drugs such as amide derivatives) are all included in the present invention.

In the present invention, (A1) is preferably the following general formula (A1a) or (A1b):

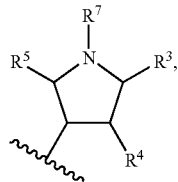
(A1a)

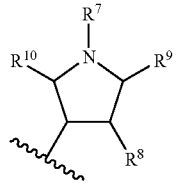
(A1b)

and more preferably the following general formula (A1c):

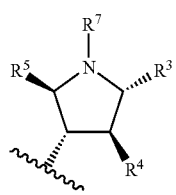
(A1c)

(A2) is preferably the following general formula (A2a) or (A2b):

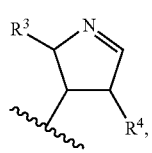
(A2a)

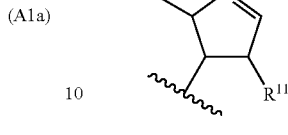
(A2b)

and more preferably the following general formula (A2c):

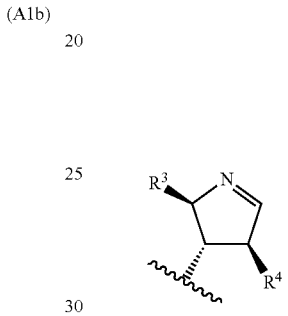
(A2c)

(A3) is preferably the following general formula (A3a):

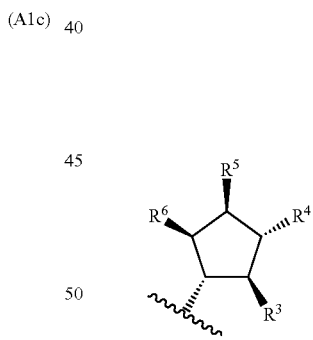
(A3a)

$R^1$ is preferably a C1-C6 alkyl group or hydroxymethyl group, and more preferably, a methyl group or hydroxymethyl group, and particularly preferably a methyl group.

$R^2$ is preferably a C1-C6 alkyl group or hydroxymethyl group, more preferably a methyl group or hydroxymethyl group, and particularly preferably a hydroxymethyl group.

R³ is preferably a C1-C6 hydroxyalkyl group, hydroxyl group, halogen atom or hydrogen atom in general formulas (A1), (A1c) and (A1a), more preferably a C1-C3 hydroxyalkyl group or hydrogen atom, and particularly preferably a hydrogen atom. In general formulas (A2), (A2a), (A2b) and (A2c), R³ is preferably a C1-C6 hydroxyalkyl group, hydroxyl group, hydrogen atom or halogen atom, more preferably a C1-C3 hydroxyalkyl group or hydrogen atom, and particularly preferably a hydroxymethyl group. In general formulas (A3) and (A3a), R³ is preferably a C1-C6 hydroxyalkyl group, amino group, hydroxyl group, hydrogen atom or halogen atom, more preferably a hydroxymethyl group, hydroxyl group or amino group, and particularly preferably a hydroxyl group.

R⁴ is preferably a C1-C6 hydroxyalkyl group, hydrogen atom, hydroxyl group or halogen atom in general formulas (A1), (A1c) and (A1a), more preferably a hydroxyl group or halogen atom, particularly preferably a hydroxyl group or fluorine atom, and most preferably a hydroxyl group. In general formulas (A2), (A2a), (A2b) and (A2c), R⁴ is preferably a C1-C6 hydroxylalkyl group, hydrogen atom, halogen atom or hydroxyl group, and more preferably a hydroxyl group. In general formulas (A3) and (A3a), R⁴ is preferably a C1-C6 hydroxyalkyl group, amino group, hydroxyl group, halogen atom or hydrogen atom, more preferably a hydroxyl group, halogen atom or hydrogen atom, and particularly preferably a hydroxyl group.

R⁵ is preferably a hydroxyl group, halogen atom, C1-C6 hydroxyalkyl group, C1-C6 haloalkyl group or hydrogen atom in general formulas (A1), (A1c) and (A1a), more preferably a C1-C6 hydroxyalkyl group, particularly preferably a C1-C3 hydroxyalkyl group, and most preferably a hydroxymethyl group. In general formulas (A3) and (A3a), R⁵ is preferably a C1-C6 hydroxyalkyl group, hydroxyl group, hydrogen atom, halogen atom or amino group (and said amino group may be substituted with one or two C1-C6 alkyl groups or C1-C6 hydroxyalkyl groups), more preferably an amino group (and said amino group may be substituted with one or two C1-C6 alkyl groups or C1-C6 hydroxyalkyl groups), and particularly preferably an amino group.

R⁶ is preferably a C1-C6 hydroxyalkyl group, amino group, hydroxyl group, hydrogen atom or halogen atom in general formulas (A3) and (A3a), more preferably a C1-C6 hydroxyalkyl group, particularly preferably a C1-C3 hydroxyalkyl group, and most preferably a hydroxymethyl group.

R⁷ is preferably a hydrogen atom, C1-C6 hydroxyalkyl group or C1-C6 alkyl group, more preferably a hydrogen atom or methyl group, and particularly preferably a hydrogen atom.

R⁸ and R⁹ are preferably C1-C3 hydroxyalkyl groups, halogen atoms, hydrogen atoms or hydroxyl groups, and more preferably hydrogen atoms or hydroxyl groups.

R¹⁰ is preferably a C1-C6 hydroxyalkyl group, more preferably a C1-C3 hydroxyalkyl group, and particularly preferably a hydroxymethyl group.

R¹¹ is preferably a hydroxyl group.

n is preferably 1.

General formula (I) is preferably the following general formula (IA) or (IB):

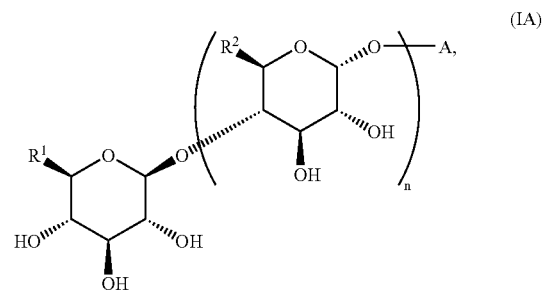

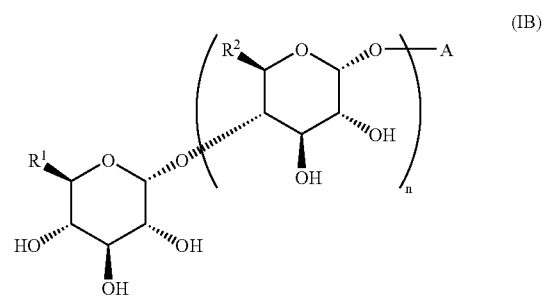

A is preferably the following general formula (A1) or (A2):

and preferably (A1).

Specific examples of oligosaccharide derivatives having the aforementioned general formulas (I), (Ia) and (Ib) of the present invention, their pharmacologically acceptable salts and their pharmacologically acceptable esters include the compounds listed to follow. However, the present invention is not limited to these exemplification compounds.

Furthermore, in the following Tables 1 to 5, ""Pr" indicates an n-propyl group, ""iPr" an i-propyl group, ""Bu" an n-butyl group, ""tBu" a t-butyl group, ""iBu" an i-butyl group, ""Pn" an n-pentyl group, and ""Hex" an n-hexyl group.

TABLE 1

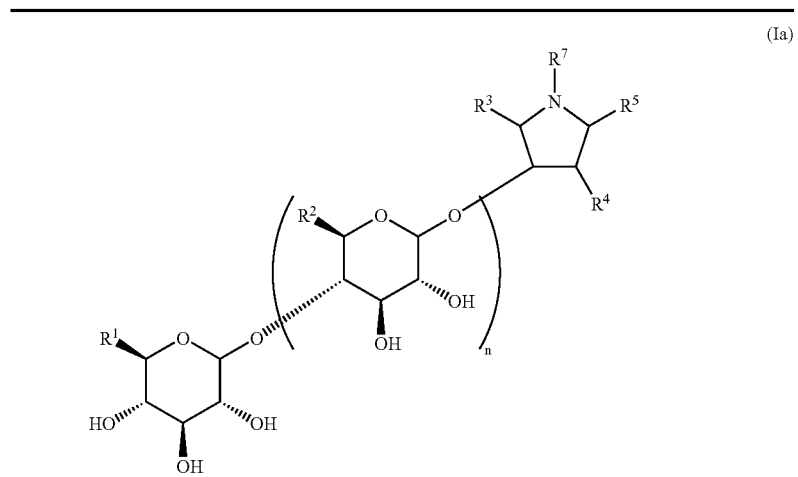

| No. | $R^1$ | $R^2$ | $R^7$ | $R^3$ | $R^4$ | $R^5$ | n |
|---|---|---|---|---|---|---|---|
| 1-1 | $CH_3$ | $CH_2OH$ | H | $CH_2OH$ | OH | H | 1 |
| 1-2 | $CH_3$ | $CH_3$ | H | $CH_2OH$ | OH | H | 1 |
| 1-3 | $CH_3$ | $CH_2F$ | H | $CH_2OH$ | OH | H | 1 |
| 1-4 | $CH_3$ | $CH_2OCH_3$ | H | $CH_2OH$ | OH | H | 1 |
| 1-5 | $CH_3$ | $CH_2CH_3$ | H | $CH_2OH$ | OH | H | 1 |
| 1-6 | $CH_3$ | $^nPr$ | H | $CH_2OH$ | OH | H | 1 |
| 1-7 | $CH_3$ | $^iPr$ | H | $CH_2OH$ | OH | H | 1 |
| 1-8 | $CH_3$ | $^nBu$ | H | $CH_2OH$ | OH | H | 1 |
| 1-9 | $CH_3$ | $^iBu$ | H | $CH_2OH$ | OH | H | 1 |
| 1-10 | $CH_3$ | $^tBu$ | H | $CH_2OH$ | OH | H | 1 |
| 1-11 | $CH_3$ | $^nPn$ | H | $CH_2OH$ | OH | H | 1 |
| 1-12 | $CH_3$ | $^nHex$ | H | $CH_2OH$ | OH | H | 1 |
| 1-13 | $CH_3$ | $CH_2OCH_2CH_3$ | H | $CH_2OH$ | OH | H | 1 |
| 1-14 | $CH_3$ | $CH_2O^iPr$ | H | $CH_2OH$ | OH | H | 1 |
| 1-15 | $CH_3$ | $CH_2O^tBu$ | H | $CH_2OH$ | OH | H | 1 |
| 1-16 | $CH_3$ | $(CH_2)_2F$ | H | $CH_2OH$ | OH | H | 1 |
| 1-17 | $CH_3$ | $(CH_2)_3F$ | H | $CH_2OH$ | OH | H | 1 |
| 1-18 | $CH_3$ | $(CH_2)_4F$ | H | $CH_2OH$ | OH | H | 1 |
| 1-19 | $CH_3$ | $(CH_2)_5F$ | H | $CH_2OH$ | OH | H | 1 |
| 1-20 | $CH_3$ | $(CH_2)_6F$ | H | $CH_2OH$ | OH | H | 1 |
| 1-21 | $CH_3$ | $CH_2Br$ | H | $CH_2OH$ | OH | H | 1 |
| 1-22 | $CH_3$ | $CH_2Cl$ | H | $CH_2OH$ | OH | H | 1 |
| 1-23 | $CH_3$ | $CH_2I$ | H | $CH_2OH$ | OH | H | 1 |
| 1-24 | $CH_3$ | $CH_2OH$ | $CH_2CH_3$ | $CH_2OH$ | OH | H | 1 |
| 1-25 | $CH_3$ | $CH_2OH$ | $^nPr$ | $CH_2OH$ | OH | H | 1 |
| 1-26 | $CH_3$ | $CH_2OH$ | $^iPr$ | $CH_2OH$ | OH | H | 1 |
| 1-27 | $CH_3$ | $CH_2OH$ | $^nBu$ | $CH_2OH$ | OH | H | 1 |
| 1-28 | $CH_3$ | $CH_2OH$ | $^tBu$ | $CH_2OH$ | OH | H | 1 |
| 1-29 | $CH_3$ | $CH_2OH$ | $^iBu$ | $CH_2OH$ | OH | H | 1 |
| 1-30 | $CH_3$ | $CH_2OH$ | $^nPn$ | $CH_2OH$ | OH | H | 1 |
| 1-31 | $CH_3$ | $CH_2OH$ | $^nHex$ | $CH_2OH$ | OH | H | 1 |
| 1-32 | $CH_3$ | $CH_2OH$ | $CH_2OH$ | $CH_2OH$ | OH | H | 1 |
| 1-33 | $CH_3$ | $CH_2OH$ | $(CH_2)_2OH$ | $CH_2OH$ | OH | H | 1 |
| 1-34 | $CH_3$ | $CH_2OH$ | $(CH_2)_3OH$ | $CH_2OH$ | OH | H | 1 |
| 1-35 | $CH_3$ | $CH_2OH$ | $(CH_2)_4OH$ | $CH_2OH$ | OH | H | 1 |
| 1-36 | $CH_3$ | $CH_2OH$ | $(CH_2)_5OH$ | $CH_2OH$ | OH | H | 1 |
| 1-37 | $CH_3$ | $CH_2OH$ | $(CH_2)_6OH$ | $CH_2OH$ | OH | H | 1 |
| 1-38 | $CH_3$ | $CH_2OH$ | $CH_2F$ | $CH_2OH$ | OH | H | 1 |
| 1-39 | $CH_3$ | $CH_2OH$ | $CH_2Cl$ | $CH_2OH$ | OH | H | 1 |
| 1-40 | $CH_3$ | $CH_2OH$ | $CH_2Br$ | $CH_2OH$ | OH | H | 1 |
| 1-41 | $CH_3$ | $CH_2OH$ | $CH_2I$ | $CH_2OH$ | OH | H | 1 |
| 1-42 | $CH_3$ | $CH_2OH$ | OH | $CH_2OH$ | OH | H | 1 |
| 1-43 | $CH_3$ | $CH_2OH$ | $OCH_3$ | $CH_2OH$ | OH | H | 1 |
| 1-44 | $CH_3$ | $CH_2OH$ | $OCH_2CH_3$ | $CH_2OH$ | OH | H | 1 |
| 1-45 | $CH_3$ | $CH_2OH$ | $O^nPr$ | $CH_2OH$ | OH | H | 1 |
| 1-46 | $CH_3$ | $CH_2OH$ | $O^iPr$ | $CH_2OH$ | OH | H | 1 |
| 1-47 | $CH_3$ | $CH_2OH$ | $O^nBu$ | $CH_2OH$ | OH | H | 1 |
| 1-48 | $CH_3$ | $CH_2OH$ | $O^tBu$ | $CH_2OH$ | OH | H | 1 |
| 1-49 | $CH_3$ | $CH_2OH$ | $O^iBu$ | $CH_2OH$ | OH | H | 1 |
| 1-50 | $CH_3$ | $CH_2OH$ | $O^nPn$ | $CH_2OH$ | OH | H | 1 |
| 1-51 | $CH_3$ | $CH_2OH$ | $O^nHex$ | $CH_2OH$ | OH | H | 1 |
| 1-52 | $CH_3$ | $CH_2OH$ | H | $CH_3$ | OH | H | 1 |
| 1-53 | $CH_3$ | $CH_2OH$ | H | $CH_2CH_3$ | OH | H | 1 |
| 1-54 | $CH_3$ | $CH_2OH$ | H | $^nPr$ | OH | H | 1 |

TABLE 1-continued

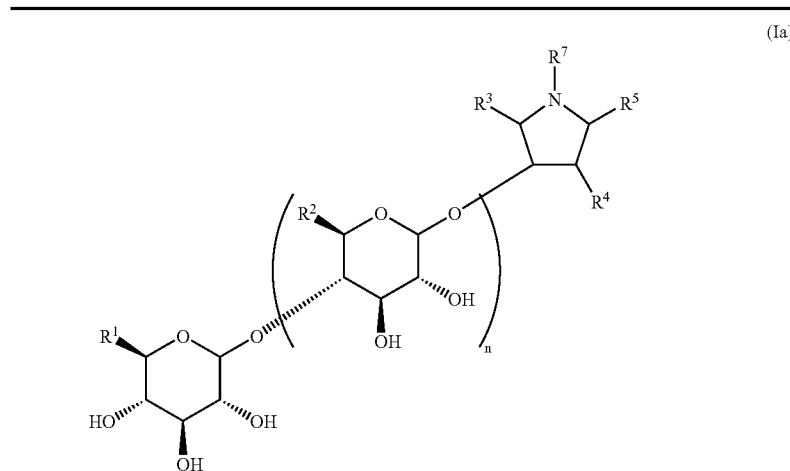

| No. | R¹ | R² | R⁷ | R³ | R⁴ | R⁵ | n |
|---|---|---|---|---|---|---|---|
| 1-55 | $CH_3$ | $CH_2OH$ | H | $^iPr$ | OH | H | 1 |
| 1-56 | $CH_3$ | $CH_2OH$ | H | $^nBu$ | OH | H | 1 |
| 1-57 | $CH_3$ | $CH_2OH$ | H | $^tBu$ | OH | H | 1 |
| 1-58 | $CH_3$ | $CH_2OH$ | H | $^iBu$ | OH | H | 1 |
| 1-59 | $CH_3$ | $CH_2OH$ | H | $^nPn$ | OH | H | 1 |
| 1-60 | $CH_3$ | $CH_2OH$ | H | $^nHex$ | OH | H | 1 |
| 1-61 | $CH_3$ | $CH_2OH$ | H | $CH_2Br$ | OH | H | 1 |
| 1-62 | $CH_3$ | $CH_2OH$ | H | $CH_2Cl$ | OH | H | 1 |
| 1-63 | $CH_3$ | $CH_2OH$ | H | $CH_2I$ | OH | H | 1 |
| 1-64 | $CH_3$ | $CH_2OH$ | H | $NH_2$ | OH | H | 1 |
| 1-65 | $CH_3$ | $CH_2OH$ | H | $N(CH_3)_2$ | OH | H | 1 |
| 1-65 | $CH_3$ | $CH_2OH$ | H | $NHCH(CH_2OH)_2$ | OH | H | 1 |
| 1-67 | $CH_3$ | $CH_2OH$ | H | OH | OH | H | 1 |
| 1-68 | $CH_3$ | $CH_2OH$ | H | H | OH | H | 1 |
| 1-69 | $CH_3$ | $CH_2OH$ | H | F | OH | H | 1 |
| 1-70 | $CH_3$ | $CH_2OH$ | H | Br | OH | H | 1 |
| 1-71 | $CH_3$ | $CH_2OH$ | H | Cl | OH | H | 1 |
| 1-72 | $CH_3$ | $CH_2OH$ | H | I | OH | H | 1 |
| 1-73 | $CH_3$ | $CH_2OH$ | H | $CH_2OH$ | $CH_3$ | H | 1 |
| 1-74 | $CH_3$ | $CH_2OH$ | H | $CH_2OH$ | $CH_2CH_3$ | H | 1 |
| 1-75 | $CH_3$ | $CH_2OH$ | H | $CH_2OH$ | $CH_2OH$ | H | 1 |
| 1-76 | $CH_3$ | $CH_2OH$ | H | $CH_2OH$ | $(CH_2)_2OH$ | H | 1 |
| 1-77 | $CH_3$ | $CH_2OH$ | H | $CH_2OH$ | $(CH_2)_3OH$ | H | 1 |
| 1-78 | $CH_3$ | $CH_2OH$ | H | $CH_2OH$ | $(CH_2)_4OH$ | H | 1 |
| 1-79 | $CH_3$ | $CH_2OH$ | H | $CH_2OH$ | $(CH_2)_5OH$ | H | 1 |
| 1-80 | $CH_3$ | $CH_2OH$ | H | $CH_2OH$ | $(CH_2)_6OH$ | H | 1 |
| 1-81 | $CH_3$ | $CH_2OH$ | H | $CH_2OH$ | $CH_2F$ | H | 1 |
| 1-82 | $CH_3$ | $CH_2OH$ | H | $CH_2OH$ | $CH_2Cl$ | H | 1 |
| 1-83 | $CH_3$ | $CH_2OH$ | H | $CH_2OH$ | $CH_2Br$ | H | 1 |
| 1-84 | $CH_3$ | $CH_2OH$ | H | $CH_2OH$ | $CH_2I$ | H | 1 |
| 1-85 | $CH_3$ | $CH_2OH$ | H | $CH_2OH$ | H | H | 1 |
| 1-86 | $CH_3$ | $CH_2OH$ | H | $CH_2OH$ | $OCH_3$ | H | 1 |
| 1-87 | $CH_3$ | $CH_2OH$ | H | $CH_2OH$ | $OCH_2CH_3$ | H | 1 |
| 1-88 | $CH_3$ | $CH_2OH$ | H | $CH_2OH$ | $O^nPr$ | H | 1 |
| 1-89 | $CH_3$ | $CH_2OH$ | H | $CH_2OH$ | $O^iPr$ | H | 1 |
| 1-90 | $CH_3$ | $CH_2OH$ | H | $CH_2OH$ | $O^nBu$ | H | 1 |
| 1-91 | $CH_3$ | $CH_2OH$ | H | $CH_2OH$ | $O^iBu$ | H | 1 |
| 1-92 | $CH_3$ | $CH_2OH$ | H | $CH_2OH$ | $O^tBu$ | H | 1 |
| 1-93 | $CH_3$ | $CH_2OH$ | H | $CH_2OH$ | $O^nPn$ | H | 1 |
| 1-94 | $CH_3$ | $CH_2OH$ | H | $CH_2OH$ | $O^nHex$ | H | 1 |
| 1-95 | $CH_3$ | $CH_2OH$ | H | $CH_2OH$ | Br | H | 1 |
| 1-96 | $CH_3$ | $CH_2OH$ | H | $CH_2OH$ | Cl | H | 1 |
| 1-97 | $CH_3$ | $CH_2OH$ | H | $CH_2OH$ | I | H | 1 |
| 1-98 | $CH_3$ | $CH_2OH$ | H | $CH_2OH$ | OH | $CH_3$ | 1 |
| 1-99 | $CH_3$ | $CH_2OH$ | H | $CH_2OH$ | OH | $CH_2CH_3$ | 1 |
| 1-100 | $CH_3$ | $CH_2OH$ | H | $CH_2OH$ | OH | $CH_2F$ | 1 |
| 1-101 | $CH_3$ | $CH_2OH$ | H | $CH_2OH$ | OH | $OCH_3$ | 1 |
| 1-102 | $CH_3$ | $CH_2OH$ | H | $CH_2OH$ | OH | $OCH_2CH_3$ | 1 |
| 1-103 | $CH_3$ | $CH_2OH$ | H | $CH_2OH$ | OH | $O^nPr$ | 1 |
| 1-104 | $CH_3$ | $CH_2OH$ | H | $CH_2OH$ | OH | $O^iPr$ | 1 |
| 1-105 | $CH_3$ | $CH_2OH$ | H | $CH_2OH$ | OH | $O^nBu$ | 1 |
| 1-106 | $CH_3$ | $CH_2OH$ | H | $CH_2OH$ | OH | $O^iBu$ | 1 |
| 1-107 | $CH_3$ | $CH_2OH$ | H | $CH_2OH$ | OH | $O^tBu$ | 1 |
| 1-108 | $CH_3$ | $CH_2OH$ | H | $CH_2OH$ | OH | $O^nPn$ | 1 |

TABLE 1-continued

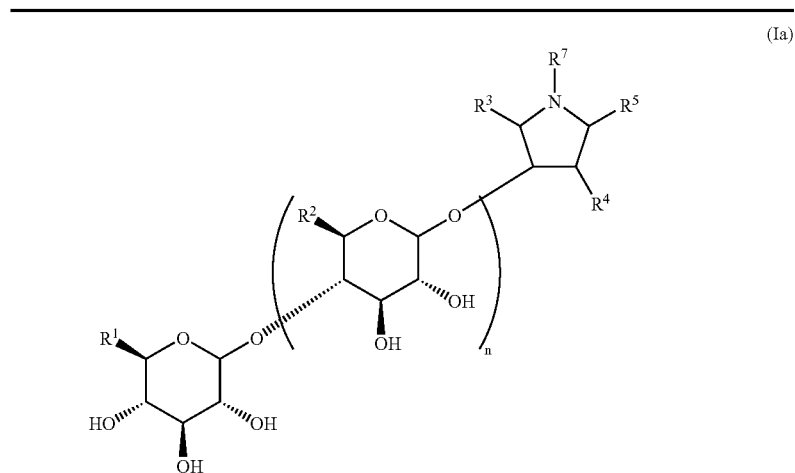

(Ia)

| No. | R¹ | R² | R⁷ | R³ | R⁴ | R⁵ | n |
|---|---|---|---|---|---|---|---|
| 1-109 | CH₃ | CH₂OH | H | CH₂OH | OH | OⁿHex | 1 |
| 1-110 | CH₃ | CH₂OH | H | CH₂OH | OH | F | 1 |
| 1-111 | CH₃ | CH₂OH | CH₃ | CH₂OH | OH | H | 1 |
| 1-112 | CH₃ | CH₃ | CH₃ | CH₂OH | OH | H | 1 |
| 1-113 | CH₃ | CH₂F | CH₃ | CH₂OH | OH | H | 1 |
| 1-114 | CH₃ | CH₂OCH₃ | CH₃ | CH₂OH | OH | H | 1 |
| 1-115 | CH₃ | CH₂OH | H | CH₂OH | F | H | 1 |
| 1-116 | CH₃ | CH₃ | H | CH₂OH | F | H | 1 |
| 1-117 | CH₃ | CH₂F | H | CH₂OH | F | H | 1 |
| 1-118 | CH₃ | CH₂OCH₃ | H | CH₂OH | F | H | 1 |
| 1-119 | CH₃ | CH₂OH | H | CH₂F | OH | H | 1 |
| 1-120 | CH₃ | CH₃ | H | CH₂F | OH | H | 1 |
| 1-121 | CH₃ | CH₂F | H | CH₂F | OH | H | 1 |
| 1-122 | CH₃ | CH₂OCH₃ | H | CH₂F | OH | H | 1 |
| 1-123 | CH₃ | CH₂OH | H | CH₂F | F | H | 1 |
| 1-124 | CH₃ | CH₃ | H | CH₂F | F | H | 1 |
| 1-125 | CH₃ | CH₂F | H | CH₂F | F | H | 1 |
| 1-126 | CH₃ | CH₂OCH₃ | H | CH₂F | F | H | 1 |
| 1-127 | CH₃ | CH₂OH | H | CH₂OH | OH | OH | 1 |
| 1-128 | CH₃ | CH₃ | H | CH₂OH | OH | OH | 1 |
| 1-129 | CH₃ | CH₂F | H | CH₂OH | OH | OH | 1 |
| 1-130 | CH₃ | CH₂OH | CH₃ | CH₂OH | OH | OH | 1 |
| 1-131 | CH₃ | CH₃ | CH₃ | CH₂OH | OH | OH | 1 |
| 1-132 | CH₃ | CH₂F | CH₃ | CH₂OH | OH | OH | 1 |
| 1-133 | CH₃ | CH₂OCH₃ | CH₃ | CH₂OH | OH | OH | 1 |
| 1-134 | CH₃ | CH₂OH | H | CH₂F | OH | OH | 1 |
| 1-135 | CH₃ | CH₃ | H | CH₂F | OH | OH | 1 |
| 1-136 | CH₃ | CH₂F | H | CH₂F | OH | OH | 1 |
| 1-137 | CH₃ | CH₂OCH₃ | H | CH₂F | OH | OH | 1 |
| 1-138 | CH₃ | CH₂OH | H | CH₂OH | F | OH | 1 |
| 1-139 | CH₃ | CH₃ | H | CH₂OH | F | OH | 1 |
| 1-140 | CH₃ | CH₂F | H | CH₂OH | F | OH | 1 |
| 1-141 | CH₃ | CH₂OCH₃ | H | CH₂OH | F | OH | 1 |
| 1-142 | CH₃ | CH₂OH | H | CH₂F | F | OH | 1 |
| 1-143 | CH₃ | CH₃ | H | CH₂F | F | OH | 1 |
| 1-144 | CH₃ | CH₂F | H | CH₂F | F | OH | 1 |
| 1-145 | CH₃ | CH₂OCH₃ | H | CH₂F | F | OH | 1 |
| 1-146 | CH₃ | CH₂OCH₃ | H | CH₂OH | OH | OH | 1 |
| 1-147 | CH₂CH₃ | CH₂OH | H | CH₂OH | OH | H | 1 |
| 1-148 | ⁿPr | CH₂OH | H | CH₂OH | OH | H | 1 |
| 1-149 | ⁱPr | CH₂OH | H | CH₂OH | OH | H | 1 |
| 1-150 | ⁿBu | CH₂OH | H | CH₂OH | OH | H | 1 |
| 1-151 | ⁱBu | CH₂OH | H | CH₂OH | OH | H | 1 |
| 1-152 | ᵗBu | CH₂OH | H | CH₂OH | OH | H | 1 |
| 1-153 | ⁿPn | CH₂OH | H | CH₂OH | OH | H | 1 |
| 1-154 | ⁿHex | CH₂OH | H | CH₂OH | OH | H | 1 |
| 1-155 | CH₂OH | CH₂OH | H | CH₂OH | OH | H | 1 |
| 1-156 | CH₂OH | CH₃ | H | CH₂OH | OH | H | 1 |
| 1-157 | CH₂OH | CH₂F | H | CH₂OH | OH | H | 1 |
| 1-158 | CH₂OH | CH₂OCH₃ | H | CH₂OH | OH | H | 1 |
| 1-159 | CH₂OH | CH₃ | H | CH₂OH | OH | H | 1 |
| 1-160 | CH₂OH | CH₂F | H | CH₂OH | OH | H | 1 |
| 1-161 | CH₂OH | CH₂OCH₃ | H | CH₂OH | OH | H | 1 |
| 1-162 | CH₂OH | CH₂CH₃ | H | CH₂OH | OH | H | 1 |

TABLE 1-continued

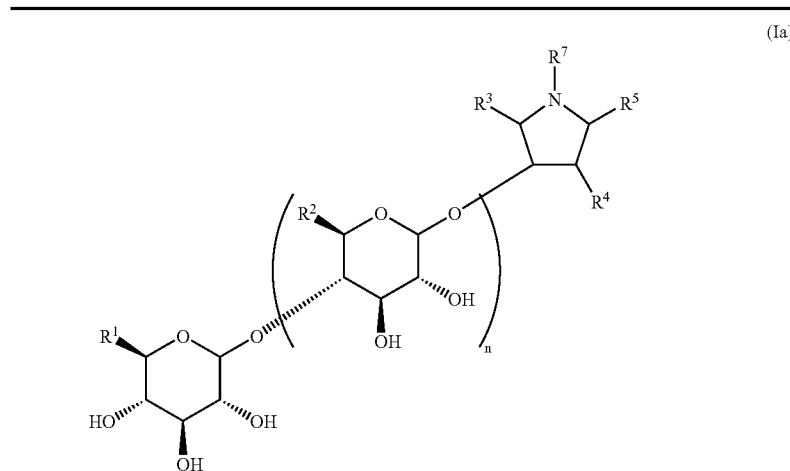

| No. | $R^1$ | $R^2$ | $R^7$ | $R^3$ | $R^4$ | $R^5$ | n |
|---|---|---|---|---|---|---|---|
| 1-163 | $CH_2OH$ | $^nPr$ | H | $CH_2OH$ | OH | H | 1 |
| 1-164 | $CH_2OH$ | $^iPr$ | H | $CH_2OH$ | OH | H | 1 |
| 1-165 | $CH_2OH$ | $^nBu$ | H | $CH_2OH$ | OH | H | 1 |
| 1-166 | $CH_2OH$ | $^iBu$ | H | $CH_2OH$ | OH | H | 1 |
| 1-167 | $CH_2OH$ | $^tBu$ | H | $CH_2OH$ | OH | H | 1 |
| 1-168 | $CH_2OH$ | $^nPn$ | H | $CH_2OH$ | OH | H | 1 |
| 1-169 | $CH_2OH$ | $^nHex$ | H | $CH_2OH$ | OH | H | 1 |
| 1-170 | $CH_2OH$ | $CH_2OCH_2CH_3$ | H | $CH_2OH$ | OH | H | 1 |
| 1-171 | $CH_2OH$ | $CH_2O^iPr$ | H | $CH_2OH$ | OH | H | 1 |
| 1-172 | $CH_2OH$ | $CH_2O^tBu$ | H | $CH_2OH$ | OH | H | 1 |
| 1-173 | $CH_2OH$ | $(CH_2)_2F$ | H | $CH_2OH$ | OH | H | 1 |
| 1-174 | $CH_2OH$ | $CH_2Br$ | H | $CH_2OH$ | OH | H | 1 |
| 1-175 | $CH_2OH$ | $CH_2Cl$ | H | $CH_2OH$ | OH | H | 1 |
| 1-176 | $CH_2OH$ | $CH_2I$ | H | $CH_2OH$ | OH | H | 1 |
| 1-177 | $CH_2OH$ | $CH_2OH$ | $CH_2CH_3$ | $CH_2OH$ | OH | H | 1 |
| 1-178 | $CH_2OH$ | $CH_2OH$ | $^nPr$ | $CH_2OH$ | OH | H | 1 |
| 1-179 | $CH_2OH$ | $CH_2OH$ | $^iPr$ | $CH_2OH$ | OH | H | 1 |
| 1-180 | $CH_2OH$ | $CH_2OH$ | $^nBu$ | $CH_2OH$ | OH | H | 1 |
| 1-181 | $CH_2OH$ | $CH_2OH$ | $^tBu$ | $CH_2OH$ | OH | H | 1 |
| 1-182 | $CH_2OH$ | $CH_2OH$ | $^iBu$ | $CH_2OH$ | OH | H | 1 |
| 1-183 | $CH_2OH$ | $CH_2OH$ | $^nPn$ | $CH_2OH$ | OH | H | 1 |
| 1-184 | $CH_2OH$ | $CH_2OH$ | $^nHex$ | $CH_2OH$ | OH | H | 1 |
| 1-185 | $CH_2OH$ | $CH_2OH$ | $CH_2OH$ | $CH_2OH$ | OH | H | 1 |
| 1-186 | $CH_2OH$ | $CH_2OH$ | $(CH_2)_2OH$ | $CH_2OH$ | OH | H | 1 |
| 1-187 | $CH_2OH$ | $CH_2OH$ | $(CH_2)_3OH$ | $CH_2OH$ | OH | H | 1 |
| 1-188 | $CH_2OH$ | $CH_2OH$ | $(CH_2)_4OH$ | $CH_2OH$ | OH | H | 1 |
| 1-189 | $CH_2OH$ | $CH_2OH$ | $(CH_2)_5OH$ | $CH_2OH$ | OH | H | 1 |
| 1-190 | $CH_2OH$ | $CH_2OH$ | $(CH_2)_6OH$ | $CH_2OH$ | OH | H | 1 |
| 1-191 | $CH_2OH$ | $CH_2OH$ | $CH_2F$ | $CH_2OH$ | OH | H | 1 |
| 1-192 | $CH_2OH$ | $CH_2OH$ | $CH_2Cl$ | $CH_2OH$ | OH | H | 1 |
| 1-193 | $CH_2OH$ | $CH_2OH$ | $CH_2Br$ | $CH_2OH$ | OH | H | 1 |
| 1-194 | $CH_2OH$ | $CH_2OH$ | $CH_2I$ | $CH_2OH$ | OH | H | 1 |
| 1-195 | $CH_2OH$ | $CH_2OH$ | OH | $CH_2OH$ | OH | H | 1 |
| 1-196 | $CH_2OH$ | $CH_2OH$ | $OCH_3$ | $CH_2OH$ | OH | H | 1 |
| 1-197 | $CH_2OH$ | $CH_2OH$ | $OCH_2CH_3$ | $CH_2OH$ | OH | H | 1 |
| 1-198 | $CH_2OH$ | $CH_2OH$ | $O^nPr$ | $CH_2OH$ | OH | H | 1 |
| 1-199 | $CH_2OH$ | $CH_2OH$ | $O^iPr$ | $CH_2OH$ | OH | H | 1 |
| 1-200 | $CH_2OH$ | $CH_2OH$ | $O^nBu$ | $CH_2OH$ | OH | H | 1 |
| 1-201 | $CH_2OH$ | $CH_2OH$ | $O^tBu$ | $CH_2OH$ | OH | H | 1 |
| 1-202 | $CH_2OH$ | $CH_2OH$ | $O^iBu$ | $CH_2OH$ | OH | H | 1 |
| 1-203 | $CH_2OH$ | $CH_2OH$ | $O^nPn$ | $CH_2OH$ | OH | H | 1 |
| 1-204 | $CH_2OH$ | $CH_2OH$ | $O^nHex$ | $CH_2OH$ | OH | H | 1 |
| 1-205 | $CH_2OH$ | $CH_2OH$ | H | $CH_3$ | OH | H | 1 |
| 1-206 | $CH_2OH$ | $CH_2OH$ | H | $CH_2CH_3$ | OH | H | 1 |
| 1-207 | $CH_2OH$ | $CH_2OH$ | H | $CH_2Br$ | OH | H | 1 |
| 1-208 | $CH_2OH$ | $CH_2OH$ | H | $CH_2Cl$ | OH | H | 1 |
| 1-209 | $CH_2OH$ | $CH_2OH$ | H | $CH_2I$ | OH | H | 1 |
| 1-210 | $CH_2OH$ | $CH_2OH$ | H | OH | OH | H | 1 |
| 1-211 | $CH_2OH$ | $CH_2OH$ | H | H | OH | H | 1 |
| 1-212 | $CH_2OH$ | $CH_2OH$ | H | F | OH | H | 1 |
| 1-213 | $CH_2OH$ | $CH_2OH$ | H | Br | OH | H | 1 |
| 1-214 | $CH_2OH$ | $CH_2OH$ | H | Cl | OH | H | 1 |
| 1-215 | $CH_2OH$ | $CH_2OH$ | H | I | OH | H | 1 |
| 1-216 | $CH_2OH$ | $CH_2OH$ | H | $CH_2OH$ | $CH_3$ | H | 1 |

TABLE 1-continued

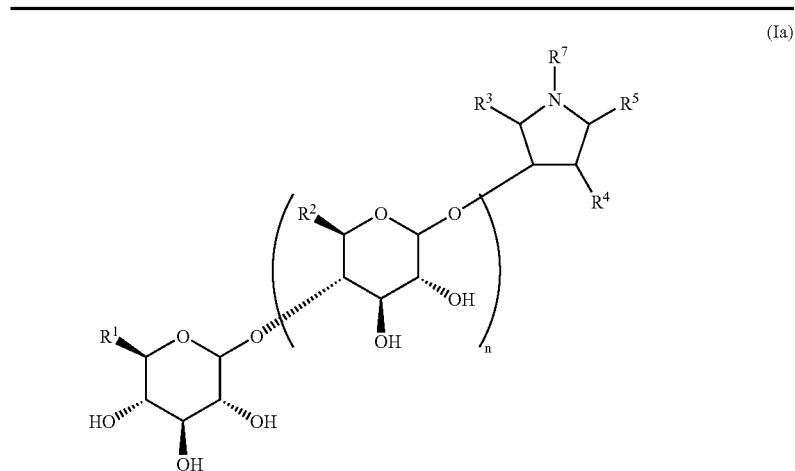

(Ia)

| No. | R$^1$ | R$^2$ | R$^7$ | R$^3$ | R$^4$ | R$^5$ | n |
|---|---|---|---|---|---|---|---|
| 1-217 | CH$_2$OH | CH$_2$OH | H | CH$_2$OH | CH$_2$CH$_3$ | H | 1 |
| 1-218 | CH$_2$OH | CH$_2$OH | H | CH$_2$OH | $^n$Pr | H | 1 |
| 1-219 | CH$_2$OH | CH$_2$OH | H | CH$_2$OH | $^i$Pr | H | 1 |
| 1-220 | CH$_2$OH | CH$_2$OH | H | CH$_2$OH | $^n$Bu | H | 1 |
| 1-221 | CH$_2$OH | CH$_2$OH | H | CH$_2$OH | $^i$Bu | H | 1 |
| 1-222 | CH$_2$OH | CH$_2$OH | H | CH$_2$OH | $^t$Bu | H | 1 |
| 1-223 | CH$_2$OH | CH$_2$OH | H | CH$_2$OH | $^n$Pn | H | 1 |
| 1-224 | CH$_2$OH | CH$_2$OH | H | CH$_2$OH | $^n$Hex | H | 1 |
| 1-225 | CH$_2$OH | CH$_2$OH | H | CH$_2$OH | CH$_2$OH | H | 1 |
| 1-226 | CH$_2$OH | CH$_2$OH | H | CH$_2$OH | CH$_2$F | H | 1 |
| 1-227 | CH$_2$OH | CH$_2$OH | H | CH$_2$OH | CH$_2$Cl | H | 1 |
| 1-228 | CH$_2$OH | CH$_2$OH | H | CH$_2$OH | CH$_2$Br | H | 1 |
| 1-229 | CH$_2$OH | CH$_2$OH | H | CH$_2$OH | CH$_2$I | H | 1 |
| 1-230 | CH$_2$OH | CH$_2$OH | H | CH$_2$OH | H | H | 1 |
| 1-231 | CH$_2$OH | CH$_2$OH | H | CH$_2$OH | OCH$_3$ | H | 1 |
| 1-232 | CH$_2$OH | CH$_2$OH | H | CH$_2$OH | OCH$_2$CH$_3$ | H | 1 |
| 1-233 | CH$_2$OH | CH$_2$OH | H | CH$_2$OH | Br | H | 1 |
| 1-234 | CH$_2$OH | CH$_2$OH | H | CH$_2$OH | Cl | H | 1 |
| 1-235 | CH$_2$OH | CH$_2$OH | H | CH$_2$OH | I | H | 1 |
| 1-236 | CH$_2$OH | CH$_2$OH | H | CH$_2$OH | OH | CH$_3$ | 1 |
| 1-237 | CH$_2$OH | CH$_2$OH | H | CH$_2$OH | OH | CH$_2$CH$_3$ | 1 |
| 1-238 | CH$_2$OH | CH$_2$OH | H | CH$_2$OH | OH | CH$_2$F | 1 |
| 1-239 | CH$_2$OH | CH$_2$OH | H | CH$_2$OH | OH | OCH$_3$ | 1 |
| 1-240 | CH$_2$OH | CH$_2$OH | H | CH$_2$OH | OH | OCH$_2$CH$_3$ | 1 |
| 1-241 | CH$_2$OH | CH$_2$OH | H | CH$_2$OH | OH | F | 1 |
| 1-242 | CH$_2$OH | CH$_2$OH | CH$_3$ | CH$_2$OH | OH | H | 1 |
| 1-243 | CH$_2$OH | CH$_3$ | CH$_3$ | CH$_2$OH | OH | H | 1 |
| 1-244 | CH$_2$OH | CH$_2$F | CH$_3$ | CH$_2$OH | OH | H | 1 |
| 1-245 | CH$_2$OH | CH$_2$OCH$_3$ | CH$_3$ | CH$_2$OH | OH | H | 1 |
| 1-246 | CH$_2$OH | CH$_2$OH | H | CH$_2$F | OH | H | 1 |
| 1-247 | CH$_2$OH | CH$_3$ | H | CH$_2$F | OH | H | 1 |
| 1-248 | CH$_2$OH | CH$_2$F | H | CH$_2$F | OH | H | 1 |
| 1-249 | CH$_2$OH | CH$_2$OH | H | CH$_2$OH | F | H | 1 |
| 1-250 | CH$_2$OH | CH$_3$ | H | CH$_2$OH | F | H | 1 |
| 1-251 | CH$_2$OH | CH$_2$F | H | CH$_2$OH | F | H | 1 |
| 1-252 | CH$_2$OH | CH$_2$OCH$_3$ | H | CH$_2$OH | F | H | 1 |
| 1-253 | CH$_2$OH | CH$_2$OCH$_3$ | H | CH$_2$F | OH | H | 1 |
| 1-254 | CH$_2$OH | CH$_2$OH | H | CH$_2$F | F | H | 1 |
| 1-255 | CH$_2$OH | CH$_3$ | H | CH$_2$F | F | H | 1 |
| 1-256 | CH$_2$OH | CH$_2$F | H | CH$_2$F | F | H | 1 |
| 1-257 | CH$_2$OH | CH$_2$OCH$_3$ | H | CH$_2$F | F | H | 1 |
| 1-258 | CH$_2$OH | CH$_2$OH | CH$_3$ | CH$_2$OH | OH | OH | 1 |
| 1-259 | CH$_2$OH | CH$_2$OH | H | CH$_2$OH | OH | OH | 1 |
| 1-260 | CH$_2$OH | CH$_3$ | H | CH$_2$OH | OH | OH | 1 |
| 1-261 | CH$_2$OH | CH$_2$F | H | CH$_2$OH | OH | OH | 1 |
| 1-262 | CH$_2$OH | CH$_2$OCH$_3$ | H | CH$_2$OH | OH | OH | 1 |
| 1-263 | CH$_2$OH | CH$_3$ | CH$_3$ | CH$_2$OH | OH | OH | 1 |
| 1-264 | CH$_2$OH | CH$_2$F | CH$_3$ | CH$_2$OH | OH | OH | 1 |
| 1-265 | CH$_2$OH | CH$_2$OCH$_3$ | CH$_3$ | CH$_2$OH | OH | OH | 1 |
| 1-266 | CH$_2$OH | CH$_2$OH | H | CH$_2$F | OH | OH | 1 |
| 1-267 | CH$_2$OH | CH$_3$ | H | CH$_2$F | OH | OH | 1 |
| 1-268 | CH$_2$OH | CH$_2$F | H | CH$_2$F | OH | OH | 1 |
| 1-269 | CH$_2$OH | CH$_2$OCH$_3$ | H | CH$_2$F | OH | OH | 1 |
| 1-270 | CH$_2$OH | CH$_2$OH | H | CH$_2$OH | F | OH | 1 |

TABLE 1-continued

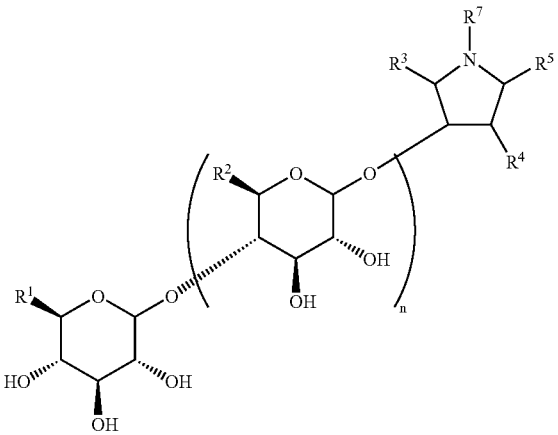

| No. | $R^1$ | $R^2$ | $R^7$ | $R^3$ | $R^4$ | $R^5$ | n |
|---|---|---|---|---|---|---|---|
| 1-271 | $CH_2OH$ | $CH_3$ | H | $CH_2OH$ | F | OH | 1 |
| 1-272 | $CH_2OH$ | $CH_2F$ | H | $CH_2OH$ | F | OH | 1 |
| 1-273 | $CH_2OH$ | $CH_2OCH_3$ | H | $CH_2OH$ | F | OH | 1 |
| 1-274 | $CH_2OH$ | $CH_2OH$ | H | $CH_2F$ | F | OH | 1 |
| 1-275 | $CH_2OH$ | $CH_3$ | H | $CH_2F$ | F | OH | 1 |
| 1-276 | $CH_2OH$ | $CH_2F$ | H | $CH_2F$ | F | OH | 1 |
| 1-277 | $CH_2OH$ | $CH_2OCH_3$ | H | $CH_2F$ | F | OH | 1 |
| 1-278 | $CH_2F$ | $CH_2OH$ | H | $CH_2OH$ | OH | H | 1 |
| 1-279 | $CH_2F$ | $CH_3$ | H | $CH_2OH$ | OH | H | 1 |
| 1-280 | $CH_2F$ | $CH_2F$ | H | $CH_2OH$ | OH | H | 1 |
| 1-281 | $CH_2F$ | $CH_2OCH_3$ | H | $CH_2OH$ | OH | H | 1 |
| 1-282 | $CH_2F$ | $CH_2CH_3$ | H | $CH_2OH$ | OH | H | 1 |
| 1-283 | $CH_2F$ | $CH_2OCH_2CH_3$ | H | $CH_2OH$ | OH | H | 1 |
| 1-284 | $CH_2F$ | $CH_2O^iPr$ | H | $CH_2OH$ | OH | H | 1 |
| 1-285 | $CH_2F$ | $CH_2O^tBu$ | H | $CH_2OH$ | OH | H | 1 |
| 1-286 | $CH_2F$ | $CH_2OH$ | H | $CH_3$ | OH | H | 1 |
| 1-287 | $CH_2F$ | $CH_2OH$ | H | $CH_2CH_3$ | OH | H | 1 |
| 1-288 | $CH_2F$ | $CH_2OH$ | H | $CH_2Br$ | OH | H | 1 |
| 1-289 | $CH_2F$ | $CH_2OH$ | H | $CH_2Cl$ | OH | H | 1 |
| 1-290 | $CH_2F$ | $CH_2OH$ | H | $CH_2I$ | OH | H | 1 |
| 1-291 | $CH_2F$ | $CH_2OH$ | H | OH | OH | H | 1 |
| 1-292 | $CH_2F$ | $CH_2OH$ | H | H | OH | H | 1 |
| 1-293 | $CH_2F$ | $CH_2OH$ | H | F | OH | H | 1 |
| 1-294 | $CH_2F$ | $CH_2OH$ | H | $CH_2OH$ | $CH_3$ | H | 1 |
| 1-295 | $CH_2F$ | $CH_2OH$ | H | $CH_2OH$ | $CH_2CH_3$ | H | 1 |
| 1-296 | $CH_2F$ | $CH_2OH$ | H | $CH_2OH$ | $CH_2OH$ | H | 1 |
| 1-297 | $CH_2F$ | $CH_2OH$ | H | $CH_2OH$ | $CH_2F$ | H | 1 |
| 1-298 | $CH_2F$ | $CH_2OH$ | H | $CH_2OH$ | H | H | 1 |
| 1-299 | $CH_2F$ | $CH_2OH$ | H | $CH_2OH$ | $OCH_3$ | H | 1 |
| 1-300 | $CH_2F$ | $CH_2OH$ | H | $CH_2OH$ | $OCH_2CH_3$ | H | 1 |
| 1-301 | $CH_2F$ | $CH_2OH$ | H | $CH_2OH$ | Br | H | 1 |
| 1-302 | $CH_2F$ | $CH_2OH$ | H | $CH_2OH$ | Cl | H | 1 |
| 1-303 | $CH_2F$ | $CH_2OH$ | H | $CH_2OH$ | I | H | 1 |
| 1-304 | $CH_2F$ | $CH_2OH$ | H | $CH_2OH$ | OH | $CH_3$ | 1 |
| 1-305 | $CH_2F$ | $CH_2OH$ | H | $CH_2OH$ | OH | $CH_2CH_3$ | 1 |
| 1-306 | $CH_2F$ | $CH_2OH$ | H | $CH_2OH$ | OH | $CH_2F$ | 1 |
| 1-307 | $CH_2F$ | $CH_2OH$ | H | $CH_2OH$ | OH | $OCH_3$ | 1 |
| 1-308 | $CH_2F$ | $CH_2OH$ | H | $CH_2OH$ | OH | $OCH_2CH_3$ | 1 |
| 1-309 | $CH_2F$ | $CH_2OH$ | H | $CH_2OH$ | OH | F | 1 |
| 1-310 | $CH_2F$ | $CH_2OH$ | $CH_3$ | $CH_2OH$ | OH | H | 1 |
| 1-311 | $CH_2F$ | $CH_3$ | $CH_3$ | $CH_2OH$ | OH | H | 1 |
| 1-312 | $CH_2F$ | $CH_2F$ | $CH_3$ | $CH_2OH$ | OH | H | 1 |
| 1-313 | $CH_2F$ | $CH_2OCH_3$ | $CH_3$ | $CH_2OH$ | OH | H | 1 |
| 1-314 | $CH_2F$ | $CH_2OH$ | H | $CH_2F$ | OH | H | 1 |
| 1-315 | $CH_2F$ | $CH_3$ | H | $CH_2F$ | OH | H | 1 |
| 1-316 | $CH_2F$ | $CH_2F$ | H | $CH_2F$ | OH | H | 1 |
| 1-317 | $CH_2F$ | $CH_2OH$ | H | $CH_2OH$ | F | H | 1 |
| 1-318 | $CH_2F$ | $CH_2OCH_3$ | H | $CH_2F$ | OH | H | 1 |
| 1-319 | $CH_2F$ | $CH_3$ | H | $CH_2OH$ | F | H | 1 |
| 1-320 | $CH_2F$ | $CH_2F$ | H | $CH_2OH$ | F | H | 1 |
| 1-321 | $CH_2F$ | $CH_2OCH_3$ | H | $CH_2OH$ | F | H | 1 |
| 1-322 | $CH_2F$ | $CH_2OH$ | H | $CH_2OH$ | OH | OH | 1 |
| 1-323 | $CH_2F$ | $CH_3$ | H | $CH_2OH$ | OH | OH | 1 |
| 1-324 | $CH_2F$ | $CH_2F$ | H | $CH_2OH$ | OH | OH | 1 |

TABLE 1-continued

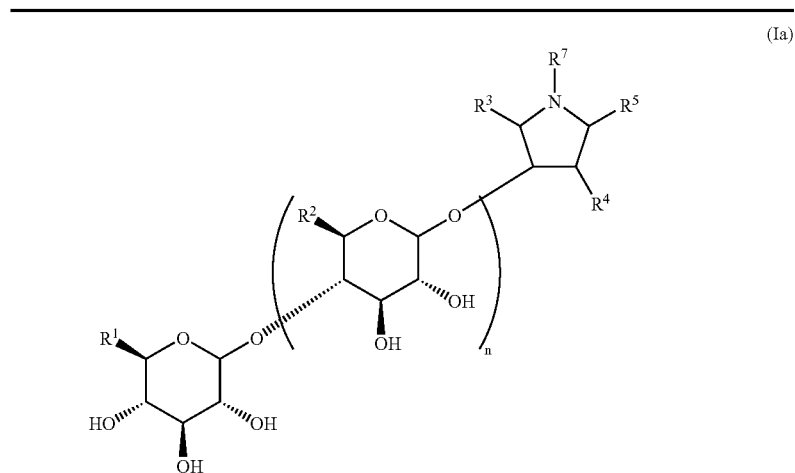

(Ia)

| No. | R¹ | R² | R⁷ | R³ | R⁴ | R⁵ | n |
|---|---|---|---|---|---|---|---|
| 1-325 | CH₂F | CH₂OCH₃ | H | CH₂OH | OH | OH | 1 |
| 1-326 | CH₂F | CH₂OH | CH₃ | CH₂OH | OH | OH | 1 |
| 1-327 | CH₂F | CH₃ | CH₃ | CH₂OH | OH | OH | 1 |
| 1-328 | CH₂F | CH₂F | CH₃ | CH₂OH | OH | OH | 1 |
| 1-329 | CH₂F | CH₂OCH₃ | CH₃ | CH₂OH | OH | OH | 1 |
| 1-330 | CH₂F | CH₂OH | H | CH₂F | OH | OH | 1 |
| 1-331 | CH₂F | CH₃ | H | CH₂F | OH | OH | 1 |
| 1-332 | CH₂F | CH₂F | H | CH₂F | OH | OH | 1 |
| 1-333 | CH₂F | CH₂OCH₃ | H | CH₂F | OH | OH | 1 |
| 1-334 | CH₂F | CH₂OH | H | CH₂F | F | H | 1 |
| 1-335 | CH₂F | CH₃ | H | CH₂F | F | H | 1 |
| 1-336 | CH₂F | CH₂F | H | CH₂F | F | H | 1 |
| 1-337 | CH₂F | CH₂OCH₃ | H | CH₂F | F | H | 1 |
| 1-338 | CH₂F | CH₂OH | H | CH₂F | F | OH | 1 |
| 1-339 | CH₂F | CH₃ | H | CH₂F | F | OH | 1 |
| 1-340 | CH₂F | CH₂F | H | CH₂F | F | OH | 1 |
| 1-341 | CH₂F | CH₂OCH₃ | H | CH₂F | F | OH | 1 |
| 1-342 | CH₂F | CH₂OH | H | CH₂OH | F | OH | 1 |
| 1-343 | CH₂F | CH₃ | H | CH₂OH | F | OH | 1 |
| 1-344 | CH₂F | CH₂F | H | CH₂OH | F | OH | 1 |
| 1-345 | CH₂F | CH₂OCH₃ | H | CH₂OH | F | OH | 1 |
| 1-346 | CH₂OCH₃ | CH₂OH | H | CH₂F | OH | H | 1 |
| 1-347 | CH₂OCH₃ | CH₃ | H | CH₂F | OH | H | 1 |
| 1-348 | CH₂OCH₃ | CH₂F | H | CH₂F | OH | H | 1 |
| 1-349 | CH₂OCH₃ | CH₂OCH₃ | H | CH₂F | OH | H | 1 |
| 1-350 | CH₂OCH₃ | CH₂OH | H | CH₂OH | F | H | 1 |
| 1-351 | CH₂OCH₃ | CH₃ | H | CH₂OH | F | H | 1 |
| 1-352 | CH₂OCH₃ | CH₂F | H | CH₂OH | F | H | 1 |
| 1-353 | CH₂OCH₃ | CH₂OCH₃ | H | CH₂OH | F | H | 1 |
| 1-354 | CH₂OCH₃ | CH₂OH | H | CH₂OH | OH | H | 1 |
| 1-355 | CH₂OCH₃ | CH₃ | H | CH₂OH | OH | H | 1 |
| 1-356 | CH₂OCH₃ | CH₂F | H | CH₂OH | OH | H | 1 |
| 1-357 | CH₂OCH₃ | CH₂OCH₃ | H | CH₂OH | OH | H | 1 |
| 1-358 | CH₂OCH₃ | CH₃ | H | CH₂OH | OH | H | 1 |
| 1-359 | CH₂OCH₃ | CH₂F | H | CH₂OH | OH | H | 1 |
| 1-360 | CH₂OCH₃ | CH₂OCH₃ | H | CH₂OH | OH | H | 1 |
| 1-361 | CH₂OCH₃ | CH₂CH₃ | H | CH₂OH | OH | H | 1 |
| 1-362 | CH₂OCH₃ | CH₂OCH₂CH₃ | H | CH₂OH | OH | H | 1 |
| 1-363 | CH₂OCH₃ | CH₂OⁱPr | H | CH₂OH | OH | H | 1 |
| 1-364 | CH₂OCH₃ | CH₂OᵗBu | H | CH₂OH | OH | H | 1 |
| 1-365 | CH₂OCH₃ | CH₂OH | H | CH₃ | OH | H | 1 |
| 1-366 | CH₂OCH₃ | CH₂OH | H | CH₂CH₃ | OH | H | 1 |
| 1-367 | CH₂OCH₃ | CH₂OH | H | OH | OH | H | 1 |
| 1-368 | CH₂OCH₃ | CH₂OH | H | H | OH | H | 1 |
| 1-369 | CH₂OCH₃ | CH₂OH | H | F | OH | H | 1 |
| 1-370 | CH₂OCH₃ | CH₂OH | H | CH₂OH | CH₃ | H | 1 |
| 1-371 | CH₂OCH₃ | CH₂OH | H | CH₂OH | CH₂CH₃ | H | 1 |
| 1-372 | CH₂OCH₃ | CH₂OH | H | CH₂OH | CH₂OH | H | 1 |
| 1-373 | CH₂OCH₃ | CH₂OH | H | CH₂OH | CH₂F | H | 1 |
| 1-374 | CH₂OCH₃ | CH₂OH | H | CH₂OH | H | H | 1 |
| 1-375 | CH₂OCH₃ | CH₂OH | H | CH₂OH | OCH₃ | H | 1 |
| 1-376 | CH₂OCH₃ | CH₂OH | H | CH₂OH | OCH₂CH₃ | H | 1 |
| 1-377 | CH₂OCH₃ | CH₂OH | H | CH₂OH | Br | H | 1 |
| 1-378 | CH₂OCH₃ | CH₂OH | H | CH₂OH | Cl | H | 1 |

TABLE 1-continued

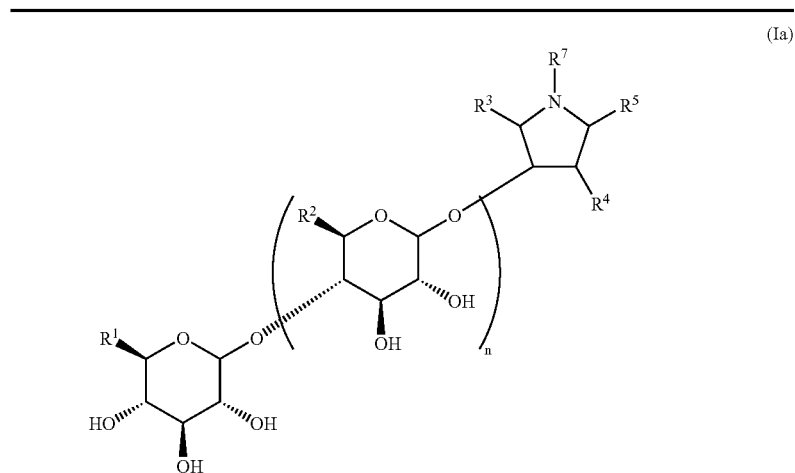

(Ia)

| No. | $R^1$ | $R^2$ | $R^7$ | $R^3$ | $R^4$ | $R^5$ | n |
|---|---|---|---|---|---|---|---|
| 1-379 | $CH_2OCH_3$ | $CH_2OH$ | H | $CH_2OH$ | I | H | 1 |
| 1-380 | $CH_2OCH_3$ | $CH_2OH$ | H | $CH_2OH$ | OH | $CH_3$ | 1 |
| 1-381 | $CH_2OCH_3$ | $CH_2OH$ | H | $CH_2OH$ | OH | $CH_2CH_3$ | 1 |
| 1-382 | $CH_2OCH_3$ | $CH_2OH$ | H | $CH_2OH$ | OH | $CH_2F$ | 1 |
| 1-383 | $CH_2OCH_3$ | $CH_2OH$ | H | $CH_2OH$ | OH | $OCH_3$ | 1 |
| 1-384 | $CH_2OCH_3$ | $CH_2OH$ | H | $CH_2OH$ | OH | $OCH_2CH_3$ | 1 |
| 1-385 | $CH_2OCH_3$ | $CH_2OH$ | H | $CH_2OH$ | OH | F | 1 |
| 1-386 | $CH_2OCH_3$ | $CH_2OH$ | $CH_3$ | $CH_2OH$ | OH | H | 1 |
| 1-387 | $CH_2OCH_3$ | $CH_3$ | $CH_3$ | $CH_2OH$ | OH | H | 1 |
| 1-388 | $CH_2OCH_3$ | $CH_2F$ | $CH_3$ | $CH_2OH$ | OH | H | 1 |
| 1-389 | $CH_2OCH_3$ | $CH_2OCH_3$ | $CH_3$ | $CH_2OH$ | OH | H | 1 |
| 1-390 | $CH_2OCH_3$ | $CH_2OH$ | H | $CH_2F$ | F | H | 1 |
| 1-391 | $CH_2OCH_3$ | $CH_3$ | H | $CH_2F$ | F | H | 1 |
| 1-392 | $CH_2OCH_3$ | $CH_2F$ | H | $CH_2F$ | F | H | 1 |
| 1-393 | $CH_2OCH_3$ | $CH_2OCH_3$ | H | $CH_2F$ | F | H | 1 |
| 1-394 | $CH_2OCH_3$ | $CH_2OH$ | $CH_3$ | $CH_2OH$ | OH | OH | 1 |
| 1-395 | $CH_2OCH_3$ | $CH_3$ | $CH_3$ | $CH_2OH$ | OH | OH | 1 |
| 1-396 | $CH_2OCH_3$ | $CH_2F$ | $CH_3$ | $CH_2OH$ | OH | OH | 1 |
| 1-397 | $CH_2OCH_3$ | $CH_2OCH_3$ | $CH_3$ | $CH_2OH$ | OH | OH | 1 |
| 1-398 | $CH_2OCH_3$ | $CH_2OH$ | H | $CH_2F$ | OH | OH | 1 |
| 1-399 | $CH_2OCH_3$ | $CH_3$ | H | $CH_2F$ | OH | OH | 1 |
| 1-400 | $CH_2OCH_3$ | $CH_2F$ | H | $CH_2F$ | OH | OH | 1 |
| 1-401 | $CH_2OCH_3$ | $CH_2OCH_3$ | H | $CH_2F$ | OH | OH | 1 |
| 1-402 | $CH_2OCH_3$ | $CH_2OH$ | H | $CH_2OH$ | F | OH | 1 |
| 1-403 | $CH_2OCH_3$ | $CH_3$ | H | $CH_2OH$ | F | OH | 1 |
| 1-404 | $CH_2OCH_3$ | $CH_2F$ | H | $CH_2OH$ | F | OH | 1 |
| 1-405 | $CH_2OCH_3$ | $CH_2OCH_3$ | H | $CH_2OH$ | F | OH | 1 |
| 1-406 | $CH_2OCH_3$ | $CH_2OH$ | H | $CH_2F$ | F | OH | 1 |
| 1-407 | $CH_2OCH_3$ | $CH_3$ | H | $CH_2F$ | F | OH | 1 |
| 1-408 | $CH_2OCH_3$ | $CH_2F$ | H | $CH_2F$ | F | OH | 1 |
| 1-409 | $CH_2OCH_3$ | $CH_2OCH_3$ | H | $CH_2F$ | F | OH | 1 |
| 1-410 | $CH_2OCH_2CH_3$ | $CH_2OH$ | H | $CH_2OH$ | OH | H | 1 |
| 1-411 | $CH_2OCH_2CH_3$ | $CH_3$ | H | $CH_2OH$ | OH | H | 1 |
| 1-412 | $CH_2OCH_2CH_3$ | $CH_2F$ | H | $CH_2OH$ | OH | H | 1 |
| 1-413 | $CH_2OCH_2CH_3$ | $CH_2OCH_3$ | H | $CH_2OH$ | OH | H | 1 |
| 1-414 | $CH_2OCH_2CH_3$ | $CH_2OH$ | $CH_3$ | $CH_2OH$ | OH | H | 1 |
| 1-415 | $CH_2OCH_2CH_3$ | $CH_3$ | $CH_3$ | $CH_2OH$ | OH | H | 1 |
| 1-416 | $CH_2OCH_2CH_3$ | $CH_2F$ | $CH_3$ | $CH_2OH$ | OH | H | 1 |
| 1-417 | $CH_2OCH_2CH_3$ | $CH_2OCH_3$ | $CH_3$ | $CH_2OH$ | OH | H | 1 |
| 1-418 | $CH_2OCH_2CH_3$ | $CH_2OH$ | H | $CH_2F$ | OH | H | 1 |
| 1-419 | $CH_2OCH_2CH_3$ | $CH_3$ | H | $CH_2F$ | OH | H | 1 |
| 1-420 | $CH_2OCH_2CH_3$ | $CH_2F$ | H | $CH_2F$ | OH | H | 1 |
| 1-421 | $CH_2OCH_2CH_3$ | $CH_2OCH_3$ | H | $CH_2F$ | OH | H | 1 |
| 1-422 | $CH_2OCH_2CH_3$ | $CH_2OH$ | H | $CH_2OH$ | F | H | 1 |
| 1-423 | $CH_2OCH_2CH_3$ | $CH_3$ | H | $CH_2OH$ | F | H | 1 |
| 1-424 | $CH_2OCH_2CH_3$ | $CH_2F$ | H | $CH_2OH$ | F | H | 1 |
| 1-425 | $CH_2OCH_2CH_3$ | $CH_2OCH_3$ | H | $CH_2OH$ | F | H | 1 |
| 1-426 | $CH_2OCH_2CH_3$ | $CH_2OH$ | H | $CH_2F$ | F | H | 1 |
| 1-427 | $CH_2OCH_2CH_3$ | $CH_3$ | H | $CH_2F$ | F | H | 1 |
| 1-428 | $CH_2OCH_2CH_3$ | $CH_2F$ | H | $CH_2F$ | F | H | 1 |
| 1-429 | $CH_2OCH_2CH_3$ | $CH_2OCH_3$ | H | $CH_2F$ | F | H | 1 |
| 1-430 | $CH_2OCH_2CH_3$ | $CH_2OH$ | H | $CH_2OH$ | OH | OH | 1 |
| 1-431 | $CH_2OCH_2CH_3$ | $CH_3$ | H | $CH_2OH$ | OH | OH | 1 |
| 1-432 | $CH_2OCH_2CH_3$ | $CH_2F$ | H | $CH_2OH$ | OH | OH | 1 |

TABLE 1-continued

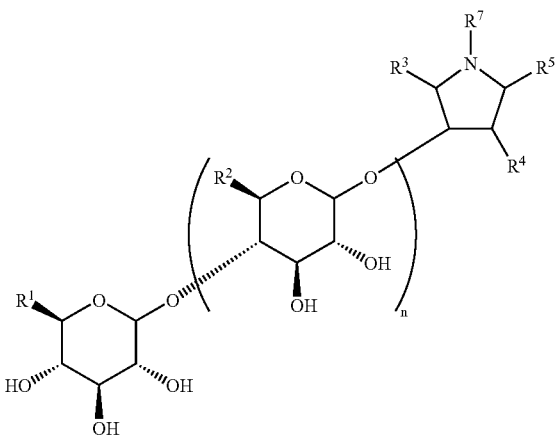

(Ia)

| No. | $R^1$ | $R^2$ | $R^7$ | $R^3$ | $R^4$ | $R^5$ | n |
|---|---|---|---|---|---|---|---|
| 1-433 | $CH_2OCH_2CH_3$ | $CH_2OCH_3$ | H | $CH_2OH$ | OH | OH | 1 |
| 1-434 | $CH_2OCH_2CH_3$ | $CH_2OH$ | $CH_3$ | $CH_2OH$ | OH | OH | 1 |
| 1-435 | $CH_2OCH_2CH_3$ | $CH_3$ | $CH_3$ | $CH_2OH$ | OH | OH | 1 |
| 1-436 | $CH_2OCH_2CH_3$ | $CH_2F$ | $CH_3$ | $CH_2OH$ | OH | OH | 1 |
| 1-437 | $CH_2OCH_2CH_3$ | $CH_2OCH_3$ | $CH_3$ | $CH_2OH$ | OH | OH | 1 |
| 1-438 | $CH_2OCH_2CH_3$ | $CH_2OH$ | H | $CH_2F$ | OH | OH | 1 |
| 1-439 | $CH_2OCH_2CH_3$ | $CH_3$ | H | $CH_2F$ | OH | OH | 1 |
| 1-440 | $CH_2OCH_2CH_3$ | $CH_2F$ | H | $CH_2F$ | OH | OH | 1 |
| 1-441 | $CH_2OCH_2CH_3$ | $CH_2OCH_3$ | H | $CH_2F$ | OH | OH | 1 |
| 1-442 | $CH_2OCH_2CH_3$ | $CH_2OH$ | H | $CH_2OH$ | F | OH | 1 |
| 1-443 | $CH_2OCH_2CH_3$ | $CH_3$ | H | $CH_2OH$ | F | OH | 1 |
| 1-444 | $CH_2OCH_2CH_3$ | $CH_2F$ | H | $CH_2OH$ | F | OH | 1 |
| 1-445 | $CH_2OCH_2CH_3$ | $CH_2OCH_3$ | H | $CH_2OH$ | F | OH | 1 |
| 1-446 | $CH_2OCH_2CH_3$ | $CH_2OH$ | H | $CH_2F$ | F | OH | 1 |
| 1-447 | $CH_2OCH_2CH_3$ | $CH_3$ | H | $CH_2F$ | F | OH | 1 |
| 1-448 | $CH_2OCH_2CH_3$ | $CH_2F$ | H | $CH_2F$ | F | OH | 1 |
| 1-449 | $CH_2OCH_2CH_3$ | $CH_2OCH_3$ | H | $CH_2F$ | F | OH | 1 |
| 1-450 | $CH_2O^nPr$ | $CH_2OH$ | H | $CH_2OH$ | OH | H | 1 |
| 1-451 | $CH_2O^iPr$ | $CH_2OH$ | H | $CH_2OH$ | OH | H | 1 |
| 1-452 | $CH_2O^nBu$ | $CH_2OH$ | H | $CH_2OH$ | OH | H | 1 |
| 1-453 | $CH_2O^iBu$ | $CH_2OH$ | H | $CH_2OH$ | OH | H | 1 |
| 1-454 | $CH_2O^tBu$ | $CH_2OH$ | H | $CH_2OH$ | OH | H | 1 |
| 1-455 | $CH_2O^nPn$ | $CH_2OH$ | H | $CH_2OH$ | OH | H | 1 |
| 1-456 | $CH_2O^nHex$ | $CH_2OH$ | H | $CH_2OH$ | OH | H | 1 |
| 1-457 | $CH_2Cl$ | $CH_2OH$ | H | $CH_2OH$ | OH | H | 1 |
| 1-458 | $CH_2Cl$ | $CH_3$ | H | $CH_2OH$ | OH | H | 1 |
| 1-459 | $CH_2Cl$ | $CH_2F$ | H | $CH_2OH$ | OH | H | 1 |
| 1-460 | $CH_2Cl$ | $CH_2OCH_3$ | H | $CH_2OH$ | OH | H | 1 |
| 1-461 | $CH_2Cl$ | $CH_2OH$ | $CH_3$ | $CH_2OH$ | OH | H | 1 |
| 1-462 | $CH_2Cl$ | $CH_3$ | $CH_3$ | $CH_2OH$ | OH | H | 1 |
| 1-463 | $CH_2Cl$ | $CH_2F$ | $CH_3$ | $CH_2OH$ | OH | H | 1 |
| 1-464 | $CH_2Cl$ | $CH_2OCH_3$ | $CH_3$ | $CH_2OH$ | OH | H | 1 |
| 1-465 | $CH_2Cl$ | $CH_2OH$ | H | $CH_2F$ | OH | H | 1 |
| 1-466 | $CH_2Cl$ | $CH_3$ | H | $CH_2F$ | OH | H | 1 |
| 1-467 | $CH_2Cl$ | $CH_2F$ | H | $CH_2F$ | OH | H | 1 |
| 1-468 | $CH_2Cl$ | $CH_2OCH_3$ | H | $CH_2F$ | OH | H | 1 |
| 1-469 | $CH_2Cl$ | $CH_2OH$ | H | $CH_2OH$ | F | H | 1 |
| 1-470 | $CH_2Cl$ | $CH_3$ | H | $CH_2OH$ | F | H | 1 |
| 1-471 | $CH_2Cl$ | $CH_2F$ | H | $CH_2OH$ | F | H | 1 |
| 1-472 | $CH_2Cl$ | $CH_2OCH_3$ | H | $CH_2OH$ | F | H | 1 |
| 1-473 | $CH_2Cl$ | $CH_2OH$ | H | $CH_2F$ | F | H | 1 |
| 1-474 | $CH_2Cl$ | $CH_3$ | H | $CH_2F$ | F | H | 1 |
| 1-475 | $CH_2Cl$ | $CH_2F$ | H | $CH_2F$ | F | H | 1 |
| 1-476 | $CH_2Cl$ | $CH_2OCH_3$ | H | $CH_2F$ | F | H | 1 |
| 1-477 | $CH_2Cl$ | $CH_2OH$ | H | $CH_2OH$ | OH | OH | 1 |
| 1-478 | $CH_2Cl$ | $CH_3$ | H | $CH_2OH$ | OH | OH | 1 |
| 1-479 | $CH_2Cl$ | $CH_2F$ | H | $CH_2OH$ | OH | OH | 1 |
| 1-480 | $CH_2Cl$ | $CH_2OCH_3$ | H | $CH_2OH$ | OH | OH | 1 |
| 1-481 | $CH_2Cl$ | $CH_2OH$ | H | $CH_2F$ | OH | OH | 1 |
| 1-482 | $CH_2Cl$ | $CH_3$ | H | $CH_2F$ | OH | OH | 1 |
| 1-483 | $CH_2Cl$ | $CH_2F$ | H | $CH_2F$ | OH | OH | 1 |
| 1-484 | $CH_2Cl$ | $CH_2OCH_3$ | H | $CH_2F$ | OH | OH | I |
| 1-485 | $CH_2Cl$ | $CH_2OH$ | H | $CH_2OH$ | F | OH | 1 |
| 1-486 | $CH_2Cl$ | $CH_3$ | H | $CH_2OH$ | F | OH | 1 |

TABLE 1-continued

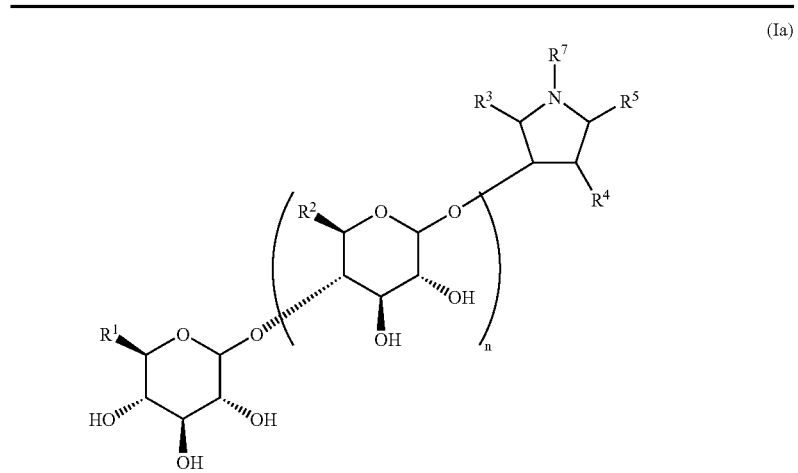

| No. | R¹ | R² | R⁷ | R³ | R⁴ | R⁵ | n |
|---|---|---|---|---|---|---|---|
| 1-487 | $CH_2Cl$ | $CH_2F$ | H | $CH_2OH$ | F | OH | 1 |
| 1-488 | $CH_2Cl$ | $CH_2OCH_3$ | H | $CH_2OH$ | F | OH | 1 |
| 1-489 | $CH_2Cl$ | $CH_2OH$ | H | $CH_2F$ | F | OH | 1 |
| 1-490 | $CH_2Cl$ | $CH_3$ | H | $CH_2F$ | F | OH | 1 |
| 1-491 | $CH_2Cl$ | $CH_2F$ | H | $CH_2F$ | F | OH | 1 |
| 1-492 | $CH_2Cl$ | $CH_2OCH_3$ | H | $CH_2F$ | F | OH | 1 |
| 1-493 | $CH_2Cl$ | $CH_2OH$ | $CH_3$ | $CH_2OH$ | OH | OH | 1 |
| 1-494 | $CH_2Cl$ | $CH_3$ | $CH_3$ | $CH_2OH$ | OH | OH | 1 |
| 1-495 | $CH_2Cl$ | $CH_2F$ | $CH_3$ | $CH_2OH$ | OH | OH | 1 |
| 1-496 | $CH_2Cl$ | $CH_2OCH_3$ | $CH_3$ | $CH_2OH$ | OH | OH | 1 |
| 1-497 | $CH_2Br$ | $CH_2OH$ | H | $CH_2OH$ | OH | H | 1 |
| 1-498 | $CH_2Br$ | $CH_3$ | H | $CH_2OH$ | OH | H | 1 |
| 1-499 | $CH_2Br$ | $CH_2F$ | H | $CH_2OH$ | OH | H | 1 |
| 1-500 | $CH_2Br$ | $CH_2OCH_3$ | H | $CH_2OH$ | OH | H | 1 |
| 1-501 | $CH_2Br$ | $CH_2OH$ | $CH_3$ | $CH_2OH$ | OH | H | 1 |
| 1-502 | $CH_2Br$ | $CH_3$ | $CH_3$ | $CH_2OH$ | OH | H | 1 |
| 1-503 | $CH_2Br$ | $CH_2F$ | $CH_3$ | $CH_2OH$ | OH | H | 1 |
| 1-504 | $CH_2Br$ | $CH_2OCH_3$ | $CH_3$ | $CH_2OH$ | OH | H | 1 |
| 1-505 | $CH_2Br$ | $CH_2OH$ | H | $CH_2F$ | OH | H | 1 |
| 1-506 | $CH_2Br$ | $CH_3$ | H | $CH_2F$ | OH | H | 1 |
| 1-507 | $CH_2Br$ | $CH_2F$ | H | $CH_2F$ | OH | H | 1 |
| 1-508 | $CH_2Br$ | $CH_2OCH_3$ | H | $CH_2F$ | OH | H | 1 |
| 1-509 | $CH_2Br$ | $CH_2OH$ | H | $CH_2OH$ | F | H | 1 |
| 1-510 | $CH_2Br$ | $CH_3$ | H | $CH_2OH$ | F | H | 1 |
| 1-511 | $CH_2Br$ | $CH_2F$ | H | $CH_2OH$ | F | H | 1 |
| 1-512 | $CH_2Br$ | $CH_2OCH_3$ | H | $CH_2OH$ | F | H | 1 |
| 1-513 | $CH_2Br$ | $CH_2OH$ | H | $CH_2F$ | F | H | 1 |
| 1-514 | $CH_2Br$ | $CH_3$ | H | $CH_2F$ | F | H | 1 |
| 1-515 | $CH_2Br$ | $CH_2F$ | H | $CH_2F$ | F | H | 1 |
| 1-516 | $CH_2Br$ | $CH_2OCH_3$ | H | $CH_2F$ | F | H | 1 |
| 1-517 | $CH_2Br$ | $CH_2OH$ | H | $CH_2OH$ | OH | OH | 1 |
| 1-518 | $CH_2Br$ | $CH_3$ | H | $CH_2OH$ | OH | OH | 1 |
| 1-519 | $CH_2Br$ | $CH_2F$ | H | $CH_2OH$ | OH | OH | 1 |
| 1-520 | $CH_2Br$ | $CH_2OH$ | $CH_3$ | $CH_2OH$ | OH | OH | 1 |
| 1-521 | $CH_2Br$ | $CH_3$ | $CH_3$ | $CH_2OH$ | OH | OH | 1 |
| 1-522 | $CH_2Br$ | $CH_2F$ | $CH_3$ | $CH_2OH$ | OH | OH | 1 |
| 1-523 | $CH_2Br$ | $CH_2OCH_3$ | $CH_3$ | $CH_2OH$ | OH | OH | 1 |
| 1-524 | $CH_2Br$ | $CH_2OH$ | H | $CH_2F$ | OH | OH | 1 |
| 1-525 | $CH_2Br$ | $CH_3$ | H | $CH_2F$ | OH | OH | 1 |
| 1-526 | $CH_2Br$ | $CH_2F$ | H | $CH_2F$ | OH | OH | 1 |
| 1-527 | $CH_2Br$ | $CH_2OCH_3$ | H | $CH_2F$ | OH | OH | 1 |
| 1-528 | $CH_2Br$ | $CH_2OH$ | H | $CH_2OH$ | F | OH | 1 |
| 1-529 | $CH_2Br$ | $CH_3$ | H | $CH_2OH$ | F | OH | 1 |
| 1-530 | $CH_2Br$ | $CH_2F$ | H | $CH_2OH$ | F | OH | 1 |
| 1-531 | $CH_2Br$ | $CH_2OCH_3$ | H | $CH_2OH$ | F | OH | 1 |
| 1-532 | $CH_2Br$ | $CH_2OH$ | H | $CH_2F$ | F | OH | 1 |
| 1-533 | $CH_2Br$ | $CH_3$ | H | $CH_2F$ | F | OH | 1 |
| 1-534 | $CH_2Br$ | $CH_2F$ | H | $CH_2F$ | F | OH | 1 |
| 1-535 | $CH_2Br$ | $CH_2OCH_3$ | H | $CH_2F$ | F | OH | 1 |
| 1-536 | $CH_2Br$ | $CH_2OCH_3$ | H | $CH_2OH$ | OH | OH | 1 |
| 1-537 | $CH_2I$ | $CH_2OH$ | H | $CH_2OH$ | OH | H | 1 |
| 1-538 | $CH_3$ | $CH_2OH$ | H | $CH_2OH$ | OH | H | 2 |
| 1-539 | $CH_3$ | $CH_3$ | H | $CH_2OH$ | OH | H | 2 |
| 1-540 | $CH_3$ | $CH_2F$ | H | $CH_2OH$ | OH | H | 2 |

TABLE 1-continued

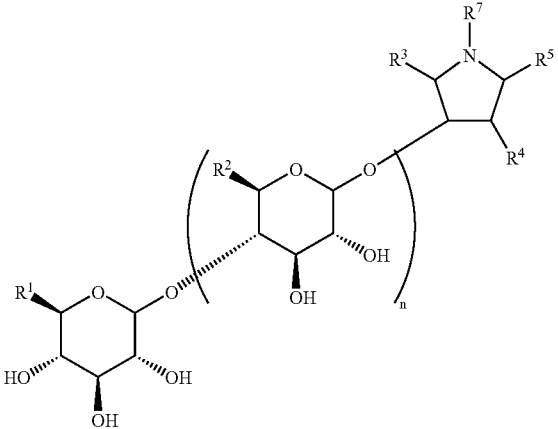

(Ia)

| No. | R¹ | R² | R⁷ | R³ | R⁴ | R⁵ | n |
|---|---|---|---|---|---|---|---|
| 1-541 | $CH_3$ | $CH_2OH$ | H | $CH_2OH$ | F | H | 2 |
| 1-542 | $CH_3$ | $CH_3$ | H | $CH_2OH$ | F | H | 2 |
| 1-543 | $CH_3$ | $CH_2F$ | H | $CH_2OH$ | F | H | 2 |
| 1-544 | $CH_3$ | $CH_2OH$ | H | $CH_2F$ | OH | H | 2 |
| 1-545 | $CH_3$ | $CH_3$ | H | $CH_2F$ | OH | H | 2 |
| 1-546 | $CH_3$ | $CH_2F$ | H | $CH_2F$ | OH | H | 2 |
| 1-547 | $CH_2OH$ | $CH_2OH$ | H | $CH_2OH$ | OH | H | 2 |
| 1-548 | $CH_2OH$ | $CH_3$ | H | $CH_2OH$ | OH | H | 2 |
| 1-549 | $CH_2OH$ | $CH_2F$ | H | $CH_2OH$ | OH | H | 2 |
| 1-550 | $CH_2F$ | $CH_2OH$ | H | $CH_2OH$ | OH | H | 2 |
| 1-551 | $CH_2F$ | $CH_3$ | H | $CH_2OH$ | OH | H | 2 |
| 1-552 | $CH_2F$ | $CH_2F$ | H | $CH_2OH$ | OH | H | 2 |
| 1-553 | $CH_2OCH_3$ | $CH_2OH$ | H | $CH_2OH$ | OH | H | 2 |
| 1-554 | $CH_2OCH_3$ | $CH_3$ | H | $CH_2OH$ | OH | H | 2 |
| 1-555 | $CH_2OCH_3$ | $CH_2F$ | H | $CH_2OH$ | OH | H | 2 |
| 1-556 | $CH_3$ | $CH_2OH$ | H | H | OH | $CH_2OH$ | 1 |
| 1-557 | $CH_3$ | $CH_2OH$ | H | $CH_2OH$ | OH | $CH_2OH$ | 1 |
| 1-558 | $CH_2OH$ | $CH_2OH$ | H | $CH_2OH$ | OH | $CH_2OH$ | 1 |

TABLE 2

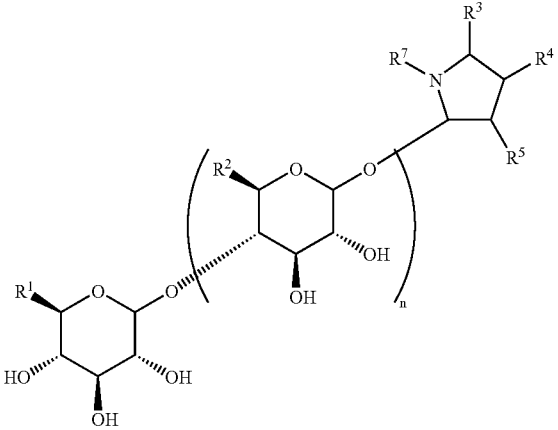

(Ia')

| No. | R¹ | R² | R⁷ | R³ | R⁴ | R⁵ | n |
|---|---|---|---|---|---|---|---|
| 2-1 | $CH_3$ | $CH_2OH$ | H | $CH_2OH$ | OH | H | 1 |
| 2-2 | $CH_3$ | $CH_3$ | H | $CH_2OH$ | OH | H | 1 |
| 2-3 | $CH_3$ | $CH_2F$ | H | $CH_2OH$ | OH | H | 1 |
| 2-4 | $CH_3$ | $CH_2OCH_3$ | H | $CH_2OH$ | OH | H | 1 |
| 2-5 | $CH_3$ | $CH_2CH_3$ | H | $CH_2OH$ | OH | H | 1 |
| 2-6 | $CH_3$ | ⁿPr | H | $CH_2OH$ | OH | H | 1 |

TABLE 2-continued

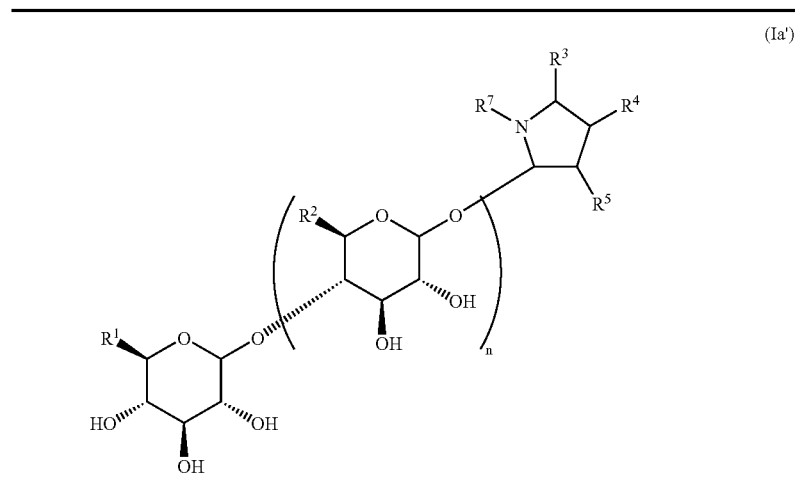

(Ia')

| No. | R¹ | R² | R⁷ | R³ | R⁴ | R⁵ | n |
|---|---|---|---|---|---|---|---|
| 2-7 | $CH_3$ | $^iPr$ | H | $CH_2OH$ | OH | H | 1 |
| 2-8 | $CH_3$ | $^nBu$ | H | $CH_2OH$ | OH | H | 1 |
| 2-9 | $CH_3$ | $^iBu$ | H | $CH_2OH$ | OH | H | 1 |
| 2-10 | $CH_3$ | $^tBu$ | H | $CH_2OH$ | OH | H | 1 |
| 2-11 | $CH_3$ | $^nPn$ | H | $CH_2OH$ | OH | H | 1 |
| 2-12 | $CH_3$ | $^nHex$ | H | $CH_2OH$ | OH | H | 1 |
| 2-13 | $CH_3$ | $CH_2OCH_2CH_3$ | H | $CH_2OH$ | OH | H | 1 |
| 2-14 | $CH_3$ | $CH_2O^iPr$ | H | $CH_2OH$ | OH | H | 1 |
| 2-15 | $CH_3$ | $CH_2O^tBu$ | H | $CH_2OH$ | OH | H | 1 |
| 2-16 | $CH_3$ | $(CH_2)_2F$ | H | $CH_2OH$ | OH | H | 1 |
| 2-17 | $CH_3$ | $(CH_2)_3F$ | H | $CH_2OH$ | OH | H | 1 |
| 2-18 | $CH_3$ | $(CH_2)_4F$ | H | $CH_2OH$ | OH | H | 1 |
| 2-19 | $CH_3$ | $(CH_2)_5F$ | H | $CH_2OH$ | OH | H | 1 |
| 2-20 | $CH_3$ | $(CH_2)_6F$ | H | $CH_2OH$ | OH | H | 1 |
| 2-21 | $CH_3$ | $CH_2Br$ | H | $CH_2OH$ | OH | H | 1 |
| 2-22 | $CH_3$ | $CH_2Cl$ | H | $CH_2OH$ | OH | H | 1 |
| 2-23 | $CH_3$ | $CH_2I$ | H | $CH_2OH$ | OH | H | 1 |
| 2-24 | $CH_3$ | $CH_2OH$ | $CH_2CH_3$ | $CH_2OH$ | OH | H | 1 |
| 2-25 | $CH_3$ | $CH_2OH$ | $^nPr$ | $CH_2OH$ | OH | H | 1 |
| 2-26 | $CH_3$ | $CH_2OH$ | $^iPr$ | $CH_2OH$ | OH | H | 1 |
| 2-27 | $CH_3$ | $CH_2OH$ | $^nBu$ | $CH_2OH$ | OH | H | 1 |
| 2-28 | $CH_3$ | $CH_2OH$ | $^tBu$ | $CH_2OH$ | OH | H | 1 |
| 2-29 | $CH_3$ | $CH_2OH$ | $^iBu$ | $CH_2OH$ | OH | H | 1 |
| 2-30 | $CH_3$ | $CH_2OH$ | $^nPn$ | $CH_2OH$ | OH | H | 1 |
| 2-31 | $CH_3$ | $CH_2OH$ | $^nHex$ | $CH_2OH$ | OH | H | 1 |
| 2-32 | $CH_3$ | $CH_2OH$ | $CH_2OH$ | $CH_2OH$ | OH | H | 1 |
| 2-33 | $CH_3$ | $CH_2OH$ | $(CH_2)_2OH$ | $CH_2OH$ | OH | H | 1 |
| 2-34 | $CH_3$ | $CH_2OH$ | $(CH_2)_3OH$ | $CH_2OH$ | OH | H | 1 |
| 2-35 | $CH_3$ | $CH_2OH$ | $(CH_2)_4OH$ | $CH_2OH$ | OH | H | 1 |
| 2-36 | $CH_3$ | $CH_2OH$ | $(CH_2)_5OH$ | $CH_2OH$ | OH | H | 1 |
| 2-37 | $CH_3$ | $CH_2OH$ | $(CH_2)_6OH$ | $CH_2OH$ | OH | H | 1 |
| 2-38 | $CH_3$ | $CH_2OH$ | $CH_2F$ | $CH_2OH$ | OH | H | 1 |
| 2-39 | $CH_3$ | $CH_2OH$ | $CH_2Cl$ | $CH_2OH$ | OH | H | 1 |
| 2-40 | $CH_3$ | $CH_2OH$ | $CH_2Br$ | $CH_2OH$ | OH | H | 1 |
| 2-41 | $CH_3$ | $CH_2OH$ | $CH_2I$ | $CH_2OH$ | OH | H | 1 |
| 2-42 | $CH_3$ | $CH_2OH$ | OH | $CH_2OH$ | OH | H | 1 |
| 2-43 | $CH_3$ | $CH_2OH$ | $OCH_3$ | $CH_2OH$ | OH | H | 1 |
| 2-44 | $CH_3$ | $CH_2OH$ | $OCH_2CH_3$ | $CH_2OH$ | OH | H | 1 |
| 2-45 | $CH_3$ | $CH_2OH$ | $O^nPr$ | $CH_2OH$ | OH | H | 1 |
| 2-46 | $CH_3$ | $CH_2OH$ | $O^iPr$ | $CH_2OH$ | OH | H | 1 |
| 2-47 | $CH_3$ | $CH_2OH$ | $O^nBu$ | $CH_2OH$ | OH | H | 1 |
| 2-48 | $CH_3$ | $CH_2OH$ | $O^tBu$ | $CH_2OH$ | OH | H | 1 |
| 2-49 | $CH_3$ | $CH_2OH$ | $O^iBu$ | $CH_2OH$ | OH | H | 1 |
| 2-50 | $CH_3$ | $CH_2OH$ | $O^nPn$ | $CH_2OH$ | OH | H | 1 |
| 2-51 | $CH_3$ | $CH_2OH$ | $O^nHex$ | $CH_2OH$ | OH | H | 1 |
| 2-52 | $CH_3$ | $CH_2OH$ | H | $CH_3$ | OH | H | 1 |
| 2-53 | $CH_3$ | $CH_2OH$ | H | $CH_2CH_3$ | OH | H | 1 |
| 2-54 | $CH_3$ | $CH_2OH$ | H | $^nPr$ | OH | H | 1 |
| 2-55 | $CH_3$ | $CH_2OH$ | H | $^iPr$ | OH | H | 1 |
| 2-56 | $CH_3$ | $CH_2OH$ | H | $^nBu$ | OH | H | 1 |
| 2-57 | $CH_3$ | $CH_2OH$ | H | $^tBu$ | OH | H | 1 |
| 2-58 | $CH_3$ | $CH_2OH$ | H | $^iBu$ | OH | H | 1 |
| 2-59 | $CH_3$ | $CH_2CH$ | H | $^nPn$ | OH | H | 1 |
| 2-60 | $CH_3$ | $CH_2OH$ | H | $^nHex$ | OH | H | 1 |

TABLE 2-continued

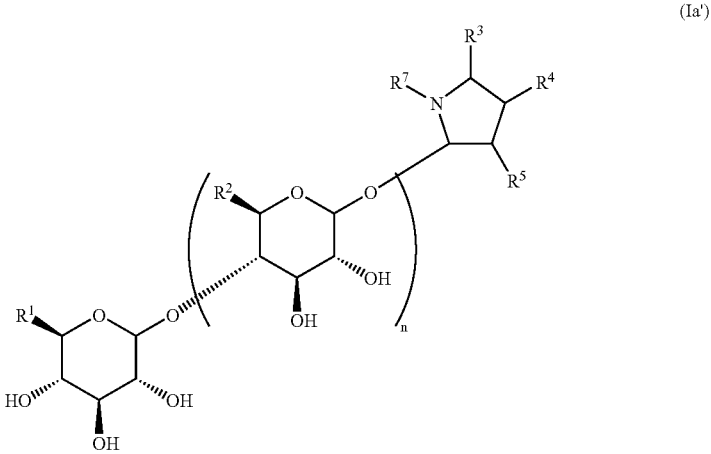

(Ia')

| No. | R¹ | R² | R⁷ | R³ | R⁴ | R⁵ | n |
|---|---|---|---|---|---|---|---|
| 2-61 | CH₃ | CH₂OH | H | CH₂Br | OH | H | 1 |
| 2-62 | CH₃ | CH₂OH | H | CH₂Cl | OH | H | 1 |
| 2-63 | CH₃ | CH₂OH | H | CH₂I | OH | H | 1 |
| 2-64 | CH₃ | CH₂OH | H | NH₂ | OH | H | 1 |
| 2-65 | CH₃ | CH₂OH | H | N(CH₃)₂ | OH | H | 1 |
| 2-66 | CH₃ | CH₂OH | H | NHCH(CH₂OH)₂ | OH | H | 1 |
| 2-67 | CH₃ | CH₂OH | H | OH | OH | H | 1 |
| 2-68 | CH₃ | CH₂OH | H | H | OH | H | 1 |
| 2-69 | CH₃ | CH₂OH | H | F | OH | H | 1 |
| 2-70 | CH₃ | CH₂OH | H | Br | OH | H | 1 |
| 2-71 | CH₃ | CH₂OH | H | Cl | OH | H | 1 |
| 2-72 | CH₃ | CH₂OH | H | I | OH | H | 1 |
| 2-73 | CH₃ | CH₂OH | H | CH₂OH | CH₃ | H | 1 |
| 2-74 | CH₃ | CH₂OH | H | CH₂OH | CH₂CH₃ | H | 1 |
| 2-75 | CH₃ | CH₂OH | H | CH₂OH | CH₂OH | H | 1 |
| 2-76 | CH₃ | CH₂OH | H | CH₂OH | (CH₂)₂OH | H | 1 |
| 2-77 | CH₃ | CH₂OH | H | CH₂OH | (CH₂)₃OH | H | 1 |
| 2-78 | CH₃ | CH₂OH | H | CH₂OH | (CH₂)₄OH | H | 1 |
| 2-79 | CH₃ | CH₂OH | H | CH₂OH | (CH₂)₅OH | H | 1 |
| 2-80 | CH₃ | CH₂OH | H | CH₂OH | (CH₂)₆OH | H | 1 |
| 2-81 | CH₃ | CH₂OH | H | CH₂OH | CH₂F | H | 1 |
| 2-82 | CH₃ | CH₂OH | H | CH₂OH | CH₂Cl | H | 1 |
| 2-83 | CH₃ | CH₂OH | H | CH₂OH | CH₂Br | H | 1 |
| 2-84 | CH₃ | CH₂OH | H | CH₂OH | CH₂I | H | 1 |
| 2-85 | CH₃ | CH₂OH | H | CH₂OH | H | H | 1 |
| 2-86 | CH₃ | CH₂OH | H | CH₂OH | OCH₃ | H | 1 |
| 2-87 | CH₃ | CH₂OH | H | CH₂OH | OCH₂CH₃ | H | 1 |
| 2-88 | CH₃ | CH₂OH | H | CH₂OH | OⁿPr | H | 1 |
| 2-89 | CH₃ | CH₂OH | H | CH₂OH | OⁱPr | H | 1 |
| 2-90 | CH₃ | CH₂OH | H | CH₂OH | OⁿBu | H | 1 |
| 2-91 | CH₃ | CH₂OH | H | CH₂OH | OⁱBu | H | 1 |
| 2-92 | CH₃ | CH₂OH | H | CH₂OH | OᵗBu | H | 1 |
| 2-93 | CH₃ | CH₂OH | H | CH₂OH | OⁿPn | H | 1 |
| 2-94 | CH₃ | CH₂OH | H | CH₂OH | OⁿHex | H | 1 |
| 2-95 | CH₃ | CH₂OH | H | CH₂OH | Br | H | 1 |
| 2-96 | CH₃ | CH₂OH | H | CH₂OH | Cl | H | 1 |
| 2-97 | CH₃ | CH₂OH | H | CH₂OH | I | H | 1 |
| 2-98 | CH₃ | CH₂OH | H | CH₂OH | OH | CH₃ | 1 |
| 2-99 | CH₃ | CH₂OH | H | CH₂OH | OH | CH₂CH₃ | 1 |
| 2-100 | CH₃ | CH₂OH | H | CH₂OH | OH | CH₂F | 1 |
| 2-101 | CH₃ | CH₂OH | H | CH₂OH | OH | OCH₃ | 1 |
| 2-102 | CH₃ | CH₂OH | H | CH₂OH | OH | OCH₂CH₃ | 1 |
| 2-103 | CH₃ | CH₂OH | H | CH₂OH | OH | OⁿPr | 1 |
| 2-104 | CH₃ | CH₂OH | H | CH₂OH | OH | OⁱPr | 1 |
| 2-105 | CH₃ | CH₂OH | H | CH₂OH | OH | OⁿBu | 1 |
| 2-106 | CH₃ | CH₂OH | H | CH₂OH | OH | OⁱBu | 1 |
| 2-107 | CH₃ | CH₂OH | H | CH₂OH | OH | OᵗBu | 1 |
| 2-108 | CH₃ | CH₂OH | H | CH₂OH | OH | OⁿPn | 1 |
| 2-109 | CH₃ | CH₂OH | H | CH₂OH | OH | OⁿHex | 1 |
| 2-110 | CH₃ | CH₂OH | H | CH₂OH | OH | F | 1 |
| 2-111 | CH₃ | CH₂OH | CH₃ | CH₂OH | OH | H | 1 |
| 2-112 | CH₃ | CH₃ | CH₃ | CH₂OH | OH | H | 1 |
| 2-113 | CH₃ | CH₂F | CH₃ | CH₂OH | OH | H | 1 |
| 2-114 | CH₃ | CH₂OCH₃ | CH₃ | CH₂OH | OH | H | 1 |

TABLE 2-continued

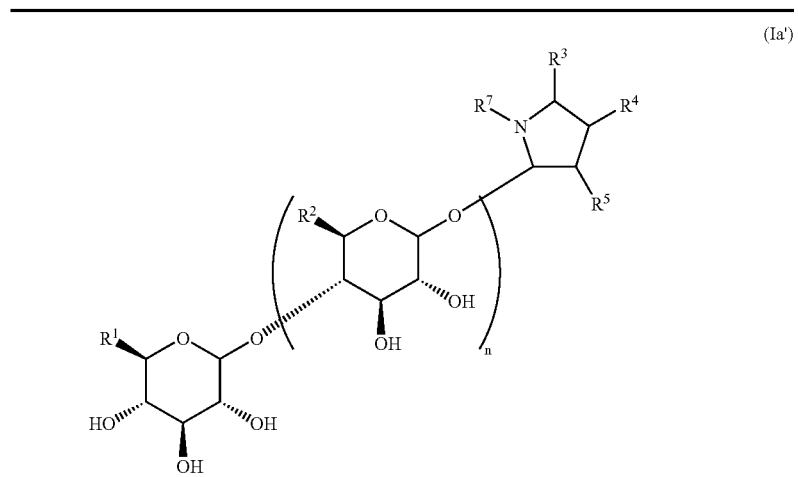

(Ia')

| No. | R$^1$ | R$^2$ | R$^7$ | R$^3$ | R$^4$ | R$^5$ | n |
|---|---|---|---|---|---|---|---|
| 2-115 | CH$_3$ | CH$_2$OH | H | CH$_2$OH | F | H | 1 |
| 2-116 | CH$_3$ | CH$_3$ | H | CH$_2$OH | F | H | 1 |
| 2-117 | CH$_3$ | CH$_2$F | H | CH$_2$OH | F | H | 1 |
| 2-118 | CH$_3$ | CH$_2$OCH$_3$ | H | CH$_2$OH | F | H | 1 |
| 2-119 | CH$_3$ | CH$_2$OH | H | CH$_2$F | OH | H | 1 |
| 2-120 | CH$_3$ | CH$_3$ | H | CH$_2$F | OH | H | 1 |
| 2-121 | CH$_3$ | CH$_2$F | H | CH$_2$F | OH | H | 1 |
| 2-122 | CH$_3$ | CH$_2$OCH$_3$ | H | CH$_2$F | OH | H | 1 |
| 2-123 | CH$_3$ | CH$_2$OH | H | CH$_2$F | F | H | 1 |
| 2-124 | CH$_3$ | CH$_3$ | H | CH$_2$F | F | H | 1 |
| 2-125 | CH$_3$ | CH$_2$F | H | CH$_2$F | F | H | 1 |
| 2-126 | CH$_3$ | CH$_2$OCH$_3$ | H | CH$_2$F | F | H | 1 |
| 2-127 | CH$_3$ | CH$_2$OH | H | CH$_2$OH | OH | OH | 1 |
| 2-128 | CH$_3$ | CH$_3$ | H | CH$_2$OH | OH | OH | 1 |
| 2-129 | CH$_3$ | CH$_2$F | H | CH$_2$OH | OH | OH | 1 |
| 2-130 | CH$_3$ | CH$_2$OH | CH$_3$ | CH$_2$OH | OH | OH | 1 |
| 2-131 | CH$_3$ | CH$_3$ | CH$_3$ | CH$_2$OH | OH | OH | 1 |
| 2-132 | CH$_3$ | CH$_2$F | CH$_3$ | CH$_2$OH | OH | OH | 1 |
| 2-133 | CH$_3$ | CH$_2$OCH$_3$ | CH$_3$ | CH$_2$OH | OH | OH | 1 |
| 2-134 | CH$_3$ | CH$_2$OH | H | CH$_2$F | OH | OH | 1 |
| 2-135 | CH$_3$ | CH$_3$ | H | CH$_2$F | OH | OH | 1 |
| 2-136 | CH$_3$ | CH$_2$F | H | CH$_2$F | OH | OH | 1 |
| 2-137 | CH$_3$ | CH$_2$OCH$_3$ | H | CH$_2$F | OH | OH | 1 |
| 2-138 | CH$_3$ | CH$_2$OH | H | CH$_2$OH | F | OH | 1 |
| 2-139 | CH$_3$ | CH$_3$ | H | CH$_2$OH | F | OH | 1 |
| 2-140 | CH$_3$ | CH$_2$F | H | CH$_2$OH | F | OH | 1 |
| 2-141 | CH$_3$ | CH$_2$OCH$_3$ | H | CH$_2$OH | F | OH | 1 |
| 2-142 | CH$_3$ | CH$_2$OH | H | CH$_2$F | F | OH | 1 |
| 2-143 | CH$_3$ | CH$_3$ | H | CH$_2$F | F | OH | 1 |
| 2-144 | CH$_3$ | CH$_2$F | H | CH$_2$F | F | OH | 1 |
| 2-145 | CH$_3$ | CH$_2$OCH$_3$ | H | CH$_2$F | F | OH | 1 |
| 2-146 | CH$_3$ | CH$_2$OCH$_3$ | H | CH$_2$OH | OH | OH | 1 |
| 2-147 | CH$_2$CH$_3$ | CH$_2$OH | H | CH$_2$OH | OH | H | 1 |
| 2-148 | $^n$Pr | CH$_2$OH | H | CH$_2$OH | OH | H | 1 |
| 2-149 | $^i$Pr | CH$_2$OH | H | CH$_2$OH | OH | H | 1 |
| 2-150 | $^n$Bu | CH$_2$OH | H | CH$_2$OH | OH | H | 1 |
| 2-151 | $^i$Bu | CH$_2$OH | H | CH$_2$OH | OH | H | 1 |
| 2-152 | $^t$Bu | CH$_2$OH | H | CH$_2$OH | OH | H | 1 |
| 2-153 | $^n$Pn | CH$_2$OH | H | CH$_2$OH | OH | H | 1 |
| 2-154 | $^n$Hex | CH$_2$OH | H | CH$_2$OH | OH | H | 1 |
| 2-155 | CH$_2$OH | CH$_2$OH | H | CH$_2$OH | OH | H | 1 |
| 2-156 | CH$_2$OH | CH$_3$ | H | CH$_2$OH | OH | H | 1 |
| 2-157 | CH$_2$OH | CH$_2$F | H | CH$_2$OH | OH | H | 1 |
| 2-158 | CH$_2$OH | CH$_2$OCH$_3$ | H | CH$_2$OH | OH | H | 1 |
| 2-159 | CH$_2$OH | CH$_3$ | H | CH$_2$OH | OH | H | 1 |
| 2-160 | CH$_2$OH | CH$_2$F | H | CH$_2$OH | OH | H | 1 |
| 2-161 | CH$_2$OH | CH$_2$OCH$_3$ | H | CH$_2$OH | OH | H | 1 |
| 2-162 | CH$_2$OH | CH$_2$CH$_3$ | H | CH$_2$OH | OH | H | 1 |
| 2-163 | CH$_2$OH | $^n$Pr | H | CH$_2$OH | OH | H | 1 |
| 2-164 | CH$_2$OH | $^i$Pr | H | CH$_2$OH | OH | H | 1 |
| 2-165 | CH$_2$OH | $^n$Bu | H | CH$_2$OH | OH | H | 1 |
| 2-166 | CH$_2$OH | $^i$Bu | H | CH$_2$OH | OH | H | 1 |
| 2-167 | CH$_2$OH | $^t$Bu | H | CH$_2$OH | OH | H | 1 |
| 2-168 | CH$_2$OH | $^n$Pn | H | CH$_2$OH | OH | H | 1 |

TABLE 2-continued

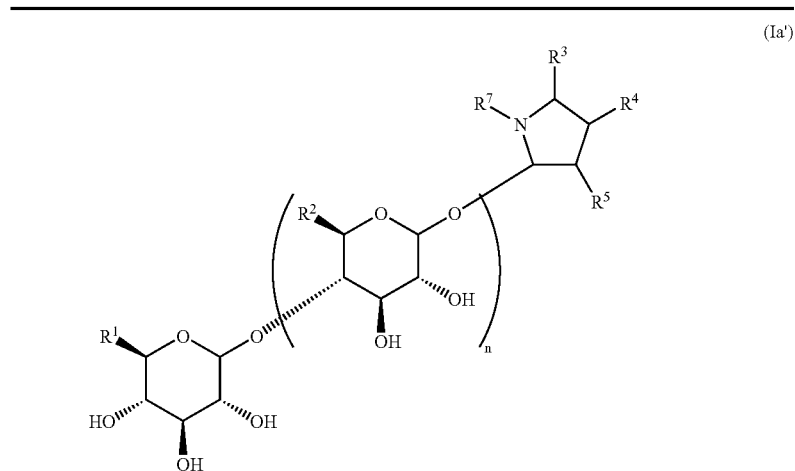

(Ia')

| No. | R$^1$ | R$^2$ | R$^7$ | R$^3$ | R$^4$ | R$^5$ | n |
|---|---|---|---|---|---|---|---|
| 2-169 | CH$_2$OH | $^n$Hex | H | CH$_2$OH | OH | H | 1 |
| 2-170 | CH$_2$OH | CH$_2$OCH$_2$CH$_3$ | H | CH$_2$OH | OH | H | 1 |
| 2-171 | CH$_2$OH | CH$_2$O$^i$Pr | H | CH$_2$OH | OH | H | 1 |
| 2-172 | CH$_2$OH | CH$_2$O$^t$Bu | H | CH$_2$OH | OH | H | 1 |
| 2-173 | CH$_2$OH | (CH$_2$)$_2$F | H | CH$_2$OH | OH | H | 1 |
| 2-174 | CH$_2$OH | CH$_2$Br | H | CH$_2$OH | OH | H | 1 |
| 2-175 | CH$_2$OH | CH$_2$Cl | H | CH$_2$OH | OH | H | 1 |
| 2-176 | CH$_2$OH | CH$_2$I | H | CH$_2$OH | OH | H | 1 |
| 2-177 | CH$_2$OH | CH$_2$OH | CH$_2$CH$_3$ | CH$_2$OH | OH | H | 1 |
| 2-178 | CH$_2$OH | CH$_2$OH | $^n$Pr | CH$_2$OH | OH | H | 1 |
| 2-179 | CH$_2$OH | CH$_2$OH | $^i$Pr | CH$_2$OH | OH | H | 1 |
| 2-180 | CH$_2$OH | CH$_2$OH | $^n$Bu | CH$_2$OH | OH | H | 1 |
| 2-181 | CH$_2$OH | CH$_2$OH | $^t$Bu | CH$_2$OH | OH | H | 1 |
| 2-182 | CH$_2$OH | CH$_2$OH | $^i$Bu | CH$_2$OH | OH | H | 1 |
| 2-183 | CH$_2$OH | CH$_2$OH | $^n$Pn | CH$_2$OH | OH | H | 1 |
| 2-184 | CH$_2$OH | CH$_2$OH | $^n$Hex | CH$_2$OH | OH | H | 1 |
| 2-185 | CH$_2$OH | CH$_2$OH | CH$_2$OH | CH$_2$OH | OH | H | 1 |
| 2-186 | CH$_2$OH | CH$_2$OH | (CH$_2$)$_2$OH | CH$_2$OH | OH | H | 1 |
| 2-187 | CH$_2$OH | CH$_2$OH | (CH$_2$)$_3$OH | CH$_2$OH | OH | H | 1 |
| 2-188 | CH$_2$OH | CH$_2$OH | (CH$_2$)$_4$OH | CH$_2$OH | OH | H | 1 |
| 2-189 | CH$_2$OH | CH$_2$OH | (CH$_2$)$_5$OH | CH$_2$OH | OH | H | 1 |
| 2-190 | CH$_2$OH | CH$_2$OH | (CH$_2$)$_6$OH | CH$_2$OH | OH | H | 1 |
| 2-191 | CH$_2$OH | CH$_2$OH | CH$_2$F | CH$_2$OH | OH | H | 1 |
| 2-192 | CH$_2$OH | CH$_2$OH | CH$_2$Cl | CH$_2$OH | OH | H | 1 |
| 2-193 | CH$_2$OH | CH$_2$OH | CH$_2$Br | CH$_2$OH | OH | H | 1 |
| 2-194 | CH$_2$OH | CH$_2$OH | CH$_2$I | CH$_2$OH | OH | H | 1 |
| 2-195 | CH$_2$OH | CH$_2$OH | OH | CH$_2$OH | OH | H | 1 |
| 2-196 | CH$_2$OH | CH$_2$OH | OCH$_3$ | CH$_2$OH | OH | H | 1 |
| 2-197 | CH$_2$OH | CH$_2$OH | OCH$_2$CH$_3$ | CH$_2$OH | OH | H | 1 |
| 2-198 | CH$_2$OH | CH$_2$OH | O$^n$Pr | CH$_2$OH | OH | H | 1 |
| 2-199 | CH$_2$OH | CH$_2$OH | O$^i$Pr | CH$_2$OH | OH | H | 1 |
| 2-200 | CH$_2$OH | CH$_2$OH | O$^n$Bu | CH$_2$OH | OH | H | 1 |
| 2-201 | CH$_2$OH | CH$_2$OH | O$^t$Bu | CH$_2$OH | OH | H | 1 |
| 2-202 | CH$_2$OH | CH$_2$OH | O$^i$Bu | CH$_2$OH | OH | H | 1 |
| 2-203 | CH$_2$OH | CH$_2$OH | O$^n$Pn | CH$_2$OH | OH | H | 1 |
| 2-204 | CH$_2$OH | CH$_2$OH | O$^n$Hex | CH$_2$OH | OH | H | 1 |
| 2-205 | CH$_2$OH | CH$_2$OH | H | CH$_3$ | OH | H | 1 |
| 2-206 | CH$_2$OH | CH$_2$OH | H | CH$_2$CH$_3$ | OH | H | 1 |
| 2-207 | CH$_2$OH | CH$_2$OH | H | CH$_2$Br | OH | H | 1 |
| 2-208 | CH$_2$OH | CH$_2$OH | H | CH$_2$Cl | OH | H | 1 |
| 2-209 | CH$_2$OH | CH$_2$OH | H | CH$_2$I | OH | H | 1 |
| 2-210 | CH$_2$OH | CH$_2$OH | H | OH | OH | H | 1 |
| 2-211 | CH$_2$OH | CH$_2$OH | H | H | OH | H | 1 |
| 2-212 | CH$_2$OH | CH$_2$OH | H | F | OH | H | 1 |
| 2-213 | CH$_2$OH | CH$_2$OH | H | Br | OH | H | 1 |
| 2-214 | CH$_2$OH | CH$_2$OH | H | Cl | OH | H | 1 |
| 2-215 | CH$_2$OH | CH$_2$OH | H | I | OH | H | 1 |
| 2-216 | CH$_2$OH | CH$_2$OH | H | CH$_2$OH | CH$_3$ | H | 1 |
| 2-217 | CH$_2$OH | CH$_2$OH | H | CH$_2$OH | CH$_2$CH$_3$ | H | 1 |
| 2-218 | CH$_2$OH | CH$_2$OH | H | CH$_2$OH | $^n$Pr | H | 1 |
| 2-219 | CH$_2$OH | CH$_2$OH | H | CH$_2$OH | $^i$Pr | H | 1 |
| 2-220 | CH$_2$OH | CH$_2$OH | H | CH$_2$OH | $^n$Bu | H | 1 |
| 2-221 | CH$_2$OH | CH$_2$OH | H | CH$_2$OH | $^i$Bu | H | 1 |
| 2-222 | CH$_2$OH | CH$_2$OH | H | CH$_2$OH | $^t$Bu | H | 1 |

TABLE 2-continued

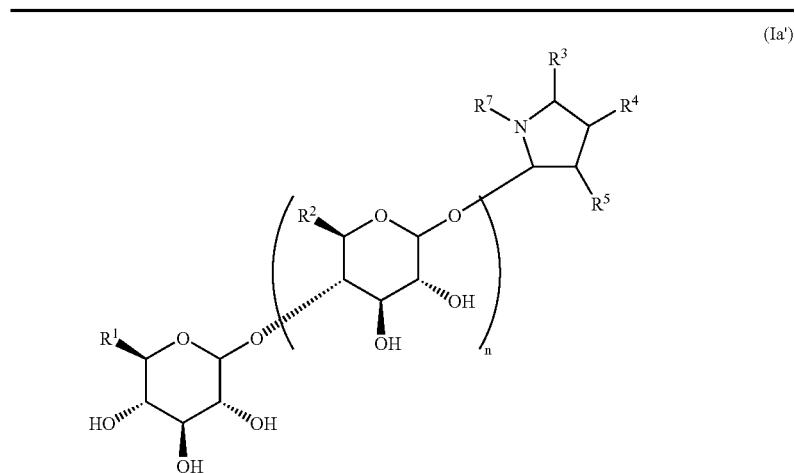

(Ia')

| No. | $R^1$ | $R^2$ | $R^7$ | $R^3$ | $R^4$ | $R^5$ | n |
|---|---|---|---|---|---|---|---|
| 2-223 | $CH_2OH$ | $CH_2OH$ | H | $CH_2OH$ | $^nPn$ | H | 1 |
| 2-224 | $CH_2OH$ | $CH_2OH$ | H | $CH_2OH$ | $^nHex$ | H | 1 |
| 2-225 | $CH_2OH$ | $CH_2OH$ | H | $CH_2OH$ | $CH_2OH$ | H | 1 |
| 2-226 | $CH_2OH$ | $CH_2OH$ | H | $CH_2OH$ | $CH_2F$ | H | 1 |
| 2-227 | $CH_2OH$ | $CH_2OH$ | H | $CH_2OH$ | $CH_2Cl$ | H | 1 |
| 2-228 | $CH_2OH$ | $CH_2OH$ | H | $CH_2OH$ | $CH_2Br$ | H | 1 |
| 2-229 | $CH_2OH$ | $CH_2OH$ | H | $CH_2OH$ | $CH_2I$ | H | 1 |
| 2-230 | $CH_2OH$ | $CH_2OH$ | H | $CH_2OH$ | H | H | 1 |
| 2-231 | $CH_2OH$ | $CH_2OH$ | H | $CH_2OH$ | $OCH_3$ | H | 1 |
| 2-232 | $CH_2OH$ | $CH_2OH$ | H | $CH_2OH$ | $OCH_2CH_3$ | H | 1 |
| 2-233 | $CH_2OH$ | $CH_2OH$ | H | $CH_2OH$ | Br | H | 1 |
| 2-234 | $CH_2OH$ | $CH_2OH$ | H | $CH_2OH$ | Cl | H | 1 |
| 2-235 | $CH_2OH$ | $CH_2OH$ | H | $CH_2OH$ | I | H | 1 |
| 2-236 | $CH_2OH$ | $CH_2OH$ | H | $CH_2OH$ | OH | $CH_3$ | 1 |
| 2-237 | $CH_2OH$ | $CH_2OH$ | H | $CH_2OH$ | OH | $CH_2CH_3$ | 1 |
| 2-238 | $CH_2OH$ | $CH_2OH$ | H | $CH_2OH$ | OH | $CH_2F$ | 1 |
| 2-239 | $CH_2OH$ | $CH_2OH$ | H | $CH_2OH$ | OH | $OCH_3$ | 1 |
| 2-240 | $CH_2OH$ | $CH_2OH$ | H | $CH_2OH$ | OH | $OCH_2CH_3$ | 1 |
| 2-241 | $CH_2OH$ | $CH_2OH$ | H | $CH_2OH$ | OH | F | 1 |
| 2-242 | $CH_2OH$ | $CH_2OH$ | $CH_3$ | $CH_2OH$ | OH | H | 1 |
| 2-243 | $CH_2OH$ | $CH_3$ | $CH_3$ | $CH_2OH$ | OH | H | 1 |
| 2-244 | $CH_2OH$ | $CH_2F$ | $CH_3$ | $CH_2OH$ | OH | H | 1 |
| 2-245 | $CH_2OH$ | $CH_2OCH_3$ | $CH_3$ | $CH_2OH$ | OH | H | 1 |
| 2-246 | $CH_2OH$ | $CH_2OH$ | H | $CH_2F$ | OH | H | 1 |
| 2-247 | $CH_2OH$ | $CH_3$ | H | $CH_2F$ | OH | H | 1 |
| 2-248 | $CH_2OH$ | $CH_2F$ | H | $CH_2F$ | OH | H | 1 |
| 2-249 | $CH_2OH$ | $CH_2OH$ | H | $CH_2OH$ | F | H | 1 |
| 2-250 | $CH_2OH$ | $CH_3$ | H | $CH_2OH$ | F | H | 1 |
| 2-251 | $CH_2OH$ | $CH_2F$ | H | $CH_2OH$ | F | H | 1 |
| 2-252 | $CH_2OH$ | $CH_2OCH_3$ | H | $CH_2OH$ | F | H | 1 |
| 2-253 | $CH_2OH$ | $CH_2OCH_3$ | H | $CH_2F$ | OH | H | 1 |
| 2-254 | $CH_2OH$ | $CH_2OH$ | H | $CH_2F$ | F | H | 1 |
| 2-255 | $CH_2OH$ | $CH_3$ | H | $CH_2F$ | F | H | 1 |
| 2-256 | $CH_2OH$ | $CH_2F$ | H | $CH_2F$ | F | H | 1 |
| 2-257 | $CH_2OH$ | $CH_2OCH_3$ | H | $CH_2F$ | F | H | 1 |
| 2-258 | $CH_2OH$ | $CH_2OH$ | $CH_3$ | $CH_2OH$ | OH | OH | 1 |
| 2-259 | $CH_2OH$ | $CH_2OH$ | H | $CH_2OH$ | OH | OH | 1 |
| 2-260 | $CH_2OH$ | $CH_3$ | H | $CH_2OH$ | OH | OH | 1 |
| 2-261 | $CH_2OH$ | $CH_2F$ | H | $CH_2OH$ | OH | OH | 1 |
| 2-262 | $CH_2OH$ | $CH_2OCH_3$ | H | $CH_2OH$ | OH | OH | 1 |
| 2-263 | $CH_2OH$ | $CH_3$ | $CH_3$ | $CH_2OH$ | OH | OH | 1 |
| 2-264 | $CH_2OH$ | $CH_2F$ | $CH_3$ | $CH_2OH$ | OH | OH | 1 |
| 2-265 | $CH_2OH$ | $CH_2OCH_3$ | $CH_3$ | $CH_2OH$ | OH | OH | 1 |
| 2-266 | $CH_2OH$ | $CH_2OH$ | H | $CH_2F$ | OH | OH | 1 |
| 2-267 | $CH_2OH$ | $CH_3$ | H | $CH_2F$ | OH | OH | 1 |
| 2-268 | $CH_2OH$ | $CH_2F$ | H | $CH_2F$ | OH | OH | 1 |
| 2-269 | $CH_2OH$ | $CH_2OCH_3$ | H | $CH_2F$ | OH | OH | 1 |
| 2-270 | $CH_2OH$ | $CH_2OH$ | H | $CH_2OH$ | F | OH | I |
| 2-271 | $CH_2OH$ | $CH_3$ | H | $CH_2OH$ | F | OH | 1 |
| 2-272 | $CH_2OH$ | $CH_2F$ | H | $CH_2OH$ | F | OH | 1 |
| 2-273 | $CH_2OH$ | $CH_2OCH_3$ | H | $CH_2OH$ | F | OH | 1 |
| 2-274 | $CH_2OH$ | $CH_2OH$ | H | $CH_2F$ | F | OH | 1 |
| 2-275 | $CH_2OH$ | $CH_3$ | H | $CH_2F$ | F | OH | 1 |
| 2-276 | $CH_2OH$ | $CH_2F$ | H | $CH_2F$ | F | OH | 1 |

TABLE 2-continued

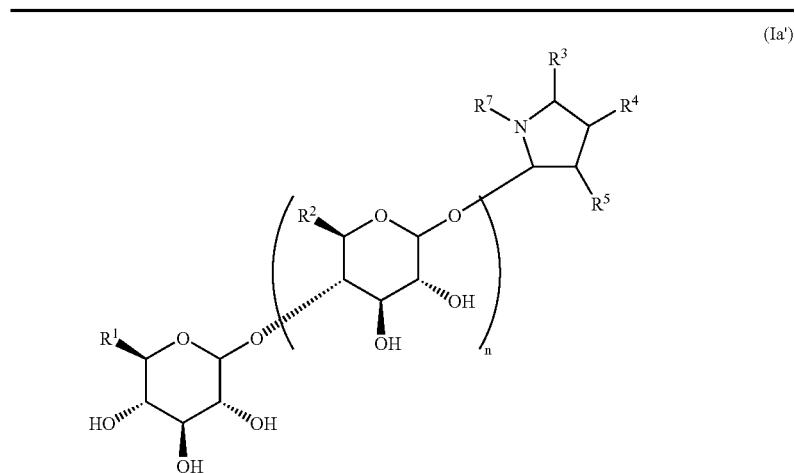

(Ia')

| No. | $R^1$ | $R^2$ | $R^7$ | $R^3$ | $R^4$ | $R^5$ | n |
|---|---|---|---|---|---|---|---|
| 2-277 | $CH_2OH$ | $CH_2OCH_3$ | H | $CH_2F$ | F | OH | 1 |
| 2-278 | $CH_2F$ | $CH_2OH$ | H | $CH_2OH$ | OH | H | 1 |
| 2-279 | $CH_2F$ | $CH_3$ | H | $CH_2OH$ | OH | H | 1 |
| 2-280 | $CH_2F$ | $CH_2F$ | H | $CH_2OH$ | OH | H | 1 |
| 2-281 | $CH_2F$ | $CH_2OCH_3$ | H | $CH_2OH$ | OH | H | 1 |
| 2-282 | $CH_2F$ | $CH_2CH_3$ | H | $CH_2OH$ | OH | H | 1 |
| 2-283 | $CH_2F$ | $CH_2OCH_2CH_3$ | H | $CH_2OH$ | OH | H | 1 |
| 2-284 | $CH_2F$ | $CH_2O^iPr$ | H | $CH_2OH$ | OH | H | 1 |
| 2-285 | $CH_2F$ | $CH_2O^tBu$ | H | $CH_2OH$ | OH | H | 1 |
| 2-286 | $CH_2F$ | $CH_2OH$ | H | $CH_3$ | OH | H | 1 |
| 2-287 | $CH_2F$ | $CH_2OH$ | H | $CH_2CH_3$ | OH | H | 1 |
| 2-288 | $CH_2F$ | $CH_2OH$ | H | $CH_2Br$ | OH | H | 1 |
| 2-289 | $CH_2F$ | $CH_2OH$ | H | $CH_2Cl$ | OH | H | 1 |
| 2-290 | $CH_2F$ | $CH_2OH$ | H | $CH_2I$ | OH | H | 1 |
| 2-291 | $CH_2F$ | $CH_2OH$ | H | OH | OH | H | 1 |
| 2-292 | $CH_2F$ | $CH_2OH$ | H | H | OH | H | 1 |
| 2-293 | $CH_2F$ | $CH_2OH$ | H | F | OH | H | 1 |
| 2-294 | $CH_2F$ | $CH_2OH$ | H | $CH_2OH$ | $CH_3$ | H | 1 |
| 2-295 | $CH_2F$ | $CH_2OH$ | H | $CH_2OH$ | $CH_2CH_3$ | H | 1 |
| 2-296 | $CH_2F$ | $CH_2OH$ | H | $CH_2OH$ | $CH_2OH$ | H | 1 |
| 2-297 | $CH_2F$ | $CH_2OH$ | H | $CH_2OH$ | $CH_2F$ | H | 1 |
| 2-298 | $CH_2F$ | $CH_2OH$ | H | $CH_2OH$ | H | H | 1 |
| 2-299 | $CH_2F$ | $CH_2OH$ | H | $CH_2OH$ | $OCH_3$ | H | 1 |
| 2-300 | $CH_2F$ | $CH_2OH$ | H | $CH_2OH$ | $OCH_2CH_3$ | H | 1 |
| 2-301 | $CH_2F$ | $CH_2OH$ | H | $CH_2OH$ | Br | H | 1 |
| 2-302 | $CH_2F$ | $CH_2OH$ | H | $CH_2OH$ | Cl | H | 1 |
| 2-303 | $CH_2F$ | $CH_2OH$ | H | $CH_2OH$ | I | H | 1 |
| 2-304 | $CH_2F$ | $CH_2OH$ | H | $CH_2OH$ | OH | $CH_3$ | 1 |
| 2-305 | $CH_2F$ | $CH_2OH$ | H | $CH_2OH$ | OH | $CH_2CH_3$ | 1 |
| 2-306 | $CH_2F$ | $CH_2OH$ | H | $CH_2OH$ | OH | $CH_2F$ | 1 |
| 2-307 | $CH_2F$ | $CH_2OH$ | H | $CH_2OH$ | OH | $OCH_3$ | 1 |
| 2-308 | $CH_2F$ | $CH_2OH$ | H | $CH_2OH$ | OH | $OCH_2CH_3$ | 1 |
| 2-309 | $CH_2F$ | $CH_2OH$ | H | $CH_2OH$ | OH | F | 1 |
| 2-310 | $CH_2F$ | $CH_2OH$ | $CH_3$ | $CH_2OH$ | OH | H | 1 |
| 2-311 | $CH_2F$ | $CH_3$ | $CH_3$ | $CH_2OH$ | OH | H | 1 |
| 2-312 | $CH_2F$ | $CH_2F$ | $CH_3$ | $CH_2OH$ | OH | H | 1 |
| 2-313 | $CH_2F$ | $CH_2OCH_3$ | $CH_3$ | $CH_2OH$ | OH | H | 1 |
| 2-314 | $CH_2F$ | $CH_2OH$ | H | $CH_2F$ | OH | H | 1 |
| 2-315 | $CH_2F$ | $CH_3$ | H | $CH_2F$ | OH | H | 1 |
| 2-316 | $CH_2F$ | $CH_2F$ | H | $CH_2F$ | OH | H | 1 |
| 2-317 | $CH_2F$ | $CH_2OH$ | H | $CH_2OH$ | F | H | 1 |
| 2-318 | $CH_2F$ | $CH_2OCH_3$ | H | $CH_2F$ | OH | H | 1 |
| 2-319 | $CH_2F$ | $CH_3$ | H | $CH_2OH$ | F | H | 1 |
| 2-320 | $CH_2F$ | $CH_2F$ | H | $CH_2OH$ | F | H | 1 |
| 2-321 | $CH_2F$ | $CH_2OCH_3$ | H | $CH_2OH$ | F | H | 1 |
| 2-322 | $CH_2F$ | $CH_2OH$ | H | $CH_2OH$ | OH | OH | 1 |
| 2-323 | $CH_2F$ | $CH_3$ | H | $CH_2OH$ | OH | OH | 1 |
| 2-324 | $CH_2F$ | $CH_2F$ | H | $CH_2OH$ | OH | OH | 1 |
| 2-325 | $CH_2F$ | $CH_2OCH_3$ | H | $CH_2OH$ | OH | OH | 1 |
| 2-326 | $CH_2F$ | $CH_2OH$ | $CH_3$ | $CH_2OH$ | OH | OH | 1 |
| 2-327 | $CH_2F$ | $CH_3$ | $CH_3$ | $CH_2OH$ | OH | OH | 1 |
| 2-328 | $CH_2F$ | $CH_2F$ | $CH_3$ | $CH_2OH$ | OH | OH | 1 |
| 2-329 | $CH_2F$ | $CH_2OCH_3$ | $CH_3$ | $CH_2OH$ | OH | OH | 1 |
| 2-330 | $CH_2F$ | $CH_2OH$ | H | $CH_2F$ | OH | OH | 1 |

TABLE 2-continued

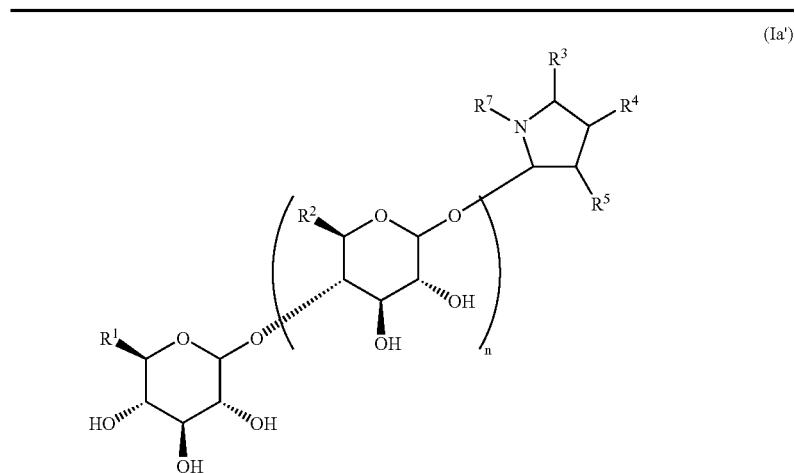

(Ia')

| No. | $R^1$ | $R^2$ | $R^7$ | $R^3$ | $R^4$ | $R^5$ | n |
|---|---|---|---|---|---|---|---|
| 2-331 | $CH_2F$ | $CH_3$ | H | $CH_2F$ | OH | OH | 1 |
| 2-332 | $CH_2F$ | $CH_2F$ | H | $CH_2F$ | OH | OH | 1 |
| 2-333 | $CH_2F$ | $CH_2OCH_3$ | H | $CH_2F$ | OH | OH | 1 |
| 2-334 | $CH_2F$ | $CH_2OH$ | H | $CH_2F$ | F | H | 1 |
| 2-335 | $CH_2F$ | $CH_3$ | H | $CH_2F$ | F | H | 1 |
| 2-336 | $CH_2F$ | $CH_2F$ | H | $CH_2F$ | F | H | 1 |
| 2-337 | $CH_2F$ | $CH_2OCH_3$ | H | $CH_2F$ | F | H | 1 |
| 2-338 | $CH_2F$ | $CH_2OH$ | H | $CH_2F$ | F | OH | 1 |
| 2-339 | $CH_2F$ | $CH_3$ | H | $CH_2F$ | F | OH | 1 |
| 2-340 | $CH_2F$ | $CH_2F$ | H | $CH_2F$ | F | OH | 1 |
| 2-341 | $CH_2F$ | $CH_2OCH_3$ | H | $CH_2F$ | F | OH | 1 |
| 2-342 | $CH_2F$ | $CH_2OH$ | H | $CH_2OH$ | F | OH | 1 |
| 2-343 | $CH_2F$ | $CH_3$ | H | $CH_2OH$ | F | OH | 1 |
| 2-344 | $CH_2F$ | $CH_2F$ | H | $CH_2OH$ | F | OH | 1 |
| 2-345 | $CH_2F$ | $CH_2OCH_3$ | H | $CH_2OH$ | F | OH | 1 |
| 2-346 | $CH_2OCH_3$ | $CH_2OH$ | H | $CH_2F$ | OH | H | 1 |
| 2-347 | $CH_2OCH_3$ | $CH_3$ | H | $CH_2F$ | OH | H | 1 |
| 2-348 | $CH_2OCH_3$ | $CH_2F$ | H | $CH_2F$ | OH | H | 1 |
| 2-349 | $CH_2OCH_3$ | $CH_2OCH_3$ | H | $CH_2F$ | OH | H | 1 |
| 2-350 | $CH_2OCH_3$ | $CH_2OH$ | H | $CH_2OH$ | F | H | 1 |
| 2-351 | $CH_2OCH_3$ | $CH_3$ | H | $CH_2OH$ | F | H | 1 |
| 2-352 | $CH_2OCH_3$ | $CH_2F$ | H | $CH_2OH$ | F | H | 1 |
| 2-353 | $CH_2OCH_3$ | $CH_2OCH_3$ | H | $CH_2OH$ | F | H | 1 |
| 2-354 | $CH_2OCH_3$ | $CH_2OH$ | H | $CH_2OH$ | OH | H | 1 |
| 2-355 | $CH_2OCH_3$ | $CH_3$ | H | $CH_2OH$ | OH | H | 1 |
| 2-356 | $CH_2OCH_3$ | $CH_2F$ | H | $CH_2OH$ | OH | H | 1 |
| 2-357 | $CH_2OCH_3$ | $CH_2OCH_3$ | H | $CH_2OH$ | OH | H | 1 |
| 2-358 | $CH_2OCH_3$ | $CH_3$ | H | $CH_2OH$ | OH | H | 1 |
| 2-359 | $CH_2OCH_3$ | $CH_2F$ | H | $CH_2OH$ | OH | H | 1 |
| 2-360 | $CH_2OCH_3$ | $CH_2OCH_3$ | H | $CH_2OH$ | OH | H | 1 |
| 2-361 | $CH_2OCH_3$ | $CH_2CH_3$ | H | $CH_2OH$ | OH | H | 1 |
| 2-362 | $CH_2OCH_3$ | $CH_2OCH_2CH_3$ | H | $CH_2OH$ | OH | H | 1 |
| 2-363 | $CH_2OCH_3$ | $CH_2O^iPr$ | H | $CH_2OH$ | OH | H | 1 |
| 2-364 | $CH_2OCH_3$ | $CH_2O^tBu$ | H | $CH_2OH$ | OH | H | 1 |
| 2-365 | $CH_2OCH_3$ | $CH_2OH$ | H | $CH_3$ | OH | H | 1 |
| 2-366 | $CH_2OCH_3$ | $CH_2OH$ | H | $CH_2CH_3$ | OH | H | 1 |
| 2-367 | $CH_2OCH_3$ | $CH_2OH$ | H | OH | OH | H | 1 |
| 2-368 | $CH_2OCH_3$ | $CH_2OH$ | H | H | OH | H | 1 |
| 2-369 | $CH_2OCH_3$ | $CH_2OH$ | H | F | OH | H | 1 |
| 2-370 | $CH_2OCH_3$ | $CH_2OH$ | H | $CH_2OH$ | $CH_3$ | H | 1 |
| 2-371 | $CH_2OCH_3$ | $CH_2OH$ | H | $CH_2OH$ | $CH_2CH_3$ | H | 1 |
| 2-372 | $CH_2OCH_3$ | $CH_2OH$ | H | $CH_2OH$ | $CH_2OH$ | H | 1 |
| 2-373 | $CH_2OCH_3$ | $CH_2OH$ | H | $CH_2OH$ | $CH_2F$ | H | 1 |
| 2-374 | $CH_2OCH_3$ | $CH_2OH$ | H | $CH_2OH$ | H | H | 1 |
| 2-375 | $CH_2OCH_3$ | $CH_2OH$ | H | $CH_2OH$ | $OCH_3$ | H | 1 |
| 2-376 | $CH_2OCH_3$ | $CH_2OH$ | H | $CH_2OH$ | $OCH_2CH_3$ | H | 1 |
| 2-377 | $CH_2OCH_3$ | $CH_2OH$ | H | $CH_2OH$ | Br | H | 1 |
| 2-378 | $CH_2OCH_3$ | $CH_2OH$ | H | $CH_2OH$ | Cl | H | 1 |
| 2-379 | $CH_2OCH_3$ | $CH_2OH$ | H | $CH_2OH$ | I | H | 1 |
| 2-380 | $CH_2OCH_3$ | $CH_2OH$ | H | $CH_2OH$ | OH | $CH_3$ | 1 |
| 2-381 | $CH_2OCH_3$ | $CH_2OH$ | H | $CH_2OH$ | OH | $CH_2CH_3$ | 1 |
| 2-382 | $CH_2OCH_3$ | $CH_2OH$ | H | $CH_2OH$ | OH | $CH_2F$ | 1 |
| 2-383 | $CH_2OCH_3$ | $CH_2OH$ | H | $CH_2OH$ | OH | $OCH_3$ | 1 |
| 2-384 | $CH_2OCH_3$ | $CH_2OH$ | H | $CH_2OH$ | OH | $OCH_2CH_3$ | 1 |

TABLE 2-continued

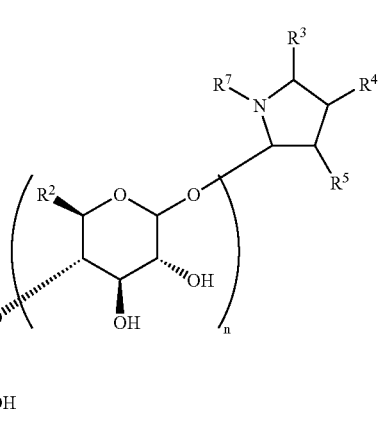

(Ia')

| No. | $R^1$ | $R^2$ | $R^7$ | $R^3$ | $R^4$ | $R^5$ | n |
|---|---|---|---|---|---|---|---|
| 2-385 | $CH_2OCH_3$ | $CH_2OH$ | H | $CH_2OH$ | OH | F | 1 |
| 2-386 | $CH_2OCH_3$ | $CH_2OH$ | $CH_3$ | $CH_2OH$ | OH | H | 1 |
| 2-387 | $CH_2OCH_3$ | $CH_3$ | $CH_3$ | $CH_2OH$ | OH | H | 1 |
| 2-388 | $CH_2OCH_3$ | $CH_2F$ | $CH_3$ | $CH_2OH$ | OH | H | 1 |
| 2-389 | $CH_2OCH_3$ | $CH_2OCH_3$ | $CH_3$ | $CH_2OH$ | OH | H | 1 |
| 2-390 | $CH_2OCH_3$ | $CH_2OH$ | H | $CH_2F$ | F | H | 1 |
| 2-391 | $CH_2OCH_3$ | $CH_3$ | H | $CH_2F$ | F | H | 1 |
| 2-392 | $CH_2OCH_3$ | $CH_2F$ | H | $CH_2F$ | F | H | 1 |
| 2-393 | $CH_2OCH_3$ | $CH_2OCH_3$ | H | $CH_2F$ | F | H | 1 |
| 2-394 | $CH_2OCH_3$ | $CH_2OH$ | $CH_3$ | $CH_2OH$ | OH | OH | 1 |
| 2-395 | $CH_2OCH_3$ | $CH_3$ | $CH_3$ | $CH_2OH$ | OH | OH | 1 |
| 2-396 | $CH_2OCH_3$ | $CH_2F$ | $CH_3$ | $CH_2OH$ | OH | OH | 1 |
| 2-397 | $CH_2OCH_3$ | $CH_2OCH_3$ | $CH_3$ | $CH_2OH$ | OH | OH | 1 |
| 2-398 | $CH_2OCH_3$ | $CH_2OH$ | H | $CH_2F$ | OH | OH | 1 |
| 2-399 | $CH_2OCH_3$ | $CH_3$ | H | $CH_2F$ | OH | OH | 1 |
| 2-400 | $CH_2OCH_3$ | $CH_2F$ | H | $CH_2F$ | OH | OH | 1 |
| 2-401 | $CH_2OCH_3$ | $CH_2OCH_3$ | H | $CH_2F$ | OH | OH | 1 |
| 2-402 | $CH_2OCH_3$ | $CH_2OH$ | H | $CH_2OH$ | F | OH | 1 |
| 2-403 | $CH_2OCH_3$ | $CH_3$ | H | $CH_2OH$ | F | OH | 1 |
| 2-404 | $CH_2OCH_3$ | $CH_2F$ | H | $CH_2OH$ | F | OH | 1 |
| 2-405 | $CH_2OCH_3$ | $CH_2OCH_3$ | H | $CH_2OH$ | F | OH | 1 |
| 2-406 | $CH_2OCH_3$ | $CH_2OH$ | H | $CH_2F$ | F | OH | 1 |
| 2-407 | $CH_2OCH_3$ | $CH_3$ | H | $CH_2F$ | F | OH | 1 |
| 2-408 | $CH_2OCH_3$ | $CH_2F$ | H | $CH_2F$ | F | OH | 1 |
| 2-409 | $CH_2OCH_3$ | $CH_2OCH_3$ | H | $CH_2F$ | F | OH | 1 |
| 2-410 | $CH_2OCH_2CH_3$ | $CH_2OH$ | H | $CH_2OH$ | OH | H | 1 |
| 2-411 | $CH_2OCH_2CH_3$ | $CH_3$ | H | $CH_2OH$ | OH | H | 1 |
| 2-412 | $CH_2OCH_2CH_3$ | $CH_2F$ | H | $CH_2OH$ | OH | H | 1 |
| 2-413 | $CH_2OCH_2CH_3$ | $CH_2OCH_3$ | H | $CH_2OH$ | OH | H | 1 |
| 2-414 | $CH_2OCH_2CH_3$ | $CH_2OH$ | $CH_3$ | $CH_2OH$ | OH | H | 1 |
| 2-415 | $CH_2OCH_2CH_3$ | $CH_3$ | $CH_3$ | $CH_2OH$ | OH | H | 1 |
| 2-416 | $CH_2OCH_2CH_3$ | $CH_2F$ | $CH_3$ | $CH_2OH$ | OH | H | 1 |
| 2-417 | $CH_2OCH_2CH_3$ | $CH_2OCH_3$ | $CH_3$ | $CH_2OH$ | OH | H | 1 |
| 2-418 | $CH_2OCH_2CH_3$ | $CH_2OH$ | H | $CH_2F$ | OH | H | 1 |
| 2-419 | $CH_2OCH_2CH_3$ | $CH_3$ | H | $CH_2F$ | OH | H | 1 |
| 2-420 | $CH_2OCH_2CH_3$ | $CH_2F$ | H | $CH_2F$ | OH | H | 1 |
| 2-421 | $CH_2OCH_2CH_3$ | $CH_2OCH_3$ | H | $CH_2F$ | OH | H | 1 |
| 2-422 | $CH_2OCH_2CH_3$ | $CH_2OH$ | H | $CH_2OH$ | F | H | 1 |
| 2-423 | $CH_2OCH_2CH_3$ | $CH_3$ | H | $CH_2OH$ | F | H | 1 |
| 2-424 | $CH_2OCH_2CH_3$ | $CH_2F$ | H | $CH_2OH$ | F | H | 1 |
| 2-425 | $CH_2OCH_2CH_3$ | $CH_2OCH_3$ | H | $CH_2OH$ | F | H | 1 |
| 2-426 | $CH_2OCH_2CH_3$ | $CH_2OH$ | H | $CH_2F$ | F | H | 1 |
| 2-427 | $CH_2OCH_2CH_3$ | $CH_3$ | H | $CH_2F$ | F | H | 1 |
| 2-428 | $CH_2OCH_2CH_3$ | $CH_2F$ | H | $CH_2F$ | F | H | 1 |
| 2-429 | $CH_2OCH_2CH_3$ | $CH_2OCH_3$ | H | $CH_2F$ | F | H | 1 |
| 2-430 | $CH_2OCH_2CH_3$ | $CH_2OH$ | H | $CH_2OH$ | OH | OH | 1 |
| 2-431 | $CH_2OCH_2CH_3$ | $CH_3$ | H | $CH_2OH$ | OH | OH | 1 |
| 2-432 | $CH_2OCH_2CH_3$ | $CH_2F$ | H | $CH_2OH$ | OH | OH | 1 |
| 2-433 | $CH_2OCH_2CH_3$ | $CH_2OCH_3$ | H | $CH_2OH$ | OH | OH | 1 |
| 2-434 | $CH_2OCH_2CH_3$ | $CH_2OH$ | $CH_3$ | $CH_2OH$ | OH | OH | 1 |
| 2-435 | $CH_2OCH_2CH_3$ | $CH_3$ | $CH_3$ | $CH_2OH$ | OH | OH | 1 |
| 2-436 | $CH_2OCH_2CH_3$ | $CH_2F$ | $CH_3$ | $CH_2OH$ | OH | OH | 1 |
| 2-437 | $CH_2OCH_2CH_3$ | $CH_2OCH_3$ | $CH_3$ | $CH_2OH$ | OH | OH | 1 |
| 2-438 | $CH_2OCH_2CH_3$ | $CH_2OH$ | H | $CH_2F$ | OH | OH | 1 |

TABLE 2-continued

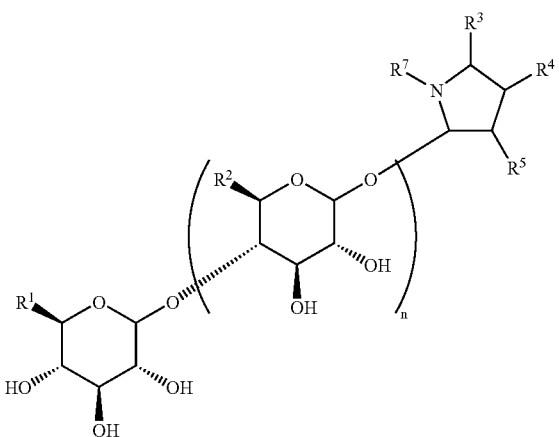

(Ia')

| No. | $R^1$ | $R^2$ | $R^7$ | $R^3$ | $R^4$ | $R^5$ | n |
|---|---|---|---|---|---|---|---|
| 2-439 | $CH_2OCH_2CH_3$ | $CH_3$ | H | $CH_2F$ | OH | OH | 1 |
| 2-440 | $CH_2OCH_2CH_3$ | $CH_2F$ | H | $CH_2F$ | OH | OH | 1 |
| 2-441 | $CH_2OCH_2CH_3$ | $CH_2OCH_3$ | H | $CH_2F$ | OH | OH | 1 |
| 2-442 | $CH_2OCH_2CH_3$ | $CH_2OH$ | H | $CH_2OH$ | F | OH | 1 |
| 2-443 | $CH_2OCH_2CH_3$ | $CH_3$ | H | $CH_2OH$ | F | OH | 1 |
| 2-444 | $CH_2OCH_2CH_3$ | $CH_2F$ | H | $CH_2OH$ | F | OH | 1 |
| 2-445 | $CH_2OCH_2CH_3$ | $CH_2OCH_3$ | H | $CH_2OH$ | F | OH | 1 |
| 2-446 | $CH_2OCH_2CH_3$ | $CH_2OH$ | H | $CH_2F$ | F | OH | 1 |
| 2-447 | $CH_2OCH_2CH_3$ | $CH_3$ | H | $CH_2F$ | F | OH | 1 |
| 2-448 | $CH_2OCH_2CH_3$ | $CH_2F$ | H | $CH_2F$ | F | OH | 1 |
| 2-449 | $CH_2OCH_2CH_3$ | $CH_2OCH_3$ | H | $CH_2F$ | F | OH | 1 |
| 2-450 | $CH_2O^nPr$ | $CH_2OH$ | H | $CH_2OH$ | OH | H | 1 |
| 2-451 | $CH_2O^iPr$ | $CH_2OH$ | H | $CH_2OH$ | OH | H | 1 |
| 2-452 | $CH_2O^nBu$ | $CH_2OH$ | H | $CH_2OH$ | OH | H | 1 |
| 2-453 | $CH_2O^iBu$ | $CH_2OH$ | H | $CH_2OH$ | OH | H | 1 |
| 2-454 | $CH_2O^tBu$ | $CH_2OH$ | H | $CH_2OH$ | OH | H | 1 |
| 2-455 | $CH_2O^nPn$ | $CH_2OH$ | H | $CH_2OH$ | OH | H | 1 |
| 2-456 | $CH_2O^nHex$ | $CH_2OH$ | H | $CH_2OH$ | OH | H | 1 |
| 2-457 | $CH_2Cl$ | $CH_2OH$ | H | $CH_2OH$ | OH | H | 1 |
| 2-458 | $CH_2Cl$ | $CH_3$ | H | $CH_2OH$ | OH | H | 1 |
| 2-459 | $CH_2Cl$ | $CH_2F$ | H | $CH_2OH$ | OH | H | 1 |
| 2-460 | $CH_2Cl$ | $CH_2OCH_3$ | H | $CH_2OH$ | OH | H | 1 |
| 2-461 | $CH_2Cl$ | $CH_2OH$ | $CH_3$ | $CH_2OH$ | OH | H | 1 |
| 2-462 | $CH_2Cl$ | $CH_3$ | $CH_3$ | $CH_2OH$ | OH | H | 1 |
| 2-463 | $CH_2Cl$ | $CH_2F$ | $CH_3$ | $CH_2OH$ | OH | H | 1 |
| 2-464 | $CH_2Cl$ | $CH_2OCH_3$ | $CH_3$ | $CH_2OH$ | OH | H | 1 |
| 2-465 | $CH_2Cl$ | $CH_2OH$ | H | $CH_2F$ | OH | H | 1 |
| 2-466 | $CH_2Cl$ | $CH_3$ | H | $CH_2F$ | OH | H | 1 |
| 2-467 | $CH_2Cl$ | $CH_2F$ | H | $CH_2F$ | OH | H | 1 |
| 2-468 | $CH_2Cl$ | $CH_2OCH_3$ | H | $CH_2F$ | OH | H | 1 |
| 2-469 | $CH_2Cl$ | $CH_2OH$ | H | $CH_2OH$ | F | H | 1 |
| 2-470 | $CH_2Cl$ | $CH_3$ | H | $CH_2OH$ | F | H | 1 |
| 2-471 | $CH_2Cl$ | $CH_2F$ | H | $CH_2OH$ | F | H | 1 |
| 2-472 | $CH_2Cl$ | $CH_2OCH_3$ | H | $CH_2OH$ | F | H | 1 |
| 2-473 | $CH_2Cl$ | $CH_2OH$ | H | $CH_2F$ | F | H | 1 |
| 2-474 | $CH_2Cl$ | $CH_3$ | H | $CH_2F$ | F | H | 1 |
| 2-475 | $CH_2Cl$ | $CH_2F$ | H | $CH_2F$ | F | H | 1 |
| 2-476 | $CH_2Cl$ | $CH_2OCH_3$ | H | $CH_2F$ | F | H | 1 |
| 2-477 | $CH_2Cl$ | $CH_2OH$ | H | $CH_2OH$ | OH | OH | 1 |
| 2-478 | $CH_2Cl$ | $CH_3$ | H | $CH_2OH$ | OH | OH | 1 |
| 2-479 | $CH_2Cl$ | $CH_2F$ | H | $CH_2OH$ | OH | OH | 1 |
| 2-480 | $CH_2Cl$ | $CH_2OCH_3$ | H | $CH_2OH$ | OH | OH | 1 |
| 2-481 | $CH_2Cl$ | $CH_2OH$ | H | $CH_2F$ | OH | OH | 1 |
| 2-482 | $CH_2Cl$ | $CH_3$ | H | $CH_2F$ | OH | OH | 1 |
| 2-483 | $CH_2Cl$ | $CH_2F$ | H | $CH_2F$ | OH | OH | 1 |
| 2-484 | $CH_2Cl$ | $CH_2OCH_3$ | H | $CH_2F$ | OH | OH | 1 |
| 2-485 | $CH_2Cl$ | $CH_2OH$ | H | $CH_2OH$ | F | OH | 1 |
| 2-486 | $CH_2Cl$ | $CH_3$ | H | $CH_2OH$ | F | OH | 1 |
| 2-487 | $CH_2Cl$ | $CH_2F$ | H | $CH_2OH$ | F | OH | 1 |
| 2-488 | $CH_2Cl$ | $CH_2OCH_3$ | H | $CH_2OH$ | F | OH | 1 |
| 2-489 | $CH_2Cl$ | $CH_2OH$ | H | $CH_2F$ | F | OH | 1 |
| 2-490 | $CH_2Cl$ | $CH_3$ | H | $CH_2F$ | F | OH | 1 |
| 2-491 | $CH_2Cl$ | $CH_2F$ | H | $CH_2F$ | F | OH | 1 |
| 2-492 | $CH_2Cl$ | $CH_2OCH_3$ | H | $CH_2F$ | F | OH | 1 |

TABLE 2-continued

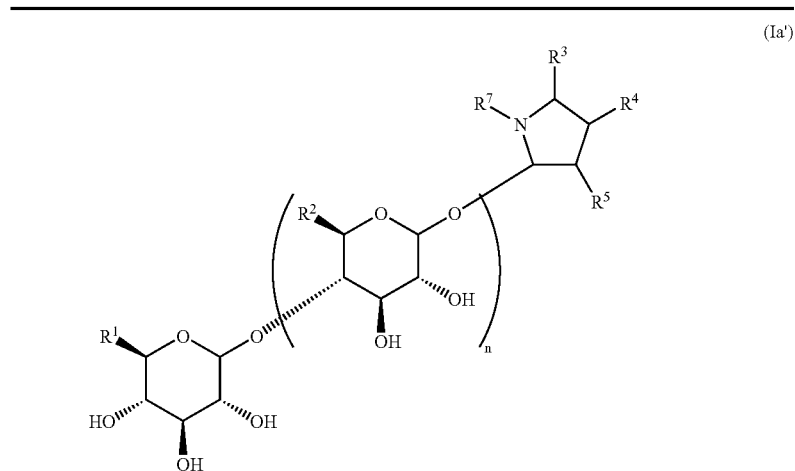

(Ia')

| No. | R¹ | R² | R⁷ | R³ | R⁴ | R⁵ | n |
|---|---|---|---|---|---|---|---|
| 2-493 | CH₂Cl | CH₂OH | CH₃ | CH₂OH | OH | OH | 1 |
| 2-494 | CH₂Cl | CH₃ | CH₃ | CH₂OH | OH | OH | 1 |
| 2-495 | CH₂Cl | CH₂F | CH₃ | CH₂OH | OH | OH | 1 |
| 2-496 | CH₂Cl | CH₂OCH₃ | CH₃ | CH₂OH | OH | OH | 1 |
| 2-497 | CH₂Br | CH₂OH | H | CH₂OH | OH | H | 1 |
| 2-498 | CH₂Br | CH₃ | H | CH₂OH | OH | H | 1 |
| 2-499 | CH₂Br | CH₂F | H | CH₂OH | OH | H | 1 |
| 2-500 | CH₂Br | CH₂OCH₃ | H | CH₂OH | OH | H | 1 |
| 2-501 | CH₂Br | CH₂OH | CH₃ | CH₂OH | OH | H | 1 |
| 2-502 | CH₂Br | CH₃ | CH₃ | CH₂OH | OH | H | 1 |
| 2-503 | CH₂Br | CH₂F | CH₃ | CH₂OH | OH | H | 1 |
| 2-504 | CH₂Br | CH₂OCH₃ | CH₃ | CH₂OH | OH | H | 1 |
| 2-505 | CH₂Br | CH₂OH | H | CH₂F | OH | H | 1 |
| 2-506 | CH₂Br | CH₃ | H | CH₂F | OH | H | 1 |
| 2-507 | CH₂Br | CH₂F | H | CH₂F | OH | H | 1 |
| 2-508 | CH₂Br | CH₂OCH₃ | H | CH₂F | OH | H | 1 |
| 2-509 | CH₂Br | CH₂OH | H | CH₂OH | F | H | 1 |
| 2-510 | CH₂Br | CH₃ | H | CH₂OH | F | H | 1 |
| 2-511 | CH₂Br | CH₂F | H | CH₂OH | F | H | 1 |
| 2-512 | CH₂Br | CH₂OCH₃ | H | CH₂OH | F | H | 1 |
| 2-513 | CH₂Br | CH₂OH | H | CH₂F | F | H | 1 |
| 2-514 | CH₂Br | CH₃ | H | CH₂F | F | H | 1 |
| 2-515 | CH₂Br | CH₂F | H | CH₂F | F | H | 1 |
| 2-516 | CH₂Br | CH₂OCH₃ | H | CH₂F | F | H | 1 |
| 2-517 | CH₂Br | CH₂OH | H | CH₂OH | OH | OH | 1 |
| 2-518 | CH₂Br | CH₃ | H | CH₂OH | OH | OH | 1 |
| 2-519 | CH₂Br | CH₂F | H | CH₂OH | OH | OH | 1 |
| 2-520 | CH₂Br | CH₂OH | CH₃ | CH₂OH | OH | OH | 1 |
| 2-521 | CH₂Br | CH₃ | CH₃ | CH₂OH | OH | OH | 1 |
| 2-522 | CH₂Br | CH₂F | CH₃ | CH₂OH | OH | OH | 1 |
| 2-523 | CH₂Br | CH₂OCH₃ | CH₃ | CH₂OH | OH | OH | 1 |
| 2-524 | CH₂Br | CH₂OH | H | CH₂F | OH | OH | 1 |
| 2-525 | CH₂Br | CH₃ | H | CH₂F | OH | OH | 1 |
| 2-526 | CH₂Br | CH₂F | H | CH₂F | OH | OH | 1 |
| 2-527 | CH₂Br | CH₂OCH₃ | H | CH₂F | OH | OH | 1 |
| 2-528 | CH₂Br | CH₂OH | H | CH₂OH | F | OH | 1 |
| 2-529 | CH₂Br | CH₃ | H | CH₂OH | F | OH | 1 |
| 2-530 | CH₂Br | CH₂F | H | CH₂OH | F | OH | 1 |
| 2-531 | CH₂Br | CH₂OCH₃ | H | CH₂OH | F | OH | 1 |
| 2-532 | CH₂Br | CH₂OH | H | CH₂F | F | OH | 1 |
| 2-533 | CH₂Br | CH₃ | H | CH₂F | F | OH | 1 |
| 2-534 | CH₂Br | CH₂F | H | CH₂F | F | OH | 1 |
| 2-535 | CH₂Br | CH₂OCH₃ | H | CH₂F | F | OH | 1 |
| 2-536 | CH₂Br | CH₂OCH₃ | H | CH₂OH | OH | OH | 1 |
| 2-537 | CH₂I | CH₂OH | H | CH₂OH | OH | H | 1 |
| 2-538 | CH₃ | CH₂OH | H | CH₂OH | OH | H | 2 |
| 2-539 | CH₃ | CH₃ | H | CH₂OH | OH | H | 2 |
| 2-540 | CH₃ | CH₂F | H | CH₂OH | OH | H | 2 |
| 2-541 | CH₃ | CH₂OH | H | CH₂OH | F | H | 2 |
| 2-542 | CH₃ | CH₃ | H | CH₂OH | F | H | 2 |
| 2-543 | CH₃ | CH₂F | H | CH₂OH | F | H | 2 |
| 2-544 | CH₃ | CH₂OH | H | CH₂F | OH | H | 2 |
| 2-545 | CH₃ | CH₃ | H | CH₂F | OH | H | 2 |
| 2-546 | CH₃ | CH₂F | H | CH₂F | OH | H | 2 |

TABLE 2-continued

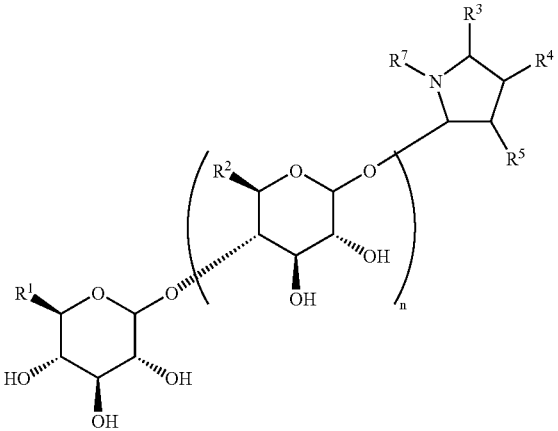

(Ia')

| No. | R¹ | R² | R⁷ | R³ | R⁴ | R⁵ | n |
|---|---|---|---|---|---|---|---|
| 2-547 | CH₂OH | CH₂OH | H | CH₂OH | OH | H | 2 |
| 2-548 | CH₂OH | CH₃ | H | CH₂OH | OH | H | 2 |
| 2-549 | CH₂OH | CH₂F | H | CH₂OH | OH | H | 2 |
| 2-550 | CH₂F | CH₂OH | H | CH₂OH | OH | H | 2 |
| 2-551 | CH₂F | CH₃ | H | CH₂OH | OH | H | 2 |
| 2-552 | CH₂F | CH₂F | H | CH₂OH | OH | H | 2 |
| 2-553 | CH₂OCH₃ | CH₂OH | H | CH₂OH | OH | H | 2 |
| 2-554 | CH₂OCH₃ | CH₃ | H | CH₂OH | OH | H | 2 |
| 2-555 | CH₂OCH₃ | CH₂F | H | CH₂OH | OH | H | 2 |

TABLE 3

(Ib')

| No. | R¹ | R² | R³ | R⁴ | n |
|---|---|---|---|---|---|
| 3-1 | CH₃ | CH₂OH | CH₂OH | OH | 1 |
| 3-2 | CH₃ | CH₃ | CH₂OH | OH | 1 |
| 3-3 | CH₃ | CH₂F | CH₂OH | OH | 1 |
| 3-4 | CH₃ | CH₂OCH₃ | CH₂OH | OH | 1 |
| 3-5 | CH₃ | CH₂OH | CH₂F | OH | 1 |
| 3-6 | CH₃ | CH₃ | CH₂F | OH | 1 |
| 3-7 | CH₃ | CH₂F | CH₂F | OH | 1 |
| 3-8 | CH₃ | CH₂OCH₃ | CH₂F | OH | 1 |
| 3-9 | CH₃ | CH₂OH | CH₂OH | CH₂OH | 1 |
| 3-10 | CH₃ | CH₃ | CH₂OH | CH₂OH | 1 |
| 3-11 | CH₃ | CH₂OH | CH₂OH | F | 1 |
| 3-12 | CH₃ | CH₃ | CH₂OH | F | 1 |

TABLE 3-continued (Ib')

| No. | R¹ | R² | R³ | R⁴ | n |
|---|---|---|---|---|---|
| 3-13 | CH₃ | CH₂F | CH₂OH | F | 1 |
| 3-14 | CH₃ | CH₂OCH₃ | CH₂OH | F | 1 |
| 3-15 | CH₃ | CH₂OH | CH₂F | F | 1 |
| 3-16 | CH₃ | CH₃ | CH₂F | F | 1 |
| 3-17 | CH₃ | CH₂F | CH₂F | F | 1 |
| 3-18 | CH₃ | CH₂OCH₃ | CH₂F | F | 1 |
| 3-19 | CH₃ | CH₂OH | CH₂OH | Cl | 1 |
| 3-20 | CH₃ | CH₃ | CH₂OH | Cl | 1 |
| 3-21 | CH₃ | CH₂OH | CH₂OH | Br | 1 |
| 3-22 | CH₃ | CH₃ | CH₂OH | Br | 1 |
| 3-23 | CH₃ | CH₂OH | CH₂OH | I | 1 |
| 3-24 | CH₃ | CH₃ | CH₂OH | I | 1 |

TABLE 3-continued

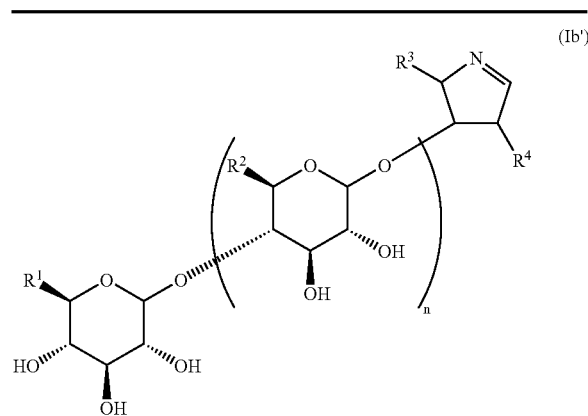

(Ib')

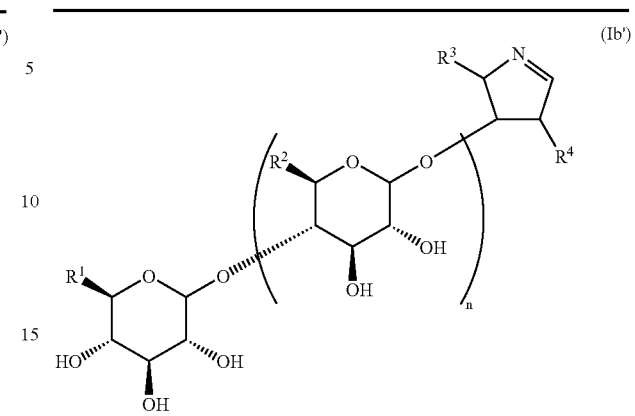

(Ib')

| No. | R$^1$ | R$^2$ | R$^3$ | R$^4$ | n |
|---|---|---|---|---|---|
| 3-25 | CH$_2$CH$_3$ | CH$_2$OH | CH$_2$OH | OH | 1 |
| 3-26 | $^n$Pr | CH$_2$OH | CH$_2$OH | OH | 1 |
| 3-27 | $^i$Pr | CH$_2$OH | CH$_2$OH | OH | 1 |
| 3-28 | $^n$Bu | CH$_2$OH | CH$_2$OH | OH | 1 |
| 3-29 | $^i$Bu | CH$_2$OH | CH$_2$OH | OH | 1 |
| 3-30 | $^t$Bu | CH$_2$OH | CH$_2$OH | OH | 1 |
| 3-31 | $^n$Pn | CH$_2$OH | CH$_2$OH | OH | 1 |
| 3-32 | $^n$Hex | CH$_2$OH | CH$_2$OH | OH | 1 |
| 3-33 | CH$_2$OH | CH$_2$OH | CH$_2$OH | OH | 1 |
| 3-34 | CH$_2$OH | CH$_3$ | CH$_2$OH | OH | 1 |
| 3-35 | CH$_2$OH | CH$_2$F | CH$_2$OH | OH | 1 |
| 3-36 | CH$_2$OH | CH$_2$OCH$_3$ | CH$_2$OH | OH | 1 |
| 3-37 | CH$_2$OH | CH$_2$OH | CH$_2$F | OH | 1 |
| 3-38 | CH$_2$OH | CH$_3$ | CH$_2$F | OH | 1 |
| 3-39 | CH$_2$OH | CH$_2$F | CH$_2$F | OH | 1 |
| 3-40 | CH$_2$OH | CH$_2$OCH$_3$ | CH$_2$F | OH | 1 |
| 3-41 | CH$_2$OH | CH$_2$OH | CH$_2$OH | F | 1 |
| 3-42 | CH$_2$OH | CH$_3$ | CH$_2$OH | F | 1 |
| 3-43 | CH$_2$OH | CH$_2$F | CH$_2$OH | F | 1 |
| 3-44 | CH$_2$OH | CH$_2$OCH$_3$ | CH$_2$OH | F | 1 |
| 3-45 | CH$_2$OH | CH$_2$OH | CH$_2$F | F | 1 |
| 3-46 | CH$_2$OH | CH$_3$ | CH$_2$F | F | 1 |
| 3-47 | CH$_2$OH | CH$_2$F | CH$_2$F | F | 1 |
| 3-48 | CH$_2$OH | CH$_2$OCH$_3$ | CH$_2$F | F | 1 |
| 3-49 | CH$_2$OCH$_3$ | CH$_2$OH | CH$_2$OH | OH | 1 |
| 3-50 | CH$_2$OCH$_3$ | CH$_3$ | CH$_2$OH | OH | 1 |
| 3-51 | CH$_2$OCH$_3$ | CH$_2$F | CH$_2$OH | OH | 1 |
| 3-52 | CH$_2$OCH$_3$ | CH$_2$OCH$_3$ | CH$_2$OH | OH | 1 |
| 3-53 | CH$_2$OCH$_3$ | CH$_2$OH | CH$_2$F | OH | 1 |
| 3-54 | CH$_2$OCH$_3$ | CH$_3$ | CH$_2$F | OH | 1 |
| 3-55 | CH$_2$OCH$_3$ | CH$_2$F | CH$_2$F | OH | 1 |
| 3-56 | CH$_2$OCH$_3$ | CH$_2$OCH$_3$ | CH$_2$F | OH | 1 |
| 3-57 | CH$_2$OCH$_3$ | CH$_2$OH | CH$_2$OH | F | 1 |
| 3-58 | CH$_2$OCH$_3$ | CH$_3$ | CH$_2$OH | F | 1 |
| 3-59 | CH$_2$OCH$_3$ | CH$_2$F | CH$_2$OH | F | 1 |
| 3-60 | CH$_2$OCH$_3$ | CH$_2$OCH$_3$ | CH$_2$OH | F | 1 |
| 3-61 | CH$_2$OCH$_3$ | CH$_2$OH | CH$_2$F | F | 1 |
| 3-62 | CH$_2$OCH$_3$ | CH$_3$ | CH$_2$F | F | 1 |
| 3-63 | CH$_2$OCH$_3$ | CH$_2$F | CH$_2$F | F | 1 |
| 3-64 | CH$_2$OCH$_3$ | CH$_2$OCH$_3$ | CH$_2$F | F | 1 |
| 3-65 | CH$_2$OCH$_2$CH$_3$ | CH$_2$OH | CH$_2$OH | OH | 1 |
| 3-66 | CH$_2$OCH$_2$CH$_3$ | CH$_3$ | CH$_2$OH | OH | 1 |
| 3-67 | CH$_2$OCH$_2$CH$_3$ | CH$_2$F | CH$_2$OH | OH | 1 |
| 3-68 | CH$_2$OCH$_2$CH$_3$ | CH$_2$OCH$_3$ | CH$_2$OH | OH | 1 |
| 3-69 | CH$_2$OCH$_2$CH$_3$ | CH$_2$OH | CH$_2$F | OH | 1 |
| 3-70 | CH$_2$OCH$_2$CH$_3$ | CH$_3$ | CH$_2$F | OH | 1 |
| 3-71 | CH$_2$OCH$_2$CH$_3$ | CH$_2$F | CH$_2$F | OH | 1 |
| 3-72 | CH$_2$OCH$_2$CH$_3$ | CH$_2$OCH$_3$ | CH$_2$F | OH | 1 |
| 3-73 | CH$_2$OCH$_2$CH$_3$ | CH$_2$OH | CH$_2$OH | F | 1 |
| 3-74 | CH$_2$OCH$_2$CH$_3$ | CH$_3$ | CH$_2$OH | F | 1 |
| 3-75 | CH$_2$OCH$_2$CH$_3$ | CH$_2$F | CH$_2$OH | F | 1 |
| 3-76 | CH$_2$OCH$_2$CH$_3$ | CH$_2$OCH$_3$ | CH$_2$OH | F | 1 |
| 3-77 | CH$_2$OCH$_2$CH$_3$ | CH$_2$OH | CH$_2$F | F | 1 |
| 3-78 | CH$_2$OCH$_2$CH$_3$ | CH$_3$ | CH$_2$F | F | 1 |
| 3-79 | CH$_2$OCH$_2$CH$_3$ | CH$_2$F | CH$_2$F | F | 1 |
| 3-80 | CH$_2$OCH$_2$CH$_3$ | CH$_2$OCH$_3$ | CH$_2$F | F | 1 |
| 3-81 | CH$_2$OCH$_2$CH$_3$ | CH$_2$OH | CH$_2$F | F | 1 |
| 3-82 | CH$_2$OCH$_2$CH$_3$ | CH$_3$ | CH$_2$F | F | 1 |
| 3-83 | CH$_2$OCH$_2$CH$_3$ | CH$_2$F | CH$_2$F | F | 1 |
| 3-84 | CH$_2$OCH$_2$CH$_3$ | CH$_2$OCH$_3$ | CH$_2$F | F | 1 |
| 3-85 | CH$_2$O$^n$Pr | CH$_2$OH | CH$_2$OH | OH | 1 |
| 3-86 | CH$_2$O$^i$Pr | CH$_2$OH | CH$_2$OH | OH | 1 |
| 3-87 | CH$_2$O$^n$Bu | CH$_2$OH | CH$_2$OH | OH | 1 |
| 3-88 | CH$_2$O$^i$Bu | CH$_2$OH | CH$_2$OH | OH | 1 |
| 3-89 | CH$_2$O$^t$Bu | CH$_2$OH | CH$_2$OH | OH | 1 |
| 3-90 | CH$_2$O$^n$Pn | CH$_2$OH | CH$_2$OH | OH | 1 |
| 3-91 | CH$_2$O$^n$Hex | CH$_2$OH | CH$_2$OH | OH | 1 |
| 3-92 | CH$_2$F | CH$_2$OH | CH$_2$OH | OH | 1 |
| 3-93 | CH$_2$F | CH$_3$ | CH$_2$OH | OH | 1 |
| 3-94 | CH$_2$F | CH$_2$F | CH$_2$OH | OH | 1 |
| 3-95 | CH$_2$F | CH$_2$OCH$_3$ | CH$_2$OH | OH | 1 |
| 3-96 | CH$_2$F | CH$_2$OH | CH$_2$F | OH | 1 |
| 3-97 | CH$_2$F | CH$_3$ | CH$_2$F | OH | 1 |
| 3-98 | CH$_2$F | CH$_2$F | CH$_2$F | OH | 1 |
| 3-99 | CH$_2$F | CH$_2$OCH$_3$ | CH$_2$F | OH | 1 |
| 3-100 | CH$_2$F | CH$_2$OH | CH$_2$OH | F | 1 |
| 3-101 | CH$_2$F | CH$_3$ | CH$_2$OH | F | 1 |
| 3-102 | CH$_2$F | CH$_2$F | CH$_2$OH | F | 1 |
| 3-103 | CH$_2$F | CH$_2$OCH$_3$ | CH$_2$OH | F | 1 |
| 3-104 | CH$_2$F | CH$_2$OH | CH$_2$F | F | 1 |
| 3-105 | CH$_2$F | CH$_3$ | CH$_2$F | F | 1 |
| 3-106 | CH$_2$F | CH$_2$F | CH$_2$F | F | 1 |
| 3-107 | CH$_2$F | CH$_2$OCH$_3$ | CH$_2$F | F | 1 |
| 3-108 | CH$_2$Cl | CH$_2$OH | CH$_2$OH | OH | 1 |
| 3-109 | CH$_2$Cl | CH$_3$ | CH$_2$OH | OH | 1 |
| 3-110 | CH$_2$Cl | CH$_2$F | CH$_2$OH | OH | 1 |
| 3-111 | CH$_2$Cl | CH$_2$OCH$_3$ | CH$_2$OH | OH | 1 |
| 3-112 | CH$_2$Cl | CH$_2$OH | CH$_2$F | OH | 1 |
| 3-113 | CH$_2$Cl | CH$_3$ | CH$_2$F | OH | 1 |
| 3-114 | CH$_2$Cl | CH$_2$F | CH$_2$F | OH | 1 |
| 3-115 | CH$_2$Cl | CH$_2$OCH$_3$ | CH$_2$F | OH | 1 |
| 3-116 | CH$_2$Cl | CH$_2$OH | CH$_2$OH | F | 1 |
| 3-117 | CH$_2$Cl | CH$_3$ | CH$_2$OH | F | 1 |
| 3-118 | CH$_2$Cl | CH$_2$F | CH$_2$OH | F | 1 |
| 3-119 | CH$_2$Cl | CH$_2$OCH$_3$ | CH$_2$OH | F | 1 |
| 3-120 | CH$_2$Cl | CH$_2$OH | CH$_2$F | F | 1 |
| 3-121 | CH$_2$Cl | CH$_3$ | CH$_2$F | F | 1 |
| 3-122 | CH$_2$Cl | CH$_2$F | CH$_2$F | F | 1 |
| 3-123 | CH$_2$Cl | CH$_2$OCH$_3$ | CH$_2$F | F | 1 |
| 3-124 | CH$_2$Br | CH$_2$OH | CH$_2$OH | OH | 1 |
| 3-125 | CH$_2$Br | CH$_3$ | CH$_2$OH | OH | 1 |
| 3-126 | CH$_2$Br | CH$_2$F | CH$_2$OH | OH | 1 |
| 3-127 | CH$_2$Br | CH$_2$OCH$_3$ | CH$_2$OH | OH | 1 |
| 3-128 | CH$_2$Br | CH$_2$OH | CH$_2$F | OH | 1 |
| 3-129 | CH$_2$Br | CH$_3$ | CH$_2$F | OH | 1 |
| 3-130 | CH$_2$Br | CH$_2$F | CH$_2$F | OH | 1 |
| 3-131 | CH$_2$Br | CH$_2$OCH$_3$ | CH$_2$F | OH | 1 |
| 3-132 | CH$_2$Br | CH$_2$OH | CH$_2$OH | F | 1 |
| 3-133 | CH$_2$Br | CH$_3$ | CH$_2$OH | F | 1 |

TABLE 3-continued

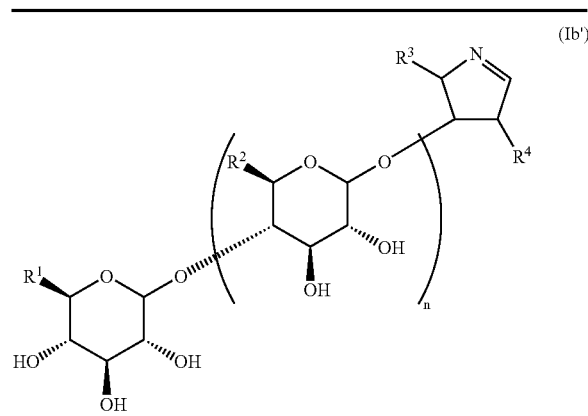

(Ib')

| No. | R¹ | R² | R³ | R⁴ | n |
|---|---|---|---|---|---|
| 3-134 | $CH_2Br$ | $CH_2F$ | $CH_2OH$ | F | 1 |
| 3-135 | $CH_2Br$ | $CH_2OCH_3$ | $CH_2OH$ | F | 1 |
| 3-136 | $CH_2Br$ | $CH_2OH$ | $CH_2F$ | F | 1 |
| 3-137 | $CH_2Br$ | $CH_3$ | $CH_2F$ | F | 1 |
| 3-138 | $CH_2Br$ | $CH_2F$ | $CH_2F$ | F | 1 |
| 3-139 | $CH_2Br$ | $CH_2OCH_3$ | $CH_2F$ | F | 1 |
| 3-140 | $CH_2I$ | $CH_2OH$ | $CH_2OH$ | OH | 1 |
| 3-141 | $CH_2I$ | $CH_3$ | $CH_2OH$ | OH | 1 |
| 3-142 | $CH_2I$ | $CH_2F$ | $CH_2OH$ | OH | 1 |
| 3-143 | $CH_3$ | $CH_2OH$ | $CH_2OH$ | OH | 2 |
| 3-144 | $CH_3$ | $CH_3$ | $CH_2OH$ | OH | 2 |
| 3-145 | $CH_3$ | $CH_2F$ | $CH_2OH$ | OH | 2 |
| 3-146 | $CH_3$ | $CH_2OCH_3$ | $CH_2OH$ | OH | 2 |
| 3-147 | $CH_2OH$ | $CH_2OH$ | $CH_2OH$ | OH | 2 |
| 3-148 | $CH_2OH$ | $CH_3$ | $CH_2OH$ | OH | 2 |
| 3-149 | $CH_2OH$ | $CH_2F$ | $CH_2OH$ | OH | 2 |
| 3-150 | $CH_2OH$ | $CH_2OCH_3$ | $CH_2OH$ | OH | 2 |

TABLE 4

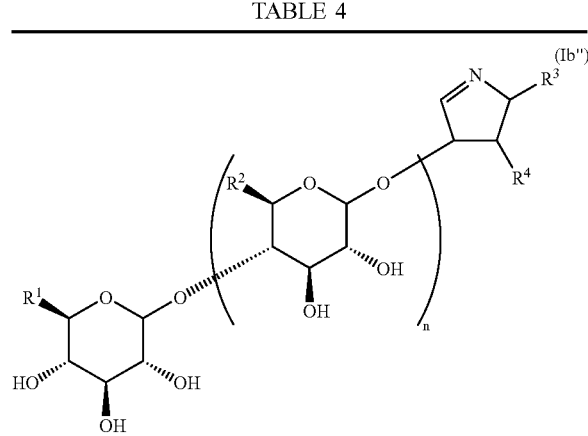

(Ib'')

| No. | R¹ | R² | R³ | R⁴ | n |
|---|---|---|---|---|---|
| 4-1 | $CH_3$ | $CH_2OH$ | $CH_2OH$ | OH | 1 |
| 4-2 | $CH_3$ | $CH_3$ | $CH_2OH$ | OH | 1 |
| 4-3 | $CH_3$ | $CH_2F$ | $CH_2OH$ | OH | 1 |
| 4-4 | $CH_3$ | $CH_2OCH_3$ | $CH_2OH$ | OH | 1 |
| 4-5 | $CH_3$ | $CH_2OH$ | $CH_2F$ | OH | 1 |
| 4-6 | $CH_3$ | $CH_3$ | $CH_2F$ | OH | 1 |
| 4-7 | $CH_3$ | $CH_2F$ | $CH_2F$ | OH | 1 |
| 4-8 | $CH_3$ | $CH_2OCH_3$ | $CH_2F$ | OH | 1 |
| 4-9 | $CH_3$ | $CH_2OH$ | $CH_2OH$ | $CH_2OH$ | 1 |
| 4-10 | $CH_3$ | $CH_3$ | $CH_2OH$ | $CH_2OH$ | 1 |
| 4-11 | $CH_3$ | $CH_2OH$ | $CH_2OH$ | F | 1 |
| 4-12 | $CH_3$ | $CH_3$ | $CH_2OH$ | F | 1 |
| 4-13 | $CH_3$ | $CH_2F$ | $CH_2OH$ | F | 1 |

TABLE 4-continued

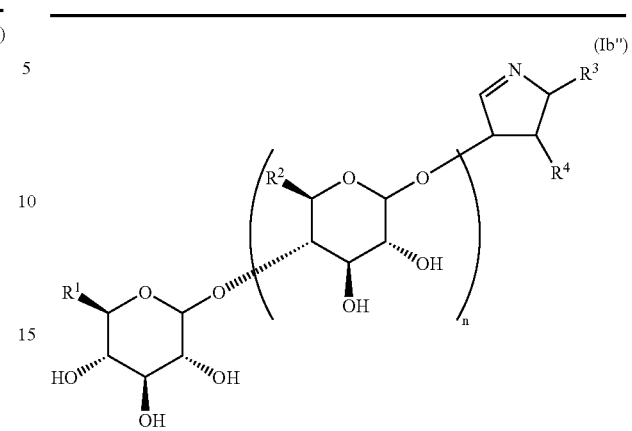

(Ib'')

| No. | R¹ | R² | R³ | R⁴ | n |
|---|---|---|---|---|---|
| 4-14 | $CH_3$ | $CH_2OCH_3$ | $CH_2OH$ | F | 1 |
| 4-15 | $CH_3$ | $CH_2OH$ | $CH_2F$ | F | 1 |
| 4-16 | $CH_3$ | $CH_3$ | $CH_2F$ | F | 1 |
| 4-17 | $CH_3$ | $CH_2F$ | $CH_2F$ | F | 1 |
| 4-18 | $CH_3$ | $CH_2OCH_3$ | $CH_2F$ | F | 1 |
| 4-19 | $CH_3$ | $CH_2OH$ | $CH_2OH$ | Cl | 1 |
| 4-20 | $CH_3$ | $CH_3$ | $CH_2OH$ | Cl | 1 |
| 4-21 | $CH_3$ | $CH_2OH$ | $CH_2OH$ | Br | 1 |
| 4-22 | $CH_3$ | $CH_3$ | $CH_2OH$ | Br | 1 |
| 4-23 | $CH_3$ | $CH_2OH$ | $CH_2OH$ | I | 1 |
| 4-24 | $CH_3$ | $CH_3$ | $CH_2OH$ | I | 1 |
| 4-25 | $CH_2CH_3$ | $CH_2OH$ | $CH_2OH$ | OH | 1 |
| 4-26 | ⁿPr | $CH_2OH$ | $CH_2OH$ | OH | 1 |
| 4-27 | ⁱPr | $CH_2OH$ | $CH_2OH$ | OH | 1 |
| 4-28 | ⁿBu | $CH_2OH$ | $CH_2OH$ | OH | 1 |
| 4-29 | ⁱBu | $CH_2OH$ | $CH_2OH$ | OH | 1 |
| 4-30 | ᵗBu | $CH_2OH$ | $CH_2OH$ | OH | 1 |
| 4-31 | ⁿPn | $CH_2OH$ | $CH_2OH$ | OH | 1 |
| 4-32 | ⁿHex | $CH_2OH$ | $CH_2OH$ | OH | 1 |
| 4-33 | $CH_2OH$ | $CH_2OH$ | $CH_2OH$ | OH | 1 |
| 4-34 | $CH_2OH$ | $CH_3$ | $CH_2OH$ | OH | 1 |
| 4-35 | $CH_2OH$ | $CH_2F$ | $CH_2OH$ | OH | 1 |
| 4-36 | $CH_2OH$ | $CH_2OCH_3$ | $CH_2OH$ | OH | 1 |
| 4-37 | $CH_2OH$ | $CH_2OH$ | $CH_2F$ | OH | 1 |
| 4-38 | $CH_2OH$ | $CH_3$ | $CH_2F$ | OH | 1 |
| 4-39 | $CH_2OH$ | $CH_2F$ | $CH_2F$ | OH | 1 |
| 4-40 | $CH_2OH$ | $CH_2OCH_3$ | $CH_2F$ | OH | 1 |
| 4-41 | $CH_2OH$ | $CH_2OH$ | $CH_2OH$ | F | 1 |
| 4-42 | $CH_2OH$ | $CH_3$ | $CH_2OH$ | F | 1 |
| 4-43 | $CH_2OH$ | $CH_2F$ | $CH_2OH$ | F | 1 |
| 4-44 | $CH_2OH$ | $CH_2OCH_3$ | $CH_2OH$ | F | 1 |
| 4-45 | $CH_2OH$ | $CH_2OH$ | $CH_2F$ | F | 1 |
| 4-46 | $CH_2OH$ | $CH_3$ | $CH_2F$ | F | 1 |
| 4-47 | $CH_2OH$ | $CH_2F$ | $CH_2F$ | F | 1 |
| 4-48 | $CH_2OH$ | $CH_2OCH_3$ | $CH_2F$ | F | 1 |
| 4-49 | $CH_2OCH_3$ | $CH_2OH$ | $CH_2OH$ | OH | 1 |
| 4-50 | $CH_2OCH_3$ | $CH_3$ | $CH_2OH$ | OH | 1 |
| 4-51 | $CH_2OCH_3$ | $CH_2F$ | $CH_2OH$ | OH | 1 |
| 4-52 | $CH_2OCH_3$ | $CH_2OCH_3$ | $CH_2OH$ | OH | 1 |
| 4-53 | $CH_2OCH_3$ | $CH_2OH$ | $CH_2F$ | OH | 1 |
| 4-54 | $CH_2OCH_3$ | $CH_3$ | $CH_2F$ | OH | 1 |
| 4-55 | $CH_2OCH_3$ | $CH_2F$ | $CH_2F$ | OH | 1 |
| 4-56 | $CH_2OCH_3$ | $CH_2OCH_3$ | $CH_2F$ | OH | 1 |
| 4-57 | $CH_2OCH_3$ | $CH_2OH$ | $CH_2OH$ | F | 1 |

TABLE 4-continued

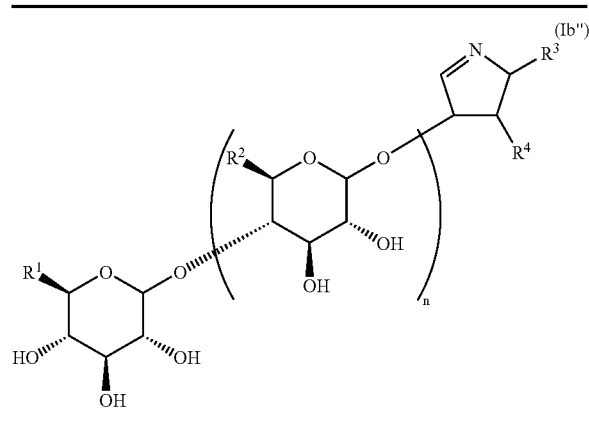

| No. | R¹ | R² | R³ | R⁴ | n |
|---|---|---|---|---|---|
| 4-58 | CH₂OCH₃ | CH₃ | CH₂OH | F | 1 |
| 4-59 | CH₂OCH₃ | CH₂F | CH₂OH | F | 1 |
| 4-60 | CH₂OCH₃ | CH₂OCH₃ | CH₂OH | F | 1 |
| 4-61 | CH₂OCH₃ | CH₂OH | CH₂F | F | 1 |
| 4-62 | CH₂OCH₃ | CH₃ | CH₂F | F | 1 |
| 4-63 | CH₂OCH₃ | CH₂F | CH₂F | F | 1 |
| 4-64 | CH₂OCH₃ | CH₂OCH₃ | CH₂F | F | 1 |
| 4-65 | CH₂OCH₂CH₃ | CH₂OH | CH₂OH | OH | 1 |
| 4-66 | CH₂OCH₂CH₃ | CH₃ | CH₂OH | OH | 1 |
| 4-67 | CH₂OCH₂CH₃ | CH₂F | CH₂OH | OH | 1 |
| 4-68 | CH₂OCH₂CH₃ | CH₂OCH₃ | CH₂OH | OH | 1 |
| 4-69 | CH₂OCH₂CH₃ | CH₂OH | CH₂F | OH | 1 |
| 4-70 | CH₂OCH₂CH₃ | CH₃ | CH₂F | OH | 1 |
| 4-71 | CH₂OCH₂CH₃ | CH₂F | CH₂F | OH | 1 |
| 4-72 | CH₂OCH₂CH₃ | CH₂OCH₃ | CH₂F | OH | 1 |
| 4-73 | CH₂OCH₂CH₃ | CH₂OH | CH₂OH | F | 1 |
| 4-74 | CH₂OCH₂CH₃ | CH₃ | CH₂OH | F | 1 |
| 4-75 | CH₂OCH₂CH₃ | CH₂F | CH₂OH | F | 1 |
| 4-76 | CH₂OCH₂CH₃ | CH₂OCH₃ | CH₂OH | F | 1 |
| 4-77 | CH₂OCH₂CH₃ | CH₂OH | CH₂F | F | 1 |
| 4-78 | CH₂OCH₂CH₃ | CH₃ | CH₂F | F | 1 |
| 4-79 | CH₂OCH₂CH₃ | CH₂F | CH₂F | F | 1 |
| 4-80 | CH₂OCH₂CH₃ | CH₂OCH₃ | CH₂F | F | 1 |
| 4-81 | CH₂OCH₂CH₃ | CH₂OH | CH₂F | F | 1 |
| 4-82 | CH₂OCH₂CH₃ | CH₃ | CH₂F | F | 1 |
| 4-83 | CH₂OCH₂CH₃ | CH₂F | CH₂F | F | 1 |
| 4-84 | CH₂OCH₂CH₃ | CH₂OCH₃ | CH₂F | F | 1 |
| 4-85 | CH₂OⁿPr | CH₂OH | CH₂OH | OH | 1 |
| 4-86 | CH₂OⁱPr | CH₂OH | CH₂OH | OH | 1 |
| 4-87 | CH₂OⁿBu | CH₂OH | CH₂OH | OH | 1 |
| 4-88 | CH₂OⁱBu | CH₂OH | CH₂OH | OH | 1 |
| 4-89 | CH₂OᵗBu | CH₂OH | CH₂OH | OH | 1 |
| 4-90 | CH₂OⁿPn | CH₂OH | CH₂OH | OH | 1 |
| 4-91 | CH₂OⁿHex | CH₂OH | CH₂OH | OH | 1 |
| 4-92 | CH₂F | CH₂OH | CH₂OH | OH | 1 |
| 4-93 | CH₂F | CH₃ | CH₂OH | OH | 1 |
| 4-94 | CH₂F | CH₂F | CH₂OH | OH | 1 |
| 4-95 | CH₂F | CH₂OCH₃ | CH₂OH | OH | 1 |
| 4-96 | CH₂F | CH₂OH | CH₂F | OH | 1 |
| 4-97 | CH₂F | CH₃ | CH₂F | OH | 1 |
| 4-98 | CH₂F | CH₂F | CH₂F | OH | 1 |
| 4-99 | CH₂F | CH₂OCH₃ | CH₂F | OH | 1 |
| 4-100 | CH₂F | CH₂OH | CH₂OH | F | 1 |
| 4-101 | CH₂F | CH₃ | CH₂OH | F | 1 |
| 4-102 | CH₂F | CH₂F | CH₂OH | F | 1 |
| 4-103 | CH₂F | CH₂OCH₃ | CH₂OH | F | 1 |
| 4-104 | CH₂F | CH₂OH | CH₂F | F | 1 |
| 4-105 | CH₂F | CH₃ | CH₂F | F | 1 |
| 4-106 | CH₂F | CH₂F | CH₂F | F | 1 |
| 4-107 | CH₂F | CH₂OCH₃ | CH₂F | F | 1 |
| 4-108 | CH₂Cl | CH₂OH | CH₂OH | OH | 1 |
| 4-109 | CH₂Cl | CH₃ | CH₂OH | OH | 1 |
| 4-110 | CH₂Cl | CH₂F | CH₂OH | OH | 1 |
| 4-111 | CH₂Cl | CH₂OCH₃ | CH₂OH | OH | 1 |
| 4-112 | CH₂Cl | CH₂OH | CH₂F | OH | 1 |
| 4-113 | CH₂Cl | CH₃ | CH₂F | OH | 1 |
| 4-114 | CH₂Cl | CH₂F | CH₂F | OH | 1 |

TABLE 4-continued

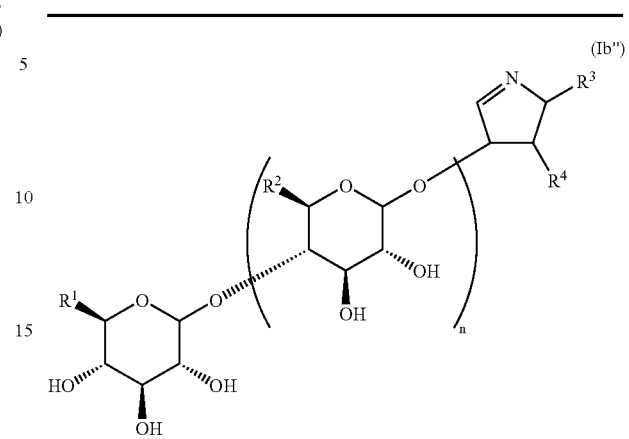

| No. | R¹ | R² | R³ | R⁴ | n |
|---|---|---|---|---|---|
| 4-115 | CH₂Cl | CH₂OCH₃ | CH₂F | OH | 1 |
| 4-116 | CH₂Cl | CH₂OH | CH₂OH | F | 1 |
| 4-117 | CH₂Cl | CH₃ | CH₂OH | F | 1 |
| 4-118 | CH₂Cl | CH₂F | CH₂OH | F | 1 |
| 4-119 | CH₂Cl | CH₂OCH₃ | CH₂OH | F | 1 |
| 4-120 | CH₂Cl | CH₂OH | CH₂F | F | 1 |
| 4-121 | CH₂Cl | CH₃ | CH₂F | F | 1 |
| 4-122 | CH₂Cl | CH₂F | CH₂F | F | 1 |
| 4-123 | CH₂Cl | CH₂OCH₃ | CH₂F | F | 1 |
| 4-124 | CH₂Br | CH₂OH | CH₂OH | OH | 1 |
| 4-125 | CH₂Br | CH₃ | CH₂OH | OH | 1 |
| 4-126 | CH₂Br | CH₂F | CH₂OH | OH | 1 |
| 4-127 | CH₂Br | CH₂OCH₃ | CH₂OH | OH | 1 |
| 4-128 | CH₂Br | CH₂OH | CH₂F | OH | 1 |
| 4-129 | CH₂Br | CH₃ | CH₂F | OH | 1 |
| 4-130 | CH₂Br | CH₂F | CH₂F | OH | 1 |
| 4-131 | CH₂Br | CH₂OCH₃ | CH₂F | OH | 1 |
| 4-132 | CH₂Br | CH₂OH | CH₂OH | F | 1 |
| 4-133 | CH₂Br | CH₃ | CH₂OH | F | 1 |
| 4-134 | CH₂Br | CH₂F | CH₂OH | F | 1 |
| 4-135 | CH₂Br | CH₂OCH₃ | CH₂OH | F | 1 |
| 4-136 | CH₂Br | CH₂OH | CH₂F | F | 1 |
| 4-137 | CH₂Br | CH₃ | CH₂F | F | 1 |
| 4-138 | CH₂Br | CH₂F | CH₂F | F | 1 |
| 4-139 | CH₂Br | CH₂OCH₃ | CH₂F | F | 1 |
| 4-140 | CH₂I | CH₂OH | CH₂OH | OH | 1 |
| 4-141 | CH₂I | CH₃ | CH₂OH | OH | 1 |
| 4-142 | CH₂I | CH₂F | CH₂OH | OH | 1 |
| 4-143 | CH₃ | CH₂OH | CH₂OH | OH | 2 |
| 4-144 | CH₃ | CH₃ | CH₂OH | OH | 2 |
| 4-145 | CH₃ | CH₂F | CH₂OH | OH | 2 |
| 4-146 | CH₃ | CH₂OCH₃ | CH₂OH | OH | 2 |
| 4-147 | CH₂OH | CH₂OH | CH₂OH | OH | 2 |
| 4-148 | CH₂OH | CH₃ | CH₂OH | OH | 2 |
| 4-149 | CH₂OH | CH₂F | CH₂OH | OH | 2 |
| 4-150 | CH₂OH | CH₂OCH₃ | CH₂OH | OH | 2 |

TABLE 5

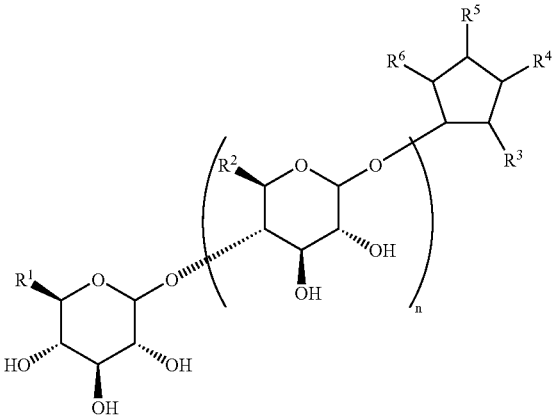

(Ic)

| | R¹ | R² | R³ | R⁴ | R⁵ | R⁶ | n |
|---|---|---|---|---|---|---|---|
| 5-1 | $CH_3$ | $CH_2OH$ | OH | OH | $NH_2$ | $CH_2OH$ | 1 |
| 5-2 | $CH_3$ | $CH_2F$ | OH | OH | $NH_2$ | $CH_2OH$ | 1 |
| 5-3 | $CH_3$ | $CH_2OH$ | OH | $CH_2OH$ | $NH_2$ | $CH_2OH$ | 1 |
| 5-4 | $CH_3$ | $CH_2F$ | OH | $CH_2OH$ | $NH_2$ | $CH_2OH$ | 1 |
| 5-5 | $CH_3$ | $CH_2OH$ | OH | $NH_2$ | H | $CH_2OH$ | 1 |
| 5-6 | $CH_3$ | $CH_2F$ | OH | $NH_2$ | H | $CH_2OH$ | 1 |
| 5-7 | $CH_3$ | $CH_2OH$ | OH | $NHCH(CH_2OH)_2$ | H | $CH_2OH$ | 1 |
| 5-8 | $CH_3$ | $CH_2F$ | OH | $NHCH(CH_2OH)_2$ | H | $CH_2OH$ | 1 |
| 5-9 | $CH_3$ | $CH_2OH$ | OH | F | $NH_2$ | $CH_2OH$ | 1 |
| 5-10 | $CH_3$ | $CH_2OH$ | OH | OH | $N(CH_3)_2$ | $CH_2OH$ | 1 |
| 5-11 | $CH_3$ | $CH_2OH$ | OH | OH | $NH(CH_3)$ | $CH_2OH$ | 1 |
| 5-12 | $CH_3$ | $CH_2OH$ | OH | OH | $N(CH_2CH_3)_2$ | $CH_2OH$ | 1 |
| 5-13 | $CH_3$ | $CH_2OH$ | OH | OH | $NH(CH_2CH_3)$ | $CH_2OH$ | 1 |
| 5-14 | $CH_3$ | $CH_2OH$ | OH | OH | $NH(^nPr)$ | $CH_2OH$ | 1 |
| 5-15 | $CH_3$ | $CH_2OH$ | OH | OH | $NH(^nBu)$ | $CH_2OH$ | 1 |
| 5-16 | $CH_3$ | $CH_2OH$ | OH | OH | $NH(^iBu)$ | $CH_2OH$ | 1 |
| 5-17 | $CH_3$ | $CH_2OH$ | OH | OH | $NH(^tBu)$ | $CH_2OH$ | 1 |
| 5-18 | $CH_3$ | $CH_2OH$ | OH | OH | $NH(^nPn)$ | $CH_2OH$ | 1 |
| 5-19 | $CH_3$ | $CH_2OH$ | OH | OH | $NH(^nHex)$ | $CH_2OH$ | 1 |
| 5-20 | $CH_3$ | $CH_2OH$ | OH | OH | $NH(CH_2OH)$ | $CH_2OH$ | 1 |
| 5-21 | $CH_3$ | $CH_2F$ | OH | OH | $N(CH_2OH)_2$ | $CH_2OH$ | 1 |
| 5-22 | $CH_3$ | $CH_2OH$ | OH | OH | $NHCH(CH_2OH)_2$ | $CH_2OH$ | 1 |
| 5-23 | $CH_3$ | $CH_2F$ | OH | OH | $NHCH(CH_2OH)_2$ | $CH_2OH$ | 1 |
| 5-24 | $CH_3$ | $CH_2OH$ | OH | OH | $NH_2$ | H | 1 |
| 5-25 | $CH_3$ | $CH_2OH$ | OH | OH | $NH_2$ | $CH_2F$ | 1 |
| 5-26 | $CH_3$ | $CH_2OH$ | OH | OH | $NH_2$ | $CH_3$ | 1 |
| 5-27 | $CH_3$ | $CH_2OH$ | OH | OH | $NH_2$ | F | 1 |
| 5-28 | $CH_3$ | $CH_2OH$ | OH | H | $NH_2$ | $CH_2OH$ | 1 |
| 5-29 | $CH_3$ | $CH_2OH$ | OH | $CH_2F$ | $NH_2$ | $CH_2OH$ | 1 |
| 5-30 | $CH_3$ | $CH_2OH$ | OH | $CH_3$ | $NH_2$ | $CH_2OH$ | 1 |
| 5-31 | $CH_3$ | $CH_2OH$ | OH | F | $NH_2$ | $CH_2OH$ | 1 |
| 5-32 | $CH_3$ | $CH_2OH$ | OH | OH | H | $CH_2OH$ | 1 |
| 5-33 | $CH_2CH_3$ | $CH_2OH$ | OH | OH | $NH_2$ | $CH_2OH$ | 1 |
| 5-34 | $CH_2CH_3$ | $CH_2OH$ | OH | $CH_2OH$ | $NH_2$ | $CH_2OH$ | 1 |
| 5-35 | $^nPr$ | $CH_2OH$ | OH | OH | $NH_2$ | $CH_2OH$ | 1 |
| 5-36 | $^iPr$ | $CH_2OH$ | OH | OH | $NH_2$ | $CH_2OH$ | 1 |
| 5-37 | $^nBu$ | $CH_2OH$ | OH | OH | $NH_2$ | $CH_2OH$ | 1 |
| 5-38 | $^iBu$ | $CH_2OH$ | OH | OH | $NH_2$ | $CH_2OH$ | 1 |
| 5-39 | $^tBu$ | $CH_2OH$ | OH | OH | $NH_2$ | $CH_2OH$ | 1 |
| 5-40 | $^nPn$ | $CH_2OH$ | OH | OH | $NH_2$ | $CH_2OH$ | 1 |
| 5-41 | $^nHex$ | $CH_2OH$ | OH | OH | $NH_2$ | $CH_2OH$ | 1 |
| 5-42 | $CH_2OH$ | $CH_2OH$ | OH | OH | $NH_2$ | $CH_2OH$ | 1 |
| 5-43 | $CH_2OH$ | $CH_2F$ | OH | OH | $NH_2$ | $CH_2OH$ | 1 |
| 5-44 | $CH_2OH$ | $CH_2F$ | OH | $CH_2OH$ | $NH_2$ | $CH_2OH$ | 1 |
| 5-45 | $CH_2OH$ | $CH_2OH$ | OH | $CH_2OH$ | $NH_2$ | $CH_2OH$ | 1 |
| 5-46 | $CH_2OH$ | $CH_2OH$ | OH | $NH_2$ | H | $CH_2OH$ | 1 |
| 5-47 | $CH_2OH$ | $CH_2F$ | OH | $NH_2$ | H | $CH_2OH$ | 1 |
| 5-48 | $CH_2OH$ | $CH_2OH$ | OH | $NHCH(CH_2OH)_2$ | H | $CH_2OH$ | 1 |
| 5-49 | $CH_2OH$ | $CH_2F$ | OH | $NHCH(CH_2OH)_2$ | H | $CH_2OH$ | 1 |
| 5-50 | $CH_2OH$ | $CH_2OH$ | OH | F | $NH_2$ | $CH_2OH$ | 1 |
| 5-51 | $CH_2OH$ | $CH_2F$ | OH | F | $NH_2$ | $CH_2OH$ | 1 |
| 5-52 | $CH_2OH$ | $CH_2OH$ | OH | OH | $NHCH(CH_2OH)_2$ | $CH_2OH$ | 1 |
| 5-53 | $CH_2OH$ | $CH_2F$ | OH | OH | $NHCH(CH_2OH)_2$ | $CH_2OH$ | 1 |
| 5-54 | $CH_2OCH_3$ | $CH_2OH$ | OH | OH | $NH_2$ | $CH_2OH$ | 1 |
| 5-55 | $CH_2OCH_3$ | $CH_2F$ | OH | OH | $NH_2$ | $CH_2OH$ | 1 |

TABLE 5-continued (Ic)
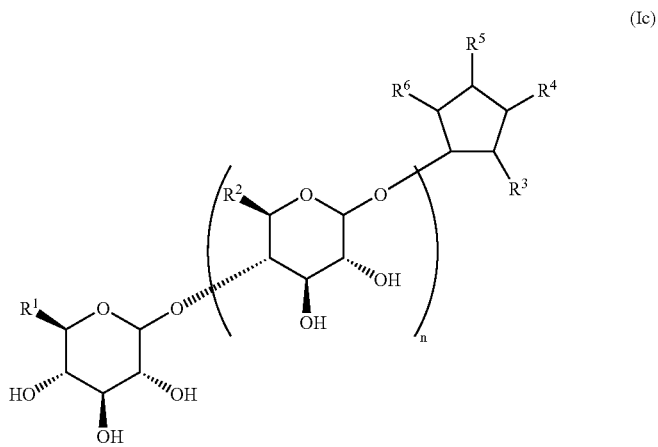

| | R¹ | R² | R³ | R⁴ | R⁵ | R⁶ | n |
|---|---|---|---|---|---|---|---|
| 5-56 | CH₂OCH₃ | CH₂OH | OH | CH₂OH | NH₂ | CH₂OH | 1 |
| 5-57 | CH₂OCH₃ | CH₂F | OH | CH₂OH | NH₂ | CH₂OH | 1 |
| 5-58 | CH₂OCH₃ | CH₂OH | OH | NH₂ | H | CH₂OH | 1 |
| 5-59 | CH₂OCH₃ | CH₂F | OH | NH₂ | H | CH₂OH | 1 |
| 5-60 | CH₂OCH₃ | CH₂OH | OH | NHCH(CH₂OH)₂ | H | CH₂OH | 1 |
| 5-61 | CH₂OCH₃ | CH₂F | OH | NHCH(CH₂OH)₂ | H | CH₂OH | 1 |
| 5-62 | CH₂OCH₃ | CH₂OH | OH | F | NH₂ | CH₂OH | 1 |
| 5-63 | CH₂OCH₃ | CH₂F | OH | F | NH₂ | CH₂OH | 1 |
| 5-64 | CH₂OCH₃ | CH₂OH | OH | OH | NHCH(CH₂OH)₂ | CH₂OH | 1 |
| 5-65 | CH₂OCH₃ | CH₂F | OH | OH | NHCH(CH₂OH)₂ | CH₂OH | 1 |
| 5-66 | CH₂F | CH₂OH | OH | OH | NH₂ | CH₂OH | 1 |
| 5-67 | CH₂F | CH₂F | OH | OH | NH₂ | CH₂OH | 1 |
| 5-68 | CH₂F | CH₂OH | OH | CH₂OH | NH₂ | CH₂OH | 1 |
| 5-69 | CH₂F | CH₂F | OH | CH₂OH | NH₂ | CH₂OH | 1 |
| 5-70 | CH₂F | CH₂OH | OH | NH₂ | H | CH₂OH | 1 |
| 5-71 | CH₂F | CH₂F | OH | NH₂ | H | CH₂OH | 1 |
| 5-72 | CH₂F | CH₂OH | OH | NHCH(CH₂OH)₂ | H | CH₂OH | 1 |
| 5-73 | CH₂F | CH₂F | OH | NHCH(CH₂OH)₂ | H | CH₂OH | 1 |
| 5-74 | CH₂F | CH₂OH | OH | F | NH₂ | CH₂OH | 1 |
| 5-75 | CH₂F | CH₂F | OH | F | NH₂ | CH₂OH | 1 |
| 5-76 | CH₂F | CH₂OH | OH | OH | NHCH(CH₂OH)₂ | CH₂OH | 1 |
| 5-77 | CH₂F | CH₂F | OH | OH | NHCH(CH₂OH)₂ | CH₂OH | 1 |
| 5-78 | CH₃ | CH₂OH | OH | OH | NH₂ | CH₂OH | 2 |
| 5-79 | CH₃ | CH₂F | OH | OH | NH₂ | CH₂OH | 2 |
| 5-80 | CH₃ | CH₂OH | OH | CH₂OH | NH₂ | CH₂OH | 2 |
| 5-81 | CH₃ | CH₂F | OH | CH₂OH | NH₂ | CH₂OH | 2 |
| 5-82 | CH₃ | CH₂OH | OH | F | NH₂ | CH₂OH | 2 |
| 5-83 | CH₂OH | CH₂OH | OH | OH | NH₂ | CH₂OH | 2 |
| 5-84 | CH₂OH | CH₂F | OH | OH | NH₂ | CH₂OH | 2 |
| 5-85 | CH₂OH | CH₂F | OH | CH₂OH | NH₂ | CH₂OH | 2 |
| 5-86 | CH₂F | CH₂OH | OH | OH | NH₂ | CH₂OH | 2 |
| 5-87 | CH₂F | CH₂F | OH | OH | NH₂ | CH₂OH | 2 |
| 5-88 | CH₂F | CH₂OH | OH | CH₂OH | NH₂ | CH₂OH | 2 |

In the above Tables, preferred compounds are 1-1, 1-115, 1-119, 1-155, 1-280, 1-354, 1-547, 1-556, 1-557, 3-1, 5-1, 5-3, 5-9, 5-22 or 5-28, more preferred are (2R,3R,4R)-4-hydroxy-2-hydroxymethyl-pyrrolidin-3-yl 4-O-(6-deoxy-α-D-glucopyranosyl)-α-D-glucopyranoside, (2R,3R,4R)-4-hydroxy-2-hydroxymethyl-pyrrolidin-3-yl 4-O-(6-deoxy-α-D-glucopyranosyl)-α-D-glucopyranoside, (2R,3R,4R)-4-hydroxy-2-hydroxymethyl-pyrrolidin-3-yl 4-O-β-D-glucopyranosyl-α-D-glucopyranoside, (2R,3R,4R)-4-hydroxy-2-hydroxymethyl-pyrrolidin-3-yl 4-O-(6-fluoro-6-deoxy-β-D-glucopyranosyl)-D-glucopyranoside, (1R,2S,3R,4R,5R)-1-amino-2,3-dihydroxy-5-hydroxymethyl-cyclopent-4-yl 4-O-(6-deoxy-α-D-glucopyranosyl)-α-D-glucopyranoside, (2R,3R,4R)-4-hydroxy-2-hydroxymethyl-pyrrolidin-3-yl 4-O-(6-methoxy-6-deoxy-β-D-glucopyranosyl)-D-glucopyranoside, (2R,3R,4R)-4-hydroxy-2-hydroxymethyl-3,4-dihydro-2H-pyrrol-3-yl 4-O-(6-deoxy-α-D-glucopyranosyl)-α-D-glucopyranoside, their pharmacologically acceptable salts and their pharmacologically acceptable esters.

A compound having the general formula (I) can be produced using, for example, a known compound for the starting raw material according to the processes described below.

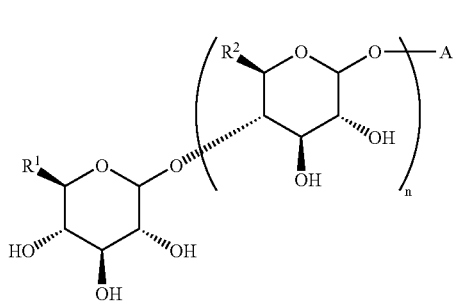

(I)

In the aforementioned formula and following description, A, $R^1$, $R^2$, $R^3$, $R^4$, $R^5$, $R^6$, $R^7$, $R^8$, $R^9$, $R^{10}$, $R^{11}$ and n are the same as previously defined. However, in the case $R^1$, $R^2$, $R^3$, $R^4$, $R^5$, $R^6$, $R^7$, $R^8$, $R^9$, $R^{10}$ or $R^{11}$ indicates a hydroxyl group or a group having a hydroxyl group, said hydroxyl group may optionally be protected.

Process A:

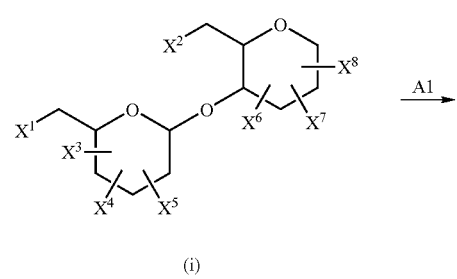

(i)

(ii)

(iii)

Process B:
Process Ba:

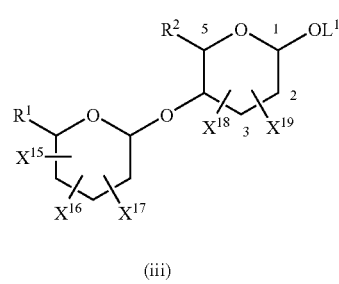

(iv)

(v)

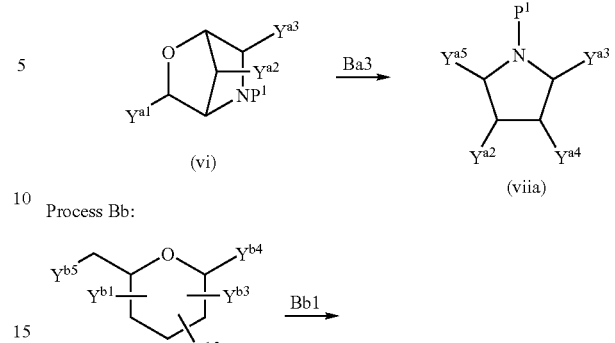

(vi)

(viia)

Process Bb:

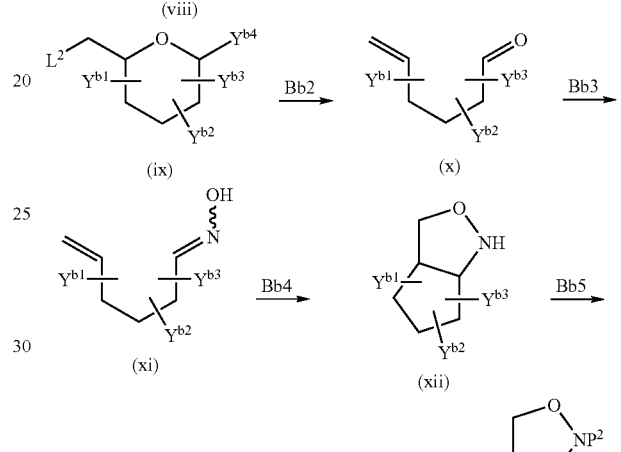

(viii)

(ix)

(x)

(xi)

(xii)

(viib)

Process Bc:

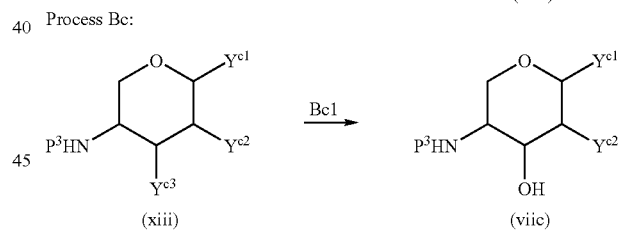

(xiii)

(viic)

Process C:

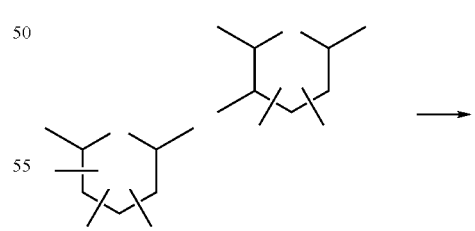

In the aforementioned steps and following description, $X^1$ to $X^{25}$, $Y^{a1}$ to $Y^{a5}$ and $Y^{c1}$ to $Y^{c3}$ are the same or different, and each represents a hydrogen atom or hydroxyl group (said hydroxyl group may optionally be protected by a protecting group), $Y^{b1}$ to $Y^{b5}$ are the same or different, and each represents a halogen atom, hydrogen atom or hydroxyl group (said hydroxyl group may optionally be protected by a protecting group), $P^1$ represents a protecting group of an amino group such as $R^6$ or a C1-C6 alkoxycarbonyl group (preferably a t-butoxycarbonyl group) or C7-C16 aralkyloxycarbonyl group (preferably a benzyloxycarbonyl group), $P^2$ and $P^3$ are the same or different, and each represents a protecting group of an amino group such as $R^7$ or a C1-C6 alkoxycarbonyl group (preferably a t-butoxycarbonyl group) or a C7-C16 aralkyloxycarbonyl group (preferably a benzyloxycarbonyl group), and $L^1$, $L^2$, $L^3$ and $L^4$ represent a hydroxyl group (said hydroxyl group may optionally be protected by a protecting group or the hydrogen atom may optionally be substituted by a leaving group) or a leaving group.

There are no particular limitations on the protecting group used to protect a hydroxyl group provided the group is typically used to protect a hydroxyl group, examples of which include "aliphatic acyl groups" such as alkyl carbonyl groups, e.g. formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosanoyl groups, carboxylated alkyl carbonyl groups, e.g. succinoyl, glutaroyl and adipoyl groups, halogeno lower alkyl carbonyl groups, e.g. chloroacetyl, dichloroacetyl, trichloroacetyl and trifluoroacetyl groups, lower alkoxy lower alkyl carbonyl groups, e.g. methoxyacetyl groups, and unsaturated alkyl carbonyl groups, e.g. (E)-2-methyl-2-butenoyl groups; "aromatic acyl groups" such as aryl carbonyl groups, e.g. benzoyl, α-naphthoyl and β-naphthoyl groups, halogenoaryl carbonyl groups, e.g. 2-bromobenzoyl and 4-chlorobenzoyl groups, lower alkylated aryl carbonyl groups, e.g. 2,4,6-trimethylbenzoyl and 4-toluoyl groups, lower alkoxylated aryl carbonyl groups, e.g. 4-anisoyl groups, carboxylated aryl carbonyl groups, e.g. 2-carboxybenzoyl, 3-carboxybenzoyl and 4-carboxybenzoyl groups, nitrated aryl carbonyl groups e.g. 4-nitrobenzoyl and 2-nitrobenzoyl groups, lower alkoxycarbonylated aryl carbonyl groups e.g. 2-(methoxycarbonyl)benzoyl groups, and arylated aryl carbonyl groups, e.g. 4-phenylbenzoyl groups; "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl groups; "tetrahydrofuranyl or tetrahydrothiofuranyl groups" such as tetrahydrofuran-2-yl and tetrahydrothiofuran-2-yl groups; "silyl groups" such as tri-lower alkyl silyl groups, e.g. trimethylsilyl, triethylsilyl, isopropyl dimethylsilyl, t-butyl dimethylsilyl, methyl diisopropylsilyl, methyl di-t-butylsilyl and triisopropylsilyl groups, and tri-lower alkyl silyl groups substituted with 1 to 2 aryl groups, e.g. diphenylmethylsilyl, diphenylbutylsilyl, diphenylisopropylsilyl and phenyldiisopropylsilyl groups; "alkoxymethyl groups" such as lower alkoxymethyl groups, e.g. methoxymethyl, 1,1-dimethyl-1-methoxymethyl, ethoxymethyl, propoxymethyl, isopropoxymethyl, butoxymethyl and t-butoxymethyl groups, lower alkoxylated lower alkoxymethyl groups, e.g. 2-methoxyethoxymethyl groups, and halogeno lower alkoxymethyl groups, e.g. 2,2,2-trichloroethoxymethyl and bis(2-chloroethoxy)methyl groups; "substituted ethyl groups" such as lower alkoxylated ethyl groups, e.g. 1-ethoxyethyl and 1-(isopropoxy)ethyl groups and halogenated ethyl groups, e.g. 2,2,2-trichloroethyl groups; "aralkyl groups" such as lower alkyl groups substituted with 1 to 3 aryl groups, e.g. benzyl, α-naphthylmethyl, β-naphthylmethyl, diphenylmethyl, triphenylmethyl, α-naphthyldiphenylmethyl and 9-anthrylmethyl groups, and lower alkyl groups substituted with 1 to 3 aryl groups in which an aryl ring is substituted with a lower alkyl, lower alkoxy, halogen or cyano group; e.g. 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, methyl and piperonyl groups; "alkoxycarbonyl groups" such as lower alkoxycarbonyl groups, e.g. methoxycarbonyl, ethoxycarbonyl, t-butoxycarbonyl and isobutoxycarbonyl groups, and lower alkoxycarbonyl groups substituted with halogen or tri-lower alkylsilyl groups, e.g. 2,2,2-trichloroethoxycarbonyl and 2-trimethylsilylethoxycarbonyl groups; "alkenyloxy carbonyl groups" such as vinyloxycarbonyl and allyloxycarbonyl groups; and, "aralkyloxy carbonyl groups" in which an aryl ring may or may not be substituted with 1 to 2 lower alkoxy or nitro groups, e.g. benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups. There are no particular limitations on reagents used to protect diols provided they are normally used to protect diols, and preferable examples include aldehyde derivatives such as benzaldehyde, ketone derivatives such as acetone, and dimethoxy compounds such as 2,2-dimethoxypropane and dimethoxybenzyl.

The process for producing Compound (I) of the present invention is comprised of the following three steps.
(1) Step A is a step wherein the left side portion of Compound (I) in the form of intermediate (iii) is produced.
(2) Step B is a step wherein the right side portion of Compound (I) in the form of Intermediate (vii) is produced, and process a, b or c can be selected corresponding to the desired Compound (I).
(3) Step C is a step wherein Compound (I) of the present invention is produced by condensing Intermediate (iii) obtained in Step A and Intermediate (vii) obtained in Step B.

The following provides an explanation of each step.
(Process A)
Raw material compound (i) can be produced by protecting and deprotecting a hydroxyl group of a known compound in accordance with known processes. In addition, protection and deprotection of a hydroxyl group can also be carried out in this step as necessary.

Protection and deprotection of a hydroxyl group can be carried in compliance with commonly known processes such as the process described in "Protective Groups in Organic Synthesis" by Green-Watts (Wiley-Interscience, USA).

In addition, deprotection can also be carried out in the manner described below.

In the case of using a silyl group for the hydroxyl group deprotecting group, it can normally be removed by treating either with a compound that forms a fluorine anion such as tetrabutyl ammonium fluoride, hydrofluoric acid, hydrofluoric acid-pyridine or potassium fluoride, or an organic acid, such as acetic acid, methanesulfonic acid, paratoluene sulfonic acid, trifluoroacetic acid or trifluoromethanesulfonic acid, or an inorganic acid such as hydrochloric acid.

Furthermore, in the case of removal by a fluorine anion, the reaction may be promoted by adding an organic acid such as formic acid, acetic acid or propionic acid.

There are no particular limitations on the solvent used provided it dissolves the starting substance to a certain extent without inhibiting the reaction, and preferable examples include ethers such as diethyl ether, diisopropyl ether, tetrahydrofuran, dioxane, dimethoxyethane and diethylene glycol dimethyl ether; nitriles such as acetonitrile and isobutyronitrile; water; organic acids such as acetic acid and mixed solvents thereof.

There are no particular limitations on the reaction temperature or reaction time, and the reaction is normally carried out at 0° C. to 100° C. (and preferably 10° C. to 30° C.) for 1 to 24 hours.

In the case the hydroxyl group protecting group is an aralkyl group or aralkyloxy carbonyl group, normally a process in which it is removed by contacting with a reducing agent in a solvent (and preferably contact reduction at normal temperature in the presence of a catalyst) or a process in which it is removed using an oxidizing agent, is used preferably.

There are no particular limitations on the solvent used during removal by catalytic reduction provided it is not involved in the present reaction, and preferable examples include alcohols such as methanol, ethanol and isopropanol; ethers such as diethyl ether, tetrahydrofuran and dioxane; aromatic hydrocarbons such as toluene, benzene and xylene; aliphatic hydrocarbons such as hexane and cyclohexane; esters such as ethyl acetate and propyl acetate; amides such as formamide, dimethylformamide, dimethylacetamide, N-methyl-2-pyrrolidone and hexamethylphosphorotriamide; fatty acids such as formic acid and acetic acid; water and mixed solvents thereof, while more preferable examples include alcohols, fatty acids, mixed solvents of alcohols and ethers, mixed solvents of alcohols and water and mixed solvents of fatty acids and water.

There are no particular limitations on the catalyst used provided it is normally used in catalytic reduction reactions, and preferable examples of catalysts used include palladium carbon, palladium black, Rainey nickel, platinum oxide, platinum black, rhodium-aluminium oxide, triphenylphosphine-rhodium chloride and palladium-barium sulfate.

There are no particular limitations on the pressure, and the reaction is normally carried out at a pressure of 1 to 10 atmospheres.

Although reaction temperature and reaction time vary depending on the types of starting substance, solvent, catalyst and so forth, they are normally 0° C. to 100° C. (and preferably 20° C. to 70° C.) and 5 minutes to 48 hours (and preferably 1 hour to 24 hours).

There are no particular limitations on the solvent used during removal by oxidation provided it is not involved in the present reaction, and water-containing organic solvents are preferable.

Preferable examples of such organic solvents include ketones such as acetone, halogenated hydrocarbons such as methylene chloride, chloroform and carbon tetrachloride, nitrites such as acetonitrile, ethers such as diethyl ether, tetrahydrofuran and dioxane, amides such as dimethylformamide, dimethylacetamide and hexamethylphosphorotriamide, and sulfoxides such as dimethyl sulfoxide.

There are no particular limitations on the oxidizing agent used provided it is a compound normally used for oxidation, and potassium persulfate, sodium persulfate, cerium ammonium nitrate (CAN) or 2,3-dichloro-5,6-dicyano-p-benzoquinone (DDQ) is used preferably.

Although reaction temperature and reaction time vary depending on the types of starting substance, solvent, catalyst and so forth, they are normally 0° C. to 150° C. and 10 minutes to 24 hours.

In addition, the protecting group can also be removed by allowing an alkali metal such as lithium metal or sodium metal to act at −78° C. to −20° C. in liquid ammonia or an alcohol such as methanol or ethanol.

Moreover, it can also be removed by using an alkyl silyl halide such as aluminium chloride-sodium iodide or trimethylsilyl iodide in a solvent.

There are no particular limitations on the solvent used provided it is not involved in the present reaction, and nitrites such as acetonitrile, halogenated hydrocarbons such as methylene chloride and chloroform, or mixed solvents thereof are used preferably.

Although reaction temperature and reaction time vary depending on the types of the starting substance, solvent and so forth, the reaction temperature and reaction time are normally 0° C. to 50° C. and 5 minutes to 3 days.

Furthermore, in the case the reaction substrate has a sulfur atom, aluminium chloride-sodium iodide is used preferably.

In the case the hydroxyl group protecting group is an aliphatic acyl group, aromatic acyl group or alkoxycarbonyl group, it is removed by treating with base in a solvent.

There are no particular limitations on the base used provided it does not have an effect on the other parts of the compound, and examples of bases that are used preferably include metal alkoxides such as sodium methoxide; alkaline metal carbonates such as sodium carbonate, potassium carbonate and lithium carbonate; alkaline metal hydroxides such as sodium hydroxide, potassium hydroxide, lithium hydroxide and barium hydroxide; and ammonias such as aqueous ammonia and concentrated ammonia-methanol.

There are no particular limitations on the solvent used provided it is normally used in hydrolysis reactions, preferable examples of which include water; organic solvents such as alcohols e.g. methanol, ethanol and n-propanol, and ethers e.g. tetrahydrofuran and dioxane; and mixed solvents of water and the aforementioned organic solvents.

Although there are no particular limitations on the reaction temperature and reaction time, and they vary according to the starting substance, solvent, base used and so forth, the reaction is normally carried out at 0° C. to 150° C. for 1 hour to 10 hours to suppress side reactions.

In the case the hydroxyl group protecting group is an alkoxy methyl group, tetrahydropyranyl group, tetrahydrothiopyranyl group, tetrahydrofuranyl group, tetrahydrothiofuranyl group or substituted ethyl group, the protecting group is normally removed by treating with acid in a solvent.

There are no particular limitations on the acid used provided it is normally used as a Bronsted acid or Lewis acid, and although preferable examples include Bronsted acids such as hydrogen chloride; inorganic acids e.g. hydrochloric acid, sulfuric acid and nitric acid; and, organic acids e.g. acetic acid, trifluoroacetic acid, methane sulfonic acid and p-toluene sulfonic acid; as well as Lewis acids such as boron trifluoride, a strongly acidic cation exchange resin such as Dowex 50W can also be used.

There are no particular limitations on the solvent used provided it dissolves the starting substance to a certain extent without inhibiting the reaction, and preferable examples include aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, tert-butanol, isoamyl alcohol, diethylene glycol, glycerin, octanol, cyclohexanol and methyl cellusorb; ketones such as acetone, methyl ethyl ketone, methyl isobutyl ketone, isophorone and cyclohexanone; water and mixed solvents thereof, while more preferable examples include halogenated hydrocarbons, esters and ethers.

Although reaction temperature and reaction time vary depending on the types, concentrations and so forth of the starting substance, solvent and acid used, they are normally −10° C. to 100° C. (and preferably −5° C. to 50° C.) and 5 minutes to 48 hours (and preferably 30 minutes to 10 hours).

In the case the hydroxyl group protecting group is an alkenyloxy carbonyl group, removal is normally achieved by treating with base under similar conditions as the removal reaction in the case the hydroxyl group protecting group is an aforementioned aliphatic acyl group, aromatic acyl group or alkoxycarbonyl group.

Furthermore, in the case of an allyloxycarbonyl group, a process in which it is removed using palladium in particular as well as triphenylphosphine or bis(methyldiphenylphosphine) (1,5-cyclooctadiene) iridium (I).hexafluorophosphate is simple and can be carried out with few side reactions.

In the case the hydroxyl group protecting group is a formyl group, it is removed by treating with base in a solvent.

There are no particular limitations on the base used provided it does not have an effect on other parts of the compounds, and an alkaline metal hydrogen carbonate such as potassium hydrogen carbonate is used preferably.

There are no particular limitations on the solvent used provided is normally used in hydrolysis reactions, and preferable examples include water; organic solvents such as alcohols e.g. methanol, ethanol and n-propanol, or ethers e.g. tetrahydrofuran and dioxane; and, mixed solvents of water and the aforementioned organic solvents.

Although reaction temperature and reaction time vary depending on the types of the starting substance, solvent and base used and there are no particular limitations on them, the reaction is normally carried out at 0° C. to 150° C. for 1 hour to 10 hours to suppress side reactions.

In the case the hydroxyl group protecting group is a halogen-substituted acetamide group such as a trifluoroacetamide group, it is removed by treating with base in a solvent.

There are no particular limitations on the base used provided it does not have an effect on other parts of the compound, and a basic resin such as Dowex 1×4 (OH−) is used preferably.

There are no particular limitations on the solvent used provided it is normally used in hydrolysis reactions, and preferable examples include water; and, alcohols such as methanol, ethanol and n-propanol, with water being more preferable.

A deprotecting group of an allyl group at the anomer position is preferably a palladium catalyst such as palladium chloride or an iridium catalyst.

There are no particular limitations on the solvent used provided it is normally used in catalytic reactions, and preferable examples include alcohol-based solvents such as methanol, ether-based solvents such as tetrahydrofuran, and water, with methanol and tetrahydrofuran being more preferable.

(Step A1)

This step is a step in which compound (ii) is produced, and is achieved by introducing a leaving group to a hydroxyl group at a desired location as necessary, followed by carrying out a nucleophilic substitution reaction with a reagent corresponding to the $R^1$ and $R^2$ groups introduced.

In the case the leaving group is a halogen atom, there are no particular limitations on the solvent used provided it dissolves the starting substance without inhibiting the reaction, with preferable examples including ethers such as diethyl ether, tetrahydrofuran and dioxane, amides such as dimethylformamide, dimethylacetamide and hexamethylphosphotriamide, halogenated hydrocarbons such as dichloromethane, chloroform and 1,2-dichloroethane, nitriles such as acetonitrile and propionitrile, esters such as ethyl formate and ethyl acetate and mixed solvents thereof, more preferable examples being halogenated hydrocarbons and ethers, and particularly preferable examples being dichloromethane and tetrahydrofuran.

There are no particular limitations on the halogenation agent used provided it is normally used in reactions between hydroxyl groups and halogen atoms, examples of which include dialkylaminosulfatrihalides such as diethylaminosulfatrifluoride (DAST), thionyl halides such as thionyl chloride, thionyl bromide and thionyl iodide, sulfuryl halides such as sulfuryl chloride, sulfuryl bromide and sulfuryl iodide, phosphorus trihalides such as phosphorus trichloride, phosphorus tribromide and phosphorus triiodide, phosphorus pentahalides such as phosphorus pentachloride, phosphorus pentabromide and phosphorus pentaiodide, and phosphorus oxyhalides such as phosphorus oxychloride, phosphorus oxybromide and phosphorus oxyiodide.

The reaction temperature is 0° C. to the heating temperature (boiling point of the solvent used), and preferably room temperature to the heating temperature (boiling point of the solvent used).

The reaction time is 10 minutes to 24 hours, and preferably 1 hour to 5 hours.

In the case the leaving group is a sulfonyl group, there are no particular limitations on the sulfonylation agent used provided it is normally used in hydroxyl group sulfonylation reactions, examples of which include alkane sulfonyl halides such as ethane sulfonyl chloride, aryl sulfonyl halides such as p-toluene sulfonyl chloride, and sulfonic acid anhydrides such as methane sulfonic acid anhydride, benzene sulfonic acid anhydride and trifluoromethane sulfonic acid anhydride. Preferable examples include methanesulfonyl chloride, p-toluenesulfonyl chloride and trifluoromethanesulfonic acid anhydride.

There are no particular limitations on the solvent used provided it dissolves the starting substance to a certain extent without inhibiting the reaction, examples of which include aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; and, ethers such as diethyl ether, diisopropyl ether, tetrahydrofuran, dioxane, dimethoxyethane and diethylene glycol dimethyl ether. Preferable examples include halogenated hydrocarbons, esters and ethers, with tetrahydrofuran being more preferable.

There are no particular limitations on the base used provided it is used as a base in normal reactions, preferable examples of which include organic bases such as triethylamine, tripropylamine, tributylamine, diisopropylethylamine, dicyclohexylamine, N-methylpiperidine, pyridine, 4-pyrrolidinopyridine, picoline, 4-(N,N-dimethylamino) pyridine, 2,6-di(t-butyl)-4-methylpyridine, quinoline, N,N-dimethylaniline, N,N-diethylaniline, 1,5-diazbicyclo[4.3.0]non-5-ene (DBN), 1,4-diazabicyclo[2.2.2]octane (DABCO)

and 1,8-diazabicyclo[5.4.0]undec-7-ene (DBU), with triethylamine and pyridine being more preferable.

The reaction temperature is 0° C. to the heating temperature (boiling point of the solvent used), and preferably 0° C. to room temperature.

The reaction time is 10 minutes to 24 hours, and preferably 10 minutes to 1 hour.

Examples of the reagent used for the reagent corresponding to groups $R^1$ and $R^2$ include commercially available reducing agents and halogenation agents.

Preferable examples of the reducing agent used include alkaline metal borohydrides such as sodium borohydride and lithium borohydride, hydrogenated aluminium compounds such as lithium aluminium hydride and aluminium triethoxide lithium hydride, and hydride reagents such as sodium tellurium hydride.

There are no particular limitations on the solvent used provided it dissolves the starting substance without inhibiting the reaction, and preferable examples include alcohols such as methanol and ethanol, ethers such as ether and tetrahydrofuran, and mixed solvents thereof.

There are no particular limitations on the halogenation agent used provided it is normally used in halogenation reactions, and preferable examples include dialkylaminosulfatrihalides such as diethylaminosulfatrifluoride (DAST), thionyl halides such as thionyl chloride, thionyl bromide and thionyl iodide, sulfuryl halides such as sulfuryl chloride, sulfuryl bromide and sulfuryl iodide, phosphorus trihalides such as phosphorus trichloride, phosphorus tribromide and phosphorus triiodide, phosphorus pentahalides such as phosphorus pentachloride, phosphorus pentabromide and phosphorous pentaiodide, and phosphorous oxyhalides such as phosphorous oxychloride, phosphorous oxybromide and phosphorous oxyiodide, with diethylaminosulfatrifluoride being more preferable.

There are no particular limitations on the solvent used provided it dissolves the starting substance to a certain extent without inhibiting the reaction, and examples include ethers such as ether and tetrahydrofuran, with tetrahydrofuran being preferable.

The reaction temperature is 0° C. to the heating temperature (boiling point of the solvent used), and preferably room temperature to the heating temperature (boiling point of the solvent used).

The reaction time is 10 minutes to 24 hours, and preferably 1 hour to 5 hours.

(Step A2)

This step is a step in which intermediate (iii) is produced, and is achieved by introducing a leaving group at position 1 of compound (ii) following the process of step A1.

(Step B)

(Process Ba)

Raw material compound (iv) can be produced following the process described in Tetrahedron, Vol. 26, 1985, p. 1469. Moreover, raw material compound (v) can be produced by protecting and deprotecting a hydroxyl group of a known compound according to a known process. In addition, hydroxyl group protection and deprotection can also be carried out as necessary in the present step in the same manner as Process A. Moreover, in the case of having a halogen atom for a substituent, a halogen atom can be introduced according to the halogenation reaction of step A1.

(Step Ba1)

This step is a step in which a bicyclic compound (v) is produced, and is achieved by reducing the azide group of compound (iv) followed by heating.

There are no particular limitations on the solvent used provided it dissolves the starting substance, and examples include water-soluble ethers such as tetrahydrofuran and dioxane, water, and mixed solvents thereof, with a mixed solvent of water and tetrahydrofuran being preferable.

Examples of azide group reducing agents include phosphines and aqueous ammonia. Although examples include trialkyl phosphines such as trimethyl phosphine and triethyl phosphine and aqueous ammonia, and triaryl phosphines such as triphenyl phosphine and aqueous ammonia, a triaryl phosphine such as triphenyl phosphine and aqueous ammonia are preferable.

In addition, a catalyst can also be used for the reducing agent. There are no particular limitations on the catalyst used provided it is normally used in catalytic reduction reactions, and examples include palladium carbonate, palladium black, palladium carbon, palladium hydroxide, Rainey nickel, platinum oxide, platinum black, rhodium-aluminium hydroxide, triphenyl phosphine-rhodium chloride and palladium-barium sulfate, with palladium carbon and palladium hydroxide being preferable.

In the case of using a catalyst for the reducing agent, there are no particular limitations on the solvent used provided it dissolves the starting substance without inhibiting the reaction, and preferable examples include alcohols such as methanol and ethanol, ethers such as tetrahydrofuran and dioxane, fatty acids such as acetic acid, and esters such as ethyl acetate, with methanol being more preferable.

The reaction temperature is 0° C. to 50° C., and preferably 0° C. to room temperature.

The reaction time is 10 minutes to 24 hours, and preferably 1 hour to 5 hours.

(Step Ba2)

This step is a step in which compound (vi) having a protected amino group is produced, and is achieved by protecting the amino group of compound (v) with a suitable protecting group.

There are no particular limitations on the solvent used provided it dissolves the starting substance without inhibiting the reaction, and preferable examples include ethers such as tetrahydrofuran, dioxane, dimethoxyethane and diethylene glycol, alcohols such as methanol and ethanol, ketones such as acetone and methyl ethyl ketone, amides such as N,N-dimethylformamide and N,N-dimethylacetamide, and sulfoxides such as dimethyl sulfoxide.

There are no particular limitations on the reagent used provided it is normally used in reactions in which a protecting group is introduced to a free amino group, and preferable examples include di-t-butyl dicarbonate, benzyloxycarbonyl chloride and p-nitrobenzyloxycarbonyl chloride, with di-t-butyl carbonate being more preferable.

There are no particular limitations on the base used provided it is used as a base in normal reactions, and preferable examples include alkaline earth carbonates, alkaline earth hydrogen carbonates and organic bases, with alkaline metal hydrogen carbonates being more preferable.

The reaction temperature is 0° C. to 50° C., and preferably 0° C. to room temperature.

The reaction time is 10 minutes to 24 hours, and preferably 1 hour to 10 hours.

(Step Ba3)

This step is a step in which pyrrolidine compound (viia) is produced, and is achieved by opening one of the rings of bicyclic compound (vi), protecting the hydroxyl group as necessary, and deprotecting the hydroxyl group at the site that glycosylates with intermediate (iii).

There are no particular limitations on the reducing agent used provided it is normally used in reduction reactions, and examples include alkali metal borohydrides such as sodium borohydride and lithium borohydride, hydrogenated aluminium compounds such as lithium aluminium hydride and aluminium triethoxide lithium hydride, and hydride reagents such as sodium tellurium hydride, with sodium borohydride being preferable.

There are no particular limitations on the solvent used provided it dissolves the starting substance to a certain extent without inhibiting the reaction, and examples include alcohols such as methanol and ethanol, ethers such as dioxane, ether and tetrahydrofuran, water and mixed solvents thereof, with methanol or tetrahydrofuran being preferable.

The reaction temperature is 0° C. to the boiling point of the solvent used, and preferably 50° C. to the boiling point of the solvent used.

The reaction time is 10 minutes to 24 hours, and preferably 1 hour to 5 hours.

(Process Bb)

Raw material compound (viii) can be produced according to the process described in Carbohydrate Research, Vol. 169, 1987, p. 23. Moreover, raw material compound (viii) can be produced by protecting and deprotecting a hydroxyl group of a known compound according to a known process. In addition, the hydroxyl group can also be protected and deprotected as necessary in the present step in the same manner as Process A. Moreover, in the case of having a halogen atom for a substituent, a halogen atom can be introduced according to the halogenation reaction of step A1.

(Step Bb1)

The present step is a step in which compound (ix) is produced, and is achieved by introducing a leaving group at the 6-position of raw material compound (viii) under the same conditions as step A1. In addition, the leaving group can be further converted to a different leaving group as necessary.

(Step Bb2)

The present step is a step in which compound (x) having an olefin terminal is produced, and is achieved by heating compound (ix) in a solvent in the presence of a catalyst.

There are no particular limitations on the solvent used provided it dissolves the starting substance without inhibiting the reaction, and preferable examples include alcohols such as methanol, ethanol and isopropanol, water, and mixed solvents thereof, with a mixed solvent of water and isopropanol being more preferable.

There are no particular limitations on the catalyst used provided it is normally used in reactions in which a double bond is reduced, and examples include zinc, palladium carbon, platinum, Rainey nickel, alkali metal borohydrides such as sodium borohydride and lithium borohydride, hydrogenated aluminium compounds such as such as lithium aluminium hydride and aluminium triethoxide lithium hydride, and hydride reagents such as sodium tellurium hydride, with zinc being preferable.

The reaction temperature is 0° C. to the boiling point of the solvent used, and preferably 50° C. to the boiling point of the solvent used.

The reaction time is 10 minutes to 24 hours, and preferably 1 hour to 5 hours.

(Step Bb3)

The present step is a step in which compound (xi) having a hydroxylamino group is produced, and is achieved by treating compound (x) with a hydroxylamine hydrochloride.

There are no particular limitations on the solvent used provided it dissolves the starting substance without inhibiting the reaction, and preferable examples include mixed solvents of alcohols such as methanol, ethanol and isopropanol, and organic bases such as pyridine, with a mixed solvent of ethanol and pyridine being particularly preferable.

The reaction temperature is 0° C. to the boiling point of the solvent used, and preferably 0° C. to 60° C.

The reaction time is 10 minutes to 24 hours, and preferably 1 hour to 5 hours.

(Step Bb4)

The present step is a step in which bicyclic compound (xii) is produced, and is achieved by cyclizing compound (xi) by heating in a solvent.

There are no particular limitations on the solvent used provided it is inactive, and preferable examples include aromatic hydrocarbons such as benzene, toluene and xylene, with toluene being particularly preferable.

The reaction temperature is 0° C. to the boiling point of the solvent used, and preferably 50° C. to the boiling point of the solvent used.

The reaction time is 10 minutes to 24 hours, and preferably 1 hour to 5 hours.

(Step Bb5)

The present step is a step in which intermediate compound (viib) is produced, and is achieved by deprotecting the hydroxyl group at the site that glycosylates with intermediate (iii), and protecting the secondary amine of compound (xii) under similar conditions to step A1.

(Process Bc)

Raw material compound (xiii) can be produced according to the process described in the Chemical Pharmaceutical Bulletin, Vol. 39, 1991, p. 2807. Moreover, raw material compound (xiii) can be produced by protecting and deprotecting the hydroxyl group of a known compound according to a known process. In addition, protection and deprotection of the hydroxyl group can also be carried out as necessary in the present step in the same manner as Process A. Moreover, in the case of having a halogen atom for a substituent, a halogen atom can be introduced according to the halogenation reaction of Step A1.

(Step Bc1)

The present step is a step in which intermediate compound (viic) is produced, and is achieved by deprotecting the hydroxyl group protecting group of raw material compound (xiii).

(Process C)

(Step C1)

The present step is a step in which desired compound (I) is produced, and is achieved by carrying out a glycosylation reaction with intermediate compounds (iii) and (vii), and deprotecting the hydroxyl group and amino group as necessary in accordance with established methods.

Preferable examples of the deprotecting group at the anomer position of compound (iii) include fluorine, bromine, chlorine, trichloroimidate, diphenyl phosphate, diethyl phosphite, thiomethyl and phenylthio groups.

There are no particular limitations on the solvent used provided it is inactive, and preferable examples include halogenated hydrocarbons such as methylene chloride and chloroform, ethers such as ether and tetrahydrofuran, and aromatic hydrocarbons such as benzene, toluene and xylene, with more preferable examples including halogenated hydrocarbons and ethers, and particularly preferable examples including methylene chloride and ether.

There are no particular limitations on the catalyst used provided it is normally used in glycosylation reactions, and preferable examples include trimethylsilyl trifluoromethanesulfonic acid, trifluoromethanesulfonic acid, boron trifluoride ether complex, toluenesulfonic acid, silver trifluoromethanesulfonic acid and tetrabutyl ammonium iodide.

The reaction temperature is 0° C. to the boiling point of the solvent used, and preferably room temperature.

The reaction time is 10 minutes to 24 hours, and preferably 1 hour to 5 hours.

In addition, compound (I) can also be produced by deprotecting the hydroxyl group after the glycosylation reaction with intermediate compounds (iii) and (viic), and then additionally subjecting to basic conditions.

In addition, in the case n=2, compound (I) can be produced using a trisaccharide derivative for the raw material compound in a process similar to processes A and C.

In addition, in the case of having a basic group, the desired compound (I) can be converted to an acid addition salt, preferably a hydrochloride, in accordance with ordinary methods.

Following completion of the reactions of each of the aforementioned steps, the desired compound is collected from the reaction mixture in accordance with ordinary methods. For example, the desired compound is obtained by suitably neutralizing the reaction mixture, or in the case of the presence of insoluble matter, removing the insoluble matter by filtration, followed by adding water and an immiscible organic solvent such as ethyl acetate, washing with water and so forth, and then separating the organic phase containing the desired compound, drying with anhydrous magnesium sulfate, for example, and finally distilling off the solvent.

The resulting desired compound can be separated and purified as necessary by suitably combining ordinary methods such as recystallization, reprecipitation or other methods normally routinely used for the separation and purification of organic compounds, examples of which include adsorption column chromatography, distribution column chromatography and other methods using a synthetic adsorbent, methods using ion exchange chromatography, and forward and/or reverse phase chromatography using silica gel or alkylated silica gel, followed by eluting with a suitable eluent.

Oligosaccharide derivatives of the present invention having the aforementioned general formulas (I), (Ia) and (Ib), their pharmacologically acceptable salts and their pharmacologically acceptable esters are administered in various forms. There are no particular limitations on the administration form, and each type of preparation form is determined according to the formulation, the age, gender and other conditions of the patient, the degree of the disease and so forth. Examples of formulations in the case of oral administration include tablets, pills, powders, granules, syrups, liquids, suspensions, emulsions, granules and capsules. Administration is performed intrarectally in the case of suppositories. Administration is preferably performed orally.

Each of these formulations can be formulated in accordance with ordinary methods using known adjuvants that can normally be used in known pharmaceutical fields, examples of which include vehicles, binders, disintegration agents, lubricants, dissolving agents, correctives and coating agents.

When forming into the form of tablets, a wide range of carriers conventionally known in this field can be used for the carrier, examples of which include vehicles such as lactose, sucrose, sodium chloride, glucose, urea, starch, calcium carbonate, kaolin, crystalline cellulose and silicic acid, binders such as water, ethanol, propanol, simple syrup, liquid glucose, liquid starch, liquid gelatin, carboxymethyl cellulose, shellac, methyl cellulose, potassium phosphate and polyvinyl pyrrolidone, disintegration agents such as dry starch, sodium alginate, powdered agar, powdered laminarin, sodium bicarbonate, calcium carbonate, polyoxyethylene sorbitan fatty acid esters, sodium lauryl sulfate, monoglyceride stearate, starch and lactose, disintegration inhibitors such as sucrose, stearine, cocoa butter and hydrogenated oils, absorption promoters such as quaternary ammonium salts and sodium lauryl sulfate, moisturizers such as glycerin and starch, adsorbents such as starch, lactose, kaolin, bentonite and colloidal silicic acid, and lubricants such as refined talc, stearates, powdered boric acid and polyethylene glycol. Moreover, tablets can be tablets provided with an ordinary coating as necessary, examples of which include sugar-coated tablets, gelatin-sealed tablets, enteric coated tablets and film-coated tablets, tablets provided with two layers of coatings or multilayer tablets.

When forming into the form of pills, a wide range of carriers conventionally known in this field can be used for the carrier, examples of which include vehicles such as glucose, lactose, starch, cocoa butter, hardened vegetable oils, kaolin and talc, binders such as powdered gum Arabic, powdered tragacanth, gelatin and ethanol, and disintegration agents such as laminaran agar.

When forming into the form of suppositories, a wide range of carriers conventionally known in this field can be used for the carrier, examples of which include polyethylene glycol, cocoa butter, higher alcohols, esters of higher alcohols, gelatin and semi-synthetic glycerides.

Moreover, other pharmaceuticals such as colorants, preservatives, fragrances, flavorings and sweeteners may also be included as necessary.

Although there are no particular limitations on the amount of active ingredient compound contained in the aforementioned pharmaceutical preparations, and it can be suitably selected over a wide range, it is suitable to normally contain an amount of 1 to 70% by weight, and preferably 1 to 30% by weight, in the total composition.

Although varying according to symptoms, age, body weight, administration method, drug form and so forth, the normal daily adult dosage has a lower limit of 0.001 mg (preferably 0.01 mg and more preferably 0.1 mg), and an upper limit of 2,000 mg (preferably 200 mg and more preferably 100 mg), and this dosage can be administered in a single administration or in multiple administrations.

BEST MODE FOR CARRYING OUT THE INVENTION

Next, the present invention is explained in more detail by way of Examples, Reference examples, Test examples and Preparation examples, but the present invention is not limited thereto.

EXAMPLE 1

(2R,3R,4R)-4-Hydroxy-2-(hydroxymethyl)pyrrolidin-3-yl 4-O-(6-deoxy-α-D-glucopyranosyl)-α-D-glucopyranoside (Exemplification Compound No. 1-1)

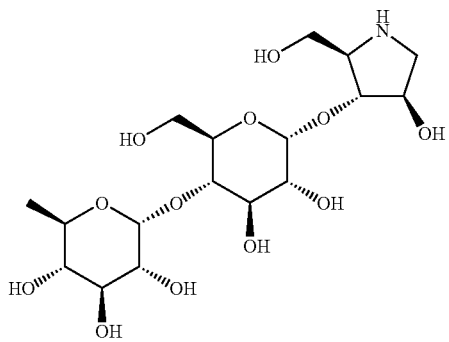

(1a) Allyl 4-O-(2,3,4,6-tetra-O-acetyl-α-D-glucopyranosyl)-2,3,6-tri-O-acetyl-D-glucopyranoside D-Maltose monohydrate (36.0 g, 100 mmol) was dissolved in pyridine (200 mL) and acetic anhydride (100 mL) and 4-dimethylaminopyridine (0.6 g, 4.90 mol) were added thereto, followed by stirring of the mixture at room temperature for 12 hours. The reaction mixture was ice-cooled and ice (30 g) was added thereto, followed by stirring of the mixture for 30 minutes. The reaction mixture was extracted with ethyl acetate (500 mL) and the organic layer was washed with diluted hydrochloric acid (1N, 200 mL), saturated aqueous sodium hydrogencarbonate (100 mL) and saturated brine (100 mL). After it was dried with anhydrous sodium sulfate, the solvent was distilled off under reduced pressure. The residue was dissolved in methylene chloride (700 mL) and allyl alcohol (34 mL, 500 mol) and trimethylsilyl trifluoromethanesulfonate (18.1 mL, 100 mmol) were added thereto, followed by stirring of the mixture at room temperature for 2 hours. The reaction mixture was added to saturated aqueous sodium hydrogencarbonate (1 L) and after it was extracted with methylene chloride (500 mL), the organic layer was washed with saturated brine (300 mL) and dried with anhydrous sodium sulfate, followed by distilling off of the solvent under reduced pressure. The residue was purified using silica gel flash column chromatography (ethyl acetate:hexane, 2:3, V/V) to obtain the desired title compound (30.0 g, yield 31%) as pale yellow amorphous matter.

$^1$H NMR (400 MHz, CDCl$_3$): δ 1.99 (3H, s), 2.00 (3H, s), 2.01 (6H, s), 2.03 (3H, s), 2.09 (3H, s), 2.14 (3H, s), 3.65-3.69 (1H, m), 3.93-4.14 (4H, m), 4.20-4.26 (2H, m), 4.30 (1H, dd, J=13.2, 5.1 Hz), 4.47 (1H, dd, J=12.4, 2.9 Hz), 4.57 (1H, d, J=8.1 Hz), 4.83-4.87 (2H, m), 5.04 (1H, t, J=9.5 Hz), 5.18-5.28 (3H, m), 5.35 (1H, t, J=9.5 Hz), 5.41 (1H, d, J=3.7 Hz), 5.79-5.88 (1H, m); MS (FAB) m/z: 677 (M+H)$^+$, 699 (M+Na)$^+$.

(1b) Allyl 4-O-(4,6-O-benzylidene-α-D-glucopyranosyl)-D-glucopyranoside

The compound (17.0 g, 25.1 mmol) synthesized in Example 1 (1a) was dissolved in methanol (250 mL) and sodium methoxide (2 mL, 9.8 mol) was added thereto under ice-cooling, followed by stirring of the mixture at room temperature for 1 hour. After Dowex 50w×8 was added to the mixture until the reaction mixture became neutral and was filtered, the solvent was distilled off under reduced pressure. The residue was dissolved in N,N-dimethylformamide (200 mL) and benzaldehyde dimethylacetal (4.65 mL, 31.0 mmol) and p-toluenesulfonic acid monohydrate (226 mg, 1.19 mmol) were added thereto, followed by stirring of the mixture at 20 mmHg and 50° C. for 5 hours. After triethylamine (1 mL) was added to the reaction mixture, the solvent was distilled off under reduced pressure. The residue was purified using silica gel flash column chromatography (ethyl acetate:hexane:methanol, 5:5:1, V/V/V) to obtain the desired title compound (10.0 g, yield 85%) as pale yellow amorphous matter.

$^1$H NMR (400 MHz, CD$_3$OD): δ 3.16 (1H, t, J=9.5 Hz), 3.28-3.32 (1H, m), 3.35 (1H, t, J=9.5 Hz), 3.42 (1H, t, J=9.5 Hz), 3.47 (1H, dd, J=9.5, 3.6 Hz), 3.54 (1H, t, J=9.5 Hz), 3.61-3.66 (2H, m), 3.71 (1H, t, J=9.5 Hz), 3.74-3.81 (2H, m), 4.02-4.07 (1H, m), 4.12 (1H, dd, J=10.3, 5.1 Hz), 4.22-4.29 (2H, m), 5.06 (1H, d, J=10.2 Hz), 5.10 (1H, d, J=4.4 Hz), 5.23 (1H, d, J=17.5 Hz), 5.81-5.91 (1H, m), 7.22-7.24 (3H, m), 7.38-7.40 (2H, m); MS (FAB) m/z: 471 (M+H)$^+$, 493 (M+Na)$^+$.

(1c) Allyl 4-O-(4,6-O-benzylidene-2,3-di-O-benzyl-α-D-glucopyranosyl)-2,3,6-tri-O-benzyl-D-glucopyranoside The compound (10.0 g, 21.3 mmol) synthesized in Example 1 (1b) was dissolved in N,N-dimethylformamide (300 mL) and sodium hydride (9.28 g, 213 mmol) was added thereto under ice-cooling, followed by stirring of the mixture under ice-cooling for 30 minutes. After benzyl bromide (25 mL, 213 mmol) was added thereto and the mixture was stirred at room temperature for 3 hours, water (100 mL) was added to the reaction mixture and the mixture was extracted with ethyl acetate (500 mL). The extract was washed with water (100 mL) and saturated brine (100 mL) and dried with anhydrous sodium sulfate, followed by distilling off of the solvent under reduced pressure. The residue was purified using silica gel flash column chromatography (hexane:ethyl acetate, 9:1, V/V) to obtain the desired title compound (18.5 g, yield 94%) as a pale yellow solid.

$^1$H NMR (400 MHz, CDCl$_3$): δ 3.49-3.68 (4H, m), 3.76-3.90 (3H, m), 3.93-4.03 (2H, m), 4.09-4.19 (3H, m), 4.42-4.78 (10H, m), 4.84-5.07 (3H, m), 5.23 (1H, t, J=9.8 Hz), 5.35 (1H, dd, J=17.5, 8.8 Hz), 5.54 (1H, d, J=3.9 Hz), 5.74 (1H, dd, J=24.5, 3.9 Hz), 5.92-6.02 (1H, m), 7.17-7.51 (5H, m); MS (FAB) m/z: 922 (M+H)$^+$, 944 (M+Na)$^+$.

(1d) Allyl 2,3,6-tri-O-benzyl-4-O-(2,3,4-tri-O-benzyl-α-D-glucopyranosyl)-D-glucopyranoside The compound (30.0 g, 32.5 mmol) synthesized in Example 1 (1c) was dissolved in diethyl ether (300 mL) and methylene chloride (150 mL) and lithium aluminium hydride (1.85 g, 48.8 mmol) and aluminium chloride (III) (6.93 g, 52.0 mmol) were added thereto, followed by heating of the mixture under reflux for 2 hours. After the reaction mixture was diluted with diethyl ether (500 mL), 1N aqueous sodium hydroxide solution (5.6 mL) was added to the reaction mixture, followed by stirring of the mixture for 1 hour. After it was extracted with ethyl acetate, the organic layer was washed with 10% aqueous hydrochloric acid solution (100 mL), saturated aqueous sodium hydrogencarbonate solution (150 mL) and saturated brine (100 mL) and dried with anhydrous sodium sulfate, followed by distilling off of the solvent under reduced pressure. The residue was purified using silica gel flash column chromatography (hexane:ethyl acetate, 4:1-3:1-2:1, V/V) to obtain the desired title compound (21.1 g, yield 71%) as a pale yellow solid.

$^1$H NMR (400 MHz, CDCl$_3$): δ 3.40-3.71 (6H, m), 3.74-3.85 (2H, m), 3.90 (2H, m), 3.99-4.07 (1H, m), 4.10-4.20 (3H, m), 4.42-4.70 (7H, m), 4.76-5.08 (6H, m), 5.23 (1H, t, J=10.7 Hz), 5.35 (1H, dd, J=18.6, 8.8 Hz), 5.64 (1H, dd, J=13.7, 3.9 Hz), 5.93-6.02 (1H, m), 7.18-7.34 (30H, m); MS (FAB) m/z: 946 (M+Na)$^+$, 924 (M+H)$^+$.

(1e) Allyl 2,3,6-tri-O-benzyl-4-O-(2,3,4-tri-O-benzyl-6-deoxy-α-D-glucopyranosyl)-D-glucopyranoside The compound (15.2 g, 16.5 mmol) synthesized in Example 1 (1d) was dissolved in pyridine (300 mL) and p-toluenesulfonyl chloride (12.5 g, 66.0 mmol) and 4-dimethylaminopyridine (2.01 g, 16.4 mmol) were added thereto, followed by stirring of the mixture at room temperature for 13 hours. After the solvent was distilled off under reduced pressure, the residue was poured into 10% aqueous hydrochloric acid solution (50 mL) and ethyl acetate (200 mL). The organic layer was washed with 10% aqueous hydrochloric acid solution (50 mL), saturated aqueous sodium hydrogencarbonate solution (20 mL) and saturated brine (20 mL) and dried with anhydrous sodium sulfate, followed by distilling off of the solvent under reduced pressure. The residue was purified using silica gel flash column chromatography (hexane:ethyl acetate, 5:1-3:1, V/V) to obtain tosylate (13.5 g, yield 76%) as a yellow oil. The tosylate (13.5 g, 12.5 mol) was dissolved in diethyl ether (300 mL) and lithium aluminium hydride (950 mg, 25 mol) was added to the reaction mixture, followed by heating of the mixture under reflux for 1 hour. 1N aqueous NaOH solution (1.0 mL) and water (1.0 mL) were added thereto and the mixture was stirred for 30 minutes. After celite filtration, the solvent was distilled off under reduced pressure. The residue was purified using silica gel flash column chromatography (hexane:ethyl acetate, 6:1, V/V) to obtain the desired title compound (10.2 g, yield 90%) as a colorless solid.

$^1$H NMR (400 MHz, CDCl$_3$): δ 1.08 (3H, d, J=5.8 Hz), 3.01 (1H, t, J=9.5 Hz), 3.35 (1H, dd, J=9.5, 3.7 Hz), 3.44-3.50 (2H, m), 3.66-3.72 (5H, m), 3.78 (1H, t, J=9.5 Hz), 3.93 (1H, t, J=9.5 Hz), 4.07 (1H, dd, J=12.8, 5.9 Hz), 4.35 (1H, dd, J=13.1, 5.1 Hz), 4.39-4.57 (7H, m), 4.69 (2H, d, J=11.7 Hz), 4.77-4.88 (3H, m), 5.13 (1H, d, J=10.0 Hz), 5.26 (1H, d, J=16.9 Hz), 5.47 (1H, d, J=3.7 Hz), 5.84-5.92 (1H, m), 7.09-7.26 (30H, m); MS (FAB) m/z: 907 (M+H)$^+$.

(1f) 4-O-(6-Deoxy-2,3,4-tri-O-benzyl-α-D-glucopyranosyl)-2,3,6-tri-O-benzyl-D-glucopyranoside The compound (10.2 g, 11.2 mmol) synthesized in Example 1 (1e) was dissolved in methanol (40 mL) and tetrahydrofuran (100 mL) and palladium chloride (II) (400 mg, 2.24 mmol) was added thereto, followed by stirring of the mixture at room temperature for 14 hours. After the reaction mixture was subjected to celite filtration, the solvent was distilled off under reduced pressure. The residue was purified using silica gel flash column chromatography (hexane:ethyl acetate, 5:1-4:1, V/V) to obtain the desired title compound (8.17 g, yield 84%) as pale yellow amorphous matter.

$^1$H NMR (400 MHz, CDCl$_3$): δ 1.14 (3H, d, J=6.6 Hz), 3.09 (1H, t, J=9.5 Hz), 3.41-3.47 (2H, m), 3.62-3.81 (4H, m), 3.96-4.05 (2H, m), 4.01-4.14 (1H, m), 4.49-4.68 (6H, m), 4.74-4.78 (2H, m), 4.84-4.96 (4H, m), 5.22 (1H, d, J=3.6 Hz), 5.51 (1H, d, J=3.7 Hz), 7.19-7.34 (30H, m); MS (FAB) m/z: 889 (M+Na)$^+$.

(1g) Methyl 3-O-benzoyl-N-benzoyloxycarbonyl-2,5-dideoxy-2,5-imino-α-D-lyxofuranoside Methyl N-benzoyloxycarbonyl-2,5-dideoxy-2,5-imino-α-D-lyxofuranoside (Tetrahedron, 1986, vol. 42, p. 5685-5692) (13.9 g, 49.8 mmol) was dissolved in methylene chloride (200 mL) and pyridine (20 mL, 249.0 mmol) and benzoyl chloride (11.6 mL, 99.6 mmol) were added thereto, followed by stirring of the mixture at room temperature for 2 hours. After 1N hydrochloric acid (200 mL) was added to the reaction mixture at 0° C. and the mixture was extracted with methylene chloride (100 mL), the organic layer was washed with saturated aqueous sodium hydrogencarbonate (200 mL) and saturated brine (200 mL) and dried with anhydrous sodium sulfate, followed by distilling off of the solvent under reduced pressure. The residue was purified using silica gel flash column chromatography (hexane:ethyl acetate, 5:1-3:1, V/V) to obtain the desired title compound (15.82 g, yield 83%) as a colorless solid.

$^1$H NMR (400 MHz, CDCl$_3$): δ 3.42-3.46 (4H, 3s), 3.60 (1H, dd, J=32.2, 10.8 Hz), 4.54 (1H, d, J=34.2 Hz), 4.64 (1H, br, d, J=7.9 Hz), 4.85 (1H, d, J=36.2 Hz), 5.13-5.22 (2H, m), 5.47 (1H, s), 7.29-7.35 (5H, m), 7.41-7.45 (2H, m), 7.59 (1H, t, J=7.8 Hz), 7.95 (2H, t, J=7.8 Hz); MS (FAB) m/z: 406 (M+Na)$^+$, 384 (M+H)$^+$.

(1h) Benzyl (2R,3R,4R)-3-benzoyloxy-4-hydroxy-2-(hydroxymethyl)pyrrolidine-1-carboxylate The compound (15.8 g, 41.3 mmol) synthesized in Example 1 (1g) was dissolved in trifluoroacetic acid:water (4:1, 160 mL) and the mixture was stirred at room temperature for 15 minutes. After water (200 mL) was added to the reaction mixture at 0° C. and the mixture was extracted with methylene chloride (300 mL), the organic layer was washed with saturated aqueous sodium hydrogencarbonate (200 mL) and saturated brine (200 mL) and dried with anhydrous sodium sulfate, followed by distilling off of the solvent under reduced pressure. The residue was dissolved in ethanol (150 mL) and the compound obtained by dissolving sodium borohydride (0.78 g, 20.7 mmol) in water (15 mL) was added thereto, followed by stirring of the mixture at 0° C. for 20 minutes. After saturated aqueous ammonium chloride (20 mL) was added to the reaction mixture at 0° C., ethanol was distilled off under reduced pressure. After water (100 mL) was added thereto and the mixture was extracted with ethyl acetate (100 mL), the organic layer was washed with saturated brine (100 mL) and dried with anhydrous sodium sulfate, followed by distilling off of the solvent under reduced pressure. The residue was purified using silica gel flash column chromatography (hexane:ethyl acetate, 1:1, V/V) to obtain the desired title compound (14.2 g, yield 89%) as a colorless oil.

$^1$H NMR (400 MHz, CDCl$_3$): δ 3.68 (1H, d, J=11.7 Hz), 3.86 (1H, dd, J=11.7, 4.4 Hz), 3.93-4.04 (2H, m), 4.25-4.32 (2H, m), 5.09-5.32 (3H, m), 7.32-7.46 (7H, m), 7.59 (1H, t, J=7.4 Hz), 7.99 (2H, d, J=8.8 Hz); MS (FAB) m/z: 372 (M+H)$^+$.

(1i) Benzyl (2R,3R,4R)-4-benzyloxy-2-benzyloxymethyl-3-hydroxypyrrolidine-1-carboxylate The compound (4.26 g, 11.5 mmol) synthesized in Example 1 (1h) was dissolved in dichloromethane:cyclohexane (1:2, 180 mL) and benzyl trichloroacetoimidate (10.6 mL, 57.5 mmol) and trifluoromethanesulfonic acid (0.15 mL, 1.7 mmol) were added thereto, followed by stirring of the mixture at room temperature for 3 hours. After saturated aqueous sodium hydrogencarbonate (10 mL) was added to the reaction mixture at 0° C. and the mixture was diluted with ethyl acetate (200 mL), it was washed with water (300 mL) and saturated brine (300 mL) and dried with anhydrous sodium sulfate, followed by distilling of the solvent under reduced pressure. The residue was purified using silica gel flash column chromatography (hexane:ethyl acetate, 10:1-5:1, V/V) to obtain 7.85 g of a pale yellow oil. Thus obtained 7.85 g of pale yellow oil was dissolved in methanol (100 mL) and 1M aqueous potassium carbonate solution (4 mL) was added thereto, followed by stirring of the mixture at room temperature for 5 hours. After methanol was distilled off under reduced pressure, water (100 mL) was added thereto and the mixture was extracted with ethyl acetate (100 mL) and then, the organic layer was washed with saturated brine (100 mL). After it was dried with anhydrous sodium sulfate, the solvent was distilled off under reduced pressure. The residue was purified using silica gel flash column chromatography hexane:ethyl acetate, 2:1, V/V) to obtain the desired title compound (4.06 g, yield 64%) as a colorless solid.

$^1$H NMR (400 MHz, CDCl$_3$): δ 3.35 (1H, dd, J=11.7, 3.7 Hz), 3.51-3.72 (1H, m), 3.66-3.89 (4H, m), 4.37-4.52 (5H, m), 4.98-5.07 (2H, m), 7.09-7.26 (15H, m); MS (FAB) m/z: 448 (M+H)$^+$.

(1j) Benzyl (2R,3R,4R)-4-benzyloxy-2-benzyloxymethyl-3-{[2,3,6-tri-O-benzyl-4-O-(2,3,4-tri-O-benzyl-6-deoxy-α-D-glucopyranosyl)-α-D-glucopyranosyl]oxy}pyrrolidine-1-carboxylate Benzyl(2R,3R,4R)-4-benzyloxy-2-benzyloxymethyl-3-{[2,3,6-tri-O-benzyl-4-O-(2,3,4-tri-O-benzyl-6-deoxy-α-D-glucopyranosyl)-β-D-glucopyranosyl]oxy}pyrrolidine-1-carboxylate The compound (13.5 g, 15.57 mmol) synthesized in Example 1 (1f) was dissolved in methylene chloride (250 mL) and trichloroacetonitrile (10 mL, 134.3 mmol) and 1,8-diazabicyclo[5.4.0]-7-undecene (2 drops) were added thereto, followed by stirring of the mixture at room temperature for 40 minutes. After the solvent was distilled off under reduced pressure, the residue was purified using silica gel flash column chromatography (hexane:ethyl acetate, 5:1, 1% triethylamine, V/V) to obtain imidate (13.0 g, 82%) as a yellow oil. The compound (5.48 g, 12.2 mmol) synthesized in Example 1 (1i) was dissolved in diethyl ether (400 mL) and imidate (13.0 g, 13.0 mmol) was added thereto. A solution of trimethylsilyl trifluoromethanesulfonate (222 μL, 1.22 mmol) in diethyl ether (2 mL) was added thereto and the mixture was stirred at room temperature for 45 minutes. After triethylamine (1 mL) was added to the reaction mixture, the solvent was distilled off under reduced pressure. The residue was purified using silica gel flash column chromatography (hexane:diethyl ether, 4:1, V/V) to obtain the desired title compound α isomer (11.6 g, 56%) as a pale yellow oil and further the β isomer (3.7 g, 18%) as a pale yellow oil.

α isomer: $^1$H NMR (400 MHz, CDCl$_3$): δ 1.20 (3H, d, J=5.9 Hz), 3.10-3.22 (2H, m), 3.30-3.38 (2H, m), 3.42 (1H, t, J=8.8 Hz), 3.50-3.70 (5H, m), 3.76-3.87 (5H, m), 4.01-4.10 (1H, m), 4.26-4.51 (9H, m), 4.61 (1H, d, J=11.0 Hz), 4.69-4.88 (8H, m), 4.96-5.16 (3H, m), 7.19-7.34 (43H, m), 7.43 (2H, d, J=7.3 Hz); MS (FAB) m/z: 1318 (M+Na)$^+$.

β isomer: $^1$H NMR (400 MHz, CDCl$_3$): δ 1.17 (3H, d, J=6.5 Hz), 3.10 (1H, t, J=9.1 Hz), 3.41-3.48 (3H, m), 3.54-3.63 (3H, m), 3.69-3.78 (4H, m), 3.81-3.92 (2H, m), 4.02 (1H, s, J=8.79 Hz), 4.25 (1H, d, J=4.39 Hz), 4.40-4.63 (13H, m), 4.73-4.79 (3H, m), 4.86-4.95 (4H, m), 5.09-5.19 (1H, m), 5.53 (1H, d, J=3.67 Hz), 7.18-7.30 (45H, m); MS (FAB) m/z: 1296 (M+H)$^+$.

(1k) (2R,3R,4R)-4-Hydroxy-2-(hydroxymethyl)pyrrolidin-3-yl 4-O-(6-deoxy-α-D-glucopyranosyl)-α-D-glucopyranoside The compound (5.60 g, 4.32 mmol) synthesized in Example 1 (1j) was dissolved in methanol (350 mL) and hydrochloric acid (4.8 mL) and 20% palladium hydroxide-carbon (2.8 g) were added thereto, followed by stirring of the mixture at room temperature under a hydrogen atmosphere for 4 hours. After celite filtration, 18% ammonia water (6 mL) was added thereto and the solvent was distilled off under reduced pressure. The residue was purified by ion exchange resin (Dowex 50w×8) column (water—5% ammonia water). Further, it was purified using silica gel flash column chromatography (ethyl acetate:methanol:water, 2:2:1, V/V) to obtain the desired title compound (1.20 g, 63%) as a colorless solid.

[α]D20 +145.7 (c 0.36, H$_2$O); $^1$H NMR (400 MHz, D$_2$O): δ 1.28 (3H, d, J=6.6 Hz), 2.93 (1H, dd, J=12.4, 3.0 Hz), 3.12-3.20 (3H, m), 3.57-3.65 (4H, m), 3.71-3.87 (6H, m), 3.92-3.98 (2H, m), 4.32-4.34 (1H, m), 5.13 (1H, d, J=3.6 Hz), 5.34 (1H, d, J=3.0 Hz); $^{13}$CNMR (125.70 MHz, D$_2$O): δ 16.72, 51.62, 60.64, 61.62, 64.84, 68.79, 70.94, 71.07, 72.13, 72.83, 73.48, 74.96, 75.64, 77.13, 84.01, 97.44, 99.88; MS (FAB) m/z: 442 (M+H)$^+$, 464 (M+Na)$^+$.

EXAMPLE 2

(2R,3R,4R)-4-Hydroxy-2-(hydroxymethyl)pyrrolidin-3-yl 4-O-(6-deoxy-β-D-glucopyranosyl)-α-D-glucopyranoside (Exemplification Compound No. 1-1)

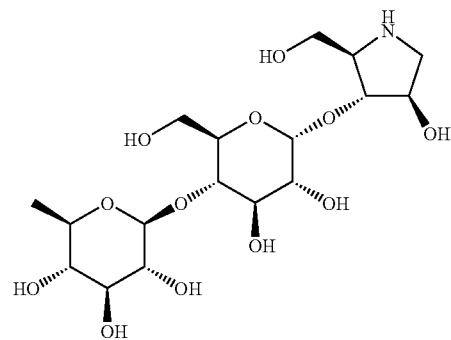

(2a) Allyl 4-O-β-D-glucopyranosyl-D-glucopyranoside

α-D-cellobiose octacetate (48.59 g, 71.6 mmol) was dissolved in methylene chloride (600 mL), and allyl alchol (29 mL, 0.43 mol) and trimethylsilyl trifluoromethanesulfonate (16 mL, 86.0 mmol) were added thereto under ice-cooling, followed by stirring of the mixture at room temperature for 1.5 hours. Water (200 mL) was added to the reaction mixture and the mixture was extracted with methylene chloride (200 mL). After the extract was washed with saturated brine (100 mL) and dried with anhydrous sodium sulfate, the solvent was distilled off under reduced pressure. The residue was dissolved in methanol (300 mL) and sodium methoxide (28 mL, 0.14 mol) was added thereto under ice-cooling, followed by stirring of the mixture at room temperature for 2 hours. After Dowex 50w×8 was added thereto until the reaction mixture became neutral and it was filtered, the solvent was distilled off under reduced pressure. The residue was purified using silica gel flash column chromatography (ethyl acetate:methanol:water, 8:2:1, V/V) to obtain the desired title compound (24.8 g, yield 91%) as pale yellow amorphous matter.

$^1$H NMR (400 MHz, CDCl$_3$): δ 3.20-3.40 (9H, m), 3.40-3.65 (4H, m), 4.00-4.40 (3H, m), 5.18 (1H, d, J=11.7 Hz), 5.35 (1H, d, J=17.6 Hz), 5.95 (1H, ddd, J=17.6, 11.7, 5.9 Hz); MS (FAB) m/z: 383 (M+H)$^+$.

(2b) Allyl 2,3,6-tri-O-benzyl-4-O-(2,3-di-O-benzyl-4,6-O-benzylidene-β-D-glucopyranosyl)-D-glucopyranoside The compound (24.8 g, 64.9 mmol) synthesized in Example 2 (2a) was dissolved in N,N-dimethylformamide (300 mL) and benzaldehyde dimethylacetal (13 mL, 84.4 mmol) and p-toluenesulfonic acid monohydrate (617 mg, 3.24 mmol) were added thereto, followed by stirring of the mixture at 20 mmH g and 50° C. for 5 hours. After triethylamine (900 μL) was added to the reaction mixture, the solvent was distilled off under reduced pressure. Water (100 mL) was added to the residue and the mixture was extracted with ethyl acetate (200 mL×5). After the extract was washed with saturated brine (100 mL) and dried with anhydrous sodium sulfate, the solvent was distilled off under reduced pressure. The residue was dissolved in N,N-dimethylformamide (400 mL) and sodium hydride (20 g, 0.45 mmol) was added thereto under ice-cooling, followed by stirring of the mixture at the same temperature for 10 minutes. Benzyl bromide (54 mL, 0.45 mmol) was added thereto and the mixture was stirred at room temperature for 2.5 hours. Water (100 mL) was added to the reaction mixture and the mixture was extracted with ethyl acetate (500 mL). After the extract was washed with water (100 mL) and saturated brine (50 mL) and dried with anhydrous sodium sulfate, the solvent was distilled off under reduced pressure. The residue was purified using silica gel flash column chromatography (hexane:ethyl acetate, 10:1-7:1, V/V) to obtain the desired title compound (46.6 g, yeild 78%) as a pale yellow solid.

$^1$H NMR (400 MHz, CDCl$_3$): δ 3.10-5.00 (26H, m), 5.18 (1H, d, J=11.7 Hz), 5.35 (1H, d, J=17.6 Hz), 5.60 (1H, s), 5.95 (1H, ddd, J=17.6, 11.7, 5.9 Hz), 7.20-7.60 (30H, m); MS (FAB) m/z: 922 (M+H)$^+$.

(2c) Allyl 2,3,6-tri-O-benzyl-4-O-(2,3,4-tri-O-benzyl-β-D-glucopyranosyl)-D-glucopyranoside The compound (63.0 g, 68.4 mmol) synthesized in Example 2 (2b) was dissolved in diethyl ether (800 mL) and methylene chloride (400 mL) and lithium aluminium hydride (10.4 g, 0.27 mol) and aluminium chloride (III) (36.4 g, 0.27 mol) were added thereto, followed by heating of the mixture under reflux for 1 hour. After the reaction mixture was diluted with diethyl ether (500 mL). 1N aqueous sodium hydroxide solution (21.0 mL) was added to the reaction mixture and the mixture was stirred for 1 hour. After extraction with ethyl acetate, the organic layer was washed with 10% aqueous hydrochloric acid solution (500 mL), saturated aqueous sodium hydrogencarbonate solution (500 mL) and saturated brine (300 mL) and dried with anhydrous sodium sulfate, followed by distilling off of the solvent reduced pressure. The residue was purified using silica gel flash column chromatography (hexane:ethyl acetate, 4:1-3:1-2:1, V/V) to obtain the desired title compound (37.8 g, yield 60%) as a pale yellow solid.

$^1$H NMR (400 MHz, CDCl$_3$): δ 3.10-5.00 (29H, m), 5.18 (1H, d, J=10.8 Hz), 5.35 (1H, d, J=22.5 Hz), 5.95 (1H, ddd, J=22.5, 10.8, 5.9 Hz), 7.20-7.60 (30H, m); MS (FAB) m/z: 924 (M+H)$^+$.

(2d) Allyl 2,3,6-tri-O-benzyl-4-O-(2,3,4-tri-O-benzyl-6-toluenesulfonyl-β-D-glucopyranosyl)-D-glucopyranoside The compound (37.8 g, 41.0 mmol) synthesized in Example 2 (2c) was dissolved in pyridine (300 mL) and p-toluenesulfonyl chloride (15.6 g, 82.0 mmol) and 4-dimethylaminopyridine (1.0 g, 0.82 mmol) were added thereto, followed by stirring of the mixture at room temperature for 13 hours. After the solvent was distilled off under reduced pressure, the residue was poured to 10% aqueous hydrochloric acid solution (50 mL) and ethyl acetate (200 mL) and the organic layer was washed with 10% aqueous hydrochloric acid solution (50 mL), saturated aqueous sodium hydrogencarbonate solution (20 mL) and saturated brine (20 mL) and dried with anhydrous sodium sulfate, followed by distilling off of the solvent under reduced pressure. The residue was purified using silica gel flash column chromatography (hexane:ethyl acetate, 5:1-3:1, V/V) to obtain the desired title compound (32.6 g, yield 74%) as a yellow oil.

$^1$H NMR (400 MHz, CDCl$_3$): δ 2.35 (3H, s), 3.10-5.00 (28H, m), 5.18 (1H, d, J=10.8 Hz), 5.35 (1H, d, J=22.5 Hz), 5.95 (1H, ddd, J=22.5, 10.8, 5.9 Hz), 7.10-7.65 (34H, m); MS (FAB) m/z: 1078 (M+H)$^+$.

(2e) Allyl 2,3,6-tri-O-benzyl-4-O-(2,3,4-tri-O-benzyl-6-deoxy-β-D-glucopyranosyl)-D-glucopyranoside The compound (32.6 g, 30.3 mol) synthesized in Example 2 (2d) was dissolved in diethyl ether (600 mL) and lithium aluminium hydride (1.72 g, 45.4 mol) was added thereto, followed by heating of the mixture under reflux for 1 hour. After the reaction mixture was diluted with diethyl ether (200 mL), 1N aqueous NaOH solution (2.0 mL) and water (2.0 mL) were added thereto, followed by stirring of the mixture for 30 minutes. After celite filtration, the solvent was distilled off under reduced pressure. The residue was purified using silica gel flash column chromatography (hexane:ethyl acetate, 7:1-6:1, V/V) to obtain the desired title compound (15.0 g, yield 55%) as a colorless solid.

¹H NMR (400 MHz, CDCl₃): δ 1.20 (3H, d, J=6.0 Hz), 3.10-5.00 (26H, m), 5.20 (1H, d, J=10.8 Hz), 5.35 (1H, d, J=22.5 Hz), 5.95 (1H, ddd, J=22.5, 10.8, 5.9 Hz), 7.10-7.65 (30H, m); MS (FAB) m/z: 908 (M+H)⁺.

(2f) 2,3,6-tri-O-Benzyl-4-O-(2,3,4-tri-O-benzyl-6-deoxy-β-D-glucopyranosyl)-D-glucopyranoside The compound (15.0 g, 16.5 mmol) synthesized in Example 2 (2e) was dissolved in methanol (150 mL) and tetrahydrofuran (30 mL) and palladium chloride (II) (586 mg, 3.31 mmol) was added thereto, followed by stirring of the mixture at room temperature for 14 hours. After the reaction mixture was subjected to celite filtration, the solvent was distilled off under reduced pressure. The residue was purified using silica gel flash column chromatography (hexane:ethyl acetate, 5:1-4:1-3:1, V/V) to obtain the desired title compound (12.0 g, yield 84%) as pale yellow amorphous matter.

¹H NMR (400 MHz, CDCl₃): δ 1.19-1.22 (3H, m), 2.96-3.66 (8H, m), 3.77-4.02 (3H, m), 4.34-4.37 (2H, m), 4.54-4.89 (10H, m), 5.00-5.19 (2H, m), 7.23-7.45 (30H, m); MS (FAB) m/z: 868 (M+H)⁺.

(2g) Benzyl (2R,3R,4R)-4-benzyloxy-2-benzyloxymethyl-3-{[2,3,6-tri-O-benzyl-4-O-(2,3,4-tri-O-benzyl-6-deoxy-β-D-glucopyranosyl)-α-D-glucopyranosyl]oxy}pyrrolidine-1-carboxylate The compound (18.8 g, 21.8 mmol) synthesized in Example 2 (2f) was dissolved in methylene chloride (400 mL) and trichloroacetonitrile (10.9 mL, 109 mmol) and 1,8-diazabicyclo[5.4.0]-7-undecene (0.33 mL, 2.18 mmol) were added thereto, followed by stirring of the mixture at room temperature for 15 minutes. After the solvent was distilled off under reduced pressure, the residue was purified using silica gel flash column chromatography (hexane:ethyl acetate, 5:1, 1% triethylamine, V/V) to obtain imidate (19.8 g, 90%) of colorless oil. The compound (9.5 g, 21.2 mmol) synthesized in Example 1 (1i) was dissolved in diethyl ether (480 mL) and trimethylsilyl trifluoromethanesulfonate (0.38 mL, 2.12 mmol) was dissolved in diethyl ether (20 mL) under a nitrogen atmosphere and the mixture was added thereto. A solution of imidate in diethyl ether (100 mL) was added to the reaction mixture and the mixture was stirred at room temperature for 3 hours. After triethylamine (0.35 mL, 2.54 mmol) was added to the reaction mixture and the solvent was distilled off under reduced pressure, the mixture was diluted with ethyl acetate (200 mL) and washed with saturated aqueous sodium hydrogencarbonate (200 mL) and saturated brine (200 mL). After the organic layer was dried with anhydrous sodium sulfate, the solvent was distilled off under reduced pressure and the residue was purified using silica gel flash column chromatography (hexane:diethyl ether, 3:1, V/V) to obtain the desired title compound (13.3 g, 47%) and its β isomer (4.5 g, 16%) as a colorless oil.

¹H NMR (400 MHz, CDCl₃): δ 1.20 (3H, d, J=5.9 Hz), 3.10-3.22 (2H, m), 3.30-3.38 (2H, m), 3.42 (1H, t, J=8.8 Hz), 3.50-3.70 (5H, m), 3.76-3.87 (5H, m), 4.01-4.10 (1H, m), 4.26-4.51 (9H, m), 4.61 (1H, d, J=11.0 Hz), 4.69-4.88 (8H, m), 4.96-5.16 (3H, m), 7.19-7.34 (43H, m), 7.43 (2H, d, J=7.3 Hz); MS (FAB) m/z: 1318 (M+Na)⁺.

(2h) (2R,3R,4R)-4-Hydroxy-2-(hydroxymethyl)pyrrolidin-3-yl 4-O-(6-deoxy-β-D-glucopyranosyl)-α-D-glucopyranoside The compound (13.3 g, 10.3 mmol) synthesized in Example 2 (2 g) was dissolved in 1% hydrochloric acid methanol solution (250 mL) and 20% palladium hydroxide-carbon (4 g) was added thereto, followed by stirring of the mixture under a hydrogen atmosphere for 2 hours. After the catalyst was removed by celite filtration, 28% ammonia water (5 mL) was added thereto and the mixture was stirred for 10 minutes. After the solvent was distilled off under reduced pressure and the residue was passed through ion exchange resin (Dowex 50w×8) column with water (200 mL), 1% ammonia water (200 mL) was flowed through. The ammonia water containing the desired compound was concentrated under reduced pressure and was purified using silica gel flash column chromatography (ethyl acetate:methanol:water, 5:2:1-1:1:1, V/V) to obtain the desired title compound (1.6 g, 35%) as a colorless solid.

[α]D²⁰ +88.8 (c 0.52, H₂O); ¹H NMR (500 MHz, D₂O): δ 1.22 (3H, d, J=6.8 Hz), 2.88 (1H, m), 3.07-3.16 (3H, m), 3.21 (1H, dd, J=7.8, 7.8 Hz), 3.36 (1H, dd, J=9.8, 9.8 Hz), 3.42 (1H, m), 3.49-3.55 (2H, m), 3.61-3.72 (5H, m), 3.75-3.83 (2H, m), 3.89 (1H, m), 4.24 (1H, m), 4.38 (1H, d, J=7.9 Hz), 5.02 (1H, d, J=3.9 Hz); ¹³C NMR (D₂O): δ 16.9, 51.7, 60.0, 61.8, 64.7, 71.0, 71.1, 71.6, 72.2, 73.6, 75.0, 75.5, 75.9, 79.2, 84.3, 97.4, 102.7; MS (FAB) m/z: 442 (M+H)⁺.

EXAMPLE 3

(2R,3R,4R)-4-Hydroxy-2-(hydroxymethyl)pyrrolidin-3-yl 4-O-β-D-glucopyranosyl-α-D-glucopyranoside (Exemplification Compound No. 1-155)

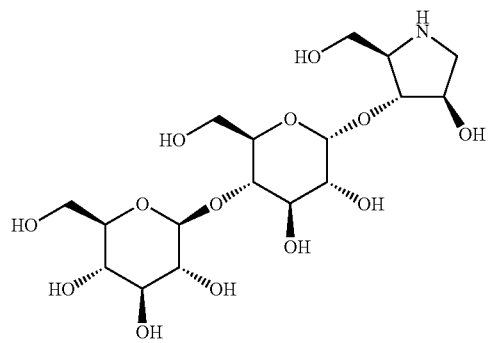

(3a) Allyl 2,3,6-tri-O-benzyl-4-O-(2,3,4,6-tetra-O-benzyl-β-D-glucopyranosyl)-D-glucopyranoside α-D-Cellobiose octaacetate (4.15 g, 6.12 mmol) was dissolved in methylene chloride (50 mL) and allyl alcohol (2.09 mL, 30.6 mmol) and trimethylsilyl trifluoromethanesulfonate (1.11 mL, 6.12 mmol) were added thereto under ice-cooling, followed by stirring of the mixture at room temperature for 4 hours. After water (20 mL) was added to the reaction mixture and the mixture was extracted with methylene chloride (50 mL), the organic layer was washed with saturated brine (20 mL) and dried with anhydrous sodium sulfate, followed by distilling off of the solvent under reduced pressure. The residue was dissolved in methanol (40 mL) and sodium methoxide (2.36 mL, 12.2 mmol)

was added thereto under ice-cooling, followed by stirring of the mixture at room temperature for 1 hour. After Dowex 50w×8 was added until the reaction mixture became neutral and the mixture was filtered, the solvent was distilled off under reduced pressure. The residue was dissolved in N,N-dimethylformamide (60 mL) and sodium hydride (2.67 g, 61.2 mmol) was added thereto under ice-cooling, followed by stirring of the mixture at the same temperature for 10 minutes. Benzyl bromide (8.01 mL, 67.3 mmol) was added thereto and the mixture was stirred at room temperature for 2 hours. After water (40 mL) was added thereto and the mixture was extracted with ethyl acetate (200 mL), the organic layer was washed with water (40 mL) and saturated brine (20 mL) and dried with anhydrous sodium sulfate, followed by distilling off of the solvent under reduced pressure. The residue was purified using silica gel flash column chromatography (hexane:ethyl acetate, 20:1-10:1-8:1, V/V) to obtain the desired title compound (4.85 g, yield 78%) as a pale yellow solid.

$^1$H NMR (400 MHz, CDCl$_3$): δ 3.29-3.71 (10H, m), 3.80-4.15 (3H, m), 4.36-4.61 (8H, m), 4.67-4.89 (8H, m), 5.04-5.11 (1H, m), 5.17-5.22 (1H, m), 5.29-5.34 (1H, m), 5.91-5.98 (1H, m), 7.07-7.41 (35H, m); MS (FAB) m/z: 1014 (M+H)$^+$.

(3b) 2,3,6-tri-O-Benzyl-4-O— (2,3,4,6-tetra-O-benzyl-β-D-glucopyranosyl)-D-glucopyranoside The compound (4.85 g, 4.79 mmol) synthesized in Example 3 (3a) was dissolved in dimethylsulfoxide (40 mL) and potassium t-butoxide (2.15 g, 19.2 mmol) was added thereto, followed by stirring of the mixture at 110° C. for 1 hour. After water (30 mL) was added to the reaction mixture and the mixture was extracted with ethyl acetate (150 mL), the organic layer was washed with saturated brine (20 mL) and dried with anhydrous sodium sulfate, followed by distilling off of the solvent under reduced pressure. The residue was dissolved in 1,4-dioxane (36 mL) and 16% aqueous sulfuric acid solution (3 mL) was added thereto, followed by stirring of the mixture at 100° C. for 1 hour. After water (30 mL) was added to the reaction mixture and the mixture was extracted with ethyl acetate (150 mL), the organic layer was washed with saturated brine (20 mL) and dried with anhydrous sodium sulfate, followed by distilling off of the solvent under reduced pressure. The residue was purified using silica gel flash column chromatography (hexane:ethyl acetate, 4:1 3:1, V/V) to obtain the desired title compound (3.15 g, yield 68%) as a brown oil.

$^1$H NMR (400 MHz, CDCl$_3$): δ 2.96-3.95 (9H, m), 4.30-4.38 (3H, m), 4.45-4.81 (7H, m), 4.98-5.10 (1H, m), 7.09-7.32 (35H, m); MS (FAB) m/z: 974 (M+H)$^+$.

(3c) (2R,3R,4R)-4-Benzyloxy-N-benzyloxycarbonyl-2-benzyloxymethyl-pyrrolidin-3-yl 2,3,6-tri-O-benzyl-4-O-(2,3,4,6-tetra-O-benzyl-β-D-glucopyranosyl)-α-D-glucopyranoside The compound (537 mg, 0.55 mmol) synthesized in Example 3 (3b) was dissolved in methylene chloride (15 mL) and trichloroacetonitrile (277 μL, 2.76 mmol) and 1,8-diazabicyclo[5.4.0]-7-undecene (2 drops) were added thereto, followed by stirring of the mixture at room temperature for 40 minutes. After the solvent was distilled off under reduced pressure, the residue was purified using silica gel flash column chromatography (hexane:ethyl acetate, 5:1, 1% triethylamine, V/V) to obtain imidate (611 mg, 99%) as a yellow oil. The compound (223 mg, 0.50 mmol) synthesized in Example 1 (1i) was dissolved in diethyl ether (10 mL) and trimethylsilyl trifluoromethanesulfonate (9 μL, 0.05 mmol) was added thereto. A solution of imidate (611 mg, 0.55 mmol) in diethyl ether (4 mL) was added dropwise thereto and the mixture was stirred at room temperature for 45 minutes. After triethylamine (4 drops) was added to the reaction mixture, the solvent was distilled off under reduced pressure. The residue was purified using silica gel flash column chromatography (hexane:diethyl ether, 2:1, V/V) to obtain the desired title compound (395 mg, 57%) as a pale yellow oil.

$^1$H NMR (400 MHz, CDCl$_3$): δ 3.24-3.86 (17H, m), 4.00-4.10 (2H, m), 4.25-4.54 (11H, m), 4.66-4.87 (8H, m), 4.95-5.12 (3H, m), 7.12-7.39 (50H, m); MS (FAB) m/z: 1402 (M+H)$^+$.

(3d) (2R,3R,4R)-4-Hydroxy-2-hydroxymethyl-pyrrolidin-3-yl 4-O-β-D-glucopyranosyl-α-D-glucopyranoside The compound (611 mg, 0.55 mmol) synthesized in Example 3 (3c) was dissolved in methanol (8 mL) and ethyl acetate (2 mL) and hydrochloric acid-methanol solution (2 mL) and 20% palladium hydroxide-carbon (400 mg) were added thereto, followed by stirring of the mixture at room temperature under a hydrogen atmosphere for 4 hours. After the celite filtration, the solvent was distilled off under reduced pressure and methanol (2 mL) and 28% ammonia water (300 μL) were added thereto, followed by stirring of the mixture at room temperature for 10 minutes. After the solvent was distilled off under reduced pressure, the residue was purified by ion exchange resin (Dowex 50w×8) column (water—1.4% ammonia water). Further, it was purified using silica gel flash column chromatography (ethyl acetate:methanol:water, 1:1:1, V/V) to obtain the desired title compound (54 mg, 42%) as colorless amorphous matter.

[α]D20 +91.9 (c 0.38, D$_2$O); $^1$H NMR (400 MHz, D$_2$O): δ 2.90 (1H, dd, J=12.5, 2.2 Hz), 3.11 (1H, dd, J=12.5, 5.1 Hz), 3.16-3.22 (2H, m), 3.28-3.43 (3H, m), 3.49-3.82 (10H, m), 3.88-3.91 (1H, m), 4.23-4.27 (1H, m), 4.40 (1H, d, J=8.1 Hz), 5.01 (1H, d, J=4.4 Hz); MS (FAB) m/z: 458 (M+H)$^+$.

EXAMPLE 4

(2R,3R,4R)-4-Hydroxy-2-hydroxymethyl-pyrrolidin-3-yl 4-O-(6-fluoro-6-deoxy-β-D-glucopyranosyl)-D-glucopyranoside (Exemplification Compound No. 1-278)

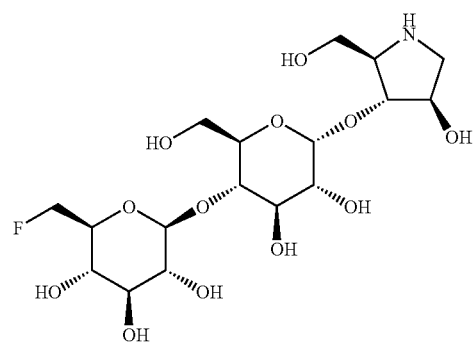

(4a) Allyl 2,3,6-tri-O-benzyl-4-O-(2,3,4-tri-O-benzyl-6-fluoro-6-deoxy-β-D-glucopyranosyl)-α-D-glucopyranoside The compound (6.43 g, 6.97 mmol) synthesized in Example 2 (2c) was dissolved in 1,2-dimethoxyethane (130 mL) and diethylaminosulfur trifluoride (2 mL, 20.50 mmol) was added thereto, followed by stirring of the mixture at 60° C. for 1 hour. Methanol (10 mL) was added to the reaction mixture under ice-cooling and the mixture was stirred for 30 minutes. After ethyl acetate (50 mL) was added thereto and the organic layer was washed with saturated aqueous sodium hydrogencarbonate solution (50 mL) and saturated brine (50 mL) and dried with anhydrous sodium sulfate, the solvent was distilled off under reduced pressure. The residue was purified using silica gel flash column chromatography (hexane:ethyl acetate, 6:1, V/V) to obtain the desired title compound (5.06 g, yield 78%) as a yellow solid.

$^1$H NMR (400 MHz, CDCl$_3$): δ 3.00-5.20 (28H, m), 5.25 (1H, d, J=8.0 Hz), 5.40 (1H, d, J=16.0 Hz), 6.00 (1H, m), 7.20-7.60 (30H, m); MS (FAB) m/z: 926 (M+H)$^+$.

(4b) Allyl 2,3,6-tri-O-benzyl-4-O-(2,3,4-tri-O-benzyl-6-fluoro-6-deoxy-β-D-glucopyranosyl)-D-glucopyranoside The compound (5.06 g, 5.47 mmol) synthesized in Example 4 (4a) was dissolved in methanol (75 mL) and tetrahydrofuran (15 mL) and palladium chloride (II) (190 mg, 1.09 mmol) was added thereto, followed by stirring of the mixture at room temperature for 14 hours. After the reaction mixture was subjected to celite filtration, the solvent was distilled off under reduced pressure. The residue was purified using silica gel flash column chromatography (hexane:ethyl acetate, 4:1-3:1-2:1, V/V) to obtain the desired title compound (3.07 g, yield 63%) as pale yellow amorphous matter.

$^1$H NMR (400 MHz, CDCl$_3$): δ 3.10-5.20 (27H, m), 7.20-7.60 (30H, m); MS (FAB) m/z: 886 (M+H)$^+$.

(4c) (2R,3R,4R)-4-Benzyloxy-N-benzyloxycarbonyl-2-(benzyloxymethyl)pyrrolidin-3-yl 2,3,6-tri-O-benzyl-4-O-(2,3,4-tri-O-benzyl-6-fluoro-6-deoxy-β-D-glucopyranosyl)-α-D-glucopyranoside The compound (646.0 mg, 0.73 mmol) synthesized in Example 4 (4b) was dissolved in methylene chloride (12 mL) and trichloroacetonitrile (0.38 mL, 3.66 mmol) and 1,8-diazabicyclo[5.4.0]undec-7-ene (1 drop) were added thereto, followed by stirring of the mixture at room temperature for 30 minutes. After the solvent was distilled off under reduced pressure, the residue was purified using silica gel flash column chromatography (hexane:ethyl acetate, 4:1, 1% triethylamine, V/V) to obtain imidate (740.2 mg, 98.5%) of yellow oil. The compound (326.7 mg, 0.73 mmol) synthesized in Example 1 (1i) was dissolved in diethyl ether (13 mL) and trimethylsilyl trifluoromethanesulfonate (6.6 μL, 0.037 mmol) was dissolved in diethyl ether (2 mL) under a nitrogen atmosphere and the mixture was added thereto. A solution of imidate (740.2 mg) in diethyl ether (5 mL) was added to the reaction mixture and the mixture was stirred at room temperature for 2 hours. After triethylamine (5.0 μL, 0.036 mmol) was added to the reaction mixture and the solvent was distilled off under reduced pressure, the residue was diluted with ethyl acetate (20 mL) and washed with saturated aqueous sodium hydrogencarbonate (20 mL) and saturated brine (20 mL). After the organic layer was dried with anhydrous sodium sulfate, the solvent was distilled off under reduced pressure and the residue containing α, β-mixture was purified using silica gel flash column chromatography (hexane:ethyl acetate, 6:1, V/V) to isolate the desired title compound α form (126.0 mg, 13%) as a colorless oil.

$^1$H NMR (400 MHz, CDCl$_3$): δ 3.00-5.20 (39H, m), 7.00-7.60 (45H, m); MS (FAB) m/z: 1315 (M+H)$^+$.

(4d) (2R,3R,4R)-4-Hydroxy-2-hydroxymethyl-pyrrolidin-3-yl 4-O-(6-fluoro-6-deoxy-β-D-glucopyranosyl)-α-D-glucopyranoside The compound (126.0 mg, 0.096 mmol) synthesized in Example 4 (4c) was dissolved in methanol (10 mL) containing 1% aqueous hydrochloric acid solution and 20% palladium hydroxide-carbon (100 mg) was added thereto, followed by stirring of the mixture under a hydrogen atmosphere for 2 hours. After the solvent was removed by celite filtration, 28% ammonia water (0.5 mL) was added thereto, followed by stirring of the mixture for 10 minutes. After the solvent was distilled off under reduced pressure and the aqueous solution (100 mL) was subjected to ion exchange resin (Dowex 50w×8), it was eluted with 1% ammonia water (100 mL). The ammonia water containing the desired compound was concentrated under reduced pressure and the residue was purified using silica gel flash column chromatography (ethyl acetate:methanol:water, 5:2:1-1:1:1, V/V) to obtain the desired title compound (23.1 mg, 52%) as colorless amorphous matter.

[α]D20 +49.6 (c 0.30, H$_2$O); $^1$H NMR (400 MHz, D$_2$O): δ 3.00-3.07 (1H, m), 3.20-3.27 (2H, m), 3.30-3.80 (21H, m), 3.95 (1H, s), 4.29 (1H, brs), 4.43 (1H, d, J=8.0 Hz), 4.50-4.80 (2H, m), 5.00 (1H, d, J=4.0 Hz); MS (FAB) m/z: 460 (M+H)$^+$.

EXAMPLE 5

(2R,3R,4R)-4-Hydroxy-2-hydroxymethyl-pyrrolidin-3-yl 4-O-(6-fluoro-6-deoxy-β-D-glucopyranosyl)-6-fluoro-6-deoxy-α-D-glucopyranoside (Exemplification Compound No. 1-280)

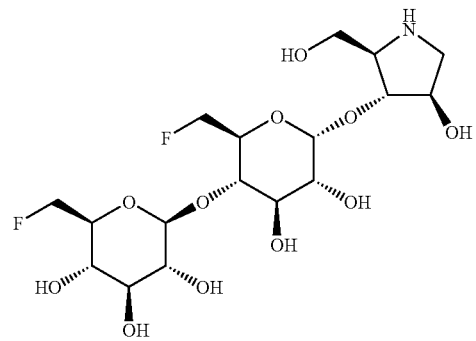

(5a) Allyl 6-O-t-butyldimethylsilyl-2,3-di-O-benzyl-4-O-(6-O-t-butyldimethylsilyl-2,3,4-tri-O-benzyl-β-D-glucopyranosyl)-D-glucopyranoside The compound (7.76 g, 20.30 mmol) synthesized in Example 2 (2a) was dissolved in N,N-dimethylformamide (160 mL) and t-butyldimethylsilyl chloride (7.65 mL, 50.75 mmol) and imidazole (4.15 g, 60.90 mmol) were added thereto, followed by stirring of the mixture at room temperature for 1 hour. After water (50 mL) was added to the reaction mixture and the mixture was extracted with ethyl acetate (100 mL), it was washed with a saturated brine (50 mL) and dried with anhydrous sodium sulfate, followed by distilling off of the solvent under reduced pressure. The residue was dissolved in N,N-dimethylformamide (120 mL) and sodium hydride (4.0 g, 91.67 mmol) was added thereto under ice-cooling, followed by stirring of the mixture at the same temperature for 10 minutes. Benzyl bromide (11 mL, 92.48 mmol) was added thereto and the mixture was stirred at room temperature for 3 hours. After water (50 mL) was added to the reaction mixture and the mixture was extracted with ethyl acetate (150 mL), the organic layer was washed with water (50 mL) and saturated brine (50 mL) and dried with anhydrous sodium sulfate, followed by distilling off of the solvent under reduced pressure. The residue was purified using silica gel flash column chromatography (hexane:ethyl acetate, 12:1, V/V) to obtain the desired title compound (8.67 g, yield 89%) as a colorless oil.

$^1$H NMR (400 MHz, CDCl$_3$): δ 0.00-0.20 (12H, m), 0.90-1.00 (18H, m), 3.00-5.20 (26H, m), 5.20 (1H, d, J=8.0 Hz), 5.35 (1H, d, J=16.0 Hz), 6.00 (1H, m), 7.20-7.60 (25H, m); MS (FAB) m/z: 1062 (M+H)$^+$.

(5b) Allyl 2,3-di-O-benzyl-4-O-(2,3,4-tri-O-benzyl-β-D-glucopyranosyl)-D-glucopyranoside The compound (8.67 g, 8.17 mmol) synthesized in Example 5 (5a) was dissolved in tetrahydrofuran (150 mL) and a solution of 1.0 M tetrabutyl ammonium fluoride in THF (20 mL, 20 mmol) was added thereto, followed by stirring of the mixture at room temperature for 5 hours. After the solvent was distilled off under reduced pressure, the residue was purified using silica gel flash column chromatography (methylene chloride:methanol, 50:1, V/V) to obtain the desired title compound (4.19 g, yield 62%) as a colorless oil.

$^1$H NMR (400 MHz, CDCl$_3$): δ 3.00-5.20 (28H, m), 5.20 (1H, d, J=12.0 Hz), 5.30 (1H, d, J=18.0 Hz), 5.98 (1H, m), 7.20-7.40 (25H, m); MS (FAB) m/z: 833 (M+H)$^+$.

(5c) Allyl 2,3-di-O-benzyl-6-fluoro-6-deoxy-4-O-(2,3,4-tri-O-benzyl-6-fluoro-6-deoxy-β-D-glucopyranosyl)-D-glucopyranoside The compound (4.19 g, 5.03 mmol) synthesized in Example 5 (5b) was dissolved in 1,2-dimethoxyethane (85 mL) and diethylaminosulfur trifluoride (2.5 mL, 25.61 mmol) was added thereto, followed by stirring of the mixture at 60° C. for 1 hour. Methanol (10 mL) was added to the reaction mixture under ice-cooling and the mixture was stirred for 30 minutes. After ethyl acetate (50 mL) was added thereto and the organic layer was washed with saturated aqueous sodium hydrogencarbonate solution (50 mL) and saturated brine (50 mL) and dried with anhydrous sodium sulfate, the solvent was distilled off under reduced pressure. The residue was purified using silica gel flash column chromatography (hexane:ethyl acetate, 5:1-4:1, V/V) to obtain the desired title compound (2.23 g, yield 53%) as a yellow solid.

$^1$H NMR (400 MHz, CDCl$_3$): δ 3.00-5.10 (26H, m), 5.23 (1H, m), 5.33 (1H, m), 5.95 (1H, m), 7.20-7.40 (25H, m); MS (FAB) m/z: 837 (M+H)$^+$.

(5d) Allyl 2,3-di-O-benzyl-6-fluoro-6-deoxy-4-O-(2,3,4-tri-O-benzyl-6-fluoro-6-deoxy-β-D-glucopyranosyl)-D-glucopyranoside The compound (2.23 g, 2.66 mmol) synthesized in Example 5 (5c) was dissolved in acetic acid (20 mL) and water (1 mL) and palladium chloride (II) (0.47 g, 2.65 mmol) and sodium acetate (0.87 g, 10.61 mmol) were added thereto, followed by stirring of the mixture at room temperature for 14 hours. After the reaction mixture was subjected to celite filtration, the solvent was distilled off under reduced pressure. The residue was purified using silica gel flash column chromatography (hexane:ethyl acetate 3:1, V/V) to obtain the desired title compound (0.73 g, yield 34%) as pale yellow amorphous matter.

$^1$H NMR (400 MHz, CDCl$_3$): δ 3.00-5.10 (25H, m), 7.20-7.60 (25H, m); MS (FAB) m/z: 797 (M+H)$^+$.

(5e) (2R,3R,4R)-4-Benzyloxy-N-benzyloxycarbonyl-2-(benzyloxymethyl)pyrrolidin-3-yl 2,3-di-O-benzyl-6-fluoro-6-deoxy-4-O-(2,3,4-tri-O-benzyl-6-fluoro-6-deoxy-β-D-glucopyranosyl)-α-D-glucopyranoside The compound (730.0 mg, 0.92 mmol) synthesized in Example 5 (5d) was dissolved in methylene chloride (13.5 mL) and trichloroacetonitrile (0.46 mL, 4.60 mmol) and 1,8-diazabicyclo[5.4.0]-7-undecene (1 drop) were added thereto, followed by stirring of the mixture at room temperature for 30 minutes. After the solvent was distilled off under reduced pressure, the residue was purified using silica gel flash column chromatography (hexane:ethyl acetate, 4:1, 1% triethylamine, V/V) to obtain imidate (675.3 mg, 78%) of yellow oil. The compound (412.3 mg, 0.92 mmol) synthesized in Example 1 (1i) was dissolved in diethyl ether (13 mL) and trimethylsilyl trifluoromethanesulfonate (8.3 µL, 0.046 mmol) was dissolved in diethyl ether (2 mL) under a nitrogen atmosphere and the mixture was added. Subsequently, a solution of imidate (675.3 mg) in diethyl ether (5 mL) was added to the reaction mixture and the mixture was stirred at room temperature for 2 hours. After triethylamine (7.0 µL, 0.050 mmol) was added to the reaction mixture and the solvent was distilled off under reduced pressure, the residue was diluted with ethyl acetate (20 mL) and the mixture was washed with saturated aqueous sodium hydrogencarbonate (20 mL) and saturated brine (20 mL). After the organic layer was dried with anhydrous sodium sulfate, the solvent was distilled off under reduced pressure. The residue containing α,β-mixture was purified using silica gel flash column chromatography (hexane:ethyl acetate, 6:1, V/V) to isolate the desired title compound α form (122.6 mg, 11%) thereof as a colorless oil.

$^1$H NMR (400 MHz, CDCl$_3$): δ 3.00-5.20 (37H, m), 7.00-7.60 (40H, m); MS (FAB) m/z: 1227 (M+H)$^+$.

(5f) (2R,3R,4R)-4-Hydroxy-2-hydroxymethyl-pyrrolidin-3-yl 4-O-(6-fluoro-6-deoxy-β-D-glucopyranosyl)-6-fluoro-6-deoxy-α-D-glucopyranoside The compound (122.6 mg, 0.10 mmol) synthesized in Example 5 (5e) was dissolved in methanol (10 mL) containing 1% aqueous hydrochloric acid solution and 20% palladium hydroxide-carbon (100 mg) was added thereto, followed by stirring of the mixture under a hydrogen atmosphere for 2 hours. After the catalyst was removed by celite filtration, 28% ammonia water (0.5 mL) was added thereto and the mixture was stirred for 10 minutes. After the solvent was distilled off under reduced pressure and the aqueous solution (100 mL) was subjected to ion exchange resin (Dowex 50w×8) column, it was eluted with 1% ammonia water (100 mL). The ammonia water containing the desired compound was concentrated under reduced pressure and the residue was purified using silica gel flash column chromatography (ethyl acetate:methanol:water, 5:2:1-1:1:1, V/V) to obtain the desired title compound (25.9 mg, 56%) as a colorless solid.

$^1$H NMR (400 MHz, D$_2$O): δ 3.20-3.90 (22H, m), 4.10 (1H, s), 4.41 (1H, d, J=8.1 Hz), 4.50-4.80 (4H, m), 5.05 (1H, d, J=6.3 Hz); MS (FAB) m/z: 462 (M+H)$^+$.

EXAMPLE 6

(1S,3R,4R,5S)-1-Amino-3-hydroxy-5-hydroxymethyl-cyclopent-4-yl 4-O-(6-deoxy-β-D-glucopyranosyl)-α-D-glucopyranoside (Exemplification Compound No. 5-28)

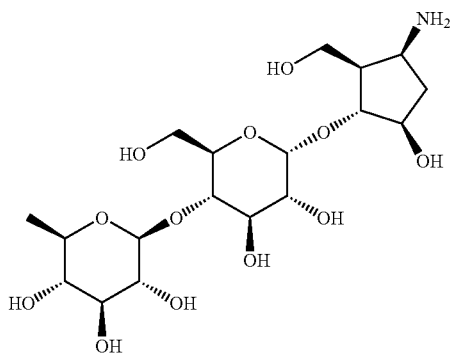

(6a) Methyl 4,6-O-benzylidene-3-O-benzyl-2-deoxy-D-glucopyranoside

2-Deoxy-D-glucose (10.1 g, 61.5 mmol) was dissolved in methanol (100 mL) and hydrochloric acid-methanol solution (50 mL) was added thereto, followed by heating of the mixture under reflux for 3 hours. After cooling to room temperature, triethylamine was added thereto until the reaction mixture became basic and the solvent was distilled off under reduced pressure. The residue was dissolved in N,N-dimethylformamide (100 mL) and benzaldehyde dimethylacetal (12.9 mL, 86.1 mmol) and p-toluenesulfonic acid monohydrate (585 mg, 3.08 mmol) were added thereto, followed by stirring of the mixture at 20 mmHg and 50° C. for 3 hours. After cooling to room temperature, water (50 mL) was added to the reaction mixture and the mixture was extracted with ethyl acetate (200 mL). The organic layer was washed with water (50 mL) and saturated brine (30 mL) and dried with anhydrous sodium sulfate, followed by distilling off of the solvent under reduced pressure. The residue was dissolved in N,N-dimethylformamide (100 mL) and 55% sodium hydride (3.99 g, 92.3 mmol) was added thereto under ice-cooling, followed by stirring of the mixture at the same temperature for 10 minutes. Benzyl bromide (11.0 mL, 92.3 mmol) was added thereto and the mixture was stirred at room temperature for 19 hours. After water (50 mL) was added to the reaction mixture and the mixture was extracted with ethyl acetate (200 mL), the organic layer was washed with water (50 mL) and saturated brine (30 mL) and dried with anhydrous sodium sulfate, followed by distilling off of the solvent under reduced pressure. The residue was purified using silica gel flash column chromatography (hexane:ethyl acetate, 20:1-10:1, V/V) to obtain the desired title compound (16.0 g, yield 73%) as a yellow solid.

$^1$H NMR (400 MHz, CDCl$_3$): δ 1.66-1.83 (1H, m), 2.24-2.34 (1H, m), 3.33 (3H, s), 3.65-3.85 (3H, m), 3.98-4.04 (1H, m), 4.22-4.35 (1H, m), 4.66-4.84 (3H, m), 5.60-5.62 (1H, m), 7.23-7.40 (8H, m), 7.49-7.52 (2H, m); MS (FAB) m/z: 357 (M+H)$^+$.

(6b) Methyl 3-O-benzyl-2-deoxy-D-glucopyranoside

The compound (2.00 g, 5.62 mmol) synthesized in Example 6 (6a) was dissolved in acetic acid (15 mL) and water (5 mL) and the mixture was stirred at 60° C. for 2 hours and 30 minutes. After cooling to room temperature, the solvent was distilled off under reduced pressure and the residue was purified using silica gel flash column chromatography (hexane:ethyl acetate, 2:1-1:2, V/V) to obtain the desired title compound (1.33 g, yield 88%) as a pale yellow oil.

$^1$H NMR (400 MHz, CDCl$_3$): δ 1.49-1.64 (1H, m), 2.11 (1H, brs), 2.25-2.36 (1H, m), 2.62 (1H, brs), 3.33 (3H, s), 3.44-3.65 (2H, m), 3.76-3.87 (3H, m), 4.41-4.52 (1H, m), 4.65-4.71 (1H, m), 4.81-4.82 (1H, m), 7.26-7.37 (5H, m); MS (FAB) m/z: 267 (M−H)$^+$.

(6c) Methyl 3-O-benzyl-2-deoxy-6-O-p-toluenesulfonyl-D-glucopyranoside

The compound (12.2 g, 45.3 mmol) synthesized in Example 6 (6b) was dissolved in pyridine (100 mL) and p-toluenesulfonyl chloride (13 g, 68.0 mmol) and 4-dimethylaminopyridine (553 mg, 4.53 mmol) were added thereto, followed by stirring of the mixture at room temperature for 12 hours. The reaction mixture was poured to 10% aqueous hydrochloric acid solution (80 mL) under ice cooling, and ethyl acetate (200 mL) and the organic layer was washed with 10% aqueous hydrochloric acid solution (80 mL), saturated aqueous sodium hydrogencarbonate solution (80 mL) and saturated brine (50 mL) and dried with anhydrous sodium sulfate, followed by distilling off of the solvent under reduced pressure. The residue was purified using silica gel flash column chromatography (hexane:ethyl acetate, 5:1-3:1, V/V) to obtain the desired title compound (16.9 g, yield: 88%) as pale yellow amorphous matter.

$^1$H NMR (400 MHz, CDCl$_3$): δ 1.54-1.61 (1H, m), 2.20-2.28 (1H, m), 2.44 (3H, s), 3.27 (3H, s), 3.41-3.48 (2H, m), 3.70-3.76 (2H, m), 4.22-4.41 (2H, m), 4.47-4.57 (1H, m), 4.63-4.68 (1H, m), 4.75-4.76 (1H, m), 7.26-7.36 (7H, m), 7.79-7.84 (2H, m); MS (FAB) m/z: 421 (M−H)$^+$.

(6d) Methyl 4-O-benzoyl-3-O-benzyl-2-deoxy-6-O-p-toluenesulfonyl-D-glucopyranoside The compound (16.9 g, 40.0 mmol) synthesized in Example 6 (6c) was dissolved in methylene chloride (150 mL) and triethylamine (22 mL, 0.16 mol), benzoyl chloride (14 mL, 0.12 mol) and 4-dimethylaminopyridine (489 mg, 4.00 mmol) were added thereto, followed by stirring of the mixture at room temperature for 18 hours. After water (80 mL) was added to the reaction mixture and the mixture was extracted with methylene chloride (100 mL), the organic layer was washed with saturated brine (50 mL) and dried with anhydrous sodium sulfate, followed by distilling off of the solvent under reduced pressure. The residue was purified using silica gel flash column chromatography (hexane:ethyl acetate, 4:1-3:1, V/V) to obtain the desired title compound (20.8 g, yield 99%) as a yellow oil.

$^1$H NMR (400 MHz, CDCl$_3$): δ 1.71-1.78 (1H, m), 2.26-2.31 (1H, m), 2.33 (3H, s), 3.32 (3H, s), 3.94-4.14 (4H, m), 4.40-4.44 (1H, m), 4.52-4.59 (1H, m), 4.80-4.81 (1H, m), 5.03-5.08 (1H, m), 7.09-7.20 (6H, m), 7.40-7.49 (3H, m), 7.57-7.62 (1H, m), 7.66-7.71 (2H, m), 7.87-7.96 (2H, m); MS (FAB) m/z: 527 (M+H)$^+$.

(6e) Methyl 4-O-benzoyl-3-O-benzyl-2,6-dideoxy-6-iode-D-glucopyranoside

The compound (2.53 g, 4.81 mmol) synthesized in Example 6 (6d) was dissolved in toluene (30 mL) and sodium iodide (3.6 g, 24.0 mmol) and 18-crown-6-ether (254 mg, 0.96 mmol) were added thereto, followed by stirring of the mixture at 100° C. under a nitrogen atmosphere for 3 hours. After cooling to room temperature, water (30 mL) was added to the reaction mixture and the mixture was extracted with ethyl acetate (100 mL). The organic layer was washed with saturated brine (30 mL) and dried with anhydrous sodium sulfate, followed by distilling off of the solvent under reduced pressure. The residue was purified using silica gel flash column chromatography (hexane:ethyl acetate, 15:1-10:1, V/V) to obtain the desired title compound (2.11 g, yield 91%) as a pale yellow oil.

$^1$H NMR (400 MHz, CDCl$_3$): δ 1.72-1.86 (1H, m), 2.31-2.41 (1H, m), 3.17-3.26 (1H, m), 3.33-3.40 (1H, m), 3.45 (3H, s), 3.69-3.86 (1H, m), 3.99-4.31 (1H, m), 4.44-4.48 (1H, m), 4.57-4.62 (1H, m), 4.90-4.91 (1H, m), 5.03-5.18 (1H, m), 7.13-7.26 (5H, m), 7.43-7.49 (2H, m), 7.58-7.62 (1H, m), 8.02-8.04 (2H, m); MS (FAB) m/z: 483 (M+H)$^+$.

(6f) 4-O-Benzoyl-3-O-benzyl-2,5,6-trideoxy-D-xylo-hex-5-enose oxime

The compound (2.11 g, 4.38 mmol) synthesized in Example 6 (6e) was dissolved in isopropanol (50 mL) and water (2 mL) and zinc powder (2 g) washed with 5% aqueous hydrochloric acid solution was added thereto, followed by heating of the mixture under reflux for 25 minutes. After cooling to room temperature, it was subjected to celite filtration and the solvent was distilled off under reduced pressure. The residue was dissolved in ethanol (50 mL) and hydroxylamine hydrochloride (913 mg, 13.1 mmol) and pyridine (1.06 mL, 13.1 mmol) were added thereto, followed by stirring of the mixture at 60° C. for 50 minutes. After cooling to room temperature, the solvent was distilled off under reduced pressure and water (20 mL) was added thereto. After the mixture was extracted with ethyl acetate (100 mL), the organic layer was washed with saturated brine (20 mL) and dried with anhydrous sodium sulfate, followed by distilling off of the solvent under reduced pressure. The residue was purified using silica gel flash column chromatography (hexane:ethyl acetate, 6:1-5:1-4:1-3:1, V/V) to obtain the desired title compound (1.14 g, yield 77%) as a colorless oil.

$^1$H NMR (400 MHz, CDCl$_3$): δ 2.47-2.55 (1H, m), 2.61-2.79 (1H, m), 3.88 (0.5H, dt, J=8.1, 5.1 Hz), 3.94 (0.5H, dt, J=8.1, 4.4 Hz), 4.65 (0.5H, d, J=11.7 Hz), 4.67 (0.5H, d, J=11.7 Hz), 4.74 (0.5H, d, J=11.7 Hz), 4.75 (0.5H, d, J=11.7 Hz), 5.33-5.36 (1H, m), 5.41-5.47 (1H, m), 5.74-5.77 (1H, m), 6.01 (1H, ddd, J=16.8, 5.9, 5.1 Hz), 6.84 (0.5H, t, J=5.1 Hz), 7.26-7.33 (5H, m), 7.43-7.48 (2.5H, m), 7.56-7.60 (1H, m), 8.06-8.08 (2H, m); MS (FAB) m/z: 340 (M+H)$^+$.

(6g) (3aR,4R,5R,6aS)-4-Benzoyloxy-5-benzyloxy-hexahydro-cyclopenta[c]isoxazole (3aS,4R,5R,6aR)-4-benzoyloxy-5-benzyloxy-hexahydro-cyclopenta[c]isoxazole The compound (5.0 g, 14.7 mmol) synthesized in Example 6 (6f) was dissolved in toluene (100 mL) and the mixture was heated under reflux for 40 hours. After cooling to room temperature, the solvent was distilled off under reduced pressure and the residue was purified using silica gel flash column chromatography (hexane:ethyl acetate, 2:1-1:1, V/V) to obtain the desired title compound (mixture) (4.08 g, yield 82%) as an orange-color oil.

$^1$H NMR (400 MHz, CDCl$_3$): δ 1.92 (0.3H, ddd, J=10.2, 5.1, 5.1 Hz), 2.00-2.13 (1.4H, m), 2.28-2.35 (0.3H, m), 2.99-3.01 (0.3H, m), 3.37 (0.7H, dd, J=8.8, 7.3 Hz), 3.43-3.49 (0.7H, m), 3.99-4.22 (4.3H, m), 4.63 (0.3H, d, J=11.7 Hz), 4.63 (1.4H, s), 4.67 (0.3H, d, J=9.5 Hz), 5.21 (0.3H, t, J=3.7 Hz), 5.28 (0.7H, d, J=3.7 Hz), 7.25-7.35 (5H, m), 7.43-7.47 (2H, m), 7.54-7.60 (1H, m), 7.99-8.08 (2H, m); MS (FAB) m/z: 340 (M+H)$^+$.

(6h) (3aR,4R,5R,6aS)-5-Benzyloxy-1-benzyloxycarbonyl-4-hydroxy-hexahydro-cyclopenta[c]isoxazole The compound (4.08 g, 12.0 mmol) synthesized in Example 6 (6 g) was dissolved in methanol (40 mL) and sodium methoxide (696 μL, 3.61 mmol) was added thereto, followed by stirring of the mixture at room temperature for 2 hours. After Dowex 50W×8 was added thereto until the reaction mixture became neutral and it was filtered, the solvent was distilled off under reduced pressure. The residue was dissolved in ethyl acetate (40 mL) and saturated aqueous sodium hydrogencarbonate solution (20 mL) and benzyloxy chloroformate (2.4 mL, 16.8 mmol) were added thereto under ice-cooling, followed by stirring of the mixture at the same temperature for 1 hour and 30 minutes. The organic layer was washed with saturated brine (50 mL) and dried with anhydrous sodium sulfate, followed by distilling off of the solvent under reduced pressure. The residue was purified using silica gel flash column chromatography (hexane:ethyl acetate, 2:1-1:1, V/V) to obtain the desired title compound (789 mg, yield 18%) as a pale yellow solid and its diastereomer (1.62 g, yield 36%) as a pale yellow oil.

$^1$H NMR (400 MHz, CDCl$_3$): δ 1.57-1.63 (1H, m), 2.47 (1H, brs), 2.50-2.56 (1H, m), 2.73-2.77 (1H, m), 3.61-3.69 (2H, m), 3.88-3.92 (1H, m), 4.01 (1H, d, J=8.8 Hz), 4.49 (1H, d, J=11.7 Hz), 4.48-4.55 (1H, m), 4.60 (1H, d, J=11.7 Hz), 5.18 (2H, s); MS (FAB) m/z: 370 (M+H)$^+$.

(6i) (3aR,4R,5R,6aS)-5-Benzyloxy-1-benzyloxycarbonyl-hexahydro-cyclopenta[c]isoxazol-4-yl 2,3,6-tri-O-benzyl-4-O-(2,3,4-tri-O-benzyl-6-deoxy-β-D-glucopyranosyl)-D-glucopyranoside The compound (751 mg, 0.87 mmol) synthesized in Example 2 (2f) was dissolved in methylene chloride (15 mL) and trichloroacetonitrile (435 μL, 4.33 mmol) and 1,8-diazabicyclo[5.4.0]-7-undecene (2 drops) were added thereto, followed by stirring of the mixture at room temperature for 1 hour. After the solvent was distilled off under reduced pressure, the residue was purified using silica gel flash column chromatography (hexane:ethyl acetate, 6:1-5:

1, 1% triethylamine, V/V) to obtain imidate (734 mg, 84%) as a yellow oil. The compound (244 mg, 0.66 mmol) synthesized in Example 6 (6h) was dissolved in diethyl ether (12 mL) and trimethylsilyl trifluoromethanesulfonate (12 μL, 0.07 mmol) was added thereto. A solution of imidate (734 mg, 0.73 mmol) in diethyl ether (3 mL) was added dropwise thereto, followed by stirring of the mixture at room temperature for 1 hour. After triethylamine (4 drops) was added to the reaction mixture, the solvent was distilled off under reduced pressure. The residue was purified using silica gel flash column chromatography (hexane:diethyl ether, 2:1-1:1, V/V) to obtain the desired title compound (α, β mixture) (516 mg, yield 64%) as colorless amorphous matter.

$^1$H NMR (400 MHz, CDCl$_3$): δ 1.19 (1.5H, d, J=2.9 Hz), 1.20 (1.5H, d, J=2.9 Hz), 1.62-1.68 (0.5H, m), 1.79-1.84 (0.5H, m), 2.39-2.45 (0.5H, m), 2.48-2.53 (0.5H, m), 2.73-2.77 (0.5H, m), 2.85-2.86 (0.5H, m), 3.10-3.60 (8H, m), 3.69-4.02 (6H, m), 4.10-4.14 (1H, m), 4.32-4.64 (8H, m), 4.69-4.87 (7H, m), 5.00 (0.5H, d, J=10.7 Hz), 5.12 (0.5H, d, J=3.9 Hz), 5.18 (1H, d, J=10.7 Hz), 7.18-7.43 (50H, m); MS (FAB) m/z: 1217 (M)$^+$.

(6j) (3aR,4R,5R,6aS)-5-Benzyloxy-1-methyloxycarbonyl-hexahydro-cyclopenta[c]isoxazol-4-yl 2,3,6-tri-O-benzyl-4-O-(2,3,4-tri-O-benzyl-6-deoxy-β-D-glucopyranosyl)-α-D-glucopyranoside The compound (516 mg, 0.42 mmol) synthesized in Example 6 (6i) was dissolved in methanol (6 mL) and toluene (6 mL) and sodium methoxide (221 μL, 1.15 mmol) was added thereto, followed by stirring of the mixture at 50° C. for 40 minutes. After cooling to room temperature, Dowex 50W×8 was added thereto until the reaction mixture became neutral and it was filtered, followed by distilling off of the solvent under reduced pressure. The residue was purified using silica gel flash column chromatography (hexane:diethyl ether, 1.5:1-1:1, v/v) to obtain the desired title compound (173 mg, yield 47%) as colorless amorphous matter.

$^1$H NMR (400 MHz, CDCl$_3$): δ 1.61-1.69 (1H, m), 2.48-2.55 (1H, m), 2.72-2.78 (1H, m), 3.13 (1H, dd, J=9.5, 8.8 Hz), 3.21 (1H, dd, J=9.5, 5.9 Hz), 3.31 (1H, dd, J=8.1, 7.3 Hz), 3.36-3.54 (5H, m), 3.59-3.62 (1H, m), 3.79 (3H, s), 3.74-3.94 (5H, m), 3.99 (1H, d, J=8.8 Hz), 4.32-4.38 (2H, m), 4.50-4.67 (7H, m), 4.76-5.00 (5H, m), 5.01 (1H, d, J=11.0 Hz), 5.12 (1H, d, J=3.7 Hz), 7.14-7.44 (35H, m); MS (FAB) m/z: 1141 (M)$^+$.

(6k) (3aR,4R,5R,6aS)-5-Benzyloxy-hexahydro-cyclopenta[c]isoxazol-4-yl 2,3,6-tri-O-benzyl-4-O-(2, 3,4-tri-O-benzyl-6-deoxy-β-D-glucopyranosyl)-α-D-glucopyranoside The compound (363 mg, 0.32 mmol) synthesized in Example 6 (6j) was dissolved in methanol (8 mL) and 1N aqueous potassium hydroxide solution (4 mL) was added thereto, followed by stirring of the mixture at 80° C. for 8 hours. After cooling to room temperature, saturated aqueous ammonium chloride solution (15 mL) was added to the reaction mixture and the mixture was extracted with ethyl acetate (100 mL). After the organic layer was washed with saturated brine (10 mL) and dried with anhydrous sodium sulfate, the solvent was distilled off under reduced pressure. The residue was purified using silica gel flash column chromatography (hexane:ethyl acetate, 1.5:1-1:1, V/V) to obtain the desired title compound (313 mg, yield 91%) as pale yellow amorphous matter.

$^1$H NMR (400 MHz, CDCl$_3$): δ 1.20 (3H, d, J=5.9 Hz), 1.56-1.64 (1H, m), 2.26-2.36 (1H, m), 2.76-2.86 (1H, m), 3.13 (1H, dd, J=9.5, 8.8 Hz), 3.19-3.25 (2H, m), 3.32 (1H, dd, J=8.8, 8.1 Hz), 3.43-3.53 (3H, m), 3.67-3.69 (2H, m), 3.81-3.95 (6H, m), 4.35-4.40 (2H, m), 4.51-4.67 (7H, m), 4.74-4.87 (6H, m), 5.01 (1H, d, J=10.3 Hz), 7.15-7.44 (35H, m); MS (FAB) m/z: 1084 (M+H)$^+$.

(6l) (1S,3R,4R,5S)-1-Amino-3-hydroxy-5-hydroxymethyl-cyclopenta-4-yl 4-O-(6-deoxy-β-D-glucopyranosyl)-α-D-glucopyranoside The compound (313 mg, 0.29 mmol) synthesized in Example 6 (6k) was dissolved in methanol (8 mL) and ethyl acetate (4 mL) and hydrochloric acid (5 drops) and 20% palladium hydroxide-carbon (300 mg) were added thereto, followed by stirring of the mixture at room temperature under a hydrogen atmosphere for 6 hours. After the celite filtration, the solvent was distilled off under reduced pressure and methanol (3 mL) and 28% water (300 μL) were added thereto, followed by stirring of the mixture at room temperature for 10 minutes. After the solvent was distilled off under reduced pressure, the residue was purified by ion exchange column (Dowex 50W×8) (water—2.8% ammonia water). Further, it was purified using silica gel flash column chromatography (ethyl acetate:methanol:water, 1:1:1, V/V) to obtain the desired title compound (107 mg, yield 81%) as a pale yellow solid.

$^1$H NMR (500 MHz, D$_2$O): δ 1.19 (1H, d, J=5.9 Hz), 1.53 (1H, dt, J=13.7, 6.8 Hz), 2.18-2.23 (1H, m), 2.27-2.33 (1H, m), 3.07 (1H, dd, J=9.8, 8.8 Hz), 3.19 (1H, dd, J=9.8, 7.8 Hz), 3.34 (1H, dd, J=9.8, 8.8 Hz), 3.37-3.41 (1H, m), 3.47-3.51 (2H, m), 3.58 (1H, dd, J=14.7, 6.8 Hz), 3.66-3.80 (6H, m), 3.86 (1H, dd, J=6.8, 4.9 Hz), 4.11-4.14 (1H, m), 4.36 (1H, d, J=7.8 Hz), 5.06 (1H, d, J=3.9 Hz); $^{13}$C NMR (125 MHz, D$_2$O): δ 16.89, 38.27, 47.74, 49.85, 59.41, 60.05, 70.97, 71.19, 71.56, 72.22, 73.64, 74.96, 75.45, 75.51, 79.24, 84.26, 97.34, 102.68; MS (FAB) m/z: 456 (M+H)$^+$.

EXAMPLE 7

(2R,3R,4R,5R)-2,5-Dihydroxymethyl-4-hydroxypyrrolidin-3-yl 4-O-(6-deoxy-β-D-glucopyranosyl)-α-D-glucopyranoside (Exemplification Compound No. 1-557)

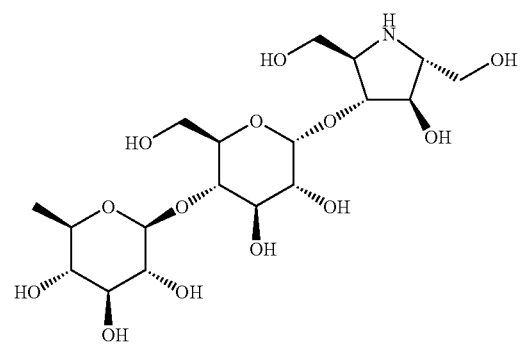

(7a) (1R,3S,4S,6R,7R)-7-Benzyloxy-6-hydroxymethyl-3-methoxy-2-oxa-5-aza-bicyclo[2,2,1]heptane Azide epoxide (Tetrahedron, 26, 1985, 1469) (2.03 g, 6.97 mmol) was dissolved in ethanol (40 mL) and Lindlar catalyst (0.4 g) was added thereto, followed by stirring of the mixture under a hydrogen atmosphere for 2 hours. After the catalyst was removed by celite filtration, it was dissolved in ethanol (40 mL) and the mixture was heated under reflux for 1 hour. After the solvent was distilled off under reduced pressure, the residue was purified using silica gel flash column chromatography (methylene chloride:ethanol, 20:1-10:1, V/V) to obtain the desired title compound (1.21 g, yield 65%) as a brown solid.

$^1$H NMR (400 MHz, CDCl$_3$): δ 2.15-2.35 (2H, br), 3.19 (1H, dd, J=5.8, 5.9 Hz), 3.35 (3H, s), 3.41 (1H, s), 3.65 (1H, dd, J=5.8, 11.7 Hz), 3.73 (1H, dd, J=5.8, 11.7 Hz), 4.11 (1H, s), 4.18 (1H s), 4.54 (1H, d, J=11.7 Hz), 4.61 (1H, d, J=11.7 Hz), 4.64 (1H, s), 7.29-7.38 (5H, m); MS (FAB) m/z: 266 (M+H)$^+$.

(7b) (1R,3R,4S,6R,7R)-7-Hydroxy-6-hydroxymethyl-3-methoxy-2-oxa-5-aza-bicyclo[2,2,1]heptane-5-carboxylic acid benzyl ester The compound (930 mg, 3.51 mmol) synthesized in Example 7 (7a) was dissolved in methanol (20 mL) and 20% palladium hydroxide-carbon (280 mg) was added thereto, followed by stirring of the mixture under a hydrogen atmosphere for 6 hours. After the catalyst was removed by celite filtration, the solvent was distilled off under reduced pressure. The residue was dissolved in ethyl acetate:saturated aqueous sodium hydrogencarbonate solution (2:1, 20 mL) and benzyl chloroformate (0.75 mL, 5.27 mmol) was added thereto, followed by stirring of the mixture at 0° C. for 2 hours. After water (20 mL) was added thereto at 0° C. and the mixture was extracted with ethyl acetate, the organic layer was washed with saturated brine (20 mL) and dried with anhydrous sodium sulfate, followed by distilling off of the solvent under reduced pressure. The residue was purified using silica gel flash column chromatography (hexane:ethyl acetate, 1:1-3:1, V/V) to obtain the desired title compound (759 mg, yield 70%) as a colorless solid.

$^1$H NMR (400 MHz, CDCl$_3$): δ 3.33 (3H, s), 3.50-4.00 (3H, m), 4.10-4.25 (3H, m), 4.61 (1H, brs), 4.60-4.74 (2H, m), 5.10-5.25 (2H, m), 7.25-7.45 (5H, m); MS (FAB) m/z: 310 (M+H)$^+$.

(7c) (1R,3S,4S,6R,7R)-7-Benzyloxy-6-t-butyldimethylsilyloxymethyl-3-methoxy-2-oxa-5-aza-bicyclo[2,2,1]heptane-5-carboxylic acid benzyl ester The compound (152 mg, 0.49 mmol) synthesized in Example 7 (7b) was dissolved in pyridine (4 mL) and t-butyldimethylsilyl chloride (82 mg, 0.54 mmol) was added thereto, followed by stirring of the mixture at 0° C. for 3 hours. After it was confirmed by TLC that the raw material was no longer present, benzoyl chloride (86 μL, 0.74 mmol) was added and the mixture was stirred at 0° C. for 1 hour. After water (20 mL) was added thereto at 0° C. and the mixture was extracted with ethyl acetate, the organic layer was washed with saturated brine (20 mL) and dried with anhydrous sodium sulfate, followed by distilling off of the solvent under reduced pressure. The residue was purified using silica gel flash column chromatography (hexane:ethyl acetate, 10:1, V/V) to obtain the desired title compound (218 mg, yield 84%) as a colorless oil.

$^1$H NMR (400 MHz, CDCl$_3$): δ −0.24-0.04 (6H, m), 0.72 (4.5H, s), 0.77 (4.5H, s), 3.34 (1.5H, s), 3.38 (1.5H, s), 3.67-3.80 (2H, m), 3.91 (0.5H m), 4.10 (0.5H, m), 4.40 (0.5H, s), 4.46 (0.5H, m), 4.66 (0.5H, s), 4.69 (1H, m), 4.78 (0.5H, m), 5.15 (2H, m), 5.44 (1H, m), 7.39-7.36 (5H, m), 7.41 (2H, m), 7.55 (1H, m), 7.95 (2H, m); MS (FAB) m/z: 528 (M+H)$^+$.

(7d) (2R,3R,4R,5R)-N-Benzyloxycarbonyl-3-benzoyl-2,5-dihydroxymethyl-4-hydroxypyrrolidine The compound (997 mg, 1.89 mmol) synthesized in Example 7 (7c) was dissolved in trifluoroacetic acid:water (4:1, 12 mL) and the mixture was stirred at room temperature for 15 minutes. After water (20 mL) was added to the reaction mixture at 0° C. and the mixture was extracted with dichloromethane (30 mL), the organic layer was washed with saturated aqueous sodium hydrogencarbonate (20 mL) and saturated brine (20 mL) and dried with anhydrous sodium sulfate, followed by distilling off of the solvent under reduced pressure. The residue was dissolved in ethanol (15 mL) and the compound obtained by dissolving sodium borohydride (35.7 mg, 0.10 mmol) in water (5 mL) was added thereto, followed by stirring of the mixture at 0° C. for 20 minutes. After saturated aqueous ammonium chloride (2 mL) was added to the reaction mixture at 0° C., ethanol was distilled off under reduced pressure. After water (15 mL) was added thereto and the mixture was extracted with ethyl acetate (15 mL), the organic layer was washed with saturated brine (15 mL) and dried with anhydrous sodium sulfate, followed by distilling off of the solvent under reduced pressure. The residue was purified using silica gel flash column chromatography (hexane:ethyl acetate, 2:1, V/V) to obtain the desired title compound (643 mg, yield 85%) as a colorless oil.

$^1$H NMR (400 MHz, CDCl$_3$): δ 3.60-3.38 (9H, m), 4.98-5.19 (4H, m), 7.20-7.30 (5H, m), 7.36. (2H, m), 7.50 (1H, m), 7.89 (2H, d, J=7.3 Hz); MS (FAB) m/z: 402 (M+H)$^+$.

(7e) (2R,3R,4R,5R)-N-Benzyloxycarbonyl-3-hydroxy-2,5-dibenzyloxymethyl-4-benzyloxypyrrolidine The compound (643 mg, 1.60 mmol) synthesized in Example 7 (7d) was dissolved in dichloromethane:cyclohexane (1:2, 18 mL) and benzyl tricloroacetoimidate (2.7 mL, 14.4 mmol) and trifluoromethanesulfonic acid (29 μL, 0.32 mmol) were added thereto, followed by stirring of the mixture at room temperature for 2 hours. After saturated aqueous sodium hydrogencarbonate (5 mL) was added to the reaction mixture at 0° C. and the mixture was diluted with ethyl acetate (200 mL), it was washed with water (30 mL) and saturated brine (30 mL) and dried with anhydrous sodium sulfate, followed by distilling off of the solvent under reduced pressure. The residue was purified using silica gel flash column chromatography (hexane:ethyl acetate, 20:1-10:1, V/V) to obtain 1080 mg of colorless oil. The thus obtained 1080 mg of colorless oil was dissolved in methanol:tetrahydrofuran (4:1, 25 mL) and potassium carbonate (44 mg, 0.32 mmol) was added thereto, followed by stirring of the mixture at room temperature for 2.5 hours. After methanol was distilled off under reduced pressure, water (15 mL) was added thereto and the mixture was extracted with ethyl acetate (15 mL). The organic layer was washed with saturated brine (15 mL) and dried with anhydrous sodium sulfate, followed by distilling off of the solvent under reduced pressure. The residue was purified using silica gel flash column chromatography (hexane:ethyl acetate, 4:1, V/V) to obtain the desired title compound (715 mg, yield 78%) as a colorless oil.

$^1$H NMR (400 MHz, CDCl$_3$): δ 3.40-3.49 (2H, m), 3.62 (1H, dd, J=4.4, 8.8 Hz), 3.79-4.12 (4H, m), 4.19 (1H, dd, J=3.7, 10.3 Hz), 4.26-4.61 (6H, m), 5.01 (1H, d, J=16.8 Hz), 5.03 (1H, d, J=16.8 Hz), 5.51 (1H, m), 7.15-7.38 (20H, m); MS (FAB) m/z: 568 (M+H)$^+$.

(7f) (2R,3R,4R,5R)-N-Benzyloxycarbonyl-2,5-dibenzyloxymethyl-4-benzyloxypyrrolidin-3-yl 2,3,6-tri-O-benzyl-4-O-(2,3,4-tri-O-benzyl-6-deoxy-β-D-glucopyranosyl)-α-D-glucopyranoside The compound (426 mg, 0.49 mmol) synthesized in Example 2 (2f) was dissolved in methylene chloride (8 mL) and trichloroacetonitrile (0.25 mL, 2.45 mmol) and 1,8-diazabicyclo[5.4.0]-7-undecene (7 μL, 0.05 mmol) were added thereto, followed by stirring of the mixture at room temperature for 15 minutes. After the solvent was distilled off under reduced pressure, the residue was purified using silica gel flash column chromatography (hexane:ethyl acetate, 5:1, 1% triethylamine, V/V) to obtain imidate (398 mg, 80%) of colorless oil. The compound (248 mg, 0.44 mmol) synthesized in Example 7 (7e) was dissolved in diethyl ether (8 mL) and trimethylsilyl trifluoromethanesulfonate (7 μL, 44 μmol) was added thereto under a nitrogen atmosphere. A solution of imidate in diethyl ether (5 mL) was added to the reaction mixture and the mixture was stirred at room temperature for 1.5 hours. After triethylamine (12 μL, 88 μmol) was added to the reaction mixture and the solvent was distilled off under reduced pressure, it was diluted with ethyl acetate (20 mL) and washed with saturated aqueous sodium hydrogencarbonate (20 mL) and saturated brine (20 mL). After the organic layer was dried with anhydrous sodium sulfate, the solvent was distilled off under reduced pressure and the residue was purified using silica gel flash column chromatography (hexane:diethyl ether, 4:1, V/V) to obtain the desired title compound (218 mg, 31%) as a colorless oil.

$^1$H NMR (500 MHz, CDCl$_3$): δ 1.23 (3H, d, J=5.9 Hz), 2.92-3.19 (4H, m), 3.26-3.73 (13H, m), 3.85 (1H, dd, J=5.1, 5.1 Hz), 3.93 (1H, dd, J=5.1, 5.1 Hz), 4.31 (1H, d, J=8.0 Hz), 5.03 (1H, d, J=3.6 Hz); MS (FAB) m/z: 472 (M+H)$^+$.

(7g) (2R,3R,4R,5R)-2,5-Dihydroxymethyl-4-hydroxypyrrolidin-3-yl 4-O-(6-deoxy-β-D-glucopyranosyl)-α-D-glucopyranoside The compound (218 mg, 0.15 mmol) synthesized in Example 7 (7f) was dissolved in 1% hydrochloric acid methanol solution (5 mL) and 20% palladium hydroxide-carbon (110 mg) was added thereto, followed by stirring of the mixture under a hydrogen atmosphere for 2 hours. After the catalyst was removed by celite filtration, 28% ammonia water (0.8 mL) was added thereto, followed by stirring of the mixture for 10 minutes. After the solvent was distilled off under reduced pressure and it was passed through ion exchange resin column with water (30 mL), 1% ammonia water (30 mL) was flowed through. The ammonia water containing the desired compound was concentrated under reduced pressure and was purified using silica gel flash column chromatography (ethyl acetate:methanol:water, 5:2:1-1:1:1, V/V) to obtain the desired title compound (47 mg, 64%) as a colorless solid.

$^1$H NMR (400 MHz, D$_2$O): δ 1.15 (3H, d, J=5.9 Hz), 2.92-3.19 (4H, m), 3.26-3.73 (13H, m), 3.85 (1H, dd, J=5.1, 5.1 Hz), 3.93 (1H, dd, J=5.1, 5.1 Hz), 4.31 (1H, d, J=8.0 Hz), 5.03 (1H, d, J=3.6 Hz); MS (FAB) m/z: 472 (M+H)$^+$.

EXAMPLE 8

(2R,3R,4R)-4-Hydroxy-2-hydroxymethyl-pyrrolidin-3-yl 4-O-(6-methoxy-6-deoxy-β-D-glucopyranosyl)-D-glucopyranoside (Exemplification Compound No. 1-354)

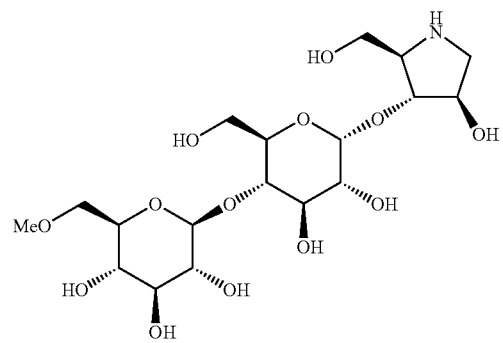

(8a) Allyl 2,3,6-tri-O-benzyl-4-O-(2,3,4-tri-O-benzyl-6-fluoro-6-deoxy-β-D-glucopyranosyl)-α-D-glucopyranoside The compound (2.19 g, 2.37 mmol) synthesized in Example 2 (2c) was dissolved in N,N-dimethylformamide (45 mL) and sodium hydride (0.12 g, 2.75 mmol) was added thereto under ice-cooling, followed by stirring of the mixture for 10 minutes. Methyl iodide (0.3 mL, 4.82 mmol) was added thereto and the mixture was stirred at room temperature for 5 hours. Methanol (5 mL) was added to the reaction mixture under ice-cooling and the mixture was stirred for 30 minutes. Ethyl acetate (20 mL) was added thereto and the organic layer was washed with water (20 mL) and saturated brine (20 mL) and dried with anhydrous sodium sulfate, followed by distilling off of the solvent under reduced pressure. The residue was purified using silica gel flash column chromatography (hexane:ethyl acetate, 6:1-5:1, V/V) to obtain the desired title compound (1.80 g, yield 81%) as a colorless oil.

$^1$H NMR (400 MHz, CDCl$_3$): δ 3.21 (3H, s), 3.30-5.00 (28H, m), 5.10 (1H, m), 5.20 (1H, m), 5.95 (1H, m), 7.20-7.40 (30H, m); MS (FAB) m/z: 938 (M+H)$^+$.

(8b) Allyl 2,3,6-tri-O-benzyl-4-O-(2,3,4-tri-O-benzyl-6-methoxy-6-deoxy-β-D-glucopyranosyl)-D-glucopyranoside The compound (1.80 g, 1.92 mmol) synthesized in Example 8 (8a) was dissolved in methanol (30 mL) and tetrahydrofuran (6 mL) and palladium chloride (II) (67.4 mg, 0.38 mmol) was added thereto, followed by stirring of the mixture at room temperature for 14 hours. After the reaction mixture was subjected to celite filtration, the solvent was distilled off under reduced pressure. The residue was purified using silica gel flash column chromatography (hexane:ethyl acetate, 5:1-4:1-3:1, V/V) to obtain the desired title compound (1.43 g, yield 83%) as colorless amorphous matter.

¹H NMR (400 MHz, CDCl₃): δ 3.20 (3H, s), 3.25-5.00 (27H, m), 5.10 (1H, m), 7.20-7.40 (30H, m); MS (FAB) m/z: 898 (M+H)⁺.

(8c) (2R,3R,4R)-4-Benzyloxy-N-benzyloxycarbonyl-2-(benzyloxymethyl)pyrrolidin-3-yl 2,3,6-tri-O-benzyl-4-O-(2,3,4-tri-O-benzyl-6-methoxy-6-deoxy-β-D-glucopyranosyl)-α-D-glucopyranoside The compound (762.6 mg, 0.85 mmol) synthesized in Example 8 (8b) was dissolved in methylene chloride (14 mL) and trichloroacetonitrile (0.43 mL, 4.29 mmol) and 1,8-diazabicyclo[5.4.0]undec-7-ene (1 drop) were added thereto, followed by stirring of the mixture at room temperature for 30 minutes. After the solvent was distilled off under reduced pressure, the residue was purified using silica gel flash column chromatography (hexane:ethyl acetate, 4:1, 1% triethylamine, V/V) to obtain imidate (567.8 mg, 64%) of colorless oil. The compound (380.8 mg, 0.85 mmol) synthesized in Example 1 (1i) was dissolved in diethyl ether (13 mL) and trimethylsilyl trifluoromethanesulfonate (8.0 μL, 0.044 mmol) was dissolved in diethyl ether (2 mL) under a nitrogen atmosphere and it was added. A solution of imidate (567.8 mg) in diethyl ether (5 mL) was added to the reaction mixture and the mixture was stirred at room temperature for 2 hours. After triethylamine (8.0 μL, 0.057 mmol) was added to the reaction mixture and the solvent was distilled off under reduced pressure, it was diluted with ethyl acetate (20 mL) and the mixture was washed with saturated aqueous sodium hydrogencarbonate solution (20 mL) and saturated brine (20 mL). After the organic layer was dried with anhydrous sodium sulfate, the solvent was distilled off under reduced pressure and the residue containing the α, β mixture was purified using silica gel flash column chromatography (hexane:diethyl ether, 3:1, V/V) to isolate the desired title compound α form (150.1 mg, 13%) thereof as colorless amorphous matter.

¹H NMR (400 MHz, CDCl₃): δ 3.20 (3H, s), 3.25-5.20 (39H, m), 7.20-7.40 (45H, m); MS (FAB) m/z: 1327 (M+H)⁺.

(8d) (2R,3R,4R)-4-Hydroxy-2-hydroxymethyl-pyrrolidin-3-yl 4-O-(6-methoxy-6-deoxy-β-D-glucopyranosyl)-α-D-glucopyranoside The compound (150.1 mg, 0.11 mmol) synthesized in Example 8 (8c) was dissolved in methanol (10 mL) containing 1% aqueous hydrochloric acid solution and 20% palladium hydroxide-carbon (100 mg) was added thereto, followed by stirring of the mixture under a hydrogen atmosphere for 2 hours. After the catalyst was removed by celite filtration, 28% ammonia water (0.5 mL) was added thereto and the mixture was stirred for 10 minutes. After the solvent was distilled off under reduced pressure and the aqueous solution (100 mL) was subjected to ion exchange resin (Dowex 50w×8) column, it was eluted with 1% ammonia water (100 mL). The ammonia water containing the desired compound was concentrated under reduced pressure and the residue was purified using silica gel flash column chromatography (ethyl acetate:methanol:water, 5:2:1-1:1:1, V/V) to obtain the desired title compound (49.1 mg, 95%) as a colorless solid.

¹H NMR (400 MHz, CDCl₃): δ 3.00-4.20 (19H, m), 3.27 (3H, s), 4.37 (1H, d, J=8.0 Hz), 4.98 (1H, d, J=3.7 Hz); MS (FAB) m/z: 472 (M+H)⁺.

EXAMPLE 9

(2R,3R,4R)-4-Fluoro-2-hydroxymethyl-pyrrolidin-3-yl 4-O-(6-deoxy-α-D-glucopyranosyl)-α-D-glucopyranoside (Exemplification Compound No. 1-115)

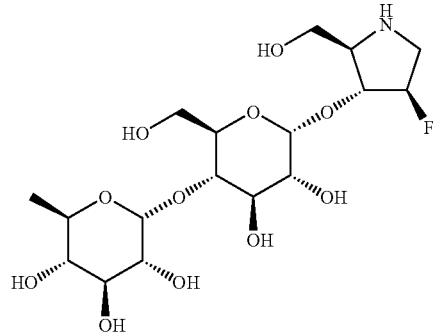

(9a) (2R,3R,4R)-3-Benzoyloxy-N-benzyloxycarbonyl-2-benzyloxymethyl-4-hydroxy-pyrrolidine The compound (3.37 g, 9.07 mmol) synthesized in Example 1 (1h) was dissolved in methylene chloride:cyclohexane (1:2, 180 mL) and benzyl trichloroacetoimidate (2.0 mL, 10.88 mmol) and trifluoromethanesulfonic acid (2.57 mL, 15.3 mmol) were added thereto, followed by stirring of the mixture at room temperature for 1 hour. After saturated aqueous sodium hydrogencarbonate solution (20 mL) was added to the reaction mixture at 0° C. and the mixture was diluted with ethyl acetate (200 mL), it was washed with water (300 mL) and saturated aqueous sodium hydrogencarbonate solution (300 mL) and dried with anhydrous sodium sulfate, followed by distilling off of the solvent under reduced pressure. The residue was purified using silica gel flash column chromatography (hexane:ethyl acetate, 5:1-2:1, V/V) to obtain 4.71 g of pale yellow oil.

¹H NMR (400 MHz, CDCl₃): δ 3.50-4.20 (4H, m), 4.45-4.80 (3H, m), 5.00-5.60 (5H, m), 7.32-7.46 (12H, m), 7.59 (1H, m), 7.99 (2H, m); MS (FAB) m/z: 462 (M+H)⁺.

(9b) (2R,3R,4S)-3-Benzoyloxy-N-benzyloxycarbonyl-2-benzyloxymethyl-4-hydroxy-pyrrolidine The compound (183 mg, 0.40 mmol) synthesized in Example 9 (9a) was dissolved in methylene chloride (4 mL) and pyridine (96 μL, 1.20 mmol) and trifluoromethanesulfonic acid anhydride (0.10 mL, 0.60 mmol) were added thereto, followed by stirring of the mixture at 0° C. for 20 minutes. After water (10 mL) was added thereto at 0° C. and the mixture was extracted with methylene chloride, the organic layer was washed with saturated brine (10 mL) and dried with anhydrous sodium sulfate, followed by distilling off of the solvent under reduced pressure. The residue was purified using silica gel flash column chromatography (hexane:ethyl acetate, 2:1, V/V) to obtain the desired title compound (92 mg, yield 50%) as a pale yellow oil.

¹H NMR (400 MHz, CDCl₃): δ 3.25-4.20 (4H, m), 4.25-4.75 (3H, m), 5.10-5.60 (5H, m), 7.32-7.46 (12H, m), 7.59 (1H, t, J=7.4 Hz), 7.99 (2H, d, J=8.8 Hz); MS (FAB) m/z: 462 (M+H)⁺.

(9c) (2R,3R,4R)-N-Benzyloxycarbonyl-2-benzyloxymethyl-4-fluoro-pyrrolidine

The compound (980 mg, 2.12 mmol) synthesized in Example 9 (9b) was dissolved in 1,2-dimethoxyethane (20 mL) and diethylaminosulfur trifluoride (0.84 mL, 6.36 mmol) was added thereto at −20° C. The temperature of the mixture was gradually raised and the mixture was stirred at 60° C. for 1 hour. After saturated aqueous sodium hydrogencarbonate solution was added thereto at 0° C. until foaming did not occur, the mixture was extracted with ethyl acetate and the organic layer was washed with saturated brine (20 mL) and dried with anhydrous sodium sulfate, follwed by distilling off of the solvent under reduced pressure. The residue was purified using silica gel flash column chromatography (hexane:ethyl acetate, 4:1, V/V) to obtain a pale yellow oil (545 mg). The thus obtained pale yellow oil (545 mg) was dissolved in methanol (10 mL) and potassium carbonate (50 mg) was added thereto, followed by stirring of the mixture at room temperature for 20 minutes. After the solvent was distilled off under reduced pressure, water (20 mL) was added thereto and the mixture was extracted with ethyl acetate. The organic layer was washed with saturated brine (20 mL). The solvent was distilled off under reduced pressure and the residue was purified using silica gel flash column chromatography (hexane:ethyl acetate, 2:1, V/V) to obtain the desired title compound (263 mg, yield 34%) as a colorless oil.

$^1$H NMR (400 MHz, CDCl$_3$): δ 3.10-4.20 (4H, m), 4.25-4.75 (3H, m), 4.80-5.20 (5H, m), 7.30-7.45 (10H, m); MS (FAB) m/z: 360 (M+H)$^+$.

(9d) (2R,3R,4R)-N-Benzyloxycarbonyl-2-benzyloxymethyl-4-fluoro-pyrrolidin-3-yl 2,3,6-tri-O-benzyl-4-O-(2,3,4-tri-O-benzyl-6-deoxy-α-D-glucopyranosyl)-α-D-glucopyranoside The compound (657 mg, 0.76 mmol) synthesized in Example 1 (1) was dissolved in methylene chloride (12 mL) and trichloroacetonitrile (0.38 mL, 3.8 mmol) and 1,8-diazabicyclo[5.4.0]-7-undecene (11 μL, 76 μmol) were added thereto, followed by stirring of the mixture at room temperature for 15 minutes. After the solvent was distilled off under reduced pressure, the residue was purified using silica gel flash column chromatography (hexane:ethyl acetate, 5:1, 1% triethylamine, V/V) to obtain imidate (767 mg, 100%) of colorless oil. The compound (263 mg, 0.73 mmol) synthesized in Example 9 (9c) was dissolved in diethyl ether (12 mL) and trimethylsilyl trifluoromethanesulfonate (13 μL, 73 μmol) was added thereto under a nitrogen atmosphere. A solution of imidate in diethyl ether (8 mL) was added to the reaction mixture and the mixture was stirred at room temperature for 1.5 hours. After triethylamine (20 μL, 146 μmol) was added to the reaction mixture and the solvent was distilled off under reduced pressure, the residue was diluted with ethyl acetate (20 mL) and the mixture was washed with saturated aqueous sodium hydrogencarbonate (20 mL) and saturated brine (20 mL). After the organic layer was dried with anhydrous sodium sulfate, the solvent was distilled off under reduced pressure and the residue was purified using silica gel flash column chromatography (hexane:diethyl ether, 4:1, V/V) to obtain the desired title compound α isomer (109 mg, 12%) and β isomer (52 mg, 6%) as a colorless oil.

$^1$H NMR (400 MHz, CDCl$_3$): δ 1.09 (3H, d, J=4.2 Hz), 3.00-5.60 (35H, m), 7.10-7.40 (40H, m); MS (FAB) m/z: 1209 (M+H)$^+$.

(9e) (2R,3R,4R)-4-Fluoro-2-hydroxymethyl-pyrrolidin-3-yl 4-O-(6-deoxy-α-D-glucopyranosyl)-α-D-glucopyranoside The compound (109 mg, 90.2 μmol) synthesized in Example 9 (9d) was dissolved in 1% hydrochloric acid methanol solution (5 mL) and 20% palladium hydroxide-carbon (55 mg) was added thereto, followed by stirring of the mixture under a hydrogen atmosphere for 1 hour. After the catalyst was removed by celite filtration, 28% ammonia water (0.2 mL) was added thereto and the mixture was stirred for 10 minutes. After the solvent was distilled off under reduced pressure and it was passed through ion exchange resin (Dowex 50w×8) column with water (30 mL), 1% ammonia water (30 mL) was flowed through. The ammonia water containing the desired compound was concentrated under reduced pressure and the residue was purified using silica gel flash column chromatography (ethyl acetate:methanol:water, 5:2:1-1:1:1, V/V) to obtain the desired title compound (26 mg, 65%) as a colorless solid.

$^1$H NMR (500 MHz, CDCl$_3$): δ 1.18 (3H, d, J=5.9 Hz), 2.98-3.16 (4H, m), 3.47-3.77 (12H, m), 4.11 (1H, dd, J=4.9, 20.5 Hz), 5.02 (1H, m), 5.23 (1H, m); MS (FAB) m/z: 444 (M+H)$^+$.

EXAMPLE 10

(2R,3R,4R)-4-Hydroxy-2-fluoromethyl-pyrrolidin-3-yl 4-O-(6-deoxy-β-D-glucopyranosyl)-α-D-glucopyranoside (Exemplification Compound No. 1-119)

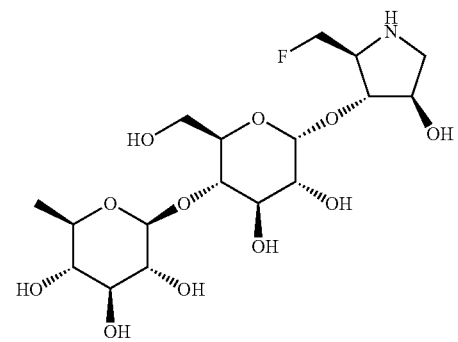

(10a) (2R,3R,4R)-3-Benzoyloxy-N-benzyloxycarbonyl-2-fluoromethyl-4-hydroxy-pyrrolidine The compound (257 mg, 0.69 mmol) synthesized in Example 1 (1h) was dissolved in 1,2-dimethoxyethane (5 mL) and diethylaminosulfur trifluoride (0.11 mL, 0.83 mmol) was added thereto at −20° C. The temperature of the mixture was gradually raised and the mixture was stirred at 60° C. for 1 hour. After saturated aqueous sodium hydrogencarbonate solution was added thereto at 0° C. until foaming did not occur, the mixture was extracted with ethyl acetate (15 mL) and the organic layer was washed with saturated brine (15 mL) and dried with anhydrous sodium sulfate, followed by distilling off of the solvent under reduced pressure. The residue was purified using silica gel flash column chromatography (hexane:ethyl acetate, 3:1, V/V) to obtain a colorless oil (113 mg, 44%).

$^1$H NMR (400 MHz, CDCl$_3$): δ 3.50-4.25 (4H, m), 4.50-5.55 (3H, m), 5.40-5.60 (2H, m), 7.20-7.50 (7H, m), 7.60 (1H, m), 8.00-8.10 (2H, m); MS (FAB) m/z: 374 (M+H)$^+$.

(10b) (2R,3R,4S)-3-Benzoyloxy-N-benzyloxycarbonyl-4-benzyloxy-2-fluoromethyl-pyrrolidine The compound (344 mg, 0.92 mmol) synthesized in Example 10 (10a) was dissolved in methylene chloride:cyclohexane (1:2, 10 mL) and benzyl trichloroacetoimidate (0.68 mL, 3.68 mmol) and trifluoromethane sulfonic acid (16 μL, 0.18 mmol) were added thereto, followed by stirring of the mixture at room temperature for 4 hours. After saturated aqueous sodium hydrogencarbonate (1 mL) was added to the reaction mixture at 0° C. and the mixture was diluted with ethyl acetate (20 mL), the mixture was washed with water (20 mL) and saturated brine (20 mL) and dried with anhydrous sodium sulfate, followed by distilling off of the solvent under reduced pressure. The residue was purified using silica gel flash column chromatography (hexane:ethyl acetate, 8:1-5:1, V/V) to obtain a colorless oil (307 mg, 68%).
$^1$H NMR (400 MHz, CDCl$_3$): δ 3.50-5.25 (7H, m), 5.50-5.75 (4H, m), 7.20-7.50 (12H, m), 7.60 (1H, m), 8.00-8.10 (2H, m); MS (FAB) m/z: 464 (M+H)$^+$.

(10c) (2R,3R,4S)-N-Benzyloxycarbonyl-4-benzyloxy-2-fluoromethyl-pyrrolidine

The compound (307 mg, 0.66 mmol) synthesized in Example 10 (10b) was dissolved in methanol (6 mL) and potassium carbonate (27 mg, 0.20 mmol) was added thereto, followed by stirring of the mixture at room temperature for 2.5 hours. After methanol was distilled off under reduced pressure, water (15 mL) was added thereto and the mixture was extracted with ethyl acetate (15 mL). The organic layer was washed with saturated brine (15 mL) and dried with anhydrous sodium sulfate, followed by distilling off of the solvent under reduced pressure. The residue was purified using silica gel flash column chromatography (hexane:ethyl acetate, 3:1, V/V) to obtain the desired title compound (176 mg, yield 74%) as a colorless oil.
$^1$H NMR (400 MHz, CDCl$_3$): δ 3.35-4.80 (7H, m), 5.50-5.75 (4H, m), 7.20-7.50 (10H, m); MS (FAB) m/z: 360 (M+H)$^+$.

(10d) (2R,3R,4R)-N-Benzyloxycarbonyl-4-benzyloxy-2-fluoromethyl-pyrrolidin-3-yl 2,3,6-tri-O-benzyl-4-O-(2,3,4-tri-O-benzyl-6-deoxy-β-D-glucopyranosyl)-α-D-glucopyranoside The compound (398 mg, 0.46 mmol) synthesized in Example 2 (2f) was dissolved in methylene chloride (8 mL) and trichloroacetonitrile (0.23 mL, 2.30 mmol) and 1,8-diazabicyclo[5.4.0]-7-undecene (7 μL, 0.05 mmol) were added thereto, followed by stirring of the mixture at room temperature for 15 minutes. After the solvent was distilled off under reduced pressure, the residue was purified using silica gel flash column chromatography (hexane:ethyl acetate, 5:1, 1% triethylamine, V/V) to obtain imidate of colorless oil. The compound (165 mg, 0.46 mmol) synthesized in Example 10 (10c) was dissolved in diethyl ether (8 mL) and trimethylsilyl trifluoromethanesulfonate (8 μL, 46 μmol) was added thereto under a nitrogen atmosphere. A solution of imidate in diethyl ether (4 mL) was added to the reaction mixture and the mixture was stirred at room temperature for 2.5 hours. After triethylamine (13 μL, 92 μmol) was added to the reaction mixture and the solvent was distilled off under reduced pressure, the residue was diluted with ethyl acetate (15 mL) and the mixture was washed with saturated aqueous sodium hydrogencarbonate (15 mL) and saturated brine (15 mL). After the organic layer was dried with anhydrous sodium sulfate, the solvent was distilled off under reduced pressure and the residue was purified using silica gel flash column chromatography (hexane:diethyl ether, 4:1, V/V) to obtain the desired title compound (53 mg, 10%) as a colorless oil.
$^1$H NMR (400 MHz, CDCl$_3$): δ 1.10 (3H, d, J=4.2 Hz), 3.00-5.60 (35H, m), 7.10-7.40 (40H, m); MS (FAB) m/z: 1209 (M+H)$^+$.

(10e) (2R,3R,4R)-4-Hydroxy-2-fluoromethyl-pyrrolidin-3-yl 4-O-(6-deoxy-β-D-glucopyranosyl)-α-D-glucopyranoside The compound (53 mg, 43.9 μmol) synthesized in Example 10 (10d) was dissolved in 1% hydrochloric acid methanol solution (5 mL) and 20% palladium hydroxide-carbon (30 mg) was added thereto, followed by stirring of the mixture under a hydrogen atmosphere for 3 hours. After the catalyst was removed by celite filtration, 28% ammonia water (0.2 mL) was added thereto and the mixture was stirred for 10 minutes. After the solvent was distilled off under reduced pressure and it was passed through ion exchange resin column with water (30 mL), 1% ammonia water (30 mL) was flowed through. The ammonia water containing the desired compound was concentrated under reduced pressure and the residue was purified using silica gel flash column chromatography (ethyl acetate:methanol:water, 5:2:1-1:1:1, V/V) to obtain the desired title compound (1.6 mg, 8%) as a colorless solid.
$^1$H NMR (500 MHz, CDCl$_3$): δ 1.18 (3H, d, J=4.0 Hz), 2.98-4.25 (16H, m), 4.50 (2H, m), 5.83 (1H, m); MS (FAB) m/z: 444 (M+H)$^+$.

EXAMPLE 11

(2R,3R,4S)-4-Hydroxy-2-hydroxymethyl-pyrrolidin-3-yl 4-O-(6-deoxy-α-D-glucopyranosyl)-α-D-glucopyranoside (Exemplification Compound No. 1-1)

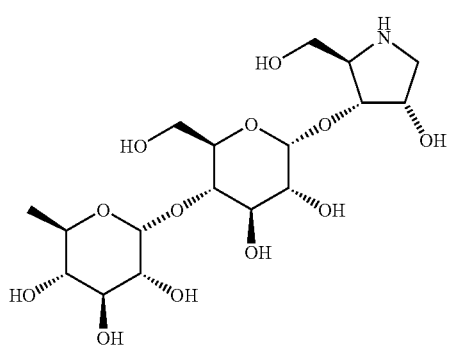

(11a) (2R,3R,4S)-N-Benzyloxycarbonyl-4-benzyloxy-2-benzyloxymethyl-3-hydroxy-pyrrolidine The compound (815 mg, 1.77 mmol) synthesized in Example 9 (9b) was dissolved in dichloromethane:cyclohexane (1:2, 45 mL) and benzyltrichloroacetoimidate (0.66 mL, 3.54 mmol) and trifluoromethanesulfonic acid (24 µL, 0.27 mmol) were added thereto, followed by stirring of the mixture at room temperature for 1.5 hours. After saturated aqueous sodium hydrogencarbonate solution (5 mL) was added to the reaction mixture at 0° C. and the mixture was diluted with ethyl acetate (200 mL), the mixture was washed with water (50 mL) and saturated aqueous sodium hydrogencarbonate solution (50 mL) and dried with anhydrous sodium sulfate, followed by distilling off of the solvent under reduced pressure. The residue was purified using silica gel flash column chromatography (hexane:ethyl acetate, 4:1, V/V) to obtain a pale yellow oil (866 mg). Thus obtained pale yellow oil (866 mg) was dissolved in methanol (15 mL) and potassium carbonate (65 mg) was added thereto, followed by stirring of the mixture at room temperature for 1 hour. After the solvent was distilled off under reduced pressure, water (20 mL) was added thereto and the mixture was extracted with ethyl acetate. The organic layer was washed with saturated brine (20 mL). The solvent was distilled off under reduced pressure and the residue was purified using silica gel flash column chromatography (hexane:ethyl acetate, 5:1-2:1, V/V) to obtain the desired title compound (233 mg, yield 30%) as a colorless oil.

$^1$H NMR (400 MHz, CDCl$_3$): δ 3.35-4.25 (6H, m), 4.25-4.70 (4H, m), 5.00-5.30 (4H, m), 7.09-7.26 (15H, m); MS (FAB) m/z: 448 (M+H)$^+$.

(11b) (2R,3R,4S)-N-Benzyloxycarbonyl-2-benzyloxymethyl-4-benzyloxy-pyrrolidin-3-yl 2,3,6-tri-O-benzyl-4-O-(2,3,4-tri-O-benzyl-6-deoxy-α-D-glucopyranosyl)-α-D-glucopyranoside The compound (513 mg, 0.59 mmol) synthesized in Example 1 (1f) was dissolved in methylene chloride (10 mL) and trichloroacetonitrile (0.3 mL, 2.95 mmol) and 1,8-diazabicyclo[5.4.0]-7-undecene (9 µL, 0.06 mmol) were added thereto, followed by stirring of the mixture at room temperature for 15 minutes. After the solvent was distilled off under reduced pressure, the residue was purified using silica gel flash column chromatography (hexane:ethyl acetate, 5:1, 1% triethylamine, V/V) to obtain imidate (447 mg, 75%) of colorless oil. The compound (233 mg, 0.52 mmol) synthesized in Example 11 (11a) was dissolved in diethyl ether (10 mL) and trimethylsilyl trifluoromethanesulfonate (9 µL, 59 µmol) was added thereto under a nitrogen atmosphere. A solution of imidate in diethyl ether (5 mL) was added to the reaction mixture and the mixture was stirred for 1.5 hours. After triethylamine (16 µL, 118 µmol) was added to the reaction mixture and the solvent was distilled off under reduced pressure, it was diluted with ethyl acetate (20 mL) and the mixture was washed with saturated aqueous sodium hydrogencarbonate (20 mL) and saturated brine (20 mL). After the organic layer was dried with anhydrous sodium sulfate, the solvent was distilled off under reduced pressure and the residue was purified using silica gel flash column chromatography (hexane:diethyl ether, 5:1-4:1, V/V) to obtain the desired title compound α isomer (58 mg, 8%) and β isomer (51 mg, 7%) as a colorless oil.

$^1$H NMR (400 MHz, CDCl$_3$): δ 1.15 (3H, d, J=5.6 Hz), 3.10-5.20 (36H, m), 1.15 (1H, d, J=6.3 Hz), 7.20-7.39 (45H, m); MS (FAB) m/z: 1297 (M+H)$^+$.

(11c) (2R,3R,4S)-4-Hydroxy-2-hydroxymethyl-pyrrolidin-3-yl 4-O-(6-deoxy-α-D-glucopyranosyl)-α-D-glucopyranoside The compound (58 mg, 44.7 µmol) synthesized in Example 11 (11b) was dissolved in 1% hydrochloric acid methanol solution (5 mL) and 20% palladium hydroxide-carbon (30 mg) was added thereto, followed by stirring of the mixture under a hydrogen atmosphere for 1.5 hours. After the catalyst was removed by celite filtration, 28% ammonia water (0.2 mL) was added thereto and the mixture was stirred for 10 minutes. After the solvent was distilled off under reduced pressure and it was passed through ion exchange resin (Dowex 50w×8) column with water (30 mL), 1% ammonia water (30 mL) was flowed through. The ammonia water containing the desired compound was concentrated under reduced pressure and the residue was purified using silica gel flash column chromatography (ethyl acetate:methanol:water, 5:2:1-1:1:1, V/V) to obtain the desired title compound (13 mg, 68%) as a colorless solid.

$^1$H NMR (400 MHz, D$_2$O): δ 1.19 (3H, d, J=4.1 Hz), 2.80-4.60 (17H, m), 5.00 (1H, d, J=3.6 Hz), 5.24 (1H, d, J=3.0 Hz); MS (FAB) m/z: 442 (M+H)$^+$.

EXAMPLE 12

(2R,3R,4R)-2-Hydroxymethyl-3-hydroxy-pyrrolidin-4-yl 4-O-(6-deoxy-β-D-glucopyranosyl)-α-D-glucopyranoside) (Exemplification Compound No. 1-556)

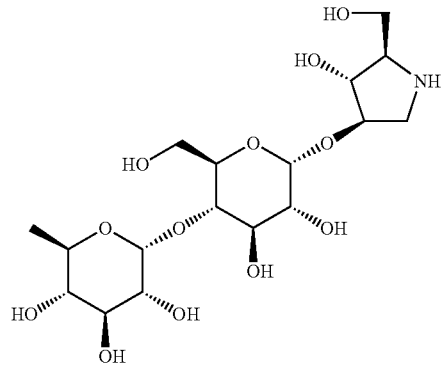

(12a) (2R,3R,4R)-N-Benzyloxycarbonyl-2-benzyloxymethyl-3-hydroxy-pyrrolidin-4-yl 2,3,6-tri-O-benzyl-4-O-(2,3,4-tri-O-benzyl-6-deoxy-β-D-glucopyranosyl)-α-D-glucopyranoside The compound (607 mg, 0.70 mmol) synthesized in Example 2 (2f) was dissolved in methylene chloride (10 mL) and trichloroacetonitrile (500 µL, 4.98 mmol) and 1,8-diazabicyclo[5.4.0]-7-undecene (2 drops) were added thereto, followed by stirring of the mixture at room temperature for 40 minutes. After the solvent was distilled off under reduced pressure, the residue was purified using silica gel flash column chromatography (hexane:ethyl acetate, 5:1, 1% triethylamine, V/V) to obtain imidate (630 mg, 89%) as a yellow oil. The compound (323 mg, 0.700 mmol) synthesized in Example 9 (9a) was dissolved in diethyl ether (10 mL) and imidate (630 mg, 0.623 mmol) was added thereto. Trimethylsilyl trifluoromethanesulfonate (6.3 µL, 34.8

μmol) was dropwise thereto and the mixture was stirred at room temperature for 45 minutes. After triethylamine (4 drops) was added to the reaction mixture, the solvent was distilled off under reduced pressure. The residue was purified using silica gel flash column chromatography (hexane:diethyl ether, 6:1, V/V) to obtain the desired title compound (610 mg, 75%) as a pale yellow oil. Subsequently the pale yellow oil (610 mg, 0.465 mmol) was dissolved in methanol (10 mL) and potassium carbonate water (1M, 1 mL, 1 mmol) was added thereto, followed by stirring of the mixture at room temperature for 3 hours. The solvent was distilled off under reduced pressure and the residue was purified using silica gel flash column chromatography (hexane:diethyl ether, 2:1, V/V) to obtain the desired title compound (280 mg, yield 50%) as a colorless solid.

$^1$H NMR (400 MHz, D$_2$O): δ 1.19 (3H, d, J=5.8 Hz), 2.83 (1H, brs), 3.12 (1H, t, J=9.3 Hz), 3.17-3.23 (1H, m), 3.29-3.37 (2H, m), 3.39-3.45 (2H, m), 3.51 (1H, dd, J=9.76, 2.93 Hz), 3.60 (1H, brt, J=7.8 Hz), 3.72-4.01 (7H, m), 4.27-4.56 (6H, m), 4.60-4.63 (2H, m), 4.73-4.75 (4H, brm), 4.78 (1H, d, J=10.75 Hz), 4.85 (1H, d, J=10.74 Hz), 4.87 (1H, d, J=9.77 Hz), 4.92 (1H, d, J=2.93 Hz), 5.01-5.12 (3H, m), 7.21-7.34 (38H, m), 7.43 (2H, d, J=6.83 Hz); MS (FAB) m/z: 1207 (M+H)$^+$.

(12b) (2R,3R,4R)-2-Hydroxymethyl-3-hydroxy-pyrrolidin-4-yl 4-O-(6-deoxy-β-D-glucopyranosyl)-α-D-glucopyranoside The compound (90 mg, 74.6 μmol) synthesized in Example 12 (12a) was dissolved in methanol (10 mL) and hydrochloric acid (140 μL) and 20% palladium hydroxide-carbon (90 mg) were added thereto, followed by stirring of the mixture at room temperature under a hydrogen atmosphere for 2 hours. After the celite filtration, ammonia water (5%) was added thereto until the pH became neutral. The solvent was distilled off under reduced pressure and the residue was purified by ion exchange resin (Dowex 50w×8) column (water—5% ammonia water). Further, it was purified using silica gel flash column chromatography (ethyl acetate:methanol:water, 1:1:1, V/V) to obtain the desired title compound (26 mg, 79%) as a colorless solid.

$^1$H NMR (400 MHz, D$_2$O): δ 1.32 (3H, d, J=5.8 Hz), 3.17-3.22 (2H, m), 3.30-3.38 (2H, m), 3.44-3.55 (2H, m), 3.60-3.64 (2H, m), 3.74-3.86 (6H, m), 3.92 (1H, brd, J=11, 72 Hz), 4.13 (1H, brs), 4.24 (1H, brs), 4.48 (1H, d, J=7.81 Hz), 5.11 (1H, d, J=2.93 Hz); MS (FAB) m/z: 442 (M+H)$^+$.

EXAMPLE 13

(2R,3R,4R)-4-Hydroxy-2-hydroxymethyl-pyrrolidin-3-yl 4-O-(6-deoxy-α-D-glucopyranosyl)-β-D-glucopyranoside (Exemplification Compound No. 1-1)

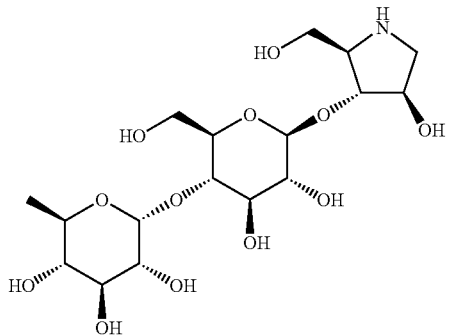

The compound β form (60 mg, 46.3 μmol) synthesized in Example 1 (1j) was dissolved in methanol (4 mL) and hydrochloric acid (56 μL) and 20% palladium hydroxide-carbon (60 mg) were added thereto, followed by stirring of the mixture at room temperature under a hydrogen atmosphere for 4 hours. After the celite filtration, 18% ammonia water (3 drops) was added thereto and the solvent was distilled off under reduced pressure. The residue was purified by ion exchange resin (Dowex 50w×8) column (water—5% ammonia water). Further, it was purified using silica gel flash column chromatography (ethyl acetate:methanol:water, 3:2:1, V/V) to obtain the desired title compound (10 mg, 49%) as a colorless solid.

$^1$H NMR (400 MHz, D$_2$O): δ 1.29 (3H, d, J=5.8 Hz), 2.93 (1H, dd, J=11.7, 3.6 Hz), 3.15-3.35 (4H, m), 3.51-3.65 (5H, m), 3.74-3.80 (5H, m), 3.93-4.00 (2H, m), 4.40 (1H, br, s), 4.56 (1H, d, J=7.3 Hz), 5.34 (1H, br, s); MS (FAB) m/z: 464 (M+Na)$^+$, 442 (M+H)$^+$.

EXAMPLE 14

(1R,2S,3R,4R,5R)-1-Amino-2,3-dihydroxy-5-hydroxymethyl-cyclopent-4-yl 4-O-(6-deoxy-α-D-glucopyranosyl)-α-D-glucopyranoside (Exemplification Compound No. 5-1)

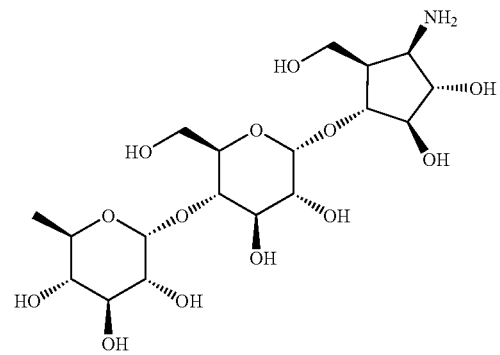

(14a) Methyl 4-O-benzoyl-2,3-di-O-benzyl-6-O-p-toluenesulfonyl-α-D-glucopyranoside Methyl 2,3-di-O-benzyl-6-O-p-toluenesulfonyl-α-D-glucopyranoside (J. Org. Chem., 2001, 66, 5965-5975) (163.9 g, 310 mmol) was dissolved in methylene chloride (1.5 L) and 4-dimethylaminopyridine (43.5 g, 352 mmol) and triethylamine (49.0 mL, 352 mmol) were added thereto. Benzoyl chloride (43.2 mL, 372 mmol) was dropwise thereto and the mixture was stirred at 0° C. for 1 hour. After diluted hydrochloric acid (2N, 500 mL) was added to the reaction mixture and the mixture was extracted with methylene chloride (1 L), the organic layer was washed with saturated aqueous sodium hydrogencarbonate (1 L) and saturated brine (1 L) and dried with anhydrous sodium sulfate, followed by distilling off of the solvent under reduced pressure. The residue was purified using silica gel flash column chromatography (hexane:ethyl acetate, 1:1, V/V) to obtain the desired title compound (196 g, yield 99%) as a colorless solid.

$^1$H NMR (400 MHz, CDCl$_3$): δ 2.34 (3H, s), 3.40 (3H, s), 3.58 (1H, dd, J=9.3, 3.4 Hz), 3.98-4.10 (4H, m), 4.57-4.65 (3H, m), 4.79 (1H, d, J=10.8 Hz), 5.06 (1H, dd, J=9.8, 9.8 Hz), 7.08-7.10 (5H, m), 7.18 (2H, d, J=7.8 Hz), 7.29-7.35 (5H, m), 7.41-7.45 (2H, m), 7.57-7.61 (1H, m), 7.67 (2H, d, J=7.8 Hz), 7.89 (2H, d, J=8.8 Hz); MS (FAB) m/z: 633 (M+H)$^+$.

(14b) Methyl 4-O-benzoyl-2,3-di-O-benzyl-6-deoxy-6-iode-α-D-glucopyranoside

The compound (196 g, 310 mmol) synthesized in Example 14 (14a) was dissolved in toluene (2 L) and sodium iodide (235 g, 1.57 mol) and 18-crown-6-ether (16.6 g, 62.8 mmol) were added thereto under a nitrogen atmosphere, followed by stirring of the mixture at 100° C. for 2 hours. The reaction mixture was cooled to room temperature and was filtered and the filtered product was washed with toluene. The filtrate and the washing liquid were washed with saturated aqueous sodium hydrogencarbonate (1 L) and saturated brine (1 L) and dried with anhydrous sodium sulfate, followed by distilling off of the solvent under reduced pressure to obtain the desired title compound (181 g, yield 99%) as a colorless solid.

$^1$H NMR (400 MHz, CDCl$_3$): δ 3.12 (1H, dd, J=11.0, 8.8 Hz), 3.29 (1H, dd, J=11.0, 2.2 Hz), 3.51 (3H, s), 3.64 (1H, dd, J=9.6, 3.7 Hz), 3.82-3.89 (1H, m), 4.06 (1H, dd, J=9.6, 8.8 Hz), 4.60-4.68 (3H, m), 4.82 (1H, d, J=11.0 Hz), 4.82 (1H, d, J=12.8 Hz), 5.06 (1H, dd, J=9.5, 9.5 Hz), 7.08-7.10 (5H, m), 7.29-7.38 (5H, m), 7.42-7.47 (2H, m), 7.57-7.61 (1H, m), 7.98 (2H, d, J=8.0 Hz); MS (FAB) m/z: 589 (M+H)$^+$.

(14c) 4-O-Benzoyl-2,3-di-O-benzyl-5,6-dideoxy-D-xylo-hex-5-enose oxime

The compound (181 g, 307 mmol) synthesized in Example 14 (14b) was dissolved in isopropanol (1.5 L) and distilled water (50 mL) and zinc powder (180 g) washed with diluted hydrochloric acid was added thereto, followed by stirring of the mixture at 100° C. for 1 hour. The reaction mixture was subjected to celite filtration, the filtered product was washed with ethanol and the filtrate and the washing liquid were distilled off under reduced pressure. The residue was dissolved in ethanol (500 mL) and hydroxylamine hydrochloride (42.7 g, 615 mmol) and pyridine (49.7 mL, 615 mmol) were added thereto, followed by stirring of the mixture at 80° C. for 40 minutes. The solvent was distilled off under reduced pressure and the residue was purified using silica gel flash column chromatography (hexane:ethyl acetate, 5:1, V/V) to obtain the desired title compound (126 g, yield 92%) as a colorless solid.

$^1$H NMR (400 MHz, CDCl$_3$): δ 3.83 (0.7H, dd, J=5.8, 4.9 Hz), 3.99 (0.3H, dd, J=6.2, 3.9 Hz), 4.23 (0.7H, dd, J=7.8, 4.9 Hz), 4.42 (1H, dd, J=11.8, 3.9 Hz), 4.65 (1H, d, J=11.7 Hz), 4.68-4.76 (3H, m), 4.97 (0.3H, dd, J=5.8, 3.9 Hz), 5.23 (1H, dd, J=10.7, 5.9 Hz), 5.31-5.37 (1H, m), 5.78-5.94 (2H, m), 7.20-7.38 (9H, m), 7.40-7.48 (3H, m), 7.53-7.59 (1H, m), 8.00-8.07 (2H, m); MS (FAB) m/z: 446 (M+H)$^+$.

(14d) (3aR,4R,5R,6S,6aR)-4-Benzoyloxy-5,6-dibenzyloxy-hexahydro-cyclopenta[c]isoxasole The compound (126 g, 282 mmol) synthesized in Example 14 (14c) was dissolved in toluene (800 mL) and the mixture was stirred at 120° C. for 8 hours. The solvent was distilled off under reduced pressure and the residue was purified using silica gel flash column chromatography (hexane:ethyl acetate, 3:1, V/V) to obtain the desired title compound (59.7 g, yield 48%) as a colorless solid.

$^1$H NMR (400 MHz, CDCl$_3$): δ 2.83-2.91 (1H, m), 3.45-3.60 (1H, m), 3.89-3.95 (2H, m), 4.11-4.18 (1H, m), 4.55 (1H, m), 4.75-4.87 (4H, m), 5.01 (1H, dd, J=7.8, 6.8 Hz), 5.09-5.13 (1H, m), 7.22-7.40 (10H, m), 7.43-7.47 (2H, m), 7.57-7.61 (1H, m), 7.97-8.00 (2H, m); MS (FAB) m/z: 446 (M+H)$^+$.

(14e) (3aR,4R,5S,6S,6aR)-1-Benzyloxycarbonyl-5,6-dibenzyloxy-4-hydroxy-hexahydro-cyclopenta[c]isoxazole The compound (59.7 g, 134 mmol) synthesized in Example 14 (14d) was dissolved in methanol (1 L) and sodium methoxide (10 mL, 49 mmol) was added thereto, followed by stirring of the mixture at room temperature for 15 minutes. After saturated aqueous ammonium chloride solution (500 mL) was added to the reaction mixture at 0° C. and the mixture was extracted with ethyl acetate (1.5 L), the organic layer was washed with saturated brine (50 mL). Saturated aqueous sodium hydrogencarbonate (500 mL) and benzyloxychloroformate (22.9 mL, 160 mmol) were added to the organic layer at 0° C. and the mixture was stirred at 0° C. for 1 hour. After the organic layer was washed with saturated brine (500 mL) and dried with anhydrous sodium sulfate, the solvent was distilled off under reduced pressure. The residue was purified using silica gel flash column chromatography (hexane:ethyl acetate, 1:1, V/V) to obtain the desired title compound (61.3 g, yield 96%) as a colorless solid.

$^1$H NMR (400 MHz, CDCl$_3$): δ 2.30 (1H, brd, J=3.7 Hz, OH), 2.91 (1H, ddd, J=8.9, 8.9, 5.7 Hz, H-3a), 3.58 (1H, dd, J=9.0, 5.7 Hz, H-3), 3.73 (1H, dd, J=8.6, 8.4 Hz, H-5), 3.82 (1H, ddd, J=8.9, 8.6, 3.7 Hz, H-4), 3.84 (1H, dd, J=8.4, 5.6 Hz, H-6), 3.98 (1H, d, J=9.0 Hz, H-3), 4.54 (1H, d, J=11.3 Hz), 4.54 (1H, dd, J=8.9, 5.6 Hz, H-6a), 4.63 (1H, d, J=11.7 Hz), 4.84 (1H, d, J=11.3 Hz), 4.87 (1H, d, J=11.7 Hz), 5.20 (1H, d, J=12.1 Hz), 5.27 (1H, d, J=12.1 Hz), 7.23-7.40 (15H, m). MS (FAB) m/z: 476 (M+H)$^+$.

(14f) (3aR,4R,5R,6S,6aR)-1-Benzyloxycarbonyl-5,6-dibenzyloxy-hexahydro-cyclopenta[c]isoxazol-4-yl 2,3,6-tri-O-benzyl-4-O-(6-deoxy-2,3,4-tri-O-benzyl-α-D-glucopyranosyl)-α-D-glucopyranoside The compound (215 mg, 0.248 mmol) synthesized in Example 1 (1f) was dissolved in methylene chloride (5 mL) and trichloroacetonitrile (460 μL, 4.61 mmol) and 1,8-diazabicyclo 5.4.0]-7-undecene (2 drops) were added thereto, followed by stirring of the mixture at room temperature for 40 minutes. After the solvent was distilled off under reduced pressure, the residue was purified using silica gel flash column chromatography (hexane:ethyl acetate, 5:1, 1% triethylamine, V/V) to obtain imidate (250 mg, 99%) as a yellow oil. The compound (100 mg, 0.21 mmol) synthesized in Example 14 (14e) was dissolved in diethyl ether (10 mL) and imidate (250 mg, 0.248 mmol) was added thereto. Trimethylsilyl trifluoromethanesulfonate (3.8 μL, 0.021 mmol) was added dropwise thereto and the mixture was stirred at room temperature for 45 minutes. After triethylamine (4 drops) was added to the reaction mixture, the solvent was distilled off under reduced pressure. The residue was purified using silica gel flash column chromatography (hexane:diethyl ether, 2:1, V/V) to obtain the desired title compound (55 mg, 17%) as a pale yellow oil.

$^1$H NMR (400 MHz, CDCl$_3$): δ 1.15 (3H, d, J=6.8 Hz), 3.01-3.12 (2H, m), 3.14 (1H, dd, J=9.8, 3.9 Hz), 3.50-3.62 (3H, m), 3.64-3.80 (2H, m), 3.80-3.96 (5H, m), 3.99-4.10 (2H, m), 4.43 (1H, d, J=11.7 Hz), 4.47 (1H, d, J=11.7 Hz), 4.50-4.62 (7H, m), 4.68-4.93 (8H, m), 5.06 (1H, d, J=11.7 Hz), 5.18-5.29 (3H, m), 5.61 (1H, d, J=3.9 Hz), 7.05-7.41 (45H, m); MS (FAB) m/z: 1324 (M+H)$^+$.

(14g) (1R,2S,3R,4R,5R)-1-Amino-2,3-dihydroxy-5-hydroxymethyl-cyclopent-4-yl 4-O-(6-deoxy-α-D-glucopyranosyl)-α-D-glucopyranoside The compound (53 mg, 40.4 mmol) synthesized in Example 14 (14f) was dissolved in methanol (10 mL) and hydrochloric acid (10 µL) and 20% palladium hydroxide-carbon (53 mg) were added thereto, followed by stirring of the mixture at room temperature under a hydrogen atmosphere for 4 hours. After celite filtration, the solvent was distilled off under reduced pressure and the residue was purified by ion exchange resin (Dowex 50w×8) column (water—5% ammonia water). Further, it was purified using silica gel flash column chromatography (ethyl acetate:methanol:water, 1:1:1, V/V) to obtain the desired title compound (5 mg, 26%) as a colorless solid.

$^1$H NMR (400 MHz, D$_2$O): δ 1.18 (3H, d, J=6.8 Hz), 2.00-2.08 (1H, m), 2.15-2.22 (1H, m), 3.03-3.09 (1H, m), 3.16-3.22 (1H, m), 3.45-3.57 (5H, m), 3.58-3.78 (8H, m), 3.81-3.89 (3H, m), 5.10 (1H, d, J=2.9 Hz), 5.23 (1H, d, J=2.9 Hz); MS (FAB) m/z: 472 (M+H)$^+$.

EXAMPLE 15

(1R,2S,3R,4R,5R)-1-Amino-2,3-dihydroxy-5-hydroxymethyl-cyclopent-4-yl 4-O-(6-deoxy-β-D-glucopyranosyl)-α-D-glucopyranoside (Exemplification Compound No. 5-1)

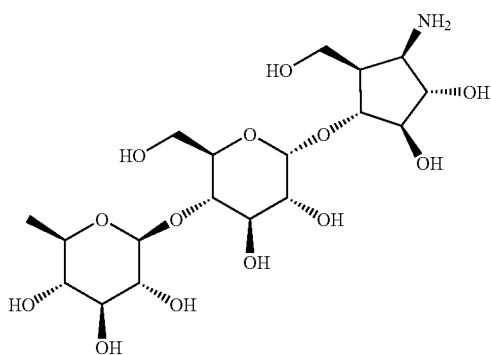

(15a) (3aR,4R,5R,6S,6aR)-1-Benzyloxycarbonyl-5,6-dibenzyloxy-hexahydro-cyclopenta[c]isoxazol-4-yl 2,3,6-tri-O-benzyl-4-O-(6-deoxy-2,3,4-tri-O-benzyl-β-D-glucopyranosyl)-α-D-glucopyranoside The compound (1.0 g, 1.15 mmol) synthesized in Example 2 (2f) was dissolved in methylene chloride (30 mL) and trichloroacetonitrile (460 µL, 4.61 mmol) and 1,8-diazabicyclo[5.4.0]-7-undecene (2 drops) were added thereto, followed by stirring of the mixture at room temperature for 40 minutes. After the solvent was distilled off under reduced pressure, the residue was purified using silica gel flash column chromatography (hexane:ethyl acetate, 5:1, 1% triethylamine, V/V) to obtain imidate (970 mg, 84%) as a yellow oil. The compound (508 mg, 1.06 mmol) synthesized in Example 14 (14e) was dissolved in diethyl ether (20 mL) and imidate (970 mg, 0.97 mmol) was added thereto. Trimethylsilyl trifluoromethanesulfonate (17 µL, 0.097 mmol) was added dropwise thereto and the mixture was stirred at room temperature for 45 minutes. After triethylamine (4 drops) was added to the reaction mixture, the solvent was distilled off under reduced pressure. The residue was purified using silica gel flash column chromatography (hexane:diethyl ether, 1:1, V/V) to obtain the desired title compound (125 mg, 9%) as a pale yellow oil.

$^1$H NMR (400 MHz, CDCl$_3$): δ 1.22 (3H, d, J=6.8 Hz), 2.81-2.87 (1H, m), 3.15 (1H, dd, J=9.8, 8.7 Hz), 3.19-3.24 (1H, m), 3.28-3.36 (2H, m), 3.40-3.45 (1H, m), 3.52 (1H, dd, J=8.8, 3.9 Hz), 3.55-3.59 (1H, m), 3.75 (1H, dd, J=10.7, 3.9 Hz), 3.79-3.84 (2H, m), 3.86-3.91 (1H, m), 3.93-4.01 (2H, m), 4.31 (1H, d, J=11.7 Hz), 4.35 (1H, d, J=7.8 Hz), 4.50 (1H, d, J=11.7 Hz), 4.52-4.59 (2H, m), 4.60-4.64 (3H, m), 4.70-4.87 (10H, m), 4.89 (1H, d, J=12.7 Hz), 5.00 (1H, d, J=10.7 Hz), 5.07 (1H, d, J=3.9 Hz), 5.21 (1H, d, J=11.7 Hz), 5.28 (1H, d, J=12.7 Hz), 7.10-7.43 (45H, m); MS (FAB) m/z: 1324 (M+H)$^+$.

(15b) (1R,2S, 3R, 4R, 5R)-1-Amino-2,3-dihydroxy-5-hydroxymethyl-cyclopent-4-yl 4-O-(6-deoxy-β-D-glucopyranosyl)-α-D-glucopyranoside The compound (115 mg, 86.8 µmol) synthesized in Example 15 (15a) was dissolved in methanol (20 mL) and ethyl acetate (1 mL) and hydrochloric acid (10 µL) and 20% palladium hydroxide-carbon (115 mg) were added thereto, followed by stirring of the mixture at room temperature under a hydrogen atmosphere for 4 hours. After celite filtration, the solvent was distilled off under reduced pressure and the residue was purified by ion exchange resin (Dowex 50w×8) column (water—5% ammonia water). Further, it was purified using silica gel flash column chromatography (ethyl acetate:methanol:water, 1:1:1, V/V) to obtain the desired title compound (30 mg, 73%) as a colorless amorphous.

[α]D20 +60.9 (c 0.11, H$_2$O); $^1$H NMR (400 MHz, D$_2$O): δ 1.21 (3H, d, J=6.8 Hz), 2.17-2.25 (1H, m), 3.05-3.10 (1H, m), 3.18-3.27 (2H, m), 3.30-3.92 (14H, m), 4.38 (1H, d, J=7.8 Hz), 5.08-5.10 (1H, m); MS (FAB) m/z: 472 (M+H)$^+$.

EXAMPLE 16

(1R,2S,3R,4R,5R)-1-(2-Hydroxy-1-hydroxymethyl-ethylamino)-2,3-dihydroxy-5-hydroxymethyl-cyclopent-4-yl 4-O-(6-deoxy-β-D-glucopyranosyl)-α-D-glucopyranoside (Exemplification Compound No. 5-22)

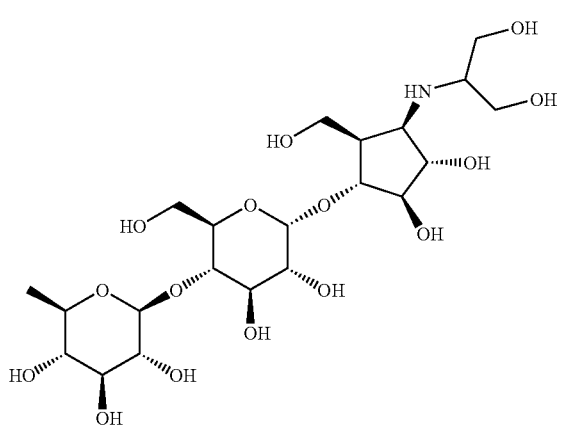

(16a) (3aR,4R,5R,6S,6aR)-4-Benzoyloxy-5,6-dibenzyloxy-1-(1,3-dihydroxyprop-2-yl)-hexahydro-cyclopenta[c]isoxazole The compound (3.07 g, 6.89 mmol) synthesized in Example 14 (14d) was dissolved in methanol (10 mL) and tetrahydrofuran (10 mL) and 1,3-dihydroxyacetone (1.86 g, 20.7 mmol) and acetic acid (1 mL) were added thereto, followed by stirring of the mixture at 70° C. for 30 minutes. Sodium cyanoborohydride (1.30 g, 20.67 mmol) was added thereto and the mixture was stirred at 70° C. for 10 hours. The solvent was distilled off under reduced pressure and the residue was purified using silica gel flash column chromatography (methylene chloride:methanol, 20:1, V/V) to obtain the desired title compound (1.20 g, yield 33%) as a colorless solid.

$^1$H NMR (400 MHz, CDCl$_3$): δ 2.35 (1H, dd, J=6.8, 4.9 Hz), 2.39 (1H, t, J=5.9 Hz), 2.77-2.82 (1H, m), 2.93-3.00 (1H, m), 3.74-3.84 (3H, m), 3.88-3.94 (1H, m), 3.96-4.08 (3H, m), 4.21-4.26 (2H, m), 4.74-4.86 (4H, m), 5.05 (1H, d, J=7.8, 5.9 Hz), 7.26-7.38 (10H, m), 7.45-7.50 (2H, m), 7.59-7.64 (1H, m), 7.98-8.02 (2H, m); MS (FAB) m/z: 520 (M+H)$^+$.

(16b) (3aR,4R,5S,6S,6aR)-5,6-Dibenzyloxy-1-(2,2-dimethyl-[1,3]dioxan-5-yl)-4-hydroxy-hexahydro-cyclopenta[c]isoxazole The compound (1.20 g, 2.31 mmol) synthesized in Example 16 (16a) was dissolved in acetone (30 mL) and 2,2-dimethoxy propane (2.27 mL, 18.5 mmol) and p-toluenesulfonic acid monohydrate (660 mg, 3.47 mmol) were added thereto, followed by stirring of the mixture at room temperature for 15 minutes. After saturated aqueous sodium hydrogencarbonate (50 mL) was added to the reaction mixture at 0° C. and the mixture was extracted with ethyl acetate (50 mL), the organic layer was washed with saturated brine (50 mL). The solvent was distilled off under reduced pressure and the residue was dissolved in methanol. Sodium methoxide (0.4 mL, 1.96 mmol) was added thereto and the mixture was stirred at room temperature for 20 minutes. After saturated aqueous ammonium chloride (50 mL) was added to the reaction mixture at 0° C. and the mixture was extracted with ethyl acetate (50 mL), the organic layer was washed with saturated brine (50 mL) and dried with anhydrous sodium sulfate, followed by distilling off of the solvent under reduced pressure. The residue was purified using silica gel flash column chromatography (hexane:ethyl acetate, 1:1, V/V) to obtain the desired title compound (840 mg, yield 80%) as a colorless solid.

$^1$H NMR (400 MHz, CDCl$_3$): δ 1.39 (3H, s), 1.47 (3H, s), 2.06 (1H, d, J=3.9 Hz), 2.85-2.96 (2H, m), 3.49 (1H, dd, J=9.8, 6.8 Hz), 3.67-3.72 (1H, m), 3.75-3.85 (6H, m), 3.89-3.97 (2H, m), 4.67 (1H, d, J=11.7 Hz), 4.68 (1H, d, J=11.7 Hz), 4.76 (1H, d, J=11.7 Hz), 4.85 (1H, d, J=11.7 Hz), 7.26-7.38 (10H, m); MS (FAB) m/z 456: (M+H)$^+$.

(16c) (3aR,4R,5S,6S,6aR)-5,6-Dibenzyloxy-1-(2,2-dimethyl-[1,3]dioxan-5-yl)-hexahydro-cyclopenta[c]isoxazol-4-yl 2,3,6-tri-O-benzyl-4-O-(6-deoxy-2,3,4-tri-O-benzyl-β-D-glucopyranosyl)-α-D-glucopyranoside The compound (600 mg, 0.692 mmol) synthesized in Example 2 (2f) was dissolved in methylene chloride (20 mL) and trichloroacetonitrile (277 μL, 2.76 mmol) and 1,8-diazabicyclo[5.4.0]-7-undecene (2 drops) were added thereto, followed by stirring of the mixture at room temperature for 40 minutes. After the solvent was distilled off under reduced pressure, the residue was purified using silica gel flash column chromatography (hexane:ethyl acetate, 5:1, 1% triethylamine, V/V) to obtain imidate (550 mg, 80%) as a yellow oil. The compound (230 mg, 0.501 mmol) synthesized in Example 16 (16b) was dissolved in diethyl ether (10 mL) and imidate (550 mg, 0.551 mmol) was added thereto. Trimethylsilyl trifluoromethanesulfonate (45 μL, 0.250 mmol) was added dropwise thereto and the mixture was stirred at room temperature for 45 minutes. After triethylamine (4 drops) was added to the reaction mixture, the solvent was distilled off under reduced pressure. The residue was purified using silica gel flash column chromatography (hexane:ethyl acetate, 3:1, V/V) to obtain the desired title compound (140 mg, 20%) as a pale yellow oil.

$^1$H NMR (400 MHz, CDCl$_3$): δ 1.22 (3H, d, J=5.8 Hz), 1.43 (3H, s), 1.49 (3H, s), 2.70-2.80 (2H, m), 3.11-3.17 (1H, m), 3.19-3.27 (1H, m), 3.30-3.54 (6H, m), 3.61-3.95 (12H, m), 4.34 (1H, d, J=11.7 Hz), 4.38 (1H, d, J=7.3 Hz), 4.52 (1H, d, J=12.5 Hz), 4.58-4.73 (5H, m), 4.73-4.90 (8H, m), 5.00 (1H, d, J=3.7 Hz), 5.03 (1H, d, J=11.0 Hz), 7.17-7.38 (38H, m), 7.43-7.47 (2H, m). MS (FAB) m/z: 1304 (M+H)$^+$.

(16d) (1R,2S,3R,4R,5R)-1-(2-Hydroxy-1-hydroxymethyl-ethylamino)-2,3-dihydroxy-5-hydroxymethyl-cyclopent-4-yl 4-O-(6-deoxy-β-D-glucopyranosyl)-α-D-glucopyranoside The compound (146 mg, 113 μmol) synthesized in Example 16 (16c) was dissolved in acetic acid (10 mL) and distilled water (2.5 mL) and the mixture was stirred at 50° C. for 1 hour. The solvent was distilled off under reduced pressure and the residue was purified using silica gel flash column chromatography (hexane:ethyl acetate, 1:1, V/V) to obtain diol (128 mg, 101 μmol) as a colorless crystal. The diol (118 mg, 93.3 μmol) was dissolved in methanol (20 mL) and ethyl acetate (1 mL) and hydrochloric acid (30 μL) and 20% palladium hydroxide-carbon (118 mg) were added thereto, followed by stirring of the mixture at room temperature under a hydrogen atmosphere for 4 hours. After celite filtration, the solvent was distilled off under reduced pressure and the residue was purified by ion exchange resin (Dowex 50w×8) column (water—5% ammonia water). Further, it was purified using silica gel flash column chromatography (ethyl acetate:methanol:water, 1:1:1, V/V) to obtain the desired title compound (43 mg, 84%) as a colorless solid.

$^1$H NMR (400 MHz, D$_2$O): δ 1.32 (3H, d, J=6.8 Hz), 2.34-2.41 (1H, m), 2.88-2.94 (1H, m), 3.16-3.22 (1H, m), 3.29-3.38 (2H, m), 3.42-3.50 (1H, m), 3.49-3.97 (16H, m), 4.48 (1H, d, J=7.8 Hz), 5.18 (1H, d, J=7.8 Hz); $^{13}$C NMR (100 MHz, D$_2$O): 616.9, 44.0, 58.5, 58.7, 60.0, 60.1, 60.6, 61.3, 70.9, 71.3, 71.6, 72.2, 73.6, 75.0, 75.5, 79.1, 79.2, 80.5, 81.9, 97.8, 102.7; MS (FAB) m/z: 546 (M+H)$^+$.

EXAMPLE 17

(1R,2S,3S,4R,5R)-1-Amino-2-fluoro-3-hydroxy-5-hydroxymethyl-cyclopent-4-yl 4-O-(6-deoxy-β-D-glucopyranosyl)-α-D-glucopyranoside (Exemplification Compound No. 5-9)

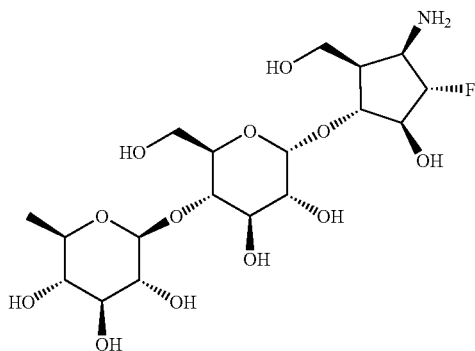

(17a) Methyl 2-deoxy-2-fluoro-D-glucopyranoside 1,3,4,6-tetra-O-Acetyl-2-deoxy-2-fluoro-β-D-glucopyranose (Carbohydr. Res., 153, 1986, 168-170) (13.4 g, 38.3 mmol) was dissolved in methanol (150 mL) and Dowex 50w×8 (19 g) was added thereto, followed by stirring of the mixture at 80° C. for 12 hours. The reaction mixture was subjected to celite filtration and the filtered product was washed with methanol. The filtrate and the washing liquid were combined and distilled off under reduced pressure. The residue was purified using silica gel flash column chromatography (methylene chloride:methanol, 10:1-5:1, V/V) to obtain the desired title compound (3.37 g, yield 45%) as a colorless solid.

$^1$H NMR (400 MHz, CD$_3$OD): δ 3.32-3.36 (1H, m), 3.43 (1.5H, s), 3.52-3.64 (2H, m), 3.54 (1.5H, s), 3.65-3.70 (1H, m), 3.80-3.92 (2.5H, m), 4.16-4.29 (0.5H, m), 4.43 (0.5H, dd, J=7.8, 2.9 Hz), 4.88 (0.5H, d, J=3.9 Hz). MS (FAB) m/z: 197 (M+H)$^+$.

(17b) Methyl 4,6-O-benzylidene-2-deoxy-2-fluoro-D-glucopyranoside

The compound (3.5 g, 17.9 mmol) synthesized in Example 17 (17a) was dissolved in dimethylformamide (70 mL) and benzaldehyde dimethylacetal (3.75 mL, 25.0 mmol) and p-toluenesulfonic acid monohydrate (170 mg, 0.892 mmol) were added thereto, followed by stirring of the mixture at 50° C. under reduced pressure for 2 hours. Triethylamine (2 mL) was added to the reaction mixture and the solvent was distilled off under reduced pressure. The residue was purified using silica gel flash column chromatography (hexane:ethyl acetate, 3:1, V/V) to obtain the desired title product (3.36 g, yield 66%) as a colorless solid.

$^1$H NMR (400 MHz, CDCl$_3$): δ 3.42-3.58 (1H, m), 3.48 (2H, s), 3.60 (1H, s), 3.70-3.90 (1.33H, m), 3.98-4.08 (0.66H, m), 4.16-4.40 (2H, m), 4.48-4.54 (1H, m), 4.94 (0.66H, d, J=4.4 Hz), 5.02-5.06 (0.33H, m), 5.52-5.54 (1H, m), 7.36-7.41 (3H, m), 7.46-7.51 (2H, m); MS (FAB) m/z: 285 (M+H)$^+$.

(17c) Methyl 4-O-benzoyl-3-O-benzyl-2-deoxy-2-fluoro-6-O-p-toluenesulfonyl-D-glucopyranoside The compound (3.36 g, 11.8 mmol) synthesized in Example 17 (17b) was dissolved in dimethylformamide (50 mL) and sodium hydride (741 mg, 17.7 mmol) was added thereto under a nitrogen atmosphere, followed by stirring of the mixture at room temperature for 30 minutes. The reaction mixture was ice-cooled and benzyl bromide (1.68 mL, 14.1 mmol) was added thereto, followed by stirring of the mixture at room temperature for 2 hours. After saturated aqueous ammonium chloride solution (50 mL) was added to the reaction mixture at 0° C. and the mixture was extracted with ethyl acetate (100 mL), the organic layer was washed with saturated brine (100 mL) and dried with anhydrous sodium sulfate, followed by distilling off of the solvent under reduced pressure. Acetic acid (16 mL) and distilled water (4 mL) were added to the residue and the mixture was stirred at 60° C. for 3 hours. The solvent was distilled off under reduced pressure and the reaction mixture was azeotroped with toluene. The residue was dissolved in pyridine (10 mL) and p-toluenesulfonic acid chloride (1.75 g, 9.20 mmol) and 4-dimethylaminopyridine (101 mg, 0.83 mmol) were added thereto under ice-cooling, followed by stirring of the mixture at room temperature for 6 hours. The reaction mixture was ice-cooled and diluted hydrochloric acid (2N, 80 mL) was added thereto. After the mixture was extracted with ethyl acetate (100 mL), the organic layer was washed with saturated aqueous sodium hydrogencarbonate (200 mL) and saturated brine (200 mL) and dried with anhydrous sodium sulfate, followed by distilling off of the solvent under reduced pressure. The residue was dissolved in methylene chloride (40 mL) and 4-dimethylaminopyridine (1.28 g, 10.5 mmol), benzoyl chloride (1.30 mL, 11.2 mmol) and triethylamine (1.46 mL, 10.5 mmol) were added thereto under ice-cooling, followed by stirring of the mixture at 0° C. for 3 hours. The reaction mixture was ice-cooled and diluted hydrochloric acid (2N, 80 mL) was added thereto. After the mixture was extracted with methylene chloride (100 mL), the organic layer was washed with saturated aqueous sodium hydrogencarbonate (200 mL) and saturated brine (100 mL) and dried with anhydrous sodium sulfate, followed by distilling off of the solvent under reduced pressure. The residue was purified using silica gel flash column chromatography (hexane:ethyl acetate, 3:1, V/V) to obtain the desired title compound (4.16 g, yield 65%) as a colorless solid.

$^1$H NMR (400 MHz, CDCl$_3$): δ 2.35 (3/2H, s), 2.36 (3/2H, s), 3.47 (3/2H, s), 3.55 (3/2H, s), 3.79-3.88 (1H, m), 4.01-4.15 (3H, m), 4.28-4.62 (3.5H, m), 4.77 (1H, dd, J=11.7, 5.1 Hz), 4.91 (0.5H, d, J=4.4 Hz), 5.05-5.12 (1H, m), 7.06-7.10 (5H, m), 7.18-7.22 (2H, m), 7.42-7.48 (2H, m), 7.58-7.65 (1H, m), 7.66-7.71 (2H, m), 7.89-7.93 (2H, m); MS (FAB) m/z: 545 (M+H)$^+$.

(17d) Methyl 4-O-benzoyl-3-O-benzyl-2,6-dideoxy-2-fluoro-6-iode-D-glucopyranoside The compound (3.83 g, 7.03 mmol) synthesized in Example 17 (17c) was dissolved in toluene (120 mL) and sodium iodide (5.27 g, 39.2 mmol) and 18-crown-6-ether (370 mg, 1.40 mmol) were added thereto under a nitrogen atmosphere, followed by stirring of the mixture at 100° C. for 2 hours. The reaction mixture was cooled to room temperature and filtered and the filtered product was washed with toluene. The filtrate and the washing liquid were washed with saturated aqueous sodium hydrogencarbonate (100 mL) and saturated brine (100 mL) and dried with anhydrous sodium sulfate, followed by distilling off of the solvent under reduced pressure. The residue was purified using silica gel flash column chromatography (hexane:ethyl acetate, 5:1, V/V) to obtain the desired title compound (3.38 g, yield 96%) as a colorless solid.

$^1$H NMR (400 MHz, CDCl$_3$): δ 3.12-3.21 (1H, m), 3.27-3.32 (1H, m) 3.57-3.62 (1H, m), 3.58 (3/2H, s), 3.65 (3/2H, s), 3.82-3.91 (1H, m), 4.38-4.68 (5/2H, m), 4.79 (1H, dd, J=11.7, 6.8 Hz), 4.99 (1/2H, dd, J=3.9 Hz), 5.06-5.13 (1H, m), 7.07-7.18 (5H, m), 7.43-7.48 (2H, m), 7.59-7.64 (1H, m), 7.95-8.00 (2H, m); MS (FAB) m/z: 501 (M+H)$^+$.

(17e) 4-O-Benzoyl-3-O-benzyl-2-fluoro-2,5,6-trideoxy-D-xylo-hex-5-enose oxime

The compound (3.37 g, 6.74 mmol) synthesized in Example 17 (17d) was dissolved in isopropanol (40 mL) and distilled water (1.3 mL) and zinc powder (4 g) washed with diluted hydrochloric acid was added thereto, followed by stirring of the mixture at 100° C. for 1 hour. The reaction mixture was subjected to celite filtration, the filtered product was washed with ethanol and the filtrate and the washing liquid were distilled off under reduced pressure. The residue was dissolved in ethanol (80 mL) and hydroxylamine hydrochloride (1.18 g, 17.1 mmol) and pyridine (1.38 mL, 17.1 mmol) were added thereto, followed by stirring of the mixture at 60° C. for 40 minutes. The solvent was distilled off under reduced pressure and the residue was purified using silica gel flash column chromatography (hexane:ethyl acetate, 5:1, V/V) to obtain the desired title compound (1.31 g, yield 54%) as a colorless solid.

$^1$H NMR (400 MHz, CDCl$_3$): δ 3.87-3.94 (0.7H, m), 4.13-4.22 (0.3H, m), 4.64-4.82 (2H, m), 5.22 (0.7H, ddd, J=46.9, 6.8, 4.9 Hz), 5.34-5.55 (2H, m), 5.75-5.88 (1.3H, m), 5.98-6.07 (1H, m), 7.24-7.62 (8H, m), 8.03-8.08 (2H, m); MS (FAB) m/z: 358 (M+H)$^+$.

(17f) (3aR,4R,5S,6S,6aR)-4-Benzoyloxy-5-benzyloxy-6-fluoro-hexahydro-cyclopenta[c]isoxazole The compound (1.31 g, 3.66 mmol) synthesized in Example 17 (17e) was dissolved in toluene (30 mL) and the mixture was stirred at 120° C. for 8 hours. The solvent was distilled off under reduced pressure and the residue was purified using silica gel flash column chromatography (hexane:ethyl acetate, 3:1, V/V) to obtain the desired title compound (965 mg, yield 74%) as a colorless solid.

$^1$H NMR (400 MHz, CDCl$_3$): δ 2.91-2.98 (1H, m), 3.50-3.58 (1H, m), 4.00-4.10 (1H, m), 4.21-4.28 (1H, m), 4.54 (1H, brd, J=7.8 Hz), 4.72 (1H, d, J=12.7 Hz), 4.83 (1H, d, J=12.7 Hz), 4.84 (1H, ddd, J=52.7, 7.8, 5.8 Hz), 4.98-5.02 (1H, m), 5.11-5.15 (1H, m), 7.28-7.36 (5H, m), 7.45-7.49 (2H, m), 7.59-7.63 (1H, m), 7.97-8.00 (2H, m); MS (FAB) m/z 358: (M+H)$^+$.

(17g) (3aR,4R,5S,6S,6aR)-5-Benzyloxy-1-benzyloxycarbonyl-6-fluoro-4-hydroxy-hexahydro-cyclopenta[c]isoxazole The compound (950 mg, 2.66 mmol) synthesized in Example 17 (17f) was dissolved in methanol (10 mL) and sodium methoxide (270 μL, 1.30 mmol) was added thereto, followed by stirring of the mixture at room temperature for 15 minutes. After saturated aqueous ammonium chloride solution (50 mL) was added to the reaction mixture at 0° C. and the mixture was extracted with ethyl acetate (50 mL), the organic layer was washed with saturated brine (50 mL) and dried with anhydrous sodium sulfate, followed by distilling off of the solvent under reduced pressure. The residue was dissolved in ethyl acetate (100 mL) and saturated aqueous sodium hydrogencarbonate (50 mL) and benzyl oxychloroformate (570 μL, 4.00 mmol) were added thereto at 0° C., followed by stirring of the mixture at 0° C. for 1 hour. The organic layer was washed with saturated brine (50 mL) and dried with anhydrous sodium sulfate, followed by distilling off of the solvent under reduced pressure. The residue was purified using silica gel flash column chromatography (hexane:ethyl acetate, 1:1, V/V) to obtain the desired title compound (1.00 g, yield 97%) as a colorless solid.

$^1$H NMR (400 MHz, CDCl$_3$): δ 2.29 (1H, brd, J=3.3 Hz, OH), 2.92-2.99 (1H, m, H-3a), 3.60 (1H, dd, J=9.0, 5.8 Hz, H-3), 3.82-3.91 (2H, m, H-5, H-4), 3.98 (1H, d, J=8.8 Hz, H-3), 4.61 (1H, d, J=12.7 Hz, CH2Ph), 4.62-4.70 (1H, m, H-6a), 4.72-4.76 (1/2H, m, H-6), 4.84 (1H, d, J=12.7 Hz, CH2Ph), 4.82-4.86 (1/2H, m, H-6), 5.21 (2H, s), 7.23-7.40 (10H, m); MS (FAB) m/z: 388 (M+H)$^+$.

(17h)(3aR,4R,5S,6S,6aR)-5-Benzyloxy-1-benzyloxycarbonyl-6-fluoro-hexahydro-cyclopenta[c]isoxazol-4-yl 2,3,6-tri-O-benzyl-4-O-(6-deoxy-2,3,4-tri-O-benzyl-β-D-glucopyranosyl)-α-D-glucopyranoside The compound (840 mg, 0.969 mmol) synthesized in Example 2 (2f) was dissolved in methylene chloride (10 mL) and trichloroacetonitrile (460 μL, 4.61 mmol) and 1,8-diazabicyclo 5.4.0]-7-undecene (2 drops) were added thereto, followed by stirring of the mixture at room temperature for 40 minutes. After the solvent was distilled off under reduced pressure, the residue was purified using silica gel flash column chromatography (hexane:ethyl acetate, 5:1, 1% triethylamine, V/V) to obtain imidate (830 mg, 85%) as a yellow oil. The compound (300 mg, 0.756 mmol) synthesized in Example 17 (17g) was dissolved in diethyl ether (15 mL) and imidate (830 mg, 0.832 mmol) was added thereto. Trimethylsilyl trifluoromethanesulfonate (13 μL, 0.0756 mmol) was added dropwise thereto and the mixture was stirred at room temperature for 45 minutes. After triethylamine (4 drops) was added to the reaction mixture, the solvent was distilled off under reduced pressure. The residue was purified using silica gel flash column chromatography (hexane:diethyl ether, 2:1, V/V) to obtain the desired title compound (86 mg, 9%) as a pale yellow oil.

$^1$H NMR (400 MHz, CDCl$_3$): δ 1.20 (3H, d, J=5.9 Hz), 2.87-2.94 (1H, m), 3.10-3.16 (1H, m), 3.19-3.24 (1H, m), 3.28-3.38 (3H, m), 3.42-3.46 (1H, m), 3.51 (1H, dd, J=9.8, 3.9 Hz), 3.55-3.59 (1H, m), 3.74 (1H, dd, J=10.7, 3.9 Hz), 3.79-3.84 (2H, m), 3.84-3.89 (1H, m), 3.94 (1H, d, J=9.8 Hz), 4.00-4.06 (1H, m), 4.31 (1H, d, J=12.7 Hz), 4.35 (1H, d, J=7.8 Hz), 4.49 (1H, d, J=12.7 Hz), 4.58-4.88 (13H, m), 5.01 (1H, d, J=10.8 Hz), 5.05 (1H, d, J=3.9 Hz), 5.18-5.26 (2H, m), 7.15-7.43 (40H, m); MS (FAB) m/z: 1236 (M+H)$^+$.

(17i) (1R,2S,3S,4R,5R)-1-Amino-2-fluoro-3-hydroxy-5-hydroxymethyl-cyclopent-4-yl 4-O-(6-deoxy-β-D-glucopyranosyl)-α-D-glucopyranoside The compound (85 mg, 68.8 μmol) synthesized in Example 17 (17h) was dissolved in methanol (20 mL) and ethyl acetate (1 mL) and hydrochloric acid (30 μL) and 20% palladium hydroxide-carbon (85 mg) were added thereto, followed by stirring of the mixture at room temperature under a hydrogen atmosphere for 4 hours. After celite filtration, the solvent was distilled off under reduced pressure and the residue was purified by ion exchange resin (Dowex 50w×8) column (water—5% ammonia water). Further, it was purified using silica gel flash column chromatography (ethyl acetate:methanol:water, 1:1:1, V/V) to obtain the desired title compound (28 mg, 86%) as colorless amorphous matter.

$^{1}$H NMR (400 MHz, $D_2O$): δ 1.21 (3H, d, J=5.9 Hz), 2.23-2.30 (1H, m), 3.04-3.10 (1H, m), 3.18-3.25 (2H, m), 3.28-3.61 (6H, m), 3.64-3.80 (5H, m), 3.86-3.91 (1H, m), 4.11-4.18 (1H, m), 4.37 (1H, d, J=8.8 Hz), 4.41-4.46 (1/2H, m), 4.52-4.57 (1/2H, m), 5.06-5.08 (1H, m); $^{13}$C NMR (100 MHz, $D_2O$): 616.9, 44.0, 58.5, 58.7, 60.0, 60.1, 60.6, 61.3, 70.9, 71.3, 71.6, 72.2, 73.6, 75.0, 75.5, 79.1, 79.2, 80.5, 81.9, 97.8, 102.7; MS (FAB) m/z: 474 (M+H)$^{+}$.

EXAMPLE 18

(2R,3R,4R)-4-Hydroxy-2-hydroxymethyl-3,4-dihydro-2H-pyrrol-3-yl 4-O-(6-deoxy-α-D-glucopyranosyl)-α-D-glucopyranoside (Exemplification Compound No. 3-1)

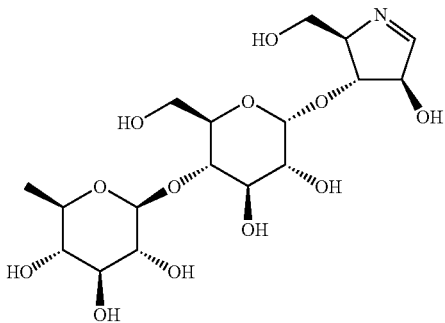

(18a) 1,2-O-Benzyl-4-deoxy-3-O-formyl-4-trifluoroacetamido-α-D-arabinoside

2-O-Benzyl-4-deoxy-3-O-formyl-4-trifluoroacetamido-D-arabinoside (Chem. Pharm. Bull., 1991, 39, 2807-2812) (0.80 g, 2.20 mmol) was dissolved in methylene chloride (50 mL) and benzyl trichloroacetoimidate (0.82 mL, 4.40 mmol) and trifluoromethanesulfonic acid (40 μL, 0.22 mmol) were added thereto, followed by stirring of the mixture at room temperature for 3 hours. After saturated aqueous sodium hydrogencarbonate (30 mL) was added to the reaction mixture at 0° C. and the mixture was diluted with ethyl acetate (100 mL), the mixture was washed with water (50 mL) and saturated brine (50 mL) and dried with anhydrous sodium sulfate, followed by distilling off of the solvent under reduced pressure. The residue was purified using silica gel flash column chromatography (hexane:ethyl acetate, 6:1, V/V) to obtain the desired title compound (0.73 g, yield 74%) as pale yellow amorphous matter.

$^{1}$H NMR (CDCl$_3$) δ: 3.55 (1H, dd, J=12.5, 2.2 Hz), 3.63 (1H, dd, J=10.3, 3.7 Hz), 4.13 (1H, d, J=13.9 Hz), 4.50 (1H, d, J=11.0 Hz), 4.53 (1H, d, J=12.5 Hz), 4.61 (1H, d, J=11.7 Hz), 4.62 (1H, br, s), 4.75 (1H, d, J=12.5 Hz), 4.90 (1H, d, J=2.9 Hz), 5.44 (1H, dd, J=10.3, 4.4 Hz), 6.69 (1H, d, J=7.33 Hz), 7.13-7.38 (10H, m), 8.00 (1H, s); MS (FAB) m/z: 476 (M+Na)$^{+}$.

(18b) 1,2-di-O-Benzyl-4-deoxy-4-trifluoroacetamido-α-D-arabinoside

The compound (0.73 g, 1.61 mmol) synthesized in Example 18 (18a) was dissolved in methanol (30 mL) and water (5 mL) and potassium hydrogencarbonate (1.00 g, 10.0 mmol) was added thereto, followed by stirring of the mixture at room temperature for 15 hours. Ethyl acetate (50 mL) was added thereto and the organic layer was washed with saturated brine (20 mL). After it was dried with anhydrous sodium sulfate, the solvent was distilled off under reduced pressure. The residue was purified using silica gel flash column chromatography (hexane:ethyl acetate, 6:1, V/V) to obtain the desired title compound (205 mg, yield 41%) as colorless amorphous matter.

$^{1}$H NMR (CDCl$_3$) δ: 2.84 (1H, d, J=2.2 Hz), 3.44 (1H, dd, J=9.5, 2.9 Hz), 3.76 (1H, dd, J=12.5, 1.5 Hz), 3.92 (1H, dd, J=12.5, 1.5 Hz), 4.20-4.28 (2H, m), 4.47 (1H, d, J=11.7 Hz), 5.53 (2H, s), 4.72 (1H, d, J=12.5 Hz), 4.91 (1H, d, J=3.7 Hz), 6.67 (1H, br, d, J=5.86 Hz), 7.12-7.38 (10H, m); MS (FAB) m/z: 426 (M+H)$^{+}$, 448 (M+Na)$^{+}$.

(18c) 1,2-di-O-Benzyl-4-deoxy-4-trifluoroacetamido-3-O-{2,3,6-tri-O-benzyl-4-O-(2,3,4-tri-O-benzyl-6-deoxy-β-D-glucopyranosyl)-α-D-glucopyranosyl)-α-D-arabinoside The compound (0.70 g, 0.81 mmol) synthesized in Example 2 (2f) was dissolved in methylene chloride (20 mL) and trichloroacetonitrile (1.00 mL, 10.0 mmol) and 2 drops of 1,8-diazabicyclo[5.4.0]-7-undecene were added thereto, followed by stirring of the mixture at room temperature for 30 minutes. After the solvent was distilled off under reduced pressure, the residue was purified using silica gel flash column chromatography (hexane:ethyl acetate, 5:1, 1% triethylamine, V/V) to obtain imidate (0.75 g, 92%) of colorless oil. The compound (205 mg, 0.48 mmol) synthesized in Example 18 (18b) and imidate (0.75 g, 0.74 mmol) were dissolved in diethyl ether (30 mL) and trimethylsilyl trifluoromethanesulfonate (8.7 μL, 0.074 mmol) was added thereto under a nitrogen atmosphere, followed by stirring of the mixture at room temperature for 3 hours. After triethylamine (0.1 mL) was added to the reaction mixture and the solvent was distilled off under reduced pressure, the residue was diluted with ethyl acetate (30 mL) and the mixture was washed with saturated aqueous sodium hydrogencarbonate (20 mL) and saturated brine (20 mL). After the organic layer was dried with anhydrous sodium sulfate, the solvent was distilled off under reduced pressure and the residue was purified using silica gel flash column chromatography (hexane:diethyl ether, 3:1, V/V) to obtain the desired title compound (185 mg, 31%) and its β isomer (250 mg, 41%) as colorless amorphous matter.

$^1$H NMR (CDCl$_3$) δ: 1.17 (3H, d, J=5.9 Hz), 3.12 (1H, t, J=9.5 Hz), 3.19-3.25 (1H, m), 3.36 (1H, t, J=9.5 Hz), 3.44-3.50 (2H, m), 3.54-3.64 (3H, m), 3.75 (1H, t, J=9.5 Hz), 3.81-3.98 (4H, m), 4.19 (1H, dd, J=8.8, 4.4 Hz), 4.35-4.39 (3H, m), 4.45 (1H, d, J=11.7 Hz), 4.49-4.54 (3H, m), 4.59-4.61 (2H, m), 4.67-4.80 (6H, m), 4.84 (1H, d, J=11.0 Hz), 4.90 (1H, d, J=1.0 Hz), 4.94 (1H, d, J=11.7 Hz), 5.02 (1H, d, J=11.0 Hz), 5.18 (1H, d, J=3.7 Hz), 6.88 (1H, br, d, J=7.3 Hz), 7.10-7.40 (40H, m); MS (FAB) m/z: 1296 (M+Na)$^+$.

(18d) 4-Deoxy-4-trifluoroacetamido-3-O-{4-O-(6-deoxy-β-D-glucopyranosyl)-α-D-glucopyranosyl}-D-arabinoside The compound (180 mg, 0.14 mmol) synthesized in Example 18 (18c) was dissolved in methanol (10 mL) and 20% palladium hydroxide-carbon (120 mg) was added thereto, followed by stirring of the mixture under a hydrogen atmosphere for 3 hours. After the catalyst was removed by celite filtration, the solvent was distilled off under reduced pressure. The residue was purified using silica gel flash column chromatography (ethyl acetate:methanol, 4:1, V/V) to obtain the desired title compound (69 mg, 88.5%) as a colorless solid.

$^1$H NMR (D$_2$O) δ: 1.32 (3H, d, J=5.9 Hz), 3.19 (1H, t, J=9.5 Hz), 3.30-3.34 (2H, m), 3.46 (1H, t, J=9.5 Hz), 3.52 (1H, br, t, J=7.4 HZ), 3.59-3.67 (3H, m), 3.72-3.88 (3H, m), 3.97-4.07 (2H, m), 4.19-4.29 (1H, m), 4.48 (1H, d, J=8.0 Hz), 4.58-4.66 (2H, m), 5.24 (1H, br, s); MS (FAB) m/z: 576 (M+Na)$^+$.

(18e) (2R,3R,4R)-4-Hydroxy-2-hydroxymethyl-3,4-dihydro-2H-pyrrol-3-yl 4-O-(6-deoxy-α-D-glucopyranosyl)-α-D-glucopyranoside The compound (47 mg, 0.085 mmol) synthesized in Example 18 (18d) was dissolved in water (10 mL) and ion exchange resin Dowex-1×4 (OH—) (3.0 g) was added thereto, followed by stirring of the mixture at room temperature for 1.5 hours. The ion exchange resin was removed and the solvent was distilled off under reduced pressure. The residue was purified using silica gel flash column chromatography (chloroform:methanol:water, 6:4:1, V/V) to obtain the desired title compound (8.0 mg, yield 21.4%) as colorless amorphous matter.

$^1$H NMR (D$_2$O) δ: 1.32 (3H, d, J=5.9 Hz), 3.16-3.21 (1H, m), 3.31-3.33 (1H, m), 3.45-3.52 (2H, m), 3.63-3.69 (2H, m), 3.80-3.96 (5H, m), 4.08 (1H, br, s), 4.25 (1H, d, J=4.9 Hz), 4.49 (1H, d, J=6.8 Hz), 4.94 (1H, d, J=4.9 Hz), 5.17 (1H, d, J=4.0 Hz), 7.68 (1H, br, s); MS (FAB) m/z: 462 (M+Na)$^+$.

EXAMPLE 19

(2R,3R,4R)-4-Hydroxy-2-hydroxymethyl-pyrrolidin-3-yl 4-O-{4-O-(β-D-glucopyranosyl)-β-D-glucopyranosyl}-α-D-glucopyranoside (Exemplification Compound No. 1-547)

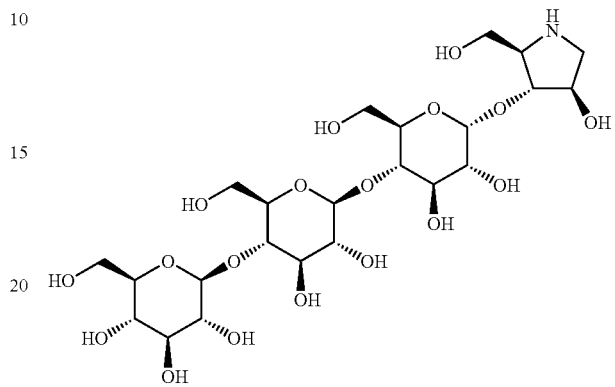

(19a) (2R,3R,4R)-4-Benzyloxy-N-benzyloxycarbonyl-2-benzyloxymethyl-pyrrolidin-3-yl 4-O-acetyl-2,3,6-tri-O-benzyl-α-D-glucopyranoside 4-O-Acetyl-2,3,6-tri-O-benzyl-glucopyranoside (Agric. Biol. Chem, 1986, 50, 2261-2272) (2.21 g, 4.49 mmol) was dissolved in methylene chloride (45 mL) and trichloroacetonitrile (2.3 mL, 22.44 mmol) and 1,8-diazabicyclo [5.4.0]-7-undecene (65 μL, 0.44 mmol) were added thereto, followed by stirring of the mixture at room temperature for 1 hour. After the solvent was distilled off under reduced pressure, the residue was purified using silica gel flash column chromatography (hexane:ethyl acetate, 2:1, 1% triethylamine, V/V) to obtain imidate (2.06 g, 72.0%) as a yellow oil. The compound (2.00 g, 4.47 mmol) synthesized in Example 1 (1i) was dissolved in diethyl ether (100 mL) and imidate (2.06 g, 3.23 mmol) was added thereto. A solution of trimethylsilyl trifluoromethanesulfonate (40 μL, 0.22 mmol) in diethyl ether (2 mL) was added dropwise thereto and the mixture was stirred at room temperature for 2 hours. After triethylamine (50 μL) was added to the reaction mixture and the solvent was distilled off under reduced pressure, the residue was diluted with ethyl acetate (20 mL) and the mixture was washed with saturated aqueous sodium hydrogencarbonate (20 mL) and saturated brine (10 mL). After the organic layer was dried with anhydrous sodium sulfate, the solvent was distilled off under reduced pressure and the residue containing the α, β mixture was purified using silica gel flash column chromatography (hexane:ethyl acetate, 5:1, V/V) to isolate the desired title compound a form (1.93 g, 46.6%) thereof as a colorless oil.

$^1$H NMR (400 MHz, CDCl$_3$) δ 1.82 (3H, s), 3.20-5.20 (26H, m), 7.10-7.40 (30H, m); MS (FAB) m/z: 922 (M+H)$^+$.

(19b) (2R,3R,4R)-4-Benzyloxy-N-benzyloxycarbonyl-2-benzyloxymethyl-pyrrolidin-3-yl 2,3,6-tri-O-benzyl-α-D-glucopyranoside The compound (1.57 g, 1.70 mmol) synthesized in Example 19 (19a) was dissolved in methanol (30 mL) and potassium carbonate (235 mg, 1.70 mmol) was added thereto, followed by stirring of the mixture at room temperature for 14 hours. The reaction mixture was diluted with ethyl acetate (10 mL) and the mixture was washed with saturated aqueous sodium hydrogencarbonate (10 mL) and saturated brine (10 mL). After the organic layer was dried with anhydrous sodium sulfate, the solvent was distilled off under reduced pressure. The residue was purified using silica gel flash column chromatography (hexane:ethyl acetate, 3:1, V/V) to obtain the desired title compound (1.41 g, 94.0%) as a colorless oil.

$^1$H NMR (400 MHz, CDCl$_3$): δ 3.40-5.20 (26H, m), 7.10-7.40 (30H, m); MS (FAB) m/z: 880 (M+H)$^+$.

(19c) Allyl 2,3,6-O-tri-benzoyl-4-O-(2,3,4,6-tetra-O-benzoyl-β-D-glucopyranosyl)-D-glucopyranoside The compound (4.0 g, 10.46 mmol) synthesized in Example 2 (2a) was dissolved in pyridine (30 mL) and benzoyl chloride (12.1 mL, 104.24 mmol) was added thereto under ice-cooling, followed by stirring of the mixture at room temperature for 14 hours. The reaction mixture was poured to 10% aqueous hydrochloric acid solution (20 mL) and methyl chloride (20 mL) and the organic layer was washed with 10% aqueous hydrochloric acid solution (20 mL), saturated aqueous sodium hydrogencarbonate solution (20 mL) and saturated brine (20 mL) and dried with anhydrous sodium sulfate, followed by distilling off of the solvent under reduced pressure. The residue was purified using silica gel flash column chromatography (hexane:ethyl acetate, 5:1-5:2, V/V) to obtain the desired title compound (8.10 g, yield 70%) as a colorless oil.

$^1$H NMR (400 MHz, CDCl$_3$): δ 3.71-4.27 (6H, m), 4.44-4.51 (1H, m), 4.58-4.63 (1H, m), 4.72 (1H, d, J=6.4 Hz), 4.93-5.81 (10H, m), 7.17-8.11 (35H, m); MS (FAB) m/z: 1111 (M+H)$^+$.

(19d) 2,3,6-O-tri-Benzoyl-4-O-(2,3,4,6-tetra-O-benzoyl-β-D-glucopyranosyl)-D-glucopyranoside The compound (8.10 g, 7.29 mmol) synthesized in Example 19 (19c) was dissolved in methanol (75 mL) and tetrahydrofuran (15 mL) and palladium chloride (II) (258 mg, 1.45 mmol) was added thereto, followed by stirring of the mixture at room temperature for 14 hours. After the reaction mixture was subjected to celite filtration, the solvent was distilled off under reduced pressure. The residue was purified using silica gel flash column chromatography (hexane:ethyl acetate, 3:1-2:1, V/V) to obtain the desired title compound (5.10 g, yield 66%) as a pale yellow solid.

$^1$H NMR (400 MHz, CDCl$_3$): δ 2.96-3.13 (1H, m), 3.79-3.92 (2H, m), 4.05-4.25 (2H, m), 4.33-4.40 (1H, m), 4.47-4.50 (1H, m), 4.60-4.63 (1H, m), 4.89-6.15 (7H, m), 7.21-8.01 (35H, m); MS (FAB) m/z: 1071 (M+H)$^+$.

(19e) (2R,3R,4R)-4-Benzyloxy-N-benzyloxycarbonyl-2-benzyloxymethyl-pyrrolidin-3-yl 2,3,6-tri-O-benzyl-4-O-{2,3,6-tri-O-benzoyl-4-O-(2,3,4,6-tetra-O-benzoyl-β-D-glucopyranosyl)-β-D-glucopyranosyl}-α-D-glucopyranoside The compound (414.4 mg, 0.39 mmol) synthesized in Example 19 (19d) was dissolved in methylene chloride (8 mL) and trichloroacetonitrile (200 μL, 1.99 mmol) and 1,8-diazabicyclo 5.4.0]-7-undecene (6 μL, 0.04 mmol) were added thereto, followed by stirring of the mixture at room temperature for 1 hour. After the solvent was distilled off under reduced pressure, the residue was purified using silica gel flash column chromatography (hexane:ethyl acetate, 2:1, 1% triethylamine, V/V) to obtain imidate (255.1 mg, 53.8%) as colorless amorphous matter. The compound (185.3 mg, 0.21 mmol) synthesized in Example 19 (19b) was dissolved in diethyl ether (8 mL) and imidate (225.1 mg, 0.21 mmol) was added thereto. A solution of trimethylsilyl trifluoromethanesulfonate (38 μL, 0.21 mmol) in diethyl ether (2 mL) was added dropwise thereto and the mixture was stirred at room temperature for 2 hours. After triethylamine (35 μL) was added to the reaction mixture and the solvent was distilled off under reduced pressure, the residue was diluted with ethyl acetate (10 mL) and washed with saturated aqueous sodium hydrogencarbonate (10 mL) and saturated brine (10 mL). After the organic layer was dried with anhydrous sodium sulfate, the solvent was distilled off under reduced pressure. The residue was purified using silica gel flash column chromatography (hexane:ethyl acetate, 4:1-3:1, V/V) to isolate the desired title compound (295.8 mg, 72.9%) as colorless amorphous matter.

$^1$H NMR (400 MHz, CDCl$_3$): δ 3.20-5.60 (40H, m), 7.10-7.40 (65H, m); MS (FAB) m/z: 1932 (M+H)$^+$.

(19f) (2R,3R,4R)-4-Benzyloxy-N-benzyloxycarbonyl-2-benzyloxymethyl-pyrrolidin-3-yl 2,3,6-tri-O-benzyl-4-O-{4-O-(β-D-glucopyranosyl)-β-D-glucopyranosyl}-α-D-glucopyranoside The compound (295.8 mg, 0.15 mmol) synthesized in Example 19 (19e) was dissolved in methanol (6 mL) and potassium carbonate (20 mg, 0.14 mmol) was added thereto, followed by stirring of the mixture at room temperature for 6 hours. The reaction mixture was diluted with ethyl acetate (10 mL) and washed with saturated aqueous sodium hydrogencarbonate (10 mL) and saturated brine (10 mL). The mixture was neutralized with methanol-hydrochloric acid and the solvent was distilled off under reduced pressure. The residue was purified using silica gel flash column chromatography (methylene chloride:methanol, 30:1-20:1-10:1, V/V) to obtain the desired title compound (100.7 mg, 55.8%) as a colorless solid.

$^1$H NMR (400 MHz, CD3OD): δ 3.20-5.60 (40H, m), 7.10-7.40 (30H, m); MS (FAB) m/z: 1204 (M+H)$^+$.

(19g) (2R,3R,4R)-4-Hydroxy-2-hydroxymethyl-pyrrolidin-3-yl 4-O-{4-O-(β-D-glucopyranosyl)-β-D-glucopyranosyl}-α-D-glucopyranoside The compound (100.7 mg, 0.084 mmol) synthesized in Example 19 (19f) was dissolved in methanol (10 mL) and 36% hydrochloric acid (280 μL) and palladium hydroxide (100 mg) were added thereto, followed by stirring of the mixture at room temperature under a hydrogen atmosphere for 4 hours. After celite filtration, 18% ammonia water (1 mL) was added thereto and the solvent was distilled off under reduced pressure. The residue was purified by ion exchange resin (Dowex 50w×8) column (water—1% ammonia water). Further, it was purified using silica gel flash column chromatography (ethyl acetate:methanol:water, 5:2:1-1:1:1, V/V) to obtain the desired title compound (10.0 mg, 19.2%) as a colorless solid.

$^1$H NMR (400 MHz, D$_2$O): δ 3.00-3.95 (25H, m), 4.38 (1H, d, J=8.1 Hz), 4.42 (1H, d, J=8.0 Hz), 5.00 (1H, d, J=2.6 Hz); MS (FAB) m/z: 620 (M+H)$^+$.

EXAMPLE 20

(2R,3R,4R)-4-Hydroxy-2-hydroxymethyl-pyrrolidin-3-yl 4-O-{4-O-(β-D-glucopyranosyl}-β-D-glucopyranosyl}-α-D-galactopyranoside (Exemplification Compound No. 1-547)

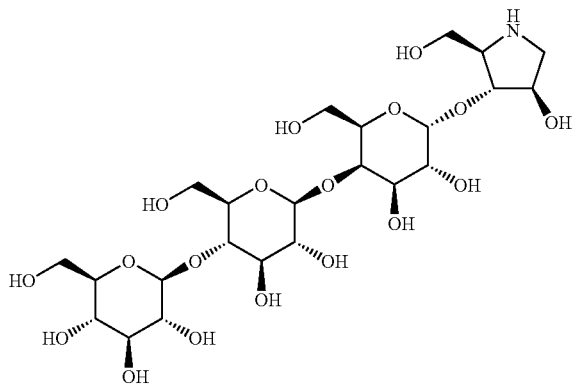

(20a) (2R,3R,4R)-4-Benzyloxy-N-benzyloxycarbonyl-2-benzyloxymethyl-pyrrolidin-3-yl 4-O-acetyl-2,3,6-tri-O-benzyl-α-D-galactopyranoside 4-O-Acetyl-2,3,6-O-tri-benzyl-D-galactopyranoside (BCSJ, 1989, 62, 3549-3566) (1.60 g, 3.25 mmol) was dissolved in methylene chloride (30 mL) and trichloroacetonitrile (1.6 mL, 15.96 mmol) and 1,8-diazabicyclo[5.4.0]-7-undecene (50 μL, 0.33 mmol) were added thereto, followed by stirring of the mixture at room temperature for 1 hour. After the solvent was distilled off under reduced pressure, the residue was purified using silica gel flash column chromatography (hexane:ethyl acetate, 6:1, 1% triethylamine, V/V) to obtain imidate (1.37 g, 66%) as a yellow oil. The compound (0.96 g, 2.01 mmol) synthesized in Example 1 (1i) was dissolved in diethyl ether (50 mL) and imidate (1.37 g, 2.15 mmol) was added thereto. A solution of trimethylsilyl trifluoromethanesulfonate (20 μL, 0.11 mmol) in diethyl ether (2 mL) was added dropwise thereto, followed by stirring of the mixture at room temperature for 2 hours. After triethylamine (10 μL) was added to the reaction mixture and the solvent was distilled off under reduced pressure, the residue was diluted with ethyl acetate (20 mL) and the mixture was washed with saturated aqueous sodium hydrogencarbonate (20 mL) and saturated brine (10 mL). After the organic layer was dried with anhydrous sodium sulfate, the solvent was distilled off under reduced pressure and the residue containing the α, β mixture was purified using silica gel flash column chromatography (hexane:ethyl acetate, 6:1-4:1, V/V) to isolate the desired title compound a isomer (0.98 g, 50%) thereof as a colorless oil.

$^1$H NMR (400 MHz, CDCl$_3$): δ2.02 (3H, s), 5.15-3.38 (25H, m), 5.61 (1H, m), 7.16-7.35 (30H, m); MS (FAB) m/z: 922 (M+H)$^+$.

(20b) (2R,3R,4R)-4-Benzyloxy-N-benzyloxycarbonyl-2-benzyloxymethyl-pyrrolidin-3-yl 2,3,6-tri-O-benzyl-α-D-galactopyranoside The compound (0.98 g, 1.06 mmol) synthesized in Example 20 (20a) was dissolved in methanol (20 mL) and potassium carbonate (147 mg, 1.06 mmol) was added thereto, followed by stirring of the mixture at room temperature for 14 hours. The reaction mixture was diluted with ethyl acetate (10 mL) and washed with saturated aqueous sodium hydrogencarbonate (10 mL) and saturated brine (10 mL). After the organic layer was dried with anhydrous sodium sulfate, the solvent was distilled off under reduced pressure. The residue was purified using silica gel flash column chromatography (hexane:ethyl acetate, 4:1, V/V) to obtain the desired title compound (772.4 mg, 83%) as a colorless oil.

$^1$H NMR (400 MHz, CDCl$_3$): δ 2.70-2.81 (1H, m), 3.46-5.15 (26H, m), 7.15-7.37 (30H, m); MS (FAB) m/z: 880 (M+H)$^+$.

(20c) (2R,3R,4R)-4-Benzyloxy-N-benzyloxycarbonyl-2-benzyloxymethyl-pyrrolidin-3-yl 2,3,6-tri-O-benzyl-4-O-{2,3,6-tri-O-benzoyl-4-O-(2,3,4,6-tetra-O-benzoyl-β-D-glucopyranosyl)-β-D-glucopyranosyl}-α-D-galactopyranoside The compound (516.8 mg, 0.48 mmol) synthesized in Example 20 (20b) was dissolved in methylene chloride (10 mL) and trichloroacetonitrile (240 μL, 2.39 mmol) and 1,8-diazabicyclo[5.4.0]-7-undecene (7.5 μL, 0.05 mmol) were added thereto, followed by stirring of the mixture at room temperature for 1 hour. After the solvent was distilled off under reduced pressure, the residue was purified using silica gel flash column chromatography (hexane:ethyl acetate, 4:1, 1% triethylamine, V/V) to obtain imidate (376.9 mg, 65%) as colorless amorphous matter. The compound (270.0 mg, 0.31 mmol) synthesized in Example 20 (20b) was dissolved in diethyl ether (15 mL) and imidate (376.9 mg, 0.31 mmol) was added thereto. A solution of trimethylsilyl trifluoromethanesulfonate (56 μL, 0.31 mmol) in diethyl ether (2 mL) was added dropwise thereto and the mixture was stirred at room temperature for 2 hours. After triethylamine (50 μL) was added to the reaction mixture and the solvent was distilled off under reduced pressure, the residue was diluted with ethyl acetate (20 mL) and washed with saturated aqueous sodium hydrogencarbonate (20 mL) and saturated brine (10 mL). After the organic layer was dried with anhydrous sodium sulfate, the solvent was distilled off under reduced pressure. The residue was purified using silica gel flash column chromatography (hexane:ethyl acetate, 4:1-3:1, V/V) to isolate the desired title compound (390.8 mg, 65%) as colorless amorphous matter.

$^1$H NMR (400 MHz, CDCl$_3$): δ 3.20-5.70 (40H, m), 7.10-7.40 (65H, m); MS (FAB) m/z: 1932 (M+H)$^+$.

(20d) (2R,3R,4R)-4-Benzyloxy-N-benzyloxycarbonyl-2-benzyloxymethyl-pyrrolidin-3-yl 2,3,6-tri-O-benzyl-4-O-{4-O-(β-D-glucopyranosyl)-β-D-glucopyranosyl}-α-D-galactopyranoside The compound (390.8 mg, 0.20 mmol) synthesized in Example 20 (20c) was dissolved in methanol (8 mL) and potassium carbonate (27.6 mg, 0.20 mmol) was added thereto, followed by stirring of the mixture at room temperature for 6 hours. The reaction mixture was diluted with ethyl acetate (10 mL) and washed with saturated aqueous sodium hydrogencarbonate (10 mL) and saturated brine (10 mL). The mixture was neutralized with methanol-hydrochloric acid and the solvent was distilled off under reduced pressure. The residue was purified using silica gel flash column chromatography (methylene chloride:methanol, 30:1-20:1-10:1, V/V) to obtain the desired title compound (146.5 mg, 61%) as a colorless solid.

$^1$H NMR (400 MHz, CD3OD): δ 1.13 3.20-4.70 (37H, m), 4.97 (1H, d, J=3.6 Hz), 5.07 (2H, s), 7.23-7.39 (30H, m); MS (FAB) m/z: 1226 (M+Na)$^+$.

(20e) (2R,3R,4R)-4-Hydroxy-2-hydroxymethyl-pyrrolidin-3-yl 4-O-{4-O-(β-D-glucopyranosyl)-β-D-glucopyranosyl}-α-D-galactopyranoside The compound (146.5 mg, 0.12 mmol) synthesized in Example 20 (20d) was dissolved in methanol (15 mL) and 36% hydrochloric acid (420 μL) and palladium hydroxide (150 mg) were added thereto, followed by stirring of the mixture at room temperature under a hydrogen atmosphere for 4 hours. After celite filtration, 18% ammonia water (1 mL) was added thereto, the solvent was distilled off under reduced pressure and the residue was purified by ion exchange resin (Dowex 50w×8) column (water—1% ammonia water). Further, it was purified using silica gel flash column chromatography (ethyl acetate:methanol:water, 5:2:1-1:1:1, V/V) to obtain acetate (23.6 mg, 32%) of the desired title compound as a colorless solid.

$^1$H NMR (400 MHz, D$_2$O): δ 3.17-3.87 (22H, m), 4.01 (1H, s), 4.11 (1H, s), 4.36 (1H, m), 4.38 (1H, d, J=8.0 Hz), 4.56 (1H, d, J=8.0 Hz), 5.04 (1H, s); MS (FAB) m/z: 620 (M+H)$^+$.

TEST EXAMPLE 1

α-Amylase Inhibitory Action (1) Preparation of Human α-Amylase Solution

"Caribzyme AMY" (International Reagents) was used for the human pancreatic α-amylase (HPA). Purified water was added to the commercially available HPA and dissolved to a concentration of 200 IU/l to prepare an α-amylase solution. The activity of the α-amylase was measured using a commercially available α-amylase assay reagent ("Neo-Amylase Test Daiichi", Daiichi Pure Chemicals).

(2) Preparation of Inhibitory Solutions

Each test compound was prepared with distilled water to a final concentration of 0.1 to 30 μg/ml, respectively.

(3) Measurement of Human α-Amylase Inhibitory Activity of Inhibitory Solutions 3.78 to 3.9 ml of distilled water and 0 to 120 μl of inhibitory solution were added to 100 μl of HPA solution and adjusted to a total volume of 4 ml. After incubating for 10 minutes at 37° C., a blue starch tablet ("Neo-Amylase Test Daiichi", Daiichi Pure Chemicals) was added followed by stirring for about 10 seconds with a mixer and heating for 30 minutes at 37° C. Subsequently, 1.0 ml of 0.5 N aqueous sodium hydroxide solution was added followed by stirring to stop the reaction, after which the mixture was centrifuged (1,500 G, 5 minutes) and the absorbance of the resulting supernatant was measured at 620 nm. A mixture to which inhibitory solution had not been added was used as a control. In addition, distilled water was added instead of α-amylase for use as a blank. The inhibition rate was calculated according to the following formula, and the final concentration of test compound required to inhibit the activity of the HPA solution by 50% (μg/ml) was taken to be the IC50 value. Those values are shown in Table 6.

Inhibition rate (%)=[1−{(Absorbance of control)−(absorbance of blank)}/{(absorbance when inhibitor added)−(absorbance of blank)}]×100

TABLE 6

| Example No. | IC50 (μg/ml) |
| --- | --- |
| 1 | $7 \times 10^{-1}$ |
| 2 | $2 \times 10^{-1}$ |
| 3 | $4 \times 10^{-1}$ |
| 4 | $3 \times 10^{-1}$ |
| 5 | 7 |
| 7 | 4 |
| 8 | $4 \times 10^{-1}$ |
| 9 | $3 \times 10$ |
| 11 | $1 \times 10$ |
| 13 | 4 |
| 14 | 1 |
| 15 | $6 \times 10^{-1}$ |
| 17 | $3 \times 10$ |
| 18 | $2 \times 10^{-3}$ |
| 19 | $6 \times 10^{-1}$ |

It was found from Table 6 that compounds of the present invention have superior α-amylase inhibitory action.

TEST EXAMPLE 2

Postprandial Hyperglycemia Inhibitory Action (1) Test Animals

Commercially available normal mice (ddY mice, males, age 8 weeks at the time of testing, supplied by Japan SLC).

(2) Experimental Methods and Results

For the dose group, a test compound and commercially available cornstarch were mixed well with 0.5% carboxymethyl cellulose to prepare a suspension that was orally administered at 0.3 mg (test compound)/2 g (cornstarch)/kg (body weight) to five mice that had been fasted in advance for 20 hours. The control group was administered with a similar suspension in the same manner with the exception of not containing the test compound.

Blood samples were collected from a tail vein of the mice before dosing and at 0.5, 1, 2 and 3 hours after dosing followed by measurement of blood glucose levels and calculation of the inhibition rate (%) according to the following formula from the area under the curve (AUC) of the increase in blood glucose levels (area under the curve of the change in increases in blood glucose levels, mg/dl×hr). Blood glucose levels were measured using a blood glucose analyzer (Glucoloader GXT, A & T).

Inhibition rate (%)=[1−(dose group AUC/control group blood glucose increase AUC)]×100

TABLE 7

| Example No. | Inhibition Rate (%) |
| --- | --- |
| 2 | 64 |

According to Table 7, compounds of the present invention were determined to have superior action in inhibiting increases in blood glucose levels. Thus, compounds of the present invention are considered to be useful as postprandial hyperglycemia therapeutic agents.

TEST EXAMPLE 3

Blood Glucose Lowering Action (1) Test Animals

Commercially available, genetically obese diabetic mice (C57BL/KsJ-db/db mice, males, age 16 weeks at the time of testing, supplied by Clea Japan).

(2) Experimental Methods and Results

A test compound was mixed into a refined laboratory animal diet (carbohydrate content: 65.95% (w/w), Oriental Yeast) to a test compound concentration of 0.005% (w/w) and allowed to be freely ingested by diabetic mice for 1 week in groups of 5 mice per group. A control group was allowed similar unrestricted access to the same feed with the exception of not containing the test compound.

Blood glucose levels were measured before the start of dosing and one week after the start of dosing. Blood samples were collected from a tail vein and blood glucose levels were measured using a blood glucose analyzer (Glucoloader GXT, A & T) to calculate the blood glucose lowering rate (%) according to the following formula.

Blood glucose lowering rate (%)=[1−(compound dose group blood glucose level/control group blood glucose level)]×100

TABLE 8

| Example No. | Blood Glucose Lowering Rate (%) |
|---|---|
| 2 | 47 |

According to Table 8, compounds of the present invention were determined to have superior blood glucose lowering action. Thus, compounds of the present invention are considered to be useful as diabetes mellitus therapeutic agents.

PREPARATION EXAMPLES

| (1) Capsules | |
|---|---|
| Compound of Example 1 | 10 mg |
| Lactose | 110 mg |
| Cornstarch | 58 mg |
| Magnesium stearate | 2 mg |
| Total | 180 mg |

Powders of each of the ingredients listed above are mixed well and passed through a 60 mesh sieve (the sieve mesh is based on the Tyler mesh). 180 mg of the resulting powder is weighed out and filled into gelatin capsules (No. 3) to prepare capsule preparations.

| (2) Tablets | |
|---|---|
| Compound of Example 1 | 10 mg |
| Lactose | 85 mg |
| Cornstarch | 34 mg |
| Crystalline cellulose | 20 mg |
| Magnesium stearate | 1 mg |
| Total | 150 mg |

Powders of each of the ingredients listed above are mixed well and compressed and molded into tablets having a weight of 150 mg each. These tablets may be coated with sugar or a film as necessary.

| (3) Granules | |
|---|---|
| Compound of Example 1 | 10 mg |
| Lactose | 839 mg |
| Cornstarch | 150 mg |
| Hydroxypropyl cellulose | 1 mg |
| Total | 1000 mg |

Powders of each of the ingredients listed above are mixed well, wetted purified water and granulated with a basket-type granulator followed by drying to obtain granules.

INDUSTRIAL APPLICABILITY

Compounds of the present invention in the form of a novel oligosaccharide derivative, its pharmacologically acceptable salts and its pharmacologically acceptable esters demonstrate superior α-amylase inhibitory action, blood glucose lowering action and lipid lowering action, and are useful as therapeutic drugs and/or preventive drugs for hyperglycemia, postprandial hyperglycemia, impaired glucose tolerance, diabetes mellitus, obesity, hyperlipemia, fatty liver, hepatomegaly, diabetic complications, neuropathy, arteriosclerosis, cataract or diabetic nephropathy (and preferably as therapeutic drugs and/or preventive drugs for hyperglycemia or diabetes mellitus).

The invention claimed is:

1. A compound represented by the general formula (I):

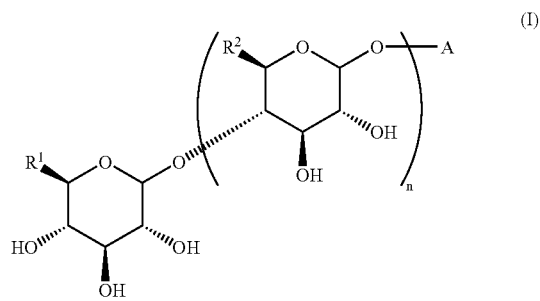

wherein

A represents the general formula (A1) or (A2):

$R^1$ and $R^2$ are the same or different, and each represent a C1-C6 alkyl group, hydroxymethyl group, C1-C6 alkoxymethyl group or C1-C6 haloalkyl group, $R^3$, $R^4$, and $R^5$ are the same or different, and each represent a C1-C6 alkyl group, C1-C6 alkoxy group, C1-C6 hydroxyalkyl group, C1-C6 haloalkyl group, amino group which amino group may optionally be substituted with one or two C1-C6 alkyl groups or C1-C6 hydroxyalkyl groups, hydroxyl group, hydrogen atom or halogen atom, $R^7$ represents a C1-C6 alkyl group, C1-C6 alkoxy group, C1-C6 hydroxyalkyl group, C1-C6 haloalkyl group, hydroxyl group or hydrogen atom, and n represents an integer of 1 or 2; or a pharmacologically acceptable salt thereof.

2. A compound according to claim 1, wherein $R^1$ and $R^2$ are the same or different and each represent a C1-C3 alkyl group, hydroxymethyl group, C1-C3 alkoxymethyl group or C1-C3 haloalkyl group; or a pharmacologically acceptable salt thereof.

3. A compound according to claim 1, wherein $R^3$, $R^4$, and $R^5$ are the same or different and each represent a C1-C3 alkyl group, C1-C3 hydroxyalkyl group, C1-C3 haloalkyl group, amino group which amino group may optionally be substituted with one or two C1-C6 hydroxyalkyl groups, hydroxyl group, hydrogen atom or halogen atom; or a pharmacologically acceptable salt thereof.

4. A compound according to claim 1, wherein $R^7$ represents a hydrogen atom; or a pharmacologically acceptable salt thereof.

5. A compound according to claim 1, represented by the general formula (Ia):

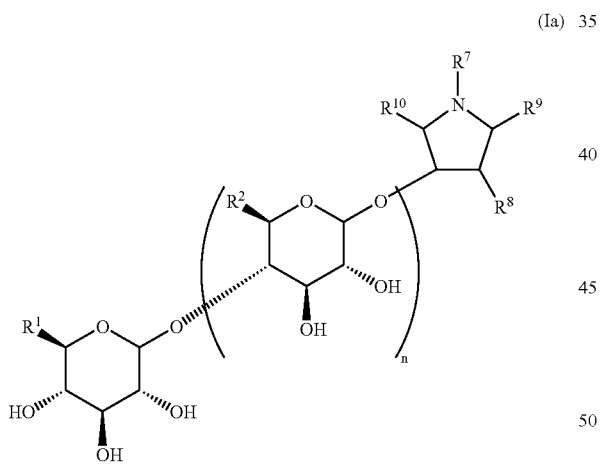

(Ia)

wherein $R^1$ and $R^2$ are the same or different, and each represent a C1-C6 alkyl group, hydroxymethyl group, C1-C6 alkoxymethyl group or C1-C6 haloalkyl group, $R^7$ represents a C1-C6 alkyl group, C1-C6 alkoxy group, C1-C6 hydroxyalkyl group, C1-C6 haloalkyl group, hydroxyl group or a hydrogen atom, $R^{10}$ represents a hydrogen atom, hydroxyl group, C1-C6 hydroxyalkyl group or C1-C6 haloalkyl group, $R^8$ and $R^9$ are the same or different and each represent a hydroxyl group, C1-C6 hydroxyalkyl group, hydrogen atom or halogen atom, and n represents an integer of 1 or 2;

or a pharmacologically acceptable salt thereof.

6. A compound according to claim 5, wherein $R^1$ is a C1-C3 alkyl group, hydroxymethyl group, C1-C3 alkoxymethyl group or C1-C3 haloalkyl group; or a pharmacologically acceptable salt thereof.

7. A compound according to claim 5, wherein $R^1$ is a methyl group or hydroxymethyl group; or a pharmacologically acceptable salt thereof.

8. A compound according to claim 5, wherein $R^2$ is a hydroxymethyl group or C1-C3 haloalkyl group; or a pharmacologically acceptable salt thereof.

9. A compound according to claim 5, wherein $R^2$ is a hydroxymethyl group; or a pharmacologically acceptable salt thereof.

10. A compound according to claim 5, wherein $R^7$ is a hydrogen atom or a pharmacologically acceptable salt thereof.

11. A compound according to claim5, wherein $R^{10}$ is a hydrogen atom, C1-C3 hydroxyalkyl group or C1-C3 haloalkyl group; or a pharmacologically acceptable salt thereof.

12. A compound according to claim 5, wherein $R^{10}$ is a C1-C3 hydroxyalkyl group; or a pharmacologically acceptable salt thereof.

13. A compound according to claim 5, wherein $R^8$ and $R^9$ are the same or different and each represent a hydroxyl group or hydrogen atom; or a pharmacologically acceptable salt thereof.

14. A compound according to claim 1, represented by the general formula (Ib):

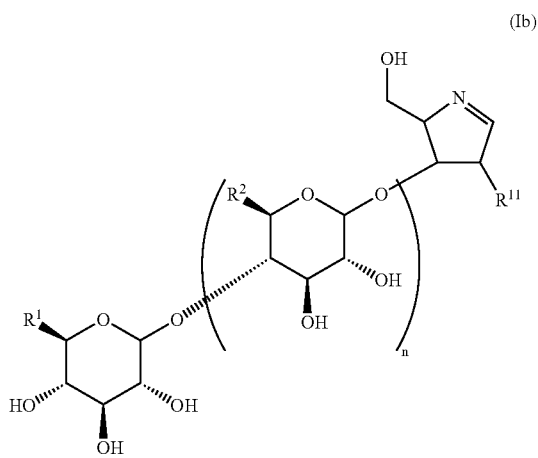

(Ib)

wherein $R^1$ and $R^2$ are the same or different, and each represent a C1-C6 alkyl group, hydroxymethyl group, C1-C6 alkoxymethyl group or C1-C6 haloalkyl group, $R^{11}$ represents a hydroxyl group, C1-C6 hydroxyalkyl group, hydrogen atom or halogen atom, and n represents an integer of 1 or 2; or a pharmacologically acceptable salt thereof.

15. A compound according to claim 14, wherein $R^{11}$ is a hydroxyl group; or a pharmacologically acceptable salt thereof.

16. A compound according to claim 14, wherein $R^1$ is a C1-C3 alkyl group, $R^2$ is a hydroxymethyl group and n is 1; or a pharmacologically acceptable salt thereof.

17. A compound according to claim 1, wherein said compound is
- (2R,3R,4R)-4-hydroxy-2-hydroxymethyl-pyrrolidin-3-yl 4-O-(6-deoxy-α-D-glucopyranosyl)-α-D-glucopyranoside,
- (2R,3R,4R)-4-hydroxy-2-hydroxymethyl-pyrrolidin-3-yl 4-O-(6-deoxy-β-D-glucopyranosyl)-α-D-glucopyranoside,
- (2R,3R,4R)-4-hydroxy-2-hydroxymethyl-pyrrolidin-3-yl 4-O-β-D-glucopyranosyl-α-D-glucopyranoside,
- (2R,3R,4R)-4-hydroxy-2-hydroxymethyl-pyrrolidin-3-yl 4-O-(6-fluoro-6-deoxy-β-D-glucopyranosyl)-D-glucopyranoside,
- (2R,3R,4R)-4-hydroxy-2-hydroxymethyl-pyrrolidin-3-yl 4-O-(6-methoxy-6-deoxy-β-D-glucopyranosyl)-D-glucopyranoside, or
- (2R,3R,4R)-4-hydroxy-2-hydroxymethyl-3,4-dihydro-2H-pyrrol-3-yl 4-O-(6-deoxy-α-D-glucopyranosyl)-α-D-glucopyranoside; or a pharmacologically acceptable salt thereof.

18. A compound or a pharmacologically acceptable salt thereof according to claim 1 or 17, and further comprising a pharmaceutically acceptable adjuvant or carrier.

19. A compound or a pharmacologically acceptable salt thereof claim 1 or 17, and further comprising a pharmaceutically acceptable adjuvant or carrier.

20. A compound or a pharmacologically acceptable salt thereof claim 1 or 17, and further comprising a pharmaceutically acceptable adjuvant or carrier.

21. A pharmaceutical composition for treating a compound or a pharmacologically acceptable salt thereof according to claim 1 or claim 17, and further comprising a pharmaceutically acceptable adjuvant or carrier.

22. A method of treating diabetes mellitus, which comprises a compound or a pharmacologically acceptable salt thereof according to claim 1 or claim 17 to a warm-blooded animal in need thereof.

* * * * *